(12) United States Patent
Carscallen et al.

(10) Patent No.: US 11,746,351 B2
(45) Date of Patent: Sep. 5, 2023

(54) ENGINEERED MICROORGANISM FOR THE PRODUCTION OF CANNABINOID BIOSYNTHETIC PATHWAY PRODUCTS

(71) Applicant: ALGAE-C INC., Caledon (CA)

(72) Inventors: William Mather Almon Carscallen, Halifax (CA); Isabel Desgagné-Penix, Trois-Rivières (CA); Jean-Francois Lemay, Shawinigan (CA)

(73) Assignee: Algae-C Inc., Caledon (CA)

( * ) Notice: Subject to any disclaimer, the term of this patent is extended or adjusted under 35 U.S.C. 154(b) by 0 days.

(21) Appl. No.: 17/052,039

(22) PCT Filed: Apr. 29, 2019

(86) PCT No.: PCT/CA2019/050557
§ 371 (c)(1),
(2) Date: Oct. 30, 2020

(87) PCT Pub. No.: WO2019/210404
PCT Pub. Date: Nov. 7, 2019

(65) Prior Publication Data
US 2021/0189402 A1 Jun. 24, 2021

Related U.S. Application Data

(60) Provisional application No. 62/664,322, filed on Apr. 30, 2018, provisional application No. 62/813,927, filed on Mar. 5, 2019.

(51) Int. Cl.
*C12N 15/52* (2006.01)
*C12N 1/12* (2006.01)
*C12N 9/88* (2006.01)
*C12P 7/42* (2006.01)

(52) U.S. Cl.
CPC .............. *C12N 15/52* (2013.01); *C12N 1/12* (2013.01); *C12N 9/88* (2013.01); *C12P 7/42* (2013.01)

(58) Field of Classification Search
CPC . C12N 15/52; C12N 1/12; C12N 9/88; C12N 15/70; C12N 9/1029; C12N 15/815; C12P 7/42; C12P 7/22; C07K 2319/00; C12Y 203/01206; C12Y 404/01026
See application file for complete search history.

(56) References Cited

U.S. PATENT DOCUMENTS

2021/0403964 A1* 12/2021 Laban ...................... C12N 1/12

FOREIGN PATENT DOCUMENTS

| WO | WO 2016/010827 | 1/2016 |
| WO | WO 2017/139496 | 8/2017 |
| WO | WO 2018/148849 | 8/2018 |
| WO | WO 2018/200888 | 11/2018 |
| WO | WO 2018/204859 | 11/2018 |
| WO | WO 2019/202510 | 10/2019 |
| WO | WO 2020/160289 | 8/2020 |

OTHER PUBLICATIONS

Branco-Vieira et al. Analyzing Phaeodactylum tricornutum lipid profile for biodiesel production. Energy Procedia 136 (2017), 369-373. (Year: 2017).*
Carvalho A et al., "Designing microorganisms for heterologous biosynthesis of cannabinoids," FEMS Yeast research, 2017 17(4)1-11 doi: 10.1093/femsyr/fox037.
Gagne et al., Identification of olivetolic acid cyclase from *Cannabis sativa* reveals a unique catalytic route to plant polyketides, P Natl Acad Sci USA, 2012, 109:12811-12816.
PCT International Search Report and Written Opinion in International Appln. No. PCT/CA2019/050557, dated Jul. 8, 2019.
Tan et al., "Synthetic pathway for the production of olivetolic acid in *Escherichia coli*," ACS Synth Biol, 2018, 7/8/:1886-1896, doi: 10.102 1/acssynbio.8b00075.
Taunt et al.,A Green biologics: The algal chloroplast as a platform for making biopharmaceuticals Bioengineered 2017, 9(1):48-54 doi: 10.1080/21655979.2017.1377867.
Altschul et al., "Basic Local Alignment Search Tool," Journal of Molecular Biology, Oct. 5, 1990, 215(3):403-410.
Altschul et al., "Gapped BLAST and PSI-BLAST: a new generation of protein database search programs," Nucleic acids research, Sep. 1, 1997, 25(17):3389-3402.
DeLoache et al, "An enzyme-coupled biosensor enables (S)-reticuline production in yeast from glucose," Nature Chemical Biology, May 18, 2015, 11(7):465-471, 9 pages.
Diaz-Santos et al., "Efficiency of different heterologous promoters in the unicellular microalga Chlamydomonas reinhardtii," Biotechnology Progress, Jan. 14, 2013, 29(2):319-328, 30 pages.
ElSohly et al., "Chemical constituents of marijuana: The complex mixture of natural cannabinoids," Life Sciences, Dec. 22, 2005, 78(5):539-548.
Flores-Sanchez et al., "In silicio expression analysis of PKS genes isolated from *Cannabis sativa* L," Genetics and Molecular Biology, Oct. 29, 2010, 33(4):703-713, 17 pages.
Fossati et al., "Reconstitution of a 10-gene pathway for synthesis of the plant alkaloid dihydrosanguinarine in *Saccharomyces cerevisiae*," Nature Communications, Feb. 11, 2014, (5):3283, 11 pages.
GenBank Accession No. AB164375.1, *Cannabis sativa* OLS mRNA for olivetol synthase, complete cds, Jun. 19, 2009, 2 pages.
GenBank Accession No. JN679224.1, "*Cannabis sativa* olivetolic cyclase mRNA, complete cds," Aug. 2, 2012, 1 page.

(Continued)

*Primary Examiner* — Iqbal H Chowdhury
(74) *Attorney, Agent, or Firm* — Fish & Richardson P.C.

(57) ABSTRACT

A genetically engineered microorganism for the production of a cannabinoid biosynthetic pathway product is described. The genetically engineered microorganism comprises at least one nucleic acid molecule encoding at least one cannabinoid biosynthetic pathway enzyme. The disclosure also relates to methods for producing a cannabinoid biosynthetic pathway product using a genetically engineered microorganism.

17 Claims, 16 Drawing Sheets

Specification includes a Sequence Listing.

(56) References Cited

OTHER PUBLICATIONS

Gibson et al., "Enzymatic assembly of DNA molecules up to several hundred kilobases," Nature Methods, Apr. 12, 2009, 6(5):343-345, 5 pages.

Karas et al., "Designer diatom episomes delivered by bacterial conjugation," Nature Communications, Apr. 21, 2015, 6:6925, 10 pages.

Karlin et al, "Applications and statistics for multiple high scoring segments in molecular sequences," Proceedings of the National Academy of Sciences, Jun. 1993, 90:5873-5877.

Karlin et al., "Methods for assessing the statistical significance of molecular sequence features by using general scoring schemes," Proceedings of the National Academy of Sciences, Mar. 1990, 87:2264-2268.

Keasling, "Synthetic biology and the development of tools for metabolic engineering," Metabolic Engineering, Feb. 1, 2012, 14(3):189-195.

Lithwick et al., "Flierarchy of sequence-dependent features associated with prokaryotic translation," Genome Research, Dec. 2003, 13:2665-2673.

Lussier et al., "Engineering microbes for plant polyketide biosynthesis," Computational and Structural Biotechnology Journal, Oct. 2012, 3(4):e201210020, 11 pages.

Marks et al., "Identification of candidate genes affecting Delta9-tetrahydrocannabinol biosynthesis in Cannabis sativa," Journal of Experimental Botany, Jul. 6, 2009, 60(13):3715-3726.

Myers et al., "Optimal alignments in linear space" Computer Applications in the Biosciences, Mar. 1988, 4(1):11-17.

PCT International Preliminary Report on Patentability in International Appln. No. PCT/CA2019/050557, dated Nov. 3, 2020, 6 pages.

Plecenikova et al., "Studies on recombination processes in two Chlamydomonas reinhardtii endogenous genes, NIT1 and ARG7," Protist, Jul. 2013, 164(4):570-582.

Schroda et al., "The HSP70A promoter as a tool for the improved expression of transgenes in Chlamydomonas," The Plant Journal, Jan. 1, 2000, 21(2):121-131.

Singh et al., "Chloroplast-derived vaccine antigens and biopharmaceuticals: protocols for expression, purification, or oral delivery and functional evaluation," Methods in Molecular Biology, 2009, 483:163-192.

Slattery et al., "An expanded plasmid-based genetic toolbox enables Cas9 genome editing and stable maintenance of synthetic pathways in Phaeodactylum tricornutum," ACS Synthetic Biology, Jan. 3, 2018, 7(2):328-338.

Stout et al., "The hexanoyl-CoA precursor for cannabinoid biosynthesis is formed by an acyl-activating enzyme in Cannabis sativa trichomes," The Plant Journal, Aug. 2012, 71(3):353-365.

Taura et al., "Characterization of olivetol synthase, a polyketide synthase putatively involved in cannabinoid biosynthetic pathway," FEBS Letters, Jun. 18, 2009, 583(12):2061-2066.

Welch et al., "Design parameters to control synthetic gene expression in Escherichia coli," PLoS One, Sep. 2009, 4(9):e7002, 10 pages.

EP Search Report in European Appln. No. 19796020.6, dated Apr. 4, 2022, 8 pages.

\* cited by examiner

Fig. 3

Cons1_TKS-FMDV-OAC

Cons2_TKS-OAC
BamHI

A)

E. coli with pC3_1    E. coli with pC4_2

ENGINEERED MICROORGANISM FOR THE PRODUCTION OF CANNABINOID BIOSYNTHETIC PATHWAY PRODUCTS

CROSS-REFERENCE TO RELATED APPLICATIONS

This application is a National Stage Application under 35 U.S.C. § 371 and claims the benefit of International Application No. PCT/CA2019/050557, filed Apr. 29, 2019, which claims the benefit of and priority from U.S. Provisional Patent Application No. 62/664,322 filed on Apr. 30, 2018, and U.S. Provisional Patent Application No. 62/813,927 filed on Mar. 5, 2019, each of which are hereby incorporated by reference in their entirety.

FIELD

The present disclosure relates to genetically engineered microorganisms for production of cannabinoid biosynthetic pathway products and cell cultures comprising thereof. The genetically engineered microorganisms comprise nucleic acid molecules having nucleic acid sequences encoding cannabinoid biosynthetic pathway enzymes for producing cannabinoid biosynthetic pathway products.

BACKGROUND

The commercialization of valuable plant natural products (PNPs) is often limited by the availability of PNP producing-plants, by the low accumulation of PNPs in planta and/or the time-consuming and often inefficient extraction methods not always economically viable. Thus, commercialization of PNPs of commercial interest is often challenging. The recent progress in genetic engineering and synthetic biology makes it possible to produce heterologous PNPs in microbes such as bacteria, yeasts and microalgae. For example, engineered microorganisms have been reported to produce the antimalarial drug artemisinin and of the opiate (morphine, codeine) painkiller precursor reticuline (Keasling 2012; Fossati et al 2014; DeLoache et al 2015). However, the latest metabolic reactions to yield the valuable end-products such as codeine and morphine in genetically modified yeast-producing reticuline have yet to be successfully achieved. In some cases, bacterial or yeast platforms do not support the assembly of complex PNP pathways. In comparison, microalgal cells have been suggested to possess advantages over other microorganisms, including the likelihood to perform similar post-translational modifications of proteins as plant and recombinant protein expression through the nuclear, mitochondrial or chloroplastic genomes (Singh et al 2009).

Cannabinoid biosynthetic pathway products such as 49-tetrahydrocanannabinol and other cannabinoids (CBs) are polyketides responsible for the psychoactive and medicinal properties of *Cannabis sativa*. More than 70 CBs have been identified so far and are all derived from fatty acid and terpenoid precursors (ElSohly and Slade 2005). The first metabolite intermediate in the CB biosynthetic pathway in *Cannabis sativa* is olivetolic acid that forms the polyketide skeleton of cannabinoids. A type III polyketide synthase (PKS; also known as tetraketide synthase (TKS) or olivetol synthase) enzyme condenses hexanoyl-CoA with three malonyl-CoA in a multi-step reaction to form trioxododecanoyl-CoA. From there, olivetolic acid cyclase (OAC) (OAC; also known as 3,5,7-trioxododecanoyl-CoA CoA-lyase) catalyzes an intramolecular aldol condensation to yield OA. In subsequent steps, CB diversification is generated by the sequential action of "decorating" enzymes on the OA backbone. The gene sequence for PKS and OAC have been identified and characterized in vitro (Lussier 2012; Gagne et al 2012; Marks et al 2009; Stout et al 2012; Taura et al 2009).

SUMMARY

The present disclosure describes an engineered microorganism such as a microalga or a cyanobacterium for production of a plant natural product such as a cannabinoid biosynthetic pathway product.

A method has been developed for the genetic transformation of the microalga *Chlamydomonas reinhardtii*, *Chlorella vulgaris*, *Dunaliella tertiolecta* and *Phaeodactylum tricornutum* with TKS and OAC genes encoding biosynthetic enzymes involved in the production of the polyketide precursor olivetolic acid. The coding sequences, without and with introns, for TKS and OAC genes were codon-optimized for enhanced expression in the selected microalgae strains. The optimized genes were synthesized, arranged in different construction cassette and inserted into transformation vectors. Different constructs comprising constitutive promoters, single or combined TKS and OAC with adaptor sequences or self-cleaving peptide sequence, ribosome binding sites, etc., were created and used to transform *Chlamydomonas reinhardtii*, *Chlorella vulgaris*, *Dunaliella tertiolecta* and *Phaeodactylum tricornutum* cells. Transformation efficiencies were determined through (i) colony growth on agar plate supplemented with antibiotic selection marker, (ii) detection of gene presence in the nuclear genome by PCR analysis and (iii) quantitative measurement of the gene expression of transgenes was detected using quantitative real-time PCR (qRT-PCR) analysis and enzymes produced were detected using SDS-PAGE and western blot to confirm the presence of the corresponding recombinant enzymes.

Accordingly, the present disclosure provides a genetically engineered microorganism that is capable of producing olivetolic acid, wherein the genetically engineered microorganism is a photosynthetic microalga or a cyanobacterium.

In an embodiment of the genetically engineered microorganism as described herein, the genetically engineered microorganism does not comprise an exogenous nucleic acid molecule encoding hexanoyl-CoA synthetase.

In an embodiment of the genetically engineered microorganism as described herein, the genetically engineered microorganism comprises at least one nucleic acid molecule that encodes tetraketide synthase and olivetolic acid cyclase.

In an embodiment of the genetically engineered microorganism as described herein, the tetraketide synthase comprises amino acid sequence with at least 90% sequence identity to sequence as shown in SEQ ID NO:15, and the olivetolic acid cyclase comprises amino acid sequence with at least 90% sequence identity to sequence as shown in SEQ ID NO:16 or 17.

In an embodiment of the genetically engineered microorganism as described herein, the at least one nucleic acid molecule comprises a promoter and two polynucleotide sequences, one encoding tetraketide synthase and the other encoding olivetolic acid cyclase, each of which is operably linked to the promoter.

In an embodiment of the genetically engineered microorganism as described herein, the at least one nucleic acid molecule comprises a first nucleic acid molecule encoding tetraketide synthase and a second nucleic acid molecule encoding olivetolic acid cyclase.

In an embodiment of the genetically engineered microorganism as described herein, the at least one nucleic acid molecule is an episomal vector.

In an embodiment of the genetically engineered microorganism as described herein, the at least one nucleic acid molecule further encodes aromatic prenyltransferase.

In an embodiment of the genetically engineered microorganism as described herein, the aromatic prenyltransferase comprises amino acid sequence with at least 90% sequence identity to sequence as shown in SEQ ID NO:18, 63, 64, or 65.

In an embodiment of the genetically engineered microorganism as described herein, the at least one nucleic acid molecule further encodes tetrahydrocannabinolic acid synthase or cannabidiolic acid synthase.

In an embodiment of the genetically engineered microorganism as described herein, the tetrahydrocannabinolic acid synthase comprises amino acid sequence with at least 90% sequence identity to sequence as shown in SEQ ID NO:20, and the cannabidiolic acid synthetase comprises amino acid sequence with at least 90% sequence identity to sequence as shown in SEQ ID NO:21.

In an embodiment of the genetically engineered microorganism as described herein, the at least one nucleic acid molecule comprises at least one polynucleotide sequence with at least 80% sequence identity to a sequence selected from SEQ ID NO: 1-4, 6-11, 13, 14, 58-60 and 68-70.

In an embodiment of the genetically engineered microorganism as described herein, the at least one nucleic acid molecule comprises at least two polynucleotide sequences with at least 80% sequence identity to a sequence selected from SEQ ID NO: 1-4, 6-11, 13, 14, 58-60 and 68-70.

In an embodiment of the genetically engineered microorganism as described herein, the at least one nucleic acid molecule comprises at least one linker sequence between the at least two polynucleotide sequences.

In an embodiment of the genetically engineered microorganism as described herein, the at least one linker sequence is a self-cleaving sequence.

In an embodiment of the genetically engineered microorganism as described herein, the microalga is Chlamydomonas reinhardtii, Chlorella vulgaris, Chlorella sorokiniana, Chlorella protothecoides, Tetraselmis chui, Nannochloropsis oculate, Scenedesmus obliquus, Acutodesmus dimorphus, Dunaliella tertiolecta, or Heamatococus plucialis.

In an embodiment of the genetically engineered microorganism as described herein, the microalga is a diatom.

In an embodiment of the genetically engineered microorganism as described herein, the microalga is Phaeodactylum tricornutum.

In an embodiment of the genetically engineered microorganism as described herein, the cyanobacterium is Arthrospira plantesis, Arthrospira maxima, Synechococcus elongatus or Aphanizomenon flos-aquae.

The present disclosure also provides a genetically engineered microorganism that is capable of producing olivetol, wherein the genetically engineered microorganism is a microalga or a cyanobacterium.

Other features and advantages of the present disclosure will become apparent from the following detailed description. It should be understood, however, that the detailed description and the specific Examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

Figure 3:
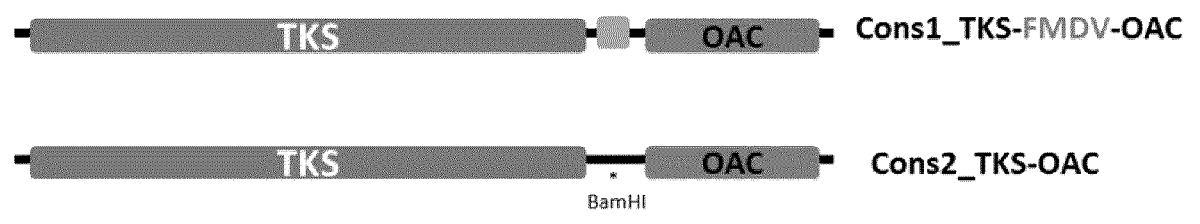

FIG. 3 shows exemplary fusion genes of tetraketide synthase (TKS) and olivetolic acid cyclase (OAC). Construct 1 (top) is TKS fused to OAC by a FMDV linker. Construct 2 (bottom is TKS fused to OAC by a peptide linker comprising a BamHI restriction site.

FIG. 9 shows SDS-PAGE gel of proteins extracted from Chlamydomonas cells transformed with pChlamy4 vectors. (A) pC4-1 transformed cells do not show an increase of two bands at, 42 (TKS) and 12 kDa (OAC) compared to control cells (lane 2). (B) pC4-2 transformed cells do not show an increase of a band at 60 kDa (expected TKS-OAC fused protein) compared to control cells (lane1). (C) Western blot using anti-FMDV-2A antibodies reveals the presence of fused and single protein construction in different C. reinhardtii positive transformants.

Figure 1:
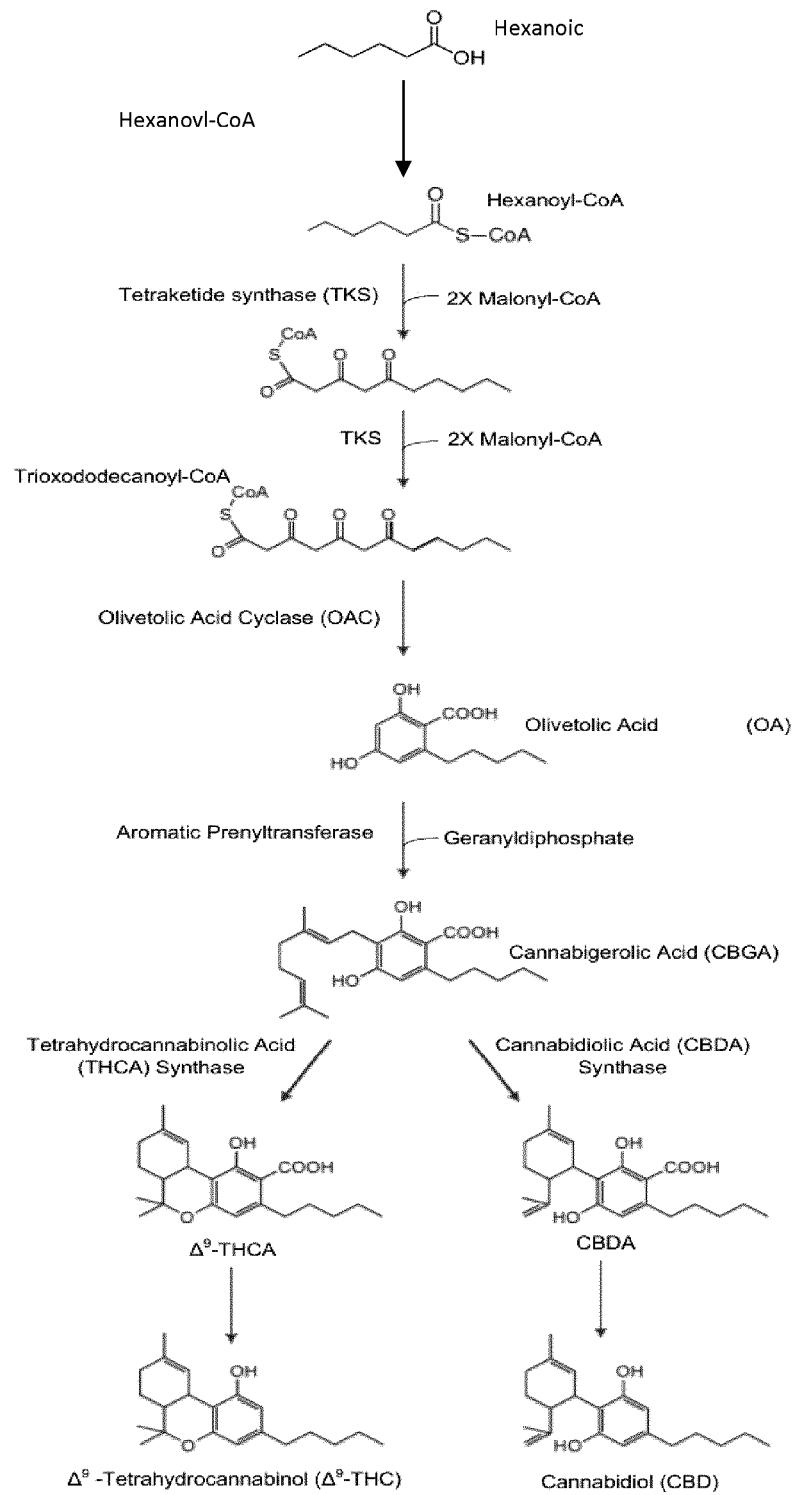
FIG. 1 shows an exemplary cannabinoid biosynthetic pathway based on enzymes from Cannabis sativa.

As used herein, the singular forms "a", "an" and "the" include plural references unless the content clearly dictates otherwise. In embodiments comprising an "additional" or "second" component, the second component as used herein is different from the other components or first component. A "third" component is different from the other, first, and second components, and further enumerated or "additional" components are similarly different.

In the absence of any indication to the contrary, reference made to a "%" content throughout this specification is to be taken as meaning % w/v (weight/volume).

As used here, the term "sequence identity" refers to the percentage of sequence identity between two nucleic acid (polynucleotide) or two amino acid (polypeptide) sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul et al (1990). BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score=50, wordlength=3 to obtain amino acid sequences homologous to a protein molecule of the present disclosure. To obtain gapped alignments for comparison purposes, Gapped BLAST can be utilized as described in Altschul et al. (1997). Alternatively, PSI-BLAST can be used to perform an iterated search which detects distant relationships between molecules (Altschul et al., 1997). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller (1988). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted. In a specific embodiment, the nucleic acids are optimized for codon usage in a specific microalgal or cyanobacterial species. In particular, the nucleic acid sequence encoding the cannabinoid biosynthetic pathway enzyme incorporates codon-optimized codons for GC-rich microalgae, such as *Chlamydomonas reinhardtii, Chlorella vulgaris, Chlorella sorokiniana, Chlorella protothecoides, Tetraselmis chui, Nannochloropsis oculate, Scenedesmus obliquus, Acutodesmus dimorphus, Dunaliella tertiolecta*, and *Heamatococus plucialis*; diatoms, such as *Phaeodactylum tricornutum* and *Thalassiosira pseudonana*; or cyanobacteria such as Arthrospira *platensis*, Arthrospira maxima, Synechococcus *elongatus*, and Aphanizomenon *flos-aquae*.

The sequences of the present disclosure may be at least 80% identical to the sequences described herein; in another example, the sequences may be at least 80%, 85%, 90%, 95%, 96%, 97%, 98%, 99%, or 100% identical at the nucleic acid or amino acid level to sequences described herein. Importantly, the proteins encoded by the variant sequences retain the activity and specificity of the proteins encoded by the reference sequences. Accordingly, the present disclosure also provides a nucleic acid molecule comprising nucleic acid sequence encoding a cannabinoid biosynthetic pathway enzyme with at least 80%, 85%, 90%, 95%, 96%, 97%, 98%, 99% or 100% sequence identity to a sequence selected from SEQ ID NO:1-14, 56-60, and 66-70. Also provided is an amino acid sequence of a cannabinoid biosynthetic pathway enzyme with at least 90%, 91%, 92%, 93%, 94%, 95%, 96%, 97%, 98%, 99%, or 100% sequence identity to a sequence selected from SEQ ID NO:15-21 and 61-65.

Nucleic acid and amino acid sequences described herein are set out in Table 1.

TABLE 1

| Sequences | |
|---|---|
| SEQ ID NO: 1 nucleic acid coding sequence of tetraketide synthase from Cannabis sativa, optimized for GC-rich microalgae | ATGAACCACCTGCGCGCTGAGGGCCCCGCCTCCGTCCTCGC CATTGGGACGGCGAACCCTGAGAACATTCTCCTGCAGGATGA GTTTCCGGATTACTACTTTCGGGTCACGAAGTCGGAGCACATG ACCCAGCTCAAGGAGAAGTTTCGGAAGATTTGCGATAAGAGC ATGATCCGCAAGCGCAACTGCTTTCTGAACGAGGAGCACCTG AAGCAGAACCCCCGGCTCGTCGAGCACGAGATGCAGACGCT |

TABLE 1-continued

| | Sequences |
|---|---|
| | CGATGCCCGGCAGGACATGCTCGTGGTCGAGGTCCCTAAGCT<br>CGGCAAGGACGCTTGCGCGAAGGCTATCAAGGAGTGGGGTC<br>AGCCCAAGTCCAAGATCACCCATCTGATTTTTACCTCCGCGTC<br>GACCACGGATATGCCTGGGGCTGACTACCACTGCGCGAAGCT<br>GCTGGGTCTCTCCCCGTCGGTGAAGCGGGTCATGATGTACCA<br>GCTGGGCTGCTACGGGGGGGGTACGGTCCTGCGCATCGCGA<br>AGGACATCGCTGAGAACAACAAGGGTGCCCGGGTCCTCGCG<br>GTGTGCTGCGACATTATGGCTTGCCTGTTTCGGGGTCCCTCG<br>GAGTCGGACCTGGAGCTGCTGGTCGGTCAGGCTATCTTTGGG<br>GATGGCGCTGCCGCCGTGATTGTCGGCGCCGAGCCGGATGA<br>GTCGGTGGGTGAGCGGCCGATCTTCGAGCTCGTCTCCACCG<br>GGCAGACGATCCTCCCTAACTCCGAGGGCACCATCGGGGGG<br>CACATTCGCGAGGCGGGGCTCATTTTTGATCTGCACAAGGAC<br>GTGCCGATGCTGATTTCCAACAACATCGAGAAGTGCCTCATCG<br>AGGCTTTCACCCCCATTGGTATTTCCGATTGGAACAGCATTTT<br>TTGGATCACCCACCCGGGCGGTAAGGCTATTCTGGATAAGGT<br>GGAGGAGAAGCTCCATCTCAAGTCCGACAAGTTTGTCGATAG<br>CCGCCATGTCCTGAGCGAGCATGGGAACATGTCCAGCTCCAC<br>GGTGCTCTTTGTCATGGACGAGCTGCGGAAGCGCTCGCTGGA<br>GGAGGGCAAGTCCACCACCGGCGACGGTTTCGAGTGGGGGG<br>TCCTGTTCGGTTTTGGTCCCGGTCTCACGGTGGAGCGGGTGG<br>TCGTGCGCTCGGTGCCCATCAAGTAC |
| SEQ ID NO: 2 nucleic acid coding sequence of olivetolic acid cyclase from Cannabis sativa, optimized for GC-rich microalgae | ATGGCGGTGAAGCACCTGATTGTCCTCAAGTTCAAGGACGAG<br>ATCACCGAGGCCCAGAAGGAGGAGTTTTTCAAGACCTACGTG<br>AACCTCGTGAACATTATCCCTGCGATGAAGGACGTGTACTGG<br>GGGAAGGATGTCACGCAGAAGAACAAGGAGGAGGGTTACAC<br>GCACATCGTCGAGGTCACGTTCGAGTCGGTCGAGACCATTCA<br>GGATTACATCATCCATCCCGCTCATGTGGGTTTTGGGGACGT<br>GTACCGCAGCTTCTGGGAGAAGCTGCTGATTTTCGATTACACC<br>CCTCGCAAG |
| SEQ ID NO: 3 nucleic acid coding sequence of olivetolic acid cyclase 2 optimized for GC-rich microalgae | ATGAAGATGAAGGCTGCGTGGAGCGCGACGATTTACTCCCTG<br>CTGAGCTGGTGCGTCGTCAAGAACGAGAAGTTCTTTCCTGAG<br>CGCACGATTGACATTTCCAAGAGCAACATGGGGCGCATGAAC<br>AACGTCGTCCTGAACTCCCTCCACACGCTCAAGTGCTACCTGA<br>ACTACGTCTCGGTGCCGTTTTTTCTGATTCTGCTCTCCCACATT<br>TTTACGCCGGTGTACATTTTTCATGGCTGGGACGATATTCATA<br>AGATTCACATTCGCCTGGAGAAGTTCTTTCTCCTGGGTTTTTG<br>CGATTTCATCTTCGAGCTGCAGTACAACCAGATGCTGCATTGC<br>CATAGCCTCTCGCAGCTGTCGTCCAGCAGCAGCTTT |
| SEQ ID NO: 4 nucleic acid coding sequence of aromatic prenyltransferase (CsPT1) from Cannabis sativa optimized for GC-rich microalgae | ATGGGGCTCAGCTCGGTGTGCACCTTCTCGTTCCAGACGAAC<br>TACCACACGCTGAACCCCCACAACAACAACCCCTAAGACCT<br>CCCTGCTCTGCTACCGCCACCCGAAGACCCCCATTAAGTACA<br>GCTACAACAACTTCCCGTCCAAGCACTGCTCCACGAAGTCGTT<br>CCACCTGCAGAACAAGTGCTCGGAGAGCCTCAGCATCGCGAA<br>GAACAGCATCCGGGCTGCGACCACGAACCAGACGGAGCCGC<br>CCGAGTCGGATAACCACTCGGTCGCTACGAAGATTCTGAACTT<br>CGGTAAGGCGTGCTGGAAGCTCCAGCGCCCCTACACCATCAT<br>TGCGTTTACGAGCTGCGCTTGCGGTCTCTTCGGGAAGGAGCT<br>CCTGCACAACACGAACCTGATCAGCTGGTCCCTCATGTTTAAG<br>GCTTTTTTTCTTCCTCGTGGCCATCCTGTGCATTGCGTCCTTCA<br>CGACCACCATCAACCAGATTTACGACCTGCACATTGACCGCAT<br>TAACAAGCCTGACCTGCCTCTGGCCTCGGGGGAGATTTCGGT<br>GAACACGGCTTGGATCATGTCGATCATCGTGGCTCTCTTTGGT<br>CTCATTATCACGATTAAGATGAAGGGCGGCCCCCTGTACATTT<br>TTGGTTACTGCTTTGGGATCTTCGGTGGGATCGTCTACAGCGT<br>GCCCCCGTTTCGGTGGAAGCAGAACCCGTCGACGGCCTTTCT<br>CCTGAACTTTCTGGCTCATATTATTACGAACTTCACCTTCTACT<br>ACGCGAGCCGCGCTGCGCTCGGGCTGCCGTTCGAGCTCCGC<br>CCGAGCTTCACGTTTCTCCTGGCCTTTATGAAGAGCATGGGTT<br>CGGCTCTCGCCCTCATTAAGGACGCTTCCGACGTGGAGGGG<br>GATACCAAGTTCGGCATCAGCACGCTCGCGTCCAAGTACGGC<br>TCCCGGAACCTCACCCTGTTTTGCTCGGGGATTGTCCTCCTGA<br>GCTACGTGGCCGCCATCCTGGCTGGCATCATCTGGCCGCAG<br>GCTTTCAACTCCAACGTCATGCTCCTCTCGCACGCGATTCTGG<br>CCTTCTGGCTGATTCTGCAGACCCGCGACTTCGCCCTCACGA<br>ACTACGACCCTGAGGCTGGTCGGCGCTTTTACGAGTTTATGT<br>GGAAGCTGTACTACGCGGAGTACCTGGTCTACGTGTTTATC |
| SEQ ID NO: 5 nucleic acid coding sequence of hexanoyl-CoA synthetase from Cannabis sativa optimized for GC-rich microalgae | ATGGGCAAGAACTACAAGTCGCTGGATTCCGTGGTGGCTTCG<br>GACTTCATCGCTCTGGGGATCACCAGCGAGGTCGCCGAGACC<br>CTCCACGGGCGCCTCGCTGAGATCGTGTGCAACTACGGTGCC<br>GCCACGCCGCAGACCTGGATTAACATCGCCAACCATATCCTG<br>TCGCCGGATCTCCCTTTCAGCCTGCATCAGATGCTGTTTTACG<br>GGTGCTACAAGGACTTCGGGCCGGCGCCTCCTGCTTGGATCC<br>CCGATCCCGAGAAGGTCAAGAGCACGAACCTGGGCGCTCTCC |

TABLE 1-continued

| | Sequences |
|---|---|
| | TCGAGAAGCGCGGGAAGGAGTTTCTCGGGGTGAAGTACAAG<br>GATCCCATCAGCTCGTTTAGCCATTTTCAGGAGTTCTCCGTCC<br>GGAACCCTGAGGTGTACTGGCGGACGGTCCTCATGGATGAGA<br>TGAAGATTTCGTTTAGCAAGGATCCGGAGTGCATTCTCCGGC<br>GGGATGATATCAACAACCCTGGGGGCAGCGAGTGGCTCCCC<br>GGTGGTTACCTGAACTCCGCCAAGAACTGCCTCAACGTCAAC<br>TCCAACAAGAAGCTGAACGATACGATGATTGTCTGGCGGGAC<br>GAGGGGAACGACGATCTGCCCCTCAACAAGCTGACCCTCGAT<br>CAGCTGCGGAAGCGGGTCTGGCTGGTCGGGTACGCTCTGGA<br>GGAGATGGGTCTCGAGAAGGGCTGCGCCATCGCGATTGACAT<br>GCCGATGCACGTGGATGCCGTGGTCATTTACCTCGCTATTGT<br>CCTGGCGGGTTACGTCGTGGTGTCGATTGCTGACAGCTTCTC<br>CGCTCCTGAGATCTCGACGCGGCTCCGGCTCTCGAAGGCCAA<br>GGCCATTTTTACGCAGGACCACATTATTCGGGGGAAGAAGCG<br>GATTCCCCTCTACTCGCGGGTGGTCGAGGCGAAGTCGCCCAT<br>GGCCATTGTCATTCCTTGCTCGGGGAGCAACATCGGCGCCGA<br>GCTCCGCGACGGGGATATCAGCTGGGATTACTTTCTGGAGCG<br>CGCCAAGGAGTTCAAGAACTGCGAGTTTACCGCTCGGGAGCA<br>GCCCGTGGATGCTTACACGAACATTCTGTTCAGCTCGGGCAC<br>GACGGGTGAGCCGAAGGCGATTCCTTGGACGCAGGCTACCC<br>CTCTGAAGGCTGCTGCGGATGGGTGGTCCCACCTCGATATCC<br>GCAAGGGGACGTGATTGTCTGGCCCACCAACCTGGGTTGGA<br>TGATGGGGCCTTGGCTGGTGTACGCCTCCCTGCTGAACGGG<br>GCTAGCATTGCTCTCTACAACGGGAGCCCTCTCGTCTCCGGC<br>TTTGCTAAGTTTGTGCAGGACGCCAAGGTGACGATGCTCGGG<br>GTCGTGCCTAGCATTGTGCGGAGCTGGAAGTCGACCAACTGC<br>GTCTCGGGCTACGATTGGTCCACCATTCGCTGCTTTTCCTCGT<br>CCGGTGAGGCCAGCAACGTGGATGAGTACCTGTGGCTGATG<br>GGTCGGGCTAACTACAAGCCGGTCATCGAGATGTGCGGCGG<br>CACGGAGATTGGGGGGGCCTTTTCGGCTGGGTCGTTTCTGCA<br>GGCTCAGTCCCTGTCGTCGTTTTCGTCGCAGTGCATGGGCTG<br>CACCCTCTACATCCTGGATAAGAACGGTTACCCTATGCCCAAG<br>AACAAGCCCGGCATCGGGGAGCTGGCGCTGGGCCCGGTCAT<br>GTTTGGTGCTTCGAAGACGCTGCTGAACGGTAACCATCACGA<br>CGTGTACTTCAAGGGTATGCCTACGCTGAACGGTGAGGTCCT<br>GCGCCGCCACGGTGACATTTTTGAGCTCACGAGCAACGGTTA<br>CTACCATGCGCATGGTCGCGCTGACGATACCATGAACATTGG<br>CGGTATCAAGATCTCGAGCATTGAGATCGAGCGCGTCTGCAA<br>CGAGGTCGACGATCGCGTGTTTGAGACCACGGCTATCGGTGT<br>CCCGCCTCTCGGCGGCGGTCCGGAGCAGCTCGTCATCTTTTT<br>CGTCCTGAAGGATTCGAACGATACCACGATCGATCTGAACCA<br>GCTGCGCCTGTCCTTTAACCTGGGCCTCCAGAAGAAGCTGAA<br>CCCTCTCTTCAAGGTGACCCGCGTGGTCCCCCTCTCCTCCCT<br>GCCTCGGACGGCTACGAACAAGATCATGCGCCGGGTCCTGC<br>GGCAGCAGTTCTCCCACTTCGAG |
| SEQ ID NO: 6 nucleic acid<br>coding sequence of<br>tetrahydrocannabinolic acid<br>synthase from Cannabis sativa<br>optimized for GC-rich<br>microalgae | ATGAACTGCTCGGCGTTTTCCTTTTGGTTTGTCTGCAAGATTAT<br>TTTTTTTTTCTCAGCTTCCACATCCAGATTTCCATTGCTAACC<br>CTCGGGAGAACTTTCTGAAGTGCTTTTCGAAGCACATCCCTAA<br>CAACGTGGCGAACCCTAAGCTGGTCTACACGCAGCATGATCA<br>GCTGTACATGTCGATCCTGAACTCCACGATCCAGAACCTCCG<br>GTTTTATCTCGGATACGACCCCTAAGCCCCTGGTGATTGTGACG<br>CCGTCCAACAACAGCCATATTCAGGCTACGATTCTCTGCTCGA<br>AGAAGGTGGGGCTCCAGATCCGGACCCGGTCCGGGGGCCAT<br>GATGCTGAGGGGATGAGCTACATCTCCCAGGTCCCCTTCGTC<br>GTGGTGGATCTGCGGAACATGCATTCGATCAAGATTGATGTCC<br>ACTCGCAGACCGCGTGGGTCGAGGCCGGCGCTACCCTCGGT<br>GAGGTCTACTACTGGATCAACGAGAAGAACGAGAACCTCAGC<br>TTCCCCGGCGGCTACTGCCCGACGGTCGGGGTCGGTGGGCA<br>CTTTTCGGGTGGGGGCTACGGCGCCCTCATGCGGAACTACG<br>GCCTCGCTGCGGACAACATTATCGATGCTCATCTCGTCAACGT<br>GGATGGCAAGGTGCTCGATCGCAAGTCGATGGGCGAGGATCT<br>CTTTTGGGCGATTCGGGCGGGGGCGGCGAGAACTTTGGCA<br>TCATTGCTGCTTGGAAGATTAAGCTCGTGGCCGTCCCTAGCAA<br>GTCGACCATTTTCTCGGTGAAGAAGAACATGGAGATTCACGGT<br>CTCGTCAAGCTCTTTAACAAGTGGCAGAACATTGCCTACAAGT<br>ACGACAAGGACCTGGTGCTGATGACCCATTTTATTACCAAGAA<br>CATTACGGACAACCACGGGAAGAACAAGACCACGGTCCATGG<br>CTACTTTTCGAGCATTTTCCATGGGGGGTCGATAGCCTCGTC<br>GACCTGATGAACAAGTCCTTCCCCGAGCTGGGCATCAAGAAG<br>ACCGACTGCAAGGAGTTTAGCTGGATCGATACCACGATTTTTT<br>ACTCGGGGGTCGTGAACTTTAACACCGCCAACTTCAAGAAGG<br>AGATCCTGCTCGATCGCTCCGCTGGCAAGAAGACGGCTTTCA<br>GCATTAAGCTCGATTACGTGAAGAAGCCCATCCCTGAGACGG<br>CTATGGTGAAGATTCTGGAGAAGCTCTACGAGGAGGACGTCG<br>GGGCTGGCATGTACGTGCTCTACCCGTACGGTGGTATCATGG<br>AGGAGATCTCGGAGTCGGCCATCCCTTTCCCCCATCGGGCGG<br>GCATCATGTACGAGCTGTGGTACACCGCCAGCTGGGAGAAGC |

TABLE 1-continued

Sequences

AGGAGGATAACGAGAAGCATATTAACTGGGTCCGGTCGGTCT
ACAACTTCACGACGCCCTACGTGAGCCAGAACCCCCGCCTCG
CTTACCTCAACTACCGGGACCTCGATCTGGGCAAGACGAACC
ATGCCTCGCCCAACAACTACACCCAGGCGCGGATTTGGGGTG
AGAAGTACTTTGGGAAGAACTTTAACCGCCTCGTCAAGGTGAA
GACGAAGGTGGATCCCAACAACTTCTTCCGCAACGAGCAGTC
CATCCCCCCCCTCCCGCCTCACCACCAT

SEQ ID NO: 7 nucleic acid coding sequence of cannabidiolic acid synthetase from Cannabis sativa optimized for GC-rich microalgae ATGAAGTGCTCCACCTTTTCCTTCTGGTTCGTCTGCAAGATCA
TTTTTTTTTTCTTCTCCTTTAACATCCAGACGTCGATCGCTAAC
CCTCGCGAGAACTTTCTGAAGTGCTTTTCCCAGTACATTCCGA
ACAACGCTACCAACCTCAAGCTCGTGTACACGCAGAACAACC
CTCTCTACATGTCCGTGCTCAACTCCACGATTCATAACCTGCG
GTTTACGAGCGACACCACCCCTAAGCCTCTCGTCATTGTGACC
CCTTCGCACGTCTCCCATATCCAGGGCACGATCCTGTGCTCC
AAGAAGGTCGGCCTGCAGATCCGGACGCGCTCCGGTGGGCA
TGATTCCGAGGGTATGTCGTACATCAGCCAGGTGCCGTTTGT
CATCGTGGATCTCCGCAACATGCGCAGCATTAAGATTGATGTC
CATTCGCAGACCGCTTGGGTCGAGGCGGGGGCGACGCTCGG
TGAGGTGTACTACTGGGTCAACGAGAAGAACGAGAACCTCTC
CCTCGCTGCCGGCTACTGCCCCACCGTCTGCGCGGGGGGGC
ATTTTGGGGCGGCGGTTACGGGCCGCTCATGCGGAACTAC
GGCCTGGCGGCGGACAACATCATCGACGCTCACCTCGTCAAC
GTCCATGGTAAGGTGCTCGATCGGAAGTCCATGGGGGAGGAC
CTGTTTTGGGCGCTCCGGGGGGGCGGCGCTGAGAGCTTTGG
TATCATTGTCGCCTGGAAGATCCGCCTCGTGGCTGTCCCGAA
GTCGACCATGTTCAGCGTCAAGAAGATTATGGAGATTCACGAG
CTGGTCAAGCTCGTGAACAAGTGGCAGAACATTGCCTACAAG
TACGACAAGGACCTGCTCCTGATGACCCATTTCATTACGCGGA
ACATCACGGACAACCAGGGGAAGAACAAGACCGCGATTCATA
CGTACTTCAGCTCCGTCTTCCTCGGCGGCGTGGATAGCCTGG
TGGACCTCATGAACAAGAGCTTTCCGGAGCTGGGCATCAAGA
AGACGGATTGCCGCCAGCTCAGCTGGATTGACACGATCATCT
TTTACTCGGGGGTGGTCAACTACGACACGGACAACTTTAACAA
GGAGATTCTGCTCGATCGGTCCGCCGGTCAGAACGGTGCCTT
TAAGATCAAGCTCGATTACGTCAAGAAGCCCATTCCCGAGAGC
GTGTTTGTCCAGATTCTCGAGAAGCTCTACGAGGAGGACATTG
GTGCCGGTATGTACGCGCTCTACCCGTACGGGGGCATTATGG
ACGAGATTAGCGAGAGCGCCATTCCTTTCCCTCATCGCGCTG
GCATTCTCTACGAGCTGTGGTACATTTGCAGCTGGGAGAAGC
AGGAGGACAACGAGAAGCACCTCAACTGGATTCGCAACATCT
ACAACTTCATGACCCCGTACGTCTCGAAGAACCCTCGGCTGG
CTTACCTGAACTACCGCGATCTCGACATTGGCATTAACGATCC
GAAGAACCCCAACAACTACACGCAGGCGCGGATCTGGGGTGA
GAAGTACTTTGGTAAGAACTTTGATCGGCTCGTGAAGGTCAAG
ACGCTCGTGGACCCTAACAACTTCTTCGCAACGAGCAGTCG
ATCCCCCCGCTGCCTCGCCACCGGCAC SEQ ID NO: 8 nucleic acid coding sequence of tetraketide synthase from Cannabis sativa optimized for diatoms ATGAATCATCTTCGCGCTGAAGGGCCGGCTTCCGTTCTCGCG
ATTGGGACGGCTAACCCTGAGAACATCTTGTTGCAAGACGAG
TTCCCAGACTACTATTTTCGTGTTACGAAATCTGAGCACATGA
CACAACTTAAAGAAAAGTTCCGTAAAATCTGCGACAAAAGTAT
GATTAGGAAGAGAAATTGCTTTCTCAACGAAGAGCACCTCAAG
CAGAACCCGAGGTTGGTTGAGCACGAAATGCAAACACTCGAC
GCGCGTCAAGATATGCTTGTAGTTGAAGTACCAAAATTGGGTA
AAGACGCTTGTGCTAAAGCGATCAAAGAGTGGGGACAACCTA
AGAGCAAAATTACTCACTTGATCTTTACTTCTGCATCGACTACT
GACATGCCCGGGCAGATTATCATTGTGCGAAGCTTTTGGGA
CTTTCACCCAGTGTCAAACGCGTAATGATGTATCAGTTGGGTT
GCTACGGCGGTGGTACAGTGCTCAGAATCGCAAAAGACATTG
CGGAAAACAACAAAGGGGCAAGAGTCCTCGCGGTTTGCTGTG
ATATCATGGCGTGCTTGTTTCGAGGACCGAGTGAATCTGACCT
CGAGTTGCTTGTTGGACAAGCAATTTTTGGAGATGGGGCCGC
AGCCGTCATCGTGGGAGCAGAGCCTGACGAGTCTGTGGGGG
AACGTCCCATCTTTGAACTCGTTAGTACCGGACAGACAATTTT
GCCCAATTCCGAAGGAACTATTGGTGGTCACATCCGAGAAGC
TGGGTTGATCTTCGATCTTCATAAAGATGTCCCGATGCTCATT
AGTAATAATATCGAAAAATGTCTCATTGAAGCGTTTACACCCAT
CGGTATTAGCGATTGGAATAGTATTTTCTGGATCACCCACCCC
GGCGGCAAGGCGATTCTTGATAAGGTGGAGGAGAAATTGCAC
TTGAAGAGTGACAAATTTGTAGACAGCCGCCACGTTCTTTCCG
AGCATGGCAATATGTCATCTTCTACGGTACTCTTTGTAATGGA
CGAACTCCGCAAGCGCTCTCTCGAGGAGGGTAAGTCAACAAC
GGGTGACGGCTTTGAGTGGGGGGTTTTGTTTGGGTTTGGCCC
CGGCTTGACCGTAGAACGTGTGGTCGTGCGTTCCGTGCCGAT
TAAGTAT TABLE 1-continued Sequences

| | |
|---|---|
| SEQ ID NO: 9 nucleic acid coding sequence of olivetolic acid cyclase from *Cannabis sativa* optimized for diatoms | ATGGCAGTTAAACACCTCATCGTCCTCAAATTCAAAGATGAGA TCACTGAGGCTCAAAAGGAGGAGTTCTTCAAAACGTATGTAAA TCTTGTGAATATTATCCCTGCGATGAAGGATGTATATTGGGGG AAGGACGTGACGCAAAAAAACAAAGAGGAAGGCTACACGCAT ATTGTCGAAGTTACTTTCGAGTCGGTTGAAACCATCCAGGATT ACATTATCCACCCCGCACATGTAGGCTTTGGTGATGTGTACCG ATCATTCTGGGAGAAATTGTTGATCTTCGATTATACGCCAAGG AAG |
| SEQ ID NO: 10 nucleic acid coding sequence of olivetolic acid cyclase 2 optimized for diatoms | ATGAAAATGAAGGCAGCTTGGTCGGCGACAATCTATTCACTCC TCTCCTGGTGCGTAGTAAAAAACGAAAAATTTTTTCCAGAGCG TACCATTGACATTAGCAAATCCAATATGGGTCGAATGAATAAC GTTGTGCTCAATAGTCTCCACACACTTAAGTGTTATTTGAACTA CGTCAGCGTCCCCTTCTTTCTCATCCTTCTTTCGCACATCTTTA CGCCTGTATACATTTTCCACGGGTGGGACGACATCCATAAAAT TCACATCCGACTCGAGAAGTTCTTCTTGTTGGGCTTCTGCGAT TTTATTTTCGAGCTCCAATACAATCAGATGCTTCACTGCCATAG CCTTTCTCAGTTGTCGTCCAGTTCATCATTC |
| SEQ ID NO: 11 nucleic acid coding sequence of aromatic prenyltransferase (CsPT1) from *Cannabis sativa* optimized for diatoms | ATGGGCCTCAGCAGTGTATGTACCTTTTCATTCCAGACTAACT ATCACACGTTGCTTAATCCGCATAACAATAACCCGAAAACTTC GTTGCTTTGTTATAGGCACCCGAAGACCCCTATCAAATATAGT TATAATAACTTTCCAAGCAAACACTGTTCGACTAAGTCCTTTCA TTTGCAAAATAAATGTTCCGAGTCTCTTAGCATTGCGAAGAACT CCATTCGTGCTGCTACTACAAATCAAACTGAGCCCCCCGAGA GTGATAATCACAGTGTAGCAACGAAGATCTTGAACTTTGGGAA GGCATGCTGGAAATTGCAACGTCCTTACACCATCATCGCGTTC ACGTCTTGCGCATGCGGCTTGTTCGGAAAGGAGCTTTTGCATA ATACGAATCTTATCAGTTGGTCGTTGATGTTCAAGGCCTTCTTT TTCCTCGTTGCAATTCTTTGTATTGCCAGCTTCACAACGACAAT TAACCAGATTTATGATCTTCATATCGATAGAATCAATAAACCCG ACTTGCCTTTGGCATCAGGAGAAATCTCTGTCAATACAGCATG GATTATGTCCATTATTGTCGCATTGTTTGGACTTATCATCACCA TCAAGATGAAGGGAGGGCCACTCTATATCTTCGGTTATTGTTT TGGAATCTTTGGCGGTATCGTATATTCTGTACCTCCGTTCAGA TGGAAACAGAACCCCAGCACGGCGTTTCTTTTGAACTTTCTTG CTCACATCATCACTAATTTTACATTTTACTATGCAAGTAGGGCA GCCCTCGGACTCCCCTTCGAGTTGAGGCCGAGTTTTACTTTTC TCCTTGCGTTTATGAAAAGTATGGGGAGTGCTCTTGCCCTTAT CAAGGATGCAAGTGATGTTGAAGGCGATACTAAATTTGGTATC AGTACCCTCGCCAGTAAATATGGGTCCAGGAATCTCACACTCT TTTGTTCAGGGATCGTTCTTCTTTCATACGTGGCTGCAATCCTT GCTGGTATTATCTGGCCCCAAGCTTTCAATAGTAATGTCATGC TCCTTAGCCATGCCATCCTTGCATTTTGGCTCATCTTGCAAAC GAGGGATTTTGCTCTCACCAACTATGATCCCGAAGCTGGAAG GCGTTTCTATGAGTTTATGTGGAAGCTTTACTACGCAGAATAT CTCGTATATGTATTCATT |
| SEQ ID NO: 12 nucleic acid coding sequence of hexanoyl- CoA synthetase from *Cannabis sativa* optimized for diatoms | ATGGGTAAGAACTACAAGTCTTTGGACTCGGTGGTCGCCCTCA GATTTTATTGCATTGGGCATCACCTCAGAGGTTGCGGAAACTC TTCATGGCAGACTCGCAGAAATTGTTTGCAACTACGGCGCGG CAACCCCACAAACGTGGATCAATATCGCTAATCACATTTTGTC GCCGGACTTGCCTTTTTCATTGCATCAGATGTTGTTTTATGGTT GTTACAAGGACTTCGGTCCCGCGCCTCCAGCTTGGATTCCGG ATCCAGAAAAGGTCAAGAGTACCAATCTCGGGGCTTTGCTTGA AAAACGAGGAAAAGAATTCCTTGGCGTAAAGTATAAGGATCCC ATCTCTAGCTTTTCGCACTTCCAGGAATTCAGTGTACGTAATC CTGAGGTTTACTGGCGTACCGTTCTTATGGATGAGATGAAAAT TTCATTTTCTAAGGACCCCGAATGTATCCTTCGTAGAGATGATA TTAACAATCCAGGGGGCTCAGAATGGTTGCCGGGTGGGTACC TTAATTCCGCTAAGAATTGCTTGAACGTCAACTCCAACAAAAA GCTCAACGACACCATGATCGTTTGGCGAGACGAGGGAAATGA CGACTTGCCTCTTAATAAGTTGACGCTCGATCAATTGAGAAAG CGAGTATGGCTCGTAGGCTATGCTCTCGAGGGAAATGGGTCTT GAGAAGGGATGCGCGATTGCAATCGATATGCCAATGCACGTC GATGCAGTAGTTATTTACCTTGCTATCGTGCTCGCCGGATATG TGGTGGTATCAATTGCAGATTCGTTAGTGCGCCCGAGATTTC AACCCGCCTTCGCCTTTCAAAAGCCAAAGCCATCTTCACCCAA GATCACATCATTAGGGGAAAGAAACGCATCCCATTGTATTCAA GGGTTGTAGAAGCGAAGAGCCCAATGGCGATCGTAATTCCCT GTTCCGGTTCCAACATCGGGGCGGAACTTCGTGACGGTGACA TTAGTTGGGATTATTTTCTCGAGAGAGCTAAGGAATTTAAAAAC TGCGAATTCACTGCAAGGGAGCAGCCGGTTGACGCGTACACA AATATTCTCTTTTCCTCCGGAACTACGGGGGAACCAAAGGCGA TCCCTTGGACGCAAGCGACACCACTTAAGGCAGCCGCCGACG GTTGGTCCCACCTTGATATTAGGAAGGGGGATGTCATCGTGT GGCCAACTAACCTCGGCTGGATGATGGGACCGTGGCTCGTCT ATGCGTCCCTCCTTAACGGAGCATCGATCGCACTCTACAATGG |

TABLE 1-continued

Sequences

ATCTCCTTTGGTATCAGGATTCGCGAAGTTCGTACAGGATGCA
AAGGTAACCATGCTTGGTGTGGTACCATCAATTGTGAGAAGCT
GGAAAAGCACTAATTGCGTGAGCGGTTATGATTGGTCAACAAT
TCGCTGTTTCTCGTCTAGTGGAGAGGCGTCCAATGTAGATGAA
TATCTCTGGCTTATGGGTAGAGCCAACTACAAACCAGTTATTG
AGATGTGCGGCGGAACCGAGATTGGAGGCGCCTTCAGTGCC
GGATCCTTCCTTCAGGCGCAGTCATTGTCGTCCTTCTCCAGTC
AGTGTATGGGCTGTACTCTCTATATTCTTGACAAGAACGGATA
CCCGATGCCGAAGAACAAGCCTGGAATTGGTGAGCTCGCACT
CGGACCAGTAATGTTTGGGGCGTCAAAAACTCTTCTCAACGG
CAACCATCACGATGTTTATTTTAAGGGTATGCCGACCCTTAAT
GGTGAGGTATTGCGCCGCCACGGTGACATTTTCGAGCTCACT
TCAAATGGATACTACCACGCGCATGGGCGAGCAGACGACACA
ATGAACATTGGGGGAATTAAGATCAGTTCGATCGAGATTGAAA
GAGTGTGTAACGAAGTTGACGACAGGGTCTTCGAGACCACAG
CCATCGGGGTACCTCCGCTCGGTGGCGGCCCGGAGCAGCTC
GTGATTTTTTTTGTCCTTAAAGACTCAAACGATACCACTATCGA
TTTGAATCAACTTAGACTCAGTTTTAATCTCGGACTTCAAAAAA
AGTTGAACCCCCTCTTCAAAGTCACCAGAGTGGTGCCCCTCTC
GAGTCTTCCCCGCACCGCTACAAATAAGATCATGCGCCGAGT
TCTTCGCCAACAGTTCAGTCACTTTGAA

SEQ ID NO: 13 nucleic acid coding sequence of tetrahydrocannabinolic acid synthase from *Cannabis sativa* optimized for diatoms ATGAACTGTTCCGCTTTCAGCTTTTGGTTCGTGTGTAAAATCAT
CTTCTTTTTCCTCTCATTCCATATTCAGATCTCTATCGCAAACC
CGCGAGAGAATTTCCTCAAATGCTTCTCGAAACACATTCCTAA
TAATGTAGCCAATCCAAAACTTGTGTATACGCAGCACGATCAG
CTCTATATGTCCATTCTTAACTCTACTATCCAGAACTTGAGATT
CATCTCTGATACCACACCCAAGCCGTTGGTGATCGTAACACCT
AGTAATAATAGTCACATCCAGGCGACGATCCTCTGCTCAAAGA
AGGTAGGACTCCAAATTAGAACGAGATCGGGCGGACACGATG
CCGAAGGAATGAGTTATATCTCCCAAGTACCGTTCGTAGTTGT
TGACCTTAGGAATATGCACTCAATTAAGATTGATGTCCACAGT
CAAACAGCATGGGTTGAGGCAGGAGCCACTCTTGGTGAAGTC
TACTACTGGATTAACGAGAAAAATGAGAACCTCTCGTTTCCTG
GCGGTTACTGTCCTACAGTGGGAGTGGGAGGTCATTTTTCGG
GCGGAGGATACGGGGCTTTGATGAGAAACTATGGGCTTGCAG
CAGATAACATTATTGACGCCCACCTCGTCAACGTAGACGGTAA
GGTATTGGATAGGAAGTCTATGGGAGAAGACTTGTTCTGGGC
GATTCGCGGAGGAGGCGGTGAAAACTTCGGAATCATCGCAGC
GTGGAAAATCAAACTCGTAGCAGTGCCATCGAAAAGTACTATC
TTCAGTGTTAAGAAAAACATGGAAATCCACGGACTTGTTAAAC
TTTTTAACAAATGGCAAAACATTGCCTATAAGTATGATAAAGAT
TTGGTGCTCATGACTCACTTCATTACCAAGAATATTACAGACAA
CCACGGTAAAAATAAGACGACTGTACATGGATACTTTAGCTCG
ATTTTCCACGGCGGCGTCGACAGCCTTGTAGATCTTATGAACA
AATCATTTCCCGAACTCGGAATTAAGAAAACGGACTGTAAGGA
ATTCAGTTGGATCGATACCACCATTTTTTACTCCGGCGTCGTT
AATTTCAACACTGCCAACTTCAAGAAGGAAATTCTCCTCGATA
GGAGCGCGGGTAAGAAAACAGCATTTTCGATTAAGTTGGATTA
TGTTAAAAAACCCATCCCTGAGACTGCCATGGTAAAAATTCTT
GAAAAACTCTATGAGGAGGACGTTGGGGCTGGCATGTACGTA
CTTTATCCATACGGAGGTATCATGGAGGAAATTAGCGAGTCGG
CAATCCCCTTCCCGCACCGCGCTGGCATCATGTATGAACTTTG
GTACACAGCAAGCTGGGAAAAGCAGGAAGATAACGAAAAACA
TATCAACTGGGTTAGGTCAGTCTATAACTTTACGACCCCCTAC
GTGTCACAGAATCCTAGATTGGCGTACCTTAATTATCGTGACC
TTGACTTGGGCAAGACGAACCACGCTTCCCCCAACAACTATAC
TCAGGCTCGTATCTGGGGTGAAAAATATTTTGGAAAAAATTTC
AACAGGTTGGTCAAAGTCAAAACCAAGGTGGATCCGAACAATT
TCTTCCGAAACGAACAATCTATTCCGCCGCTTCCACCGCACCA
CCAC SEQ ID NO: 14 nucleic acid coding sequence of cannabidiolic acid synthetase from *Cannabis sativa* optimized for diatoms ATGAAGTGTTCTACGTTCTCCTTCTGGTTCGTTTGCAAAATCAT
TTTCTTCTTCTTTAGCTTTAATATCCAGACTTCCATCGCGAACC
CGCGCGAGTTTCCTCAAGTGCTTCTCACAATATATTCCGAA
TAATGCGACGAACCTTAAGCTCGTATATACGCAAAATAATCCA
CTTTACATGAGTGTGCTCAATAGTACTATTCATAACTTGCGCTT
TACGTCTGATACCACACCGAAGCCCCTCGTAATCGTCACACCT
TCACACGTGTCGCATATTCAGGGGACTATTTTGTGCTCGAAGA
AGGTGGGCTTGCAAATCAGAACGCGTTCAGGAGGTCATGACT
CTGAAGGGATGAGCTACATTTCACAGGTACCTTTTGTGATTGT
CGACTTGCGAAACATGGAGATCTATCAAGATCGACGTCCATAGC
CAAACTGCGTGGGTAGAAGCGGGCGCTACATTGGGGGAGGT
GTATTACTGGGTGAATGAAAGAACGAGAACCTCTCTCTCGCT
GCCGGTTACTGCCCCACAGTCTGTGCTGGTGGACACTTTGGA
GGTGGAGGGTACGGTCCTCTTATGCGAAACTATGGATTGGCT
GCCGACAACATTATTGACGCTCACTTGGTAAACGTTCATGGTA
AGGTACTTGACCGTAAGTCTATGGGCGAAGACCTCTTTTGGG

TABLE 1-continued

Sequences

CACTTCGCGGTGGTGGCGCTGAATCTTTCGGTATCATCGTCG
CGTGGAAGATTAGATTGGTAGCGGTCCCTAAGTCCACAATGTT
CAGTGTGAAAAAGATTATGGAGATCCACGAACTTGTTAAACTT
GTCAACAAATGGCAAAACATTGCGTATAAGTACGACAAAGATT
TGTTGCTCATGACGCACTTTATCACACGAAACATCACTGACAA
CCAGGGGAAGAACAAAACAGCAATCCACACGTACTTCTCGTCT
GTGTTCCTTGGCGGGGTAGATTCACTCGTCGATCTCATGAATA
AAAGCTTCCCGGAGTTGGGGATTAAAAAAACAGATTGCAGGC
AACTCTCCTGGATCGATACAATTATTTTTTACAGCGGAGTGGT
CAATTACGACACGGACAACTTCAATAAGGAGATCCTCCTCGAT
AGGTCAGCCGGGCAGAACGGAGCCTTTAAGATCAAACTCGAT
TACGTCAAGAAGCCGATCCCAGAGTCTGTATTTGTTCAAATTC
TTGAAAAACTTTACGAAGAGGATATTGGGGCTGGGATGTACGC
TTTGTATCCTTATGGGGGTATTATGGACGAGATCTCAGAATCG
GCAATCCCCTTCCCCCATAGGGCCGGAATCTTGTACGAACTTT
GGTACATCTGCTCCTGGGAAAAGCAGGAGGATAACGAGAAGC
ACTTGAACTGGATCAGAAACATTTATAATTTTATGACCCCTTAC
GTCTCGAAAAACCCTCGACTTGCCTACTTGAATTACAGGGATC
TCGACATCGGTATTAATGACCCTAAGAATCCAAATAACTATAC
GCAGGCCCGTATTTGGGGAGAAAAATATTTTGGTAAGAACTTT
GATCGCTTGGTCAAAGTTAAAACGTTGGTTGATCCCAATAACT
TCTTCAGAAATGAGCAGTCGATCCCCCCATTGCCTAGACATCG
CCAT

| SEQ ID NO: 15 amino acid sequence of tetraketide synthase from Cannabis sativa | MNHLRAEGPASVLAIGTANPENILLQDEFPDYYFRVTKSEHMTQL KEKFRKICDKSMIRKRNCFLNEEHLKQNPRLVEHEMQTLDARQD MLVVEVPKLGKDACAKAIKEWGQPKSKITHLIFTSASTTDMPGAD YHCAKLLGLSPSVKRVMMYQLGCYGGGTVLRIAKDIAENNKGAR VLAVCCDIMACLFRGPSESDLELLVGQAIFGDGAAAVIVGAEPDE SVGERPIFELVSTGQTILPNSEGTIGGHIREAGLIFDLHKDVPMLIS NNIEKCLIEAFTPIGISDWNSIFWITHPGGKAILDKVEEKLHLKSDK FVDSRHVLSEHGNMSSSTVLFVMDELRKRSLEEGKSTTGDGFE WGVLFGFGPGLTVERVVVRSVPIKY |
| --- | --- |
| SEQ ID NO: 16 amino acid sequence of olivetolic acid cyclase from Cannabis sativa | MAVKHLIVLKFKDEITEAQKEEFFKTYVNLVNIIPAMKDVYWGKDV TQKNKEEGYTHIVEVTFESVETIQDYIIHPAHVGFGDVYRSFWEKL LIFDYTPRK |
| SEQ ID NO: 17 amino acid sequence of olivetolic acid cyclase 2 | MKMKAAWSATIYSLLSWCVVKNEKFFPERTIDISKSNMGRMNNV VLNSLHTLKCYLNYVSVPFFLILLSHIFTPVYIFHGWDDIHKIHIRLE KFFLLGFCDFIFELQYNQMLHCHSLSQLSSSSSF |
| SEQ ID NO: 18 amino acid sequence of aromatic prenyltransferase (CsPT1) from Cannabis sativa | MGLSSVCTFSFQTNYHTLLNPHNNNPKTSLLCYRHPKTPIKYSYN NFPSKHCSTKSFHLQNKCSESLSIAKNSIRAATTNQTEPPESDNH SVATKILNFGKACWKLQRPYTIIAFTSCACGLFGKELLHNTNLISW SLMFKAFFFLVAILCIASFTTTINQIYDLHIDRINKPDLPLASGEISVN TAWIMSIIVALFGLIITIKMKGGPLYIFGYCFGIFGGIVYSVPPFRWK QNPSTAFLLNFLAHIITNFTFYYASRAALGLPFELRPSFTFLLAFMK SMGSALALIKDASDVEGDTKFGISTLASKYGSRNLTLFCSGIVLLS YVAAILAGIIWPQAFNSNVMLLSHAILAFWLILQTRDFALTNYDPEA GRRFYEFMWKLYYAEYLVYVFIDYKDDDDK |
| SEQ ID NO: 19 amino acid sequence of hexanoyl-CoA synthetase from Cannabis sativa | MGKNYKSLDSVVASDFIALGITSEVAETLHGRLAEIVCNYGAATP QTWINIANHILSPDLPFSLHQMLFYGCYKDFGPAPPAWIPDPEKV KSTNLGALLEKRGKEFLGVKYKDPISSFSHFQEFSVRNPEVYWR TVLMDEMKISFSKDPECILRRDDINNPGGSEWLPGGYLNSAKNCL NVNSNKKLNDTMIVWRDEGNDDLPLNKLTLDQLRKRVWLVGYAL EEMGLEKGCAIAIDMPMHVDAVVIYLAIVLAGYVVVSIADSFSAPEI STRLRLSKAKAIFTQDHIIRGKKRIPLYSRVVEAKSPMAIVIPCSGS NIGAELRDGDISWDYFLERAKEFKNCEFTAREQPVDAYTNILFSS GTTGEPKAIPWTQATPLKAAADGWSHLDIRKGDVIVWPTNLGWM MGPWLVYASLLNGASIALYNGSPLVSGFAKFVQDAKVTMLGVVP SIVRSWKSTNCVSGYDWSTIRCFSSSGEASNVDEYLWLMGRAN YKPVIEMCGGTEIGGAFSAGSFLQAQSLSSFSSQCMGCTLYILDK NGYPMPKNKPGIGELALGPVMFGASKTLLNGNHHDVYFKGMPTL NGEVLRRHGDIFELTSNGYYHAHGRADDTMNIGGIKISSIEIERVC NEVDDRVFETTAIGVPPLGGGPEQLVIFFVLKDSNDTTIDLNQLRL SFNLGLQKKLNPLFKVTRVVPLSSLPRTATNKIMRRVLRQQFSHF E |
| SEQ ID NO: 20 amino acid sequenceof tetrahydrocannabinolic acid synthase from Cannabis sativa | MNCSAFSFWFVCKIIFFFLSFHIQISIANPRENFLKCFSKHIPNNVA NPKLVYTQHDQLYMSILNSTIQNLRFISDTTPKPLVIVTPSNNSHIQ ATILCSKKVGLQIRTRSGGHDAEGMSYISQVPFVVVDLRNMHSIKI DVHSQTAVWEAGATLGEVYYWINEKNENLSFPGGYCPTVGVGG HFSGGGYGALMRNYGLAADNIIDAHLVNVDGKVLDRKSMGEDLF WAIRGGGGENFGIIAAWKIKLVAVPSKSTIFSVKKNMEIHGLVKLF NKWQNIAYKYDKDLVLMTHFITKNITDNHGKNKTTVHGYFSSIFH GGVDSLVDLMNKSFPELGIKKTDCKEFSWIDTTIFYSGVVNFNTA |

TABLE 1-continued

| | Sequences |
|---|---|
| | NFKKEILLDRSAGKKTAFSIKLDYVKKPIPETAMVKILEKLYEEDVG AGMYVLYPYGGIMEEISESAIPFPHRAGIMYELWYTASWEKQED NEKHINVWRSVYNFTTPYVSQNPRLAYLNYRDLDLGKTNHASPN NYTQARIWGEKYFGKNFNRLVKVKTKVDPNNFFRNEQSIPPLPP HHHEQKLISEEDL |
| SEQ ID NO: 21 amino acid sequence of cannabidiolic acid synthetase from *Cannabis sativa* | MKCSTFSFWFVCKIIFFFFSFNIQTSIANPRENFLKCFSQYIPNNAT NLKLVYTQNNPLYMSVLNSTIHNLRFTSDTTPKPLVIVTPSHVSHI QGTILCSKKVGLQIRTRSGGHDSEGMSYISQVPFVIVDLRNMRSI KIDVHSQTAVWEAGATLGEVYYWVNEKNENLSLAAGYCPTVCA GGHFGGGGYGPLMRNYGLAADNIIDAHLVNVHGKVLDRKSMGE DLFWALRGGGAESFGIIVAWKIRLVAVPKSTMFSVKKIMEIHELVK LVNKWQNIAYKYDKDLLLMTHFITRNITDNQGKNKTAIHTYFSSVF LGGVDSLVDLMNKSFPELGIKKTDCRQLSWIDTIIFYSGVVNYDTD NFNKEILLDRSAGQNGAFKIKLDYVKKPIPESVFVQILEKLYEEDIG AGMYALYPYGGIMDEISESAIPFPHRAGILYELWYICSWEKQEDN EKHLNWIRNIYNFMTPYVSKNPRLAYLNYRDLDIGINDPKNPNNY TQARIWGEKYFGKNFDRLVKVKTLVDPNNFFRNEQSIPPLPRHR H |
| SEQ ID NO: 22 nucleic acid coding sequence of 6His optimized for GC-rich microalgae | CATCACCACCATCACCAT |
| SEQ ID NO: 23 nucleic acid coding sequence of MYC optimized for GC-rich microalgae | GAGCAGAAGCTCATTTCCGAGGAGGACCTG |
| SEQ ID NO: 24 nucleic acid coding sequence of FLAG optimized for GC-rich microalgae | GATTACAAGGATGATGATGACAAG |
| SEQ ID NO: 25 nucleic acid coding sequence of V5 optimized for GC-rich microalgae | GGGAAGCCCATCCCTAACCCTCTCCTGGGGCTCGACTCGACG |
| SEQ ID NO: 26 nucleic acid coding sequence of HA optimized for GC-rich microalgae | TACCCCTACGATGTGCCGGACTACGCT |
| SEQ ID NO: 27 nucleic acid coding sequence of HSV optimized for GC-rich microalgae | CAGCCTGAGCTCGCGCCTGAGGACCCCGAGGACTGC |
| SEQ ID NO: 28 nucleic acid coding sequence of 6His optimized for diatoms | CATCACCATCATCACCAT |
| SEQ ID NO: 29 nucleic acid coding sequence of MYC optimized for diatoms | GAACAGAAGCTCATTTCAGAAGAGGACTTG |
| SEQ ID NO: 30 nucleic acid coding sequence of FLAG optimized for diatoms | GATTACAAAGACGACGACGACAAG |
| SEQ ID NO: 31 nucleic acid coding sequence of V5 optimized for diatoms | GGTAAACCGATTCCGAATCCCCTTTTGGGTCTCGACTCCACA |
| SEQ ID NO: 32 nucleic acid coding sequence of HA optimized for diatoms | TATCCCTATGACGTGCCGGACTACGCC |
| SEQ ID NO: 33 nucleic acid coding sequence of HSV optimized for diatoms | CAACCAGAGCTTGCACCTGAAGACCCTGAGGATTGC |
| SEQ ID NO: 34 nucleic acid sequence of FBAC2-1 Intron | GTACGTACGCGTAACATATTGTAGCCAATTTGGTGTCGACGGC ATGGTCTCGCAGGGAACGATAGAAAAACGTTGACACCTAGAA ACGGGGGCTCTGGCACGGCAGCTCTCCACGGATTCTCTCGCA GTATTACACGGGCTATGCAGTGGACAGGGATACCAAACGTAT |

TABLE 1-continued

Sequences

|  |  |
|---|---|
|  | GTTGGTGTCTTAATGTAAACTTTGCCCGTAAATTCCGTCCATAT<br>CGATCGAATCCTTACCGTCAAGGGAGACCTCCAGTTCCCATG<br>GTCGAGGGGCTTTCGTGGACCATCCCGCCGCAAGATCCATCC<br>GCTGGTGTGACGTCGAGCAGCGCCGAACGGTGTCAGTGACG<br>TGGCATCCCTCCCCCATCCACAGCAAACACGAGTAGTTTTGGT<br>CGCGTTTATACCGCGCTCCAAACCCCAGAATTGGCCGTCGCG<br>GTTTTCCGTACCGTTGGTCTCACACTGGTCCCGCGTTTTTTCT<br>TTGATTCCACAATCAG |
| SEQ ID NO: 35 nucleic acid<br>sequence of TUFA-1 Intron | GTAAGACTCTGCAGGCTCCACGTGAACGAGTACCTCGAACGG<br>TATGGTACCGTCACAATACACGGTTTCTGCCCTTGTTAGCTCA<br>CACGTTTGCTGTCCTTTCTACTCGTTCTTCCCTGTTGTTGATCC<br>TTGTTAG |
| SEQ ID NO: 36 nucleic acid<br>sequence of EIF6-1 Intron | GTACGTTTTGTTGTGGTCTATTGACAACTGTAGAGTGCGTGAA<br>GCATTTACATCTTGAAATGGTACATCTGACGCTTTTTGTCATCT<br>TGAAG |
| SEQ ID NO: 37 nucleic acid<br>sequence of RPS4-1 Intron | GTAAGAATACTCATTCTTCGTCAATGAGATTGTTGAGTCTCTGA<br>TAGGAACCGAAAATGTAGGAAGGAAGCGCTGGCAACTTTCTG<br>ATGAAAGATGTTTCTGATGAAAGACGTTTGCCGTTGACAAACA<br>TCCGTCCCACGAAAGTAGTGTCGGGAAACGTTGGCTCACTCG<br>GTTGATTCTTTTTCTCCTTTAATAG |
| SEQ ID NO: 38 nucleic acid<br>sequence of Elongation Factor-<br>1 alpha Promoter pEF-1α | CGAAACGAATAGAAGCTCCCCGAGGTCGGGTGTTGTTTGGGA<br>GGTTCATGGTGGTTTCGGTGTCGCTTGCTCGCTCGCTCGTTC<br>GCAGTGACAGACAGTTCGTGAGACACGGAGAACCGTTGGCGTC<br>CGAGTTCGGGTGCCGCATTTCGTCGTCTCCACGATTCAATTCT<br>TGCCCATCAGACGAGTCCCGAATTCCGTGACTCTGGATGCGA<br>TTTACTTTCTAACTGTAAGCGAAACTCAACGATTCCGTACGTTG<br>TTTTCTATTTTACAGTGAGTCTTCGATACCACCGTACAACCATC<br>GTTCGTGTACCGTCTGGTAGTCCCACGTGTCGACAACGTGTG<br>GCTCTGGACCGATGAGTTGTTTGCCGTTCGGAAACGAGCAGT<br>ACCAAGGAATTCACAGAAACACAGCCCATGTAACACAACGACC<br>GCGAATCGTTTCGGTGCTCTCGCTTCGCGTACGGGCGGGCG<br>GTCCTCCCGAGCAGCGAGAGGAGTCCGCAGCGTCATAGTTGC<br>AATCCGGGCCCCCCTCGCGTTGTTCACTCTCTCGTCTAGTAGA<br>GAAACTTCCATCGGATCGTATCATAATATTGTATCGTATAATAT<br>CACGTAATC |
| SEQ ID NO: 39 nucleic acid<br>sequence of 40SRPS8<br>Promoter p40SRPS8 | CCCTGCGATAGACCTTTTCCAAACTCACGCAGTCCAAGAAAAC<br>AAAGGGGTGAGAAGTATACGCACCTTTCGGTTTCGGCATAATT<br>CTTAAACTCTTGTGGTCACTTTCTTGTGAAGAAGCTAGGGGCA<br>CTCGTTTTCCCTCAGAGCCTGCAAACACAAAATTCCTGCAGTC<br>AATTGTCCCAACACTCGGCAAACCGTATGCGCAAGCAACGAT<br>GCGCAGAAGGCCGTGGATGGATGGCGACTCGCGATATGGCT<br>TCTTGGGTCGCCAGTGTGGTACGTCCGGCGTATGTCAATACG<br>CGAATTCGGACGACTGGCATCTCTAGGAGGAGGATTCCTTCTT<br>TTATGACATGTTTATTTTATATACATTGATGCTTTCCGACAGTC<br>GGAAGTAATAAATGAATTTATTTCAAGACTACCTATACTCCTTT<br>GACTTGTTCGACTAATCTTACCGCTTACTAAAATCTCGAAATCA<br>CGCTTGACCTCTCGCACGCAAATTTTTGCTGCTGGACGCTACG<br>CACTCGGCCCAATTCTTCTCGGTCCTCGTCGTCGCAATTGTCG<br>TTGCGTTGATCTTGCACCGAAGGAATCAGAGAATAGAATACC |
| SEQ ID NO: 40 nucleic acid<br>sequence of Histone H4<br>Promoter pH4-1B | CGTCGGTCTCTTTCCCGGGAAACGGGTACACTCCTCCGCGCC<br>AACAACATATTACTACTACTACCAAGAACGTCCACGGCCTTGT<br>CGTGCGTTACGCTCTCCCAACGCGTGCGGGGTAAATTACGTC<br>TCGGTTTGCTAAGTAGCGCACAGCTAAATAGATGACCGTTATT<br>GTATTTAAGATCATTCAATATTGATTGCATTGTACTTTGCGTCA<br>AACTGAAATTCCCTCGTACTAACGGTTAACCCGTCAACCCTAA<br>GCGTTCGCCCAAAGTAGTCAACCGGGACACGCGAACCGACAT<br>TGGGCAGATCTTTCACAGACAGAAAACCATTTCCAATCCAAAT<br>AAGCATGACTATTACACACCCATTCGTAGCGCGAGGACAAACT<br>GATAGCTCCAACAAAATGCGCCAACATCGTACATTGTAAGAAG<br>CTTACGGAACACTATGTATGTAGAACCATACGAACAGCAACTA<br>GTACTGGCCATCGAGCAGCGGTGACTCCCGGCTTTCGTAGCG<br>CTGTGAAGGTTACACTCTCACAATTCGCTCTCGGCTACAACCG<br>ACAAAAGTCTTACTCACAGTCAATACCGAAAACAAACAACAGC<br>CAAC |
| SEQ ID NO: 41 nucleic acid<br>sequence of Tubulin gamma<br>chain Promoter pγ-Tubulin | TTCGTTGATATTTTTATTCAAATGTATCGGGAGGAGTAGAGGTT<br>GATTAACTGTAAACAATTTCCTATTTACTGTTAAGGACCAGCTG<br>CTGCAGTAGGTATGGCCTATCCACTAAACGCACTCACGGAAC<br>GCCTCGCGAAATTTACCCACGGCCAACTTACATTACCGCCTTT<br>TGTGAATTGGAAACGCCGCATGATTCTCAAATGCGCAGAATTT<br>CAAACGGTAGCTTGCGTGTGGAGACTCGCTCATTGACAGTGAA<br>ACTACCTTGTGTCCTCGGATTTTCAGATATACCTATACAGTTCA |

TABLE 1-continued

| | Sequences |
|---|---|
| | TGGCAAAATTTCGTTCATGAACGCACGTGATCCATTGCTCGCG<br>ATTCCCGTTTTTGATTGTGAACGCGGGATTACATGCGTGCGGT<br>GACGGTAGTCCAGACACAGATATTTGCAATACCGGGCCCTTTT<br>CACTACAGACCCTGTAGGGGTATGTTGACGAGAATGAACTCG<br>CAGACTGCCAAAATCGCTTTGGCTGATCCCAAGTTTTGGCACT<br>CCATCGTAATTTGTCATATTCCATACGGTAGCTTCGACTGAATC<br>CAGACAAACAATTTAGTCCAGCTGCGCTTCTACTTGCAAT |
| SEQ ID NO: 42 nucleic acid sequence of Ribulose-1,5-bisphosphate carboxylase/oxygenase small subunit N-methyltransferase I Promoter pRBCMT | ACACGGAGGATCTATCTACAGCAGCGATGAGGGCGCCCGAGA<br>AAGAAAGAACGATTGCCGTACTATTCTCTTTGACCTTTGGGCG<br>CTCGCTCGTATCTTTGAAGCGACTGTTGGGGTCTCAGGGTCC<br>AAAAAACAGAAACTGGATTGACAGTGTGTCTGGACCTTGTCGA<br>ACCTTACAGTTACATTACAGTTAATTGTCACTGTAAATAGTCTA<br>TCGCTGGATTACGTCATCGCGTGACTGGGTGGGAATCCTTCTT<br>GTTGACAGTGAATCTACGGTATACTATTCCTTGGGCGCTTGTA<br>CTTGTGTCTCGAGATTGCCGACAGTGACGTCAATTCGGCACC<br>CACACCTTCCACCCGCCGAACCAAAATCAACAACACGAAGCA<br>CACGACCGACCGACTGTACACGTGAAGGAGCAAACCATCGAA<br>CGAAAGGAGCCTTCCACGGACACAACCCGAAAGCTCGACACC<br>CTTCACCCACGCAAAGTATCTCTTCGTGATCCTACC |
| SEQ ID NO: 43 nucleic acid sequence of Fucoxanthin-chlorophyll a/c binding protein B Promoter pFcpB | GAAACATACCTTCAGCGTCGTCTTCACTGTCACAGTCAACTGA<br>CAGTAATCTTTGGCCCGTAGAGGTTCGAAATTCAATCTATTAAA<br>TACAGCAGGATAAGACACAAGAGCGACATCCTGACATCAACTC<br>CGTGAACAGCAAATCCTGGTTGAACACGTATCCTTTTGGGGG<br>CCTCCAGCTACGACGCTCGCCCCAGCTGGGGCTTCCTTACTA<br>TACACAGCGCATATTTCGCGGTTGCCAGAAGTCAAG |
| SEQ ID NO: 44 nucleic acid sequence of Fucoxanthin-chlorophyll a/c binding protein C Promoter pFcpC | GAGCACAAGAGGTGACAAAAGCCACCGGCTGGATCGCACTTC<br>TCGGAATTTCCCCCCTACTATCAAACAAATTCGAATTGCCAAA<br>GGTGAAGgGACTAACTGTAAATCCTGATCAATCAAGGTCTCAA<br>TCAAGTACAATGGGCTACAATGATATTTAGATGGGAACACAAT<br>GAAACaAATTGAAACTTCTACTGACAGGAGCGCAATTGACTTG<br>TGTAGCTTTTCATGAGCACTTGATTGCTACCaATTGTGAACGG<br>GATGGGGAAAGACTCGAAAAGGTGCATGCTTCCGATAATCTA<br>CTATATTTTCTAGAATCAAATAATATTTAAATGAATGAGGTCCT<br>CAGCGTACGTTAAGCCTACTTATTTAGAACGAGAAGTCAGACC<br>GAGGGGTACTAAAATTCTAAGGGTTGAGAGGTATCTTGATTCC<br>GGGTCTATGGAAGCCCATCCTTGTTGAAGCTTGAACACGATCC<br>TTGTGAAAGGCCGACGTTGCGCGAAAAAACAGCCTGCCGATT<br>TCTTTCCTTCTTTCTCGTCTCAACCTATATACTTTCATAATCTCT<br>GTTAGAGTTTACCAACAACACATATATACATTTCGACAAA |
| SEQ ID NO: 45 nucleic acid sequence of Fucoxanthin-chlorophyll a/c binding protein D Promoter pFcpD | ACTAGCTTGATTGGGATATCTCGCTCATGTTTGTCGCGTGCTA<br>TGTCTTTTTAGGTACTTTGAACCTACGTTCGTACTTGTATAATA<br>TGATCATCGTATTATCGTTTTTCATCCGTCCAGCGCAAAATGCA<br>TTAGCAGCTAGTCCTAGCGTGCGGAGCTACCTGgACAGGTGC<br>ATGACGGATGCGTGTCCTTCAGTGAcTTTCTAATTAACAGTAAC<br>TTCTTTACTTATGTTTCAGTTTGTAAGAAGCGGGATTCGCTCGT<br>CGGTTGACATCTGATTGGACTGCGTCGGCACaTGAAAACTACA<br>TTGTGAAATCTGCTAAAACTCCGGGTATCTCTGACACAAAACG<br>ATTCGGCTTCGCAATTTCAACATTACGGTCAAGGCTAACGTAT<br>CTTTTCTCGGTCAACTTCAGATTAtGCCGATTAAATTGTCGTAGC<br>TTTCAAGGCGTTTTGAGTACTGCGGCAGTTGTTGAACCTGCAA<br>GGAGAAGATCTCGACAACAGAATAAAGCGAAAATGGGTCTC<br>ATGCACTAACACTCAGgCCTCCCTCATAATCTCTGTTTGAGTTT<br>ACCAACAACACATATATACATTTCGACAAA |
| SEQ ID NO: 46 nucleic acid sequence of Elongation Factor-1 alpha Terminator tEF-1α | ATGCGGGAGTGGACCGCGACGATCCGTCCGGAAAAcAATACT<br>AGGTGCTATCACAGGGGCGCGTTTTGGAGAGACGTTCTGCGG<br>AAACACGAATTTAGAATACGTAACTAACATATAAACTGGATAGC<br>CCTCGCATCGGAACTTAGAATGTTCGCCTCAATTTTTAGTTTAG<br>CGTGGAGCAGAGATACCTTTCCATTTGGCAAAATCTACCTTTC<br>GTGAGGGACATCTTGAGAAATAAGCGGACTTGTAGACTAGGA<br>CCGTGGTAACCTCCTCTCAATCTACCAATGTTGTCTGATTTCC<br>GAGCCGCGCGGCTGAAAATCGTCTAGCACTTGGATGCGAGAG<br>CAAATGTCAAGTCCTGCTCTGTCCTGTTGGACGCTTTCCTCTC<br>ACCGCGAGAGGGCTTTCACTCGCGAAACACGTATTTCATATTC<br>AAACTCTATGAAGTTTAAAGTAGATGTATCTACAAACGGTCCTA<br>AGTTTGGGTAAGAATTTTCGACTGCAT |
| SEQ ID NO: 47 nucleic acid sequence of 40SRPS8 Terminator t40SRPS8 | AGATAAGAATATCTCATTGTGAACATCTATGATTTACCAATTTT<br>ATTCTTTGTTTACAGTTAGACGCCAGTAATTGTGCTGTTTCTCT<br>CAAGTCTGTGTCAATACAAACTACGAAACTTGGCAATTTTTCTC<br>TTGAATATGAGCACGAGATTGAAACGCACAAAGGAAATTAGTT<br>TCCATCCTTTGACAAAGTTTGTTGCTGTTTAGAGAACAGATGTC<br>AAAATTAACGTGCCATGGAATTGAACCATGGTGCGCTATCCCC<br>AAATCACGTCGTTTGACCTCGTCACATTTAAGGTATATCAAGC |

TABLE 1-continued

| | Sequences |
|---|---|
| | ATATTCACTTATATCTTGACATCCTCCCTGCTTGATATTCCTTT<br>GCCCTTGAGCCATCTTCCCCACACGCTGGAGATGACCCCTGC<br>CCCTCCTTTCTTTATCCACCCGAGTAAGGTGTCGACAAGTCAC<br>TTTGCCCCTGAGCCATCCTCCCCACTCAGGAGATGACCCCTA<br>CCCCTTTCTTCTTTATCCACCCC |
| SEQ ID NO: 48 nucleic acid sequence of Histone H4 Terminator tH4-1B | GCTTGCGCTTGATCCTCGACTTTGTTGCTCGTCTTTAAAACCTT<br>GGAACGATTATATACAATCACCAACTCAAAAACCGGATTTTCTA<br>AAATCCACCCAAACAACCAAAGAAAATACTTCTCATTGCATTTA<br>TGAATCACAGCAGACCTGCGTCCTTTTAAAACTTAGATCCTGT<br>TTTCTTATAAAAAACAGATCAAATTTTCTGGGAGTTCATTGACT<br>CTGCCAGTCAGAATCAATCCTGCAGTAATTCTTTATTTACAGGT<br>GAAAGTAAAAGAGAATCCCAATTTTTTGCTTGTACATTAAGGTC<br>CTCCTTACATTACAGCTAATTTCAAAATAAGATGAAGTTGGATT<br>CGTGTCCTTTCATGGTGATGTGATATTCTGCACTATACCAA<br>ACACCGTGAAATGTCAGCTAGAGCTTGTCATGAGGCAGTTGCT<br>GCCAATCACTACATATAGATCCTTCACGGAGAAAAGTTGGCTT<br>CATTCTCTGTTGCTAATCGGCT |
| SEQ ID NO: 49 nucleic acid sequence of Tubulin gamma chain Terminator tγ-Tubulin | AGCAAACTCATTATGATGCATGGGAGTGCGACCGAGTTTCGAA<br>CGATGCTAACGAACATTATTAGTGGAAGGCAGTCATTGTTGTA<br>TGCGTCAAAGTATATAATCAGACGGACAGTAGTTCATTTTAAAC<br>TTTTGTTCGGAAAGCGTTGATCATTCATCGGGGAATCGCGCTA<br>ACGAGCAGTAATTGGAGTTGTAACTGCAGGCTCAACGCGTTTC<br>TGGCTCCCGTGGGTTACCATAATGCTAACTATCATTCTTTATTT<br>GCAGTATCACCAGTCCAAGAATTATTCGTGGTCATTTCTGATG<br>CTACTGTGGAGAAGTGAGAGTAATTTCGCCGACTTTGAAGTGA<br>AGACGCGTCTCCGAACGTAGATTGTTGGTATTGTACCATTGAA<br>GGAGAGTTTTTGAACTCAGGTTGTTGATCGTAATGTCCGCGAC<br>ATCCTGGCGCACTACACGCCAATGACCATAACATGTCTTGGTC<br>GCCCTCCTCGTAAGTCATCGCCATT |
| SEQ ID NO: 50 nucleic acid sequence of Ribulose-1,5-bisphosphatecarboxylase/ oxygenase small subunit N-methyltransferase 1 Terminator tRBCMT | AAATACAAATTCATGTACCTAAACGATAGTATGGATGATGGGA<br>GTAATTGCACTATAATTGTAGAACCTTGTAAGAGGAAAAAATGA<br>TCTTACTGTGTTATTTCCTCTTGAAAGAATCTATGGATAAAATA<br>AGAGAGGACGCTAGGTGGTAACATTCCGGCAAAACACTGGCG<br>CCTAAATTTTTGCCGGAATCGTCAATTGCAACGGTTGTACCGG<br>TGCTTTGTTTTAGTGTTTCGCCTTGCTACCCTTCAGGAACCGG<br>TAACGAACACCTCCGCCACCCCGGACCCGCTCTGTTTTAGTTT<br>GAATGGACTTGCGCAAAGAATCCTTATCATTCGCCTGTGACCG<br>GGTTCCTTCCTTGGCCAAATTTGCCAGAAAGGTTTCCCGATCA<br>ATGCTAGGGGTGCTTCCGCCTCCACTTGCCGTGGGAGTGTTC<br>CCACCGCTACTTGCCGTTGGAGTGCTATCACTATCGGAGCCTT<br>GGATCGTGTTGGGCGTACCGGTAGTGCC |
| SEQ ID NO: 51 nucleic acid sequence of carboxylase/ oxygenase small subunit N-methyltransferase I Terminator tFcpB | TTTACTTGCTGGGTAGGCCGTTTCTGGAATAACATATTAGATTC<br>TAACTGGTTCGAAGCATTGCGTTGCTGTAACATTCCCGTTCAC<br>AAAAATACAGAACAGTCTAGAAGTTCGCGACGACATAATTTTTT<br>CTCTTTAGGAGGCCGGGGTTGTAATTGTTCTAGGGCTGTTCCA<br>ATAGAGAAGATAAGATGATCAAACATACCAGCCGCGCGCTTGATT<br>GGACGGAGTACGTTTGCATCAGCTATTTTTCAAAAGCGCTGCA<br>CGACGCACACTCTATGAACACTTCAAGACTCTCAACGCAAGTG<br>ACAACCATCCTCTCCAAAAGGCTATCTTTCGGGGCACCTGTAA<br>TATAAAAAAGCATGGCAGTGCATTCCATGCAAAAAATGTCTAAT<br>CTGGTTGGGTTTTAAAGTCCGTATCGAGCACAGAGGTGACAAA<br>AGCCACCGGCTGGATCGCACTTCTCGGAATTTCCCCCCTACT<br>ATCAAACAAATTCGAATTGCCAAAGGTG |
| SEQ ID NO: 52 nucleic acid sequence of Fucoxanthin-chlorophyll a/c binding protein B Terminator tFcpC | TTTTGTTACATTGACTTCAAGGAGTCGAGGAATCGATACTGCC<br>GTCGTTTCCAGGATCCGAGGTTTCTATAGACTCTCTATAGACT<br>CTGTTAACCTAATAGAATCAGACATACCTCTCCTGCTATTTTGT<br>TTTTATGAATTTGGCTTTTGCCTCTCTAGTCAGATTTGAATGTT<br>ATTTTCCGCCAGGTGTGTTAGTCGGGCTCTCGTTTGAGTTACA<br>AGAGGGATTGAGTGGCGAGGATTCACTCTAATGTAAATATGAC<br>TGTGAACAAAACTTTAAAATTACTACGCATCTTCTTTGACTGTC<br>AGATATTCGTCGGTGACAGCAGTCAATGCCTGCAAATTGTCCT<br>CCTGGGTCGCAATTTGGTTTTGGATTGACCTGGTATGCATTAT<br>GAAGAAAAAATTCGTTATTAGCCAACTGCCTAGCGTGCACAT<br>TGCATGGTTAGACCTCCTTGACGACTGTGAGCCTACATCCTTC<br>TGCAACAAGCTGCAAT |

TABLE 1-continued

| Sequences | |
|---|---|
| SEQ ID NO: 53 nucleic acid sequence of Fucoxanthin-chlorophyll a/c binding protein C Terminator tFcpD | TTTTGTTACATTTACTGACTTCAAGGAGTCGAGGAATCGATACT GCCGTCGTTTCCAGGATCCGAGGTTTCATAAACTCTGTTAACG TTATAGAAACAGACTTACCTCTCCTACGCCATTCACGTAATATT CGCAATATGCTATTCTTCCTCTGAAGACCAGGTTTATGTGCTG CCTGAAACTATTTCAATAAGTCAGCTGCACTTGCACAGGGTTT CACAAGGAAAGCGTGTCTTTTTTTCCAACGTAGGCGTCGCTTT CGTCTGACTCTTACTCTTACATTCACAGCCAATACTTACAATTA GTAAAAAACCTGTGCTCGAGAGTGAAAACGTC |
| SEQ ID NO: 54 nucleic acid sequence of self-cleaving linker FMDV2a optimized for GC-rich microalgae | GCTCCTGTCAAGCAGACCCTGAACTTTGACCTGCTCAAGCTC GCCGGTGATGTGGAGAGCAACCCCGGCCCC |
| SEQ ID NO: 55 nucleic acid sequence of self-cleaving linker FMDV2a optimized for diatoms | GCCCCGGTGAAACAAACCCTTAATTTCGATTTGTTGAAATTGG CTGGAGATGTTGAGTCTAATCCAGGCCCC |
| SEQ ID NO: 56 nucleic acid coding sequence of Steely1 from *Dictyostelium discoideum* optimized for diatoms | ATGAACAAGAACTCGAAGATTCAATCGCCGAACTCGTCGGAC GTGGCTGTGATTGGAGTGGGATTTCGATTTCCGGGAAACTCG AACGACCCGGAATCGTTGTGGAACAACTTGTTGGACGGATTT GACGCTATTACGCAAGTGCCGAAGGAACGATGGGCTACGTCG TTTCGAGAAATGGGATTGATTAAGAACAAGTTTGGAGGATTTTT GAAGGACTCGGAATGGAAGAACTTTGACCCGTTGTTTTTTGGA ATTGGACCGAAGGAAGCTCCGTTTATTGACCCGCAACAACGAT TGTTGTTGTCGATTGTGTGGGAATCGTTGGAAGACGCTTACAT TCGACCGGACGAATTGCGAGGATCGAACACGGGAGTGTTTAT TGGAGTGTCGAACAACGACTACACGAAGTTGGGATTTCAAGA CAACTACTCGATTTCGCCGTACACGATGACGGGATCGAACTC GTCGTTGAACTCGAACCGAATTTCGTACTGCTTTGACTTTCGA GGACCGTCGATTACGGTGGACACGGCTTGCTCGTCGTCGTTG GTGTCGGTGAACTTGGGAGTGCAATCGATTCAAATGGGAGAA TGCAAGATTGCTATTTGCGGAGGAGTGAACGCTTTGTTTGACC CGTCGACGTCGGTGGCTTTTTCGAAGTTGGGAGTGTTGTCGG AAAACGGACGATGCAACTCGTTTTCGGACCAAGCTTCGGGAT ACGTGCGATCGGAAGGAGCTGGAGTGGTGGTGTTGAAGTCGT TGGAACAAGCTAAGTTGGACGGAGACCGAATTTACGGAGTGA TTAAGGGAGTGTCGTCGAACGAAGACGGAGCTTGAACGGAG ACAAGAACTCGTTGACGACGCCGTCGTGCGAAGCTCAATCGA TTAACATTTCGAAGGCTATGGAAAAGGCTTCGTTGTCGCCGTC GGACATTTACTACATTGAAGCTCACGGAACGGGAACGCCGGT GGGAGACCCGATTGAAGTGAAGGCTTTGTCGAAGATTTTTTCG AACTCGAACAACAACCAATTGAACAACTTTTCGACGGACGGAA ACGACAACGACGACGACGACGACAACACGTCGCCGGAA CCGTTGTTGATTGGATCGTTTAAGTCGAACATTGGACACTTGG AATCGGCTGCTGGAATTGCTTCGTTGATTAAGTGCTGCTTGAT GTTGAAGAACCGAATGTTGGTGCCGTCGATTAACTGCTCGAAC TTGAACCCGTCGATTCCGTTTGACCAATACAACATTTCGGTGA TTCGAGAAATTCGACAATTTCCGACGGACAAGTTGGTGAACAT TGGAATTAACTCGTTTGGATTTGGAGGATCGAACTGCCACTTG ATTATTCAAGAATACAACAACAACTTTAAGAACAACTCGACGAT TTGCAACAACAACAACAACAACAACAACATTGACTACTTG ATTCCGATTTCGTCGAAGACGAAGAAGTCGTTGGACAAGTACT TGATTTTGATTAAGACGAACTCGAACTACCACAAGGACATTTC GTTTGACGACTTTGTGAAGTTTCAAATTAAGTCGAAGCAATACA ACTTGTCGAACGAATGACGACGATTGCTAACGACTGGAACTC GTTTATTAAGGGATCGAACGAATTTCACAACTTGATTGAATCGA AGGACGGAGAAGGAGGATCGTCGTCGTCGAACCGAGGAATT GACTCGGCTAACCAAATTAACACGACGACGACGTCGACGATT AACGACATTGAACCGTTGTTGGTGTTTGTGTTTTGCGGACAAG GACCGCAATGGAACGGAATGATTAAGACGTTGTACAACTCGG AAAACGTGTTTAAGAACACGGTGGACCACGTGGACTCGATTTT GTACAAGTACTTTGGATACTCGATTTTGAACGTGTTGTCGAAG ATTGACGACAACGACGACTCGATTAACCACCCGATTGTGGCTC AACCGTCGTTGTTTTTGTTGCAAATTGGATTGGTGGAATTGTTT AAGTACTGGGGAATTTACCCGTCGATTTCGGTGGACACTCG TTTGGAGAAGTGTCGTCGTACTACTTGTCGGGAATTATTTCGT TGGAAACGGCTTGCAAGATTGTGTACGTGCGATCGTCGAACC AAAACAAGACGATGGGATCGGGAAAGATGTTGGTGGTGTCGA TGGGATTTAAGCAATGGAACGACCAATTTTCGGCTGAATGGTC GGACATTGAAATTGCTTGCTACAACGCTCCGGACTCGATTGTG GTGACGGGAAACGAAGAACGATTGAAGGAATTGTCGATTAAG TTGTCGGACGAATCGAACCAAATTTTTAACACGTTTTTGCGATC GCCGTGCTCGTTTCACTCGTCGCACCAAGAAGTGATTAAGGG ATCGATGTTTGAAGAATTGTCGAACTTGCAATCGACGGGAGAA ACGGAAATTCCGTTGTTTTCGACGGTGACGGGACGACAAGTG TTGTCGGGACACGTGACGGCTAACACATTTACGACAACGTG CGAGAACCGGTGTTGTTTCAAAAGACGATTGAATCGATTACGT |

TABLE 1-continued

Sequences

```
CGTACATTAAGTCGCACTACCCGTCGAACCAAAAGGTGATTTA
CGTGGAAATTGCTCCGCACCCGACGTTGTTTTCGTTGATTAAG
AAGTCGATTCCGTCGTCGAACAAGAACTCGTCGTCGGTGTTGT
GCCCGTTGAACCGAAAGGAAAACTCGAACAACTCGTACAAGA
AGTTTGTGTCGCAATTGTACTTTAACGGAGTGAACGTGGACTT
TAACTTTCAATTGAACTCGATTTGCGACAACGTGAACAACGAC
CACCACTTGAACAACGTGAAGCAAAACTCGTTTAAGGAAACGA
CGAACTCGTTGCCGCGATACCAATGGGAACAAGACGAATACT
GGTCGGAACCGTTGATTTCGCGAAAGAACCGATTGGAAGGAC
CGACGACGTCGTTGTTGGGACACCGAATTATTTACTCGTTTCC
GGTGTTTCAATCGGTGTTGGACTTGCAATCGGACAACTACAAG
TACTTGTTGGACCACTTGGTGAACGGAAAGCCGGTGTTTCCG
GGAGCTGGATACTTGGACATTATTATTGAATTTTTTGACTACCA
AAAGCAACAATTGAACTCGTCGGACTCGTCGAACTCGTACATT
ATTAACGTGGACAAGATTCAATTTTTGAACCCGATTCACTTGAC
GGAAAACAAGTTGCAAACGTTGCAATCGTCGTTTGAACCGATT
GTGACGAAGAAGTCGGCTTTTTCGGTGAACTTTTTTATTAAGG
ACACGGTGGAAGACCAATCGAAGGTGAAGTCGATGTCGGACG
AAACGTGGACGAACACGTGCAAGGCTACGATTTCGTTGGAAC
AACAACAACCGTCGCCGTCGTCGACGTTGACGTTGTCGAAGA
AGCAAGACTTGCAAATTTTGCGAAACCGATGCGACATTTCGAA
GTTGGACAAGTTTGAATTGTACGACAAGATTTCGAAGAACTTG
GGATTGCAATACAACTCGTTGTTTCAAGTGGTGGACACGATTG
AAACGGGAAAGGACTGCTCGTTTGCTACGTTGTCGTTGCCGG
AAGACACGTTGTTTACGACGATTTTGAACCCGTGCTTGTTGGA
CAACTGCTTTCACGGATTGTTGACGTTGATTAACGAAAAGGGA
TCGTTTGTGGTGGAATCGATTTCGTCGGTGTCGATTTACTTGG
AAAACATTGGATCGTTTAACCAAACGTCGGTGGGAAACGTGCA
ATTTTACTTGTACACGACGATTTCGAAGGCTACGTCGTTTTCGT
CGGAAGGAACGTGCAAGTTGTTACGAAGGACGGATCGTTGA
TTTTGTCGATTGGAAAGTTTATTATTAAGTCGACGAACCCGAA
GTCGACGAAGACGAACGAAACGATTGAATCGCCGTTGGACGA
AACGTTTTCGATTGAATGGCAATCGAAGGACTCGCCGATTCCG
ACGCCGCAACAAATTCAACAACAATCGCCGTTGAACTCGAACC
CGTCGTTTATTCGATCGACGATTTTGAAGGACATTCAATTTGAA
CAATACTGCTCGTCGATTATTCACAAGGAATTGATTAACCACG
AAAAGTACAAGAACCAACAATCGTTTGACATTAACTCGTTGGA
AAACCACTTGAACGACGACCAATTGATGGAATCGTTGTCGATT
TCGAAGGAATACTTGCGATTTTTTACGCGAATTATTTCGATTAT
TAAGCAATACCCGAAGATTTTGAACGAAAAGGAATTGAAGGAA
TTGAAGGAAATTATTGAATTGAAGTACCCGTCGGAAGTGCAAT
TGTTGGAATTTGAAGTGATTGAAAAGGTGTCGATGATTATTCC
GAAGTTGTTGTTTGAAAACGACAAGCAATCGTCGATGACGTTG
TTTCAAGACAACTTGTTGACGCGATTTTACTCGAACTCGAACT
CGACGCGATTTTACTTGGAACGAGTGTCGGAAATGGTGTTGG
AATCGATTCGACCGATTGTGCGAGAAAAGCGAGTGTTTCGAAT
TTTGGAAATTGGAGCTGGAACGGGATCGTTGTCGAACGTGGT
GTTGACGAAGTTGAACACGTACTTGTCGACGTTGAACTCGAAC
GGAGGATCGGGATACAACATTATTATTGAATACACGTTTACGG
ACATTTCGGCTAACTTTATTATTGGAGAAATTCAAGAACGATG
TGCAACTTGTACCCGAACGTGACGTTTAAGTTTTCGGTGTTGG
ACTTGGAAAAGGAAATTATTAACTCGTCGGACTTTTTGATGGG
AGACTACGACATTGTGTTGATGGCTTACGTGATTCACGCTGTG
TCGAACATTAAGTTTTCGATTGAACAATTGTACAAGTTGTTGTC
GCCGCGAGGATGGTTGTTGTGCATTGAACCGAAGTCGAACGT
GGTGTTTTCGGACTTGGTGTTTGGATGCTTTAACCAATGGTGG
AACTACTACGACGACATTCGAACGACGCACTGCTCGTTGTCG
GAATCGCAATGGAACCAATTGTTGTTGAACCAATCGTTGAACA
ACGAATCGTCGTCGTCGTCGAACTGCTACGGAGGATTTTCGA
ACGTGTCGTTTATTGGAGGAGAAAAGGACGTGGACTCGCACT
CGTTTATTTTGCACTGCCAAAAGGAATCGATTTCGCAAATGAA
GTTGGCTACGACGATTAACAACGGATTGTCGTCGGGATCGATT
GTGATTGTGTTGAACTCGCAACAATTGACGAACATGAAGTCGT
ACCCGAAGGTGATTGAATACATTCAAGAAGCTACGTCGTTGTG
CAAGACGATTGAAATTATTGACTCGAAGGACGTGTTGAACTCG
ACGAACTCGGTGTTGGAAAAGATTCAAAAGTCGTTGTTGGTGT
TTTGCTTGTTGGGATACGACTTGTTGGAAAACAACTACCAAGA
ACAATCGTTTGAATACGTGAAGTTGTTGAACTTGATTTCGACG
ACGGCTTCGTCGTCGAACGACAAGAAGCCGCCGAAGGTGTTG
TTGATTACGAAGCAATCGGAACGAATTTCGCGATCGTTTTACT
CGCGATCGTTGATTGGAATTTCGCGAACGTCGATGAACGAATA
CCCGAACTTGTCGATTACGTCGATTGACTTGGACACGAACGAC
TACTCGTTGCAATCGTTGTTGAAGCCGATTTTTTCGAACTCGA
AGTTTTCGGACAACGAATTATTTTTAAGAAGGGATTGATGTTT
GTGTCGCGAATTTTTAAGAACAAGCAATTGTTGGAATCGTCGA
ACGCTTTTGAAACGGACTCGTCGAACTTGTACTGCAAGGCTTC
GTCGGACTTGTCGTACAAGTACGCTATTAAGCAATCGATGTTG
ACGGAAAACCAAATTGAAATTAAGGTGGAATGCGTGGGAATTA
```

TABLE 1-continued

Sequences

```
ACTTTAAGGACAACTTGTTTTACAAGGGATTGTTGCCGCAAGA
AATTTTTCGAATGGGAGACATTTACAACCCGCCGTACGGATTG
GAATGCTCGGGAGTGATTACGCGAATTGGATCGAACGTGACG
GAATACTCGGTGGGACAAAACGTGTTTGGATTTGCTCGACACT
CGTTGGGATCGCACGTGGTGACGAACAAGGACTTGGTGATTT
TGAAGCCGGACACGATTTCGTTTTCGGAAGCTGCTTCGATTCC
GGTGGTGTACTGCACGGCTTGGTACTCGTTGTTTAACATTGGA
CAATTGTCGAACGAAGAATCGATTTTGATTCACTCGGCCACGG
GAGGAGTGGGATTGGCTTCGTTGAACTTGTTGAAGATGAAGA
ACCAACAACAACCGTTGACGAACGTGTACGCTACGGTGG
GATCGAACGAAAAGAAGAAGTTTTTGATTGACAACTTTAACAA
CTTGTTTAAGGAAGACGGAGAAAACATTTTTTCGACGCGAGAC
AAGGAATACTCGAACCAATTGGAATCGAAGATTGACGTGATTT
TGAACACGTTGTCGGGAGAATTTGTGGAATCGAACTTTAAGTC
GTTGCGATCGTTTGGACGATTGATTGACTTGTCGGCTACGCAC
GTGTACGCTAACCAACAAATTGGATTGGGAAACTTTAAGTTTG
ACCACTTGTACTCGGCTGTGGACTTGGAACGATTGATTGACGA
AAAGCCGAAGTTGTTGCAATCGATTTTGCAACGAATTACGAAC
TCGATTGTGAACGGATCGTTGGAAAAGATTCCGATTACGATTT
TTCCGTCGACGGAAACGAAGGACGCTATTGAATTGTTGTCGAA
GCGATCGCACATTGGAAAGGTGGTGGTGGACTGCACGGACAT
TTCGAAGTGCAACCCGGTGGGAGACGTGATTACGAACTTTTC
GATGCGATTGCCGAAGCCGAACTACCAATTGAACTTGAACTCG
ACGTTGTTGATTACGGGACAATCGGGATTGTCGATTCCGTTGT
TGAACTGGTTGTTGTCGAAGTCGGGAGGAAACGTGAAGAACG
TGGTGATTATTTCGAAGTCGACGATGAAGTGGAAGTTGCAAAC
GATGATTTCGCACTTTGTGTCGGGATTTGGAATTCACTTTAACT
ACGTGCAAGTGGACATTTCGAACTACGACGCTTTGTCGGAAG
CTATTAAGCAATTGCCGTCGGACTTGCCGCCGATTACGTCGGT
GTTTCACTTGGCTGCTATTTACAACGACGTGCCGATGGACCAA
GTGACGATGTCGACGGTGGAATCGGTGCACAACCCGAAGGTG
TTGGGAGCTGTGAACTTGCACCGAATTTCGGTGTCGTTTGGAT
GGAAGTTGAACCACTTTGTGTTGTTTTCGTCGATTACGGCTAT
TACGGGATACCCGGACCAATCGATTTACAACTCGGCTAACTCG
ATTTTGGACGCTTTGTCGAACTTTCGACGATTTATGGGATTGC
CGTCGTTTTCGATTAACTTGGGACCGATGAAGGACGAAGGAA
AGGTGTCGACGAACAAGTCGATTAAGAAGTTGTTTAAGTCGCG
AGGATTGCCGTCGTTGTCGTTGAACAAGTTGTTTGGATTGTTG
GAAGTGGTGATTAACAACCCGTCGAACCACGTGATTCCGTCG
CAATTGATTTGCTCGCCGATTGACTTTAAGACGTACATTGAATC
GTTTTCGACGATGCGACCGAAGTTGTTGCACTTGCAACCGAC
GATTTCGAAGCAACAATCGTCGATTATTAACGACTCGACGAAG
GCTTCGTCGAACATTTCGTTGCAAGACAAGATTACGTCGAAGG
TGTCGGACTTGTTGTCGATTCCGATTTCGAAGATTAACTTTGA
CCACCCGTTGAAGCACTACGGATTGGACTCGTTGTTGACGGT
GCAATTTAAGTCGTGGATTGACAAGGAATTTGAAAAGAACTTG
TTTACGCACATTCAATTGGCTACGATTTCGATTAACTCGTTTTT
GGAAAAGGTGAACGGATTGTCGACGAACAACAACAACAACAA
CAACTCGAACGTGAAGTCGTCGCCGTCGATTGTGAAGGAAGA
AATTGTGACGTTGGACAAGGACCAACAACCGTTGTTGTTGAAG
GAACACCAACACATTATTATTTCGCCGGACATTCGAATTAACAA
GCCGAAGCGAGAATCGTTGATTCGAACGCCGATTTTGAACAA
GTTTAACCAAATTACGGAATCGATTATTACGCCGTCGACGCCG
TCGTTGTCGCAATCGGACGTGTTGAAGACGCCGCCGATTAAG
TCGTTGAACAACACGAAGAACTCGTCGTTGATTAACACGCCGC
CGATTCAATCGGTGCAACAACACCAAAAGCAACAACAAAAGGT
GCAAGTGATTCAACAACAACAACAACCGTTGTCGCGATTGTCG
TACAAGTCGAACAACAACTCGTTTGTGTTGGGAATTGGAATTT
CGGTGCCGGGAGAACCGATTTCGCAACAATCGTTGAAGGACT
CGATTTCGAACGACTTTTCGGACAAGGCTGAAACGAACGAAAA
GGTGAAGCGAATTTTTGAACAATCGCAAATTAAGACGCGACAC
TTGGTGCGAGACTACACGAAGCCGGAAAACTCGATTAAGTTTC
GACACTTGGAAACGATTACGGACGTGAACAACCAATTTAAGAA
GGTGGTGCCGGACTTGGCTCAACAAGCTTGCTTGCGAGCTTT
GAAGGACTGGGGAGGAGACAAGGGAGACATTACGCACATTGT
GTCGGTGACGTCGACGGGAATTATTATTCCGGACGTGAACTTT
AAGTTGATTGACTTGTTGGGATTGAACAAGGACGTGGAACGA
GTGTCGTTGAACTTGATGGGATGCTTGGCTGGATTGTCGTCGT
TGCGAACGGCTGCTTCGTTGGCTAAGGCTTCGCCGCGAAACC
GAATTTTGGTGGTGTGCACGGAAGTGTGCTCGTTGCACTTTTC
GAACACGGACGGAGGAGACCAAATGGTGGCTTCGTCGATTTT
TGCTGACGGATCGGCTGCTTACATTATTGGATGCAACCCGCG
AATTGAAGAAACGCCGTTGTACGAAGTGATGTGCTCGATTAAC
CGATCGTTTCCGAACACGGAAAACGCTATGGTGTGGGACTTG
GAAAAGGAAGGATGGAACTTGGGATTGGACGCTTCGATTCCG
ATTGTGATTGGATCGGGAATTGAAGCTTTTGTGGACACGTTGT
TGGACAAGGCTAAGTTGCAAACGTCGACGGCTATTTCGGCTA
AGGACTGCGAATTTTTGATTCACACGGGAGGAAAGTCGATTTT
```

TABLE 1-continued

| | Sequences |
|---|---|
| | GATGAACATTGAAAACTCGTTGGGAATTGACCCGAAGCAAACG<br>AAGAACACGTGGGACGTGTACCACGCTTACGGAAACATGTCG<br>TCGGCTTCGGTGATTTTTGTGATGGACCACGCTCGAAAGTCGA<br>AGTCGTTGCCGACGTACTCGATTTCGTTGGCTTTTGGACCGG<br>GATTGGCTTTTGAAGGATGCTTTTTGAAGAACGTGGTGTAA |
| SEQ ID NO: 57 nucleic acid coding sequence of Steely2 from *Dictyostelium discoideum* optimized for diatoms | ATGAACAACAACAAGTCGATTAACGACTTGTCGGGAAACTCGA<br>ACAACAACATTGCTAACTCGAACATTAACAACTACAACAACTTG<br>ATTAAGAAGGAACCGATTGCTATTATTGGAATTGGATGCCGAT<br>TTCCGGGAAACGTGTCGAACTACTCGGACTTTGTGAACATTAT<br>TAAGAACGGATCGGACTGCTTGACGAAGATTCCGGACGACCG<br>ATGGAACGCTGACATTATTTCGCGAAAGCAATGGAAGTTGAAC<br>AACCGAATTGGAGGATACTTGAAGAACATTGACCAATTTGACA<br>ACCAATTTTTTGGAATTTCGCCGAAGGAAGCTCAACACATTGA<br>CCCGCAACAACGATTGTTGTTGCACTTGGCTATTGAAACGTTG<br>GAAGACGGAAAGATTTCGTTGGACGAAATTAAGGGAAAGAAG<br>GTGGGAGTGTTTATTGGATCGTCGTCGGGAGACTACTTGCGA<br>GGATTTGACTCGTCGGAAATTAACCAATTTACGACGCCGGGAA<br>CGAACTCGTCGTTTTTGTCGAACCGATTGTCGTACTTTTTGGA<br>CGTGAACGGACCGTCGATGACGGTGAACACGGCTTGCTCGG<br>CTTCGATGGTGGCTATTCACTTGGGATTGCAATCGTTGTGGAA<br>CGGAGAATCGGAATTGTCGATGGTGGGAGGAGTGAACATTAT<br>TTCGTCGCCGTTGCAATCGTTGGACTTTGGAAAGGCTGGATTG<br>TTGAACCAAGAAACGGACGGACGATGCTACTCGTTTGACCCG<br>CGAGCTTCGGGATACGTGCGATCGGAAGGAGGAGGAATTTTG<br>TTGTTGAAGCCGTTGTCGGCTGCTTTGCGAGACAACGACGAA<br>ATTTACTCGTTGTTGTTGAACTCGGCTAACAACTCGAACGGAA<br>AGACGCCGACGGGAATTACGTCGCCGCGATCGTTGTGCCAAG<br>AAAAGTTGATTCAACAATTGTTGCGAGAATCGTCGGACCAATT<br>TTCGATTGACGACATTGGATACTTTGAATGCCACGGAACGGGA<br>ACGCAAATGGGAGACTTGAACGAAATTACGGCTATTGGAAAGT<br>CGATTGGAATGTTGAAGTCGCACGACGACCCGTTGATTATTGG<br>ATCGGTGAAGGCTTCGATTGGACACTTGGAAGGAGCTTCGGG<br>AATTTGCGGAGTGATTAAGTCGATTATTTGCTTGAAGGAAAAG<br>ATTTTGCCGCAACAATGCAAGTTTTCGTCGTACAACCCGAAGA<br>TTCCGTTTGAAACGTTGAACTTGAAGGTGTTGACGAAGACGCA<br>ACCGTGGAACAACTCGAAGCGAATTTGCGGAGTGAACTCGTT<br>TGGAGTGGGAGGATCGAACTCGTCGTTGTTTTTGTCGTCGTTT<br>GACAAGTCGACGACGATTACGGAACCGACGACGACGACGAC<br>GATTGAATCGTTGCCGTCGTCGTCGTCGTCGTTTGACAACTTG<br>TCGGTGTCGTCGTCGATTTCGACGAACAACGACAACGACAAG<br>GTGTCGAACATTGTGAACAACCGATACGGATCGTCGATTGAC<br>GTGATTACGTTGTCGGTGACGTCGCCGGACAAGGAAGACTTG<br>AAGATTCGAGCTAACGACGTGTTGGAATCGATTAAGACGTTGG<br>ACGACAACTTTAAGATTCGAGACATTTCGAACTTGACGAACAT<br>TCGAACGTCGCACTTTTCGAACCGAGTGGCTATTATTGGAGAC<br>TCGATTGACTCGATTAAGTTGAACTTGCAATCGTTTATTAAGGG<br>AGAAAACAACAACAACAAGTCGATTATTTTGCCGTTGATTAACA<br>ACGGAAACAACAACAACAACAACAACAACTCGTCGGGATC<br>GTCGTCGTCGTCGTCGAACAACAACAACATTTGCTTTATTTTT<br>CGGGACAAGGACAACAATGGAACAAGATGATTTTTGACTTGTA<br>CGAAAACAACAAGACGTTTAAGAACGAAATGAACAACTTTTCG<br>AAGCAATTTGAAATGATTTCGGGATGGTCGATTATTGACAAGT<br>TGTACAACTCGGGAGGAGGAGGAAACGAAGAATTGATTAACG<br>AAACGTGGTTGGCTCAACCGTCGATTGTGGCTGTGCAATACTC<br>GTTGATTAAGTTGTTTTCGAAGGACATTGGAATTGAAGGATCG<br>ATTGTGTTGGGACACTCGTTGGGAGAATTGATGGCTGCTTACT<br>ACTGCGGAATTATTAACGACTTTAACGACTTGTTGAAGTTGTTG<br>TACATTCGATCGACGTTGCAAAACAAGACGAACGGATCGGGA<br>CGAATGCACGTGTGCTTGTCGTCGAAGGCTGAAATTGAACAAT<br>TGATTTCGCAATTGGGATTTAACGGACGAATTGTGATTTGCGG<br>AAACAACACGATGAAGTCGTGCACGATTTCGGGAGACAACGA<br>ATCGATGAACCAATTTACGAAGTTGATTTCGTCGAACAATAC<br>GGATCGGTGGTGCACAAGGAAGTGCGAACGAACTCGGCTTTT<br>CACTCGCACCAAATGGACATTATTAAGGACGAATTTTTTAAGTT<br>GTTTAACCAATACTTTCCGACGAACCAAATTTCGACGAACCAA<br>ATTTACGACGGAAAGTCGTTTTACTCGACGTGCTACGGAAAGT<br>ACTTGACGCCGATTGAATGCAAGCAATTGTTGTCGTCGCCGAA<br>CTACTGGTGGAAGAACATTCGAGAATCGGTGTTGTTTAAGGAA<br>TCGATTGAACAAATTTTGCAAAACCACCAACAATCGTTGACGTT<br>TATTGAAATTACGTGCCACCCGATTTTGAACTACTTTTTGTCGC<br>AATTGTTGAAGTCGTCGTCGAAGTCGAACACGTTGTTGTTGTC<br>GACGTTGTCGAAGAACTCGAACTCGATTGACCAATTGTTGATT<br>TTGTGCTCGAAGTTGTACGTGAACAACTTGTCGTCGATTAAGT<br>GGAACTGGTTTTACGACAAGCAACAACAACAACAATCGGAATC<br>GTTGGTGTCGTCGAACTTTAAGTTGCCGGGACGACGATGAA<br>GTTGGAAAAGTACTGGATTGAAAACTGCCAACGACAAATGGAC<br>CGAATTAAGCCGCCGATGTTTATTTCGTTGGACCGAAAGTTGT |

TABLE 1-continued

| Sequences |
|---|
| TTTCGGTGACGCCGTCGTTTGAAGTGCGATTGAACCAAGACC |
| GATTTCAATACTTGAACGACCACCAAATTCAAGACATTCCGTT |
| GGTGCCGTTTTCGTTTTACATTGAATTGGTGTACGCTTCGATTT |
| TTAACTCGATTTCGACGACGACGACGAACACGACGGCTTCGA |
| CGATGTTTGAAATTGAAAACTTTACGATTGACTCGTCGATTATT |
| ATTGACCAAAAGAAGTCGACGTTGATTGGAATTAACTTTAACTC |
| GGACTTGACGAAGTTTGAAATTGGATCGATTAACTCGATTGGA |
| TCGGGATCGTCGTCGAACAACAACTTTATTGAAAACAAGTGGA |
| AGATTCACTCGAACGGAATTATTAAGTACGGAACGAACTACTT |
| GAAGTCGAACTCGAAGTCGAACTCGTTTAACGAATCGACGAC |
| GACGACGACGACGACGACGACGACGAAGTGCTTTAAGTC |
| GTTTAACTCGAACGAATTTTACAACGAAATTATTAAGTACAACT |
| ACAACTACAAGTCGACGTTTCAATGCGTGAAGGAATTTAAGCA |
| ATTTGACAAGCAAGGAACGTTTTACTACTCGGAAATTCAATTTA |
| AGAAGAACGACAAGCAAGTGATTGACCAATTGTTGTCGAAGCA |
| ATTGCCGTCGGACTTTCGATGCATTCACCCGTGCTTGTTGGAC |
| GCTGTGTTGCAATCGGCTATTATTCCGGCTACGAACAAGACGA |
| ACTGCTCGTGGATTCCGATTAAGATTGGAAAGTTGTCGGTGAA |
| CATTCCGTCGAACTCGTACTTTAACTTTAAGGACCAATTGTTGT |
| ACTGCTTGATTAAGCCGTCGACGTCGACGTCGACGTCGCCGT |
| CGACGTACTTTCGTCGGACATTCAAGTGTTTGACAAGAAGAA |
| CAACAACTTGATTTGCGAATTGACGAACTTGGAATTTAAGGGA |
| ATTAACTCGTCGTCGTCGTCGTCGTCGTCGTCGACGATTA |
| ACTCGAACGTGGAAGCTAACTACGAATCGAAGATTGAAGAAAC |
| GAACCACGACGAAGACGAAGACGAAGAATTGCCGTTGGTGTC |
| GGAATACGTGTGGTGCAAGGAAGAATTGATTAACCAATCGATT |
| AAGTTTACGGACAACTACCAAACGGTGATTTTTTGCTCGACGA |
| ACTTGAACGGAAACGACTTGTTGGACTCGATTATTACGTCGGC |
| TTTGGAAAACGGACACGACGAAAACAAGATTTTTATTGTGTCG |
| CCGCCGCCGGTGGAATCGGACCAATACAACAACCGAATTATT |
| ATTAACTACACGAACAACGAATCGGACTTTGACGCTTTGTTTG |
| CTATTATTAACTCGACGACGTCGATTTCGGGAAAGTCGGGATT |
| GTTTTCGACGCGATTTATTATTTTGCCGAACTTTAACTCGATTA |
| CGTTTTCGTCGGGAAACTCGACGCCGTTGATTACGAACGTGA |
| ACGGAAACGGAAACGGAAAGTCGTGCGGAGGAGGAGGAGGA |
| TCGACGAACAACACGATTTCGAACTCGTCGTCGTCGATTTCGT |
| CGATTGACAACGGAAACAACGAAGACGAAGAAATGGTGTTGA |
| AGTCGTTTAACGACTCGAACTTGTCGTTGTTTCACTTGCAAAA |
| GTCGATTATTAAGAACAACATTAAGGGACGATTGTTTTTGATTA |
| CGAACGGAGGACAATCGATTTCGTCGTCGACGCCGACGTCGA |
| CGTACAACGACCAATCGTACGTGAACTTGTCGCAATACCAATT |
| GATTGGACAAATTCGAGTGTTTTCGAACGAATACCCGATTATG |
| GAATGCTCGATGATTGACATTCAAGACTCGACGCGAATTGACT |
| TGATTACGGACCAATTGAACTCGACGAAGTTGTCGAAGTTGGA |
| AATTGCTTTTCGAGACAACATTGGATACTCGTACAAGTTGTTGA |
| AGCCGTCGATTTTTGACAACTCGTCGTTGCCGTCGTCGTCGTC |
| GGAAATTGAAACGACGGCTACGACGAAGGACGAAGAAAAGAA |
| CAACTCGATTAACTACAACAACAACTACTACCGAGTGGAATTG |
| TCGGACAACGGAATTATTTCGGACTTGAAGATTAAGCAATTTC |
| GACAAATGAAGTGCGGAGTGGGACAAGTGTTGGTGCGAGTGG |
| AAATGTGCACGTTGAACTTTCGAGACATTTTGAAGTCGTTGGG |
| ACGAGACTACGACCCGATTCACTTGAACTCGATGGGAGACGA |
| ATTTTCGGGAAAGGTGATTGAAATTGGAGAAGGAGTGAACAAC |
| TTGTCGGTGGGACAATACGTGTTTGGAATTAACATGTCGAAGT |
| CGATGGGATCGTTTGTGTGCTGCAACTCGGACTTGGTGTTTCC |
| GATTCCGATTCCGACGCCGTCGTCGTCGTCGTCGTCGAACGA |
| AAACATTGACGACCAAGAAATTATTTCGAAGTTGTTGAACCAAT |
| ACTGCACGATTCCGATTGTGTTTTTGACGTCGTGGTACTCGAT |
| TGTGATTCAAGGACGATTGAAGAAGGGAGAAAAGATTTTGATT |
| CACTCGGGATGCGGAGGAGTGGGATTGGCTACGATTCAAATT |
| TCGATGATGATTGGAGCTGAAATTCACGTGACGGTGGGATCG |
| AACGAAAAGAAGCAATACTTGATTAAGGAATTTGGAATTGACG |
| AAAAGCGAATTTACTCGTCGCGATCGTTGCAATTTTACAACGA |
| CTTGATGGTGAACACGGACGGACAAGGAGTGGACATGGTGTT |
| GAACTCGTTGTCGGGAGAATACTTGGAAAAGTCGATTCAATGC |
| TTGTCGCAATACGGACGATTTATTGAAATTGGAAAGAAGGACA |
| TTTACTCGAACTCGTCGATTCACTTGGAACCGTTAAGAACAA |
| CTTGTCGTTTTTTGCTGTGGACATTGCTCAAATGACGGAAAAC |
| CGACGAGACTACTTGCGAGAAATTATGATTGACCAATTGTTGC |
| CGTGCTTTAAGAACGGATCGTTGAAGCCGTTGAACCAACACTG |
| CTTTAACTCGCCGTGCGACTTGGTGAAGGCTATTCGATTTATG |
| TCGTCGGGAAACCACATTGGAAAGATTTTGATTAACTGGTCGA |
| ACTTGAACAACGACAAGCAATTTATTAACCACCACTCGGTGGT |
| GCACTTGCCGATTCAATCGTTTTCGAACCGATCGACGTACATT |
| TTTACGGGATTTGGAGGATTGACGCAAACGTTGTTGAAGTACT |
| TTTCGACGGAATCGGACTTGACGAACGTGATTATTGTGTCGAA |
| GAACGGATTGGACGACAACTCGGGATCGGGATCGGGAAACAA |
| CGAAAAGTTGAAGTTGATTAACCAATTGAAGGAATCGGGATTG |

TABLE 1-continued

Sequences

AACGTGTTGGTGGAAAAGTGCGACTTGTCGTCGATTAAGCAA
GTGTACAAGTTGTTTAACAAGATTTTTGACAACGACGCTTCGG
GATCGGACTCGGGAGACTTTTCGGACATTAAGGGAATTTTTCA
CTTTGCTTCGTTGATTAACGACAAGCGAATTTTGAAGCACAAC
TTGGAATCGTTTAACTACGTGTACAACTCGAAGGCTACGTCGG
CTTGGAACTTGCACCAAGTGTCGTTGAAGTACAACTTGAACTT
GGACCACTTTCAAACGATTGGATCGGTGATTACGATTTTGGGA
AACATTGGACAATCGAACTACACGTGCGCTAACCGATTTGTGG
AAGGATTGACGCACTTGCGAATTGGAATGGGATTGAAGTCGT
CGTGCATTCACTTGGCTTCGATTCCGGACGTGGGAATGGCTT
CGAACGACAACGTGTTGAACGACTTGAACTCGATGGGATTTGT
GCCGTTTCAATCGTTGAACGAAATGAACTTGGGATTTAAGAAG
TTGTTGTCGTCGCCGAACCCGATTGTGGTGTTGGGAGAAATTA
ACGTGGACCGATTTATTGAAGCTACGCCGAACTTTCGAGCTAA
GGACAACTTTATTATTACGTCGTTGTTTAACCGAATTGACCCGT
TGTTGTTGGTGAACGAATCGCAAGACTTTATTATTAACAACAAC
ATTAACAACAACGGAGGAGGAGGAGACGGATCGTTTGACGAC
TTGAACCAATTGGAAGACGAAGGACAACAAGGATTTGGAAAC
GGAGACGGATACGTGGACGACAACATTGACTCGGTGTCGATG
TTGTCGGGAACGTCGTCGATTTTTGACAACGACTTTTACACGA
AGTCGATTCGAGGAATGTTGTGCGACATTTTGGAATTGAAGGA
CAAGGACTTGAACAACACGGTGTCGTTTTCGGACTACGGATTG
GACTCGTTGTTGTCGTCGGAATTGTCGAACACGATTCAAAAGA
ACTTTTCGATTTTGATTCCGTCGTTGACGTTGGTGGACAACTC
GACGATTAACTCGACGGTGGAATTGATTAAGAACAAGTTGAAG
AACTCGACGACGTCGTCGATTTCGTCGTCGGTGTCGAAGAAG
GTGTCGTTTAAGAAGAACACGCAACCGTTGATTATTCCGACGA
CGGCTCCGATTTCGATTATTAAGACGCAATCGTACATTAAGTC
GGAAATTATTGAATCGTTGCCGATTTCGTCGTCGACGACGATT
AAGCCGTTGGTGTTTGACAACTTGGTGTACTCGTCGTCGTCGT
CGAACAACTCGAACTCGAAGAACGAATTGACGTCGCCGCCGC
CGTCGGCTAAGCGAGAATCGGTGTTGCCGATTATTTCGGAAG
ACAACAACTCGGACAACGACTCGTCGATGGCTACGGTGATTTA
CGAAATTTCGCCGATTGCTGCTCCGTACCACCGATACCAAACG
GACGTGTTGAAGGAAATTACGCAATTGACGCCGCACAAGGAA
TTTATTGACAACATTTACAAGAAGTCGAAGATTCGATCGCGATA
CTGCTTTAACGACTTTTCGGAAAAGTCGATGGCTGACATTAAC
AAGTTGGACGCTGGAGAACGAGTGGCTTTGTTTCGAGAACAA
ACGTACCAAACGGTGATTAACGCTGGAAAGACGGTGATTGAA
CGAGCTGGAATTGACCCGATGTTGATTTCGCACGTGGTGGGA
GTGACGTCGACGGGAATTATGGCTCCGTCGTTTGACGTGGTG
TTGATTGACAAGTTGGGATTGTCGATTAACACGTCGCGAACGA
TGATTAACTTTATGGGATGCGGAGCTGCTGTGAACTCGATGCG
AGCTGCTACGGCTTACGCTAAGTTGAAGCCGGGAACGTTTGT
GTTGGTGGTGGCTGTGGAAGCTTCGGCTACGTGCATGAAGTT
TAACTTTGACTCGCGATCGGACTTGTTGTCGCAAGCTATTTTTA
CGGACGGATGCGTGGCTACGTTGGTGACGTGCCAACCGAAGT
CGTCGTTGGTGGGAAAGTTGGAAATTATTGACGACTTGTCGTA
CTTGATGCCGGACTCGCGAGACGCTTTGAACTTGTTTATTGGA
CCGACGGGAATTGACTTGGACTTGCGACCGGAATTGCCGATT
GCTATTAACCGACACATTAACTCGGCTATTACGTCGTGGTTGA
AGAAGAACTCGTTGCAAAAGTCGGACATTGAATTTTTTGCTAC
GCACCCGGGAGGAGCTAAGATTATTTCGGCTGTGCACGAAGG
ATTGGGATTGTCGCCGGAAGACTTGTCGGACTCGTACGAAGT
GATGAAGCGATACGGAAACATGATTGGAGTGTCGACGTACTA
CGTGTTGCGACGAATTTTGGACAAGAACCAAACGTTGTTGCAA
GAAGGATCGTTGGGATACAACTACGGAATGGCTATGGCTTTTT
CGCCGGGAGCTTCGATTGAAGCTATTTTGTTTAAGTTGATTAA
GTAA

| SEQ ID NO: 58 nucleic acid coding sequence of Orf2 from *Streptomyces* Sp. Strain Cl190 optimized for diatoms | ATGTCGGAAGCTGCTGACGTGGAACGAGTGTACGCTGCTATG
GAAGAAGCTGCTGGATTGTTGGGAGTGGCTTGCGCTCGAGAC
AAGATTTACCCGTTGTTGTCGACGTTTCAAGACACGTTGGTGG
AAGGAGGATCGGTGGTGGTGTTTCGATGGCTTCGGGACGAC
ACTCGACGGAATTGGACTTTTCGATTTCGGTGCCGACGTCGC
ACGGAGACCCGTACGCTACGGTGGTGGAAAAGGGATTGTTTC
CGGCTACGGGACACCCGGTGGACGACTTGTTGGCTGACACG
CAAAAGCACTTGCCGGTGTCGATGTTTGCTATTGACGGAGAA
GTGACGGGAGGATTTAAGAAGACGTACGCTTTTTTTCCGACG
GACAACATGCCGGGAGTGGCTGAATTGTCGGCTATTCCGTCG
ATGCCGCCGGCTGTGGCTGAAAACGCTGAATTGTTTGCTCGA
TACGGATTGGACAAGGTGCAAATGACGTCGATGGACTACAAG
AAGCGACAAGTGAACTTGTACTTTTCGGAATTGTCGGCTCAAA
CGTTGGAAGCTGAATCGGTGTTGGCTTTGGTGCGAGAATTGG
GATTGCACGTGCCGAACGAATTGGGATTGAAGTTTTGCAAGC
GATCGTTTTCGGTGTACCCGACGTTGAACTGGGAAACGGGAA
AGATTGACCGATTGTGCTTTGCTGTGATTTCGAACGACCCGAC
GTTGGTGCCGTCGTCGGACGAAGGAGACATTGAAAAGTTTCA |

| | |
|---|---|
| | CAACTACGCTACGAAGGCTCCGTACGCTTACGTGGGAGAAAA<br>GCGAACGTTGGTGTACGGATTGACGTTGTCGCCGAAGGAAGA<br>ATACTACAAGTTGGGAGCTTACTACCACATTACGGACGTGCAA<br>CGAGGATTGTTGAAGGCTTTTGACTCGTTGGAAGACTAA |
| SEQ ID NO: 59 nucleic acid coding sequence of CsPT4 from *Cannabis sativa* optimized for diatoms | ATGGGATTGTCGTTGGTGTGCACGTTTTCGTTTCAAACGAACT<br>ACCACACGTTGTTGAACCCGCACAACAAGAACCCGAAGAACT<br>CGTTGTTGTCGTACCAACACCCGAAGACGCCGATTATTAAGTC<br>GTCGTACGACAACTTTCCGTCGAAGTACTGCTTGACGAAGAAC<br>TTTCACTTGTTGGGATTGAACTCGCACAACCGAATTTCGTCGC<br>AATCGCGATCGATTCGAGCTGGATCGGACCAAATTGAAGGAT<br>CGCCGCACCACGAATCGGACAACTCGATTGCTACGAAGATTTT<br>GAACTTTGGACACACGTGCTGGAAGTTGCAACGACCGTACGT<br>GGTGAAGGGAATGATTTCGATTGCTTGCGGATTGTTTGGACGA<br>GAATTGTTTAACAACCGACACTTGTTTTCGTGGGGATTGATGT<br>GGAAGGCTTTTTTTGCTTTGGTGCCGATTTTGTCGTTTAACTTT<br>TTTGCTGCTATTATGAACCAAATTTACGACGTGGACATTGACC<br>GAATTAACAAGCCGGACTTGCCGTTGGTGTCGGGAGAAATGT<br>CGATTGAAACGGCTTGGATTTTGTCGATTATTGTGGCTTTGAC<br>GGGATTGATTGTGACGATTAAGTTGAAGTCGGCTCCGTTGTTT<br>GTGTTTATTTACATTTTTGGAATTTTTGCTGGATTTGCTTACTC<br>GGTGCCGCCGATTCGATGGAAGCAATACCCGTTTACGAACTTT<br>TTGATTACGATTTCGTCGCACGTGGGATTGGCTTTTACGTCGT<br>ACTCGGCTACGACGTCGGCTTTGGGATTGCCGTTTGTGTGGC<br>GACCGGCTTTTTCGTTTATTATTGCTTTTATGACGGTGATGGG<br>AATGACGATTGCTTTTGCTAAGGACATTTCGGACATTGAAGGA<br>GACGCTAAGTACGGAGTGTCGACGGTGGCTACGAAGTTGGGA<br>GCTCGAAACATGACGTTTGTGGTGTCGGGAGTGTTGTTGTTGA<br>ACTACTTGGTGTCGATTTCGATTGGAATTATTTGGCCGCAAGT<br>GTTTAAGTCGAACATTATGATTTTGTCGCACGCTATTTTGGCTT<br>TTTGCTTGATTTTTCAAACGCGAGAATTGGCTTTGGCTAACTAC<br>GCTTCGGCTCCGTCGCGACAATTTTTTGAATTTATTTGGTTGTT<br>GTACTACGCTGAATACTTTGTGTACGTGTTTATTTAA |
| SEQ ID NO: 60 nucleic acid coding sequence of HlPT1 from *Humulus lupulus* optimized for diatoms | ATGGAATTGTCGTCGGTGTCGTCGTTTTCGTTGGGAACGAACC<br>CGTTTATTTCGATTCCGCACAACAACAACAACTTGAAGGTGTC<br>GTCGTACTGCTGCAAGTCGAAGTCGCGAGTGATTAACTCGAC<br>GAACTCGAAGCACTGCTCGCCGAACAACAACTCGAACAACAA<br>CACGTCGAACAAGACGACGCACTTGTTGGGATTGTACGGACA<br>ATCGCGATGCTTGTTGAAGCCGTTGTCGTTTATTTCGTGCAAC<br>GACCAACGAGGAAACTCGATTCGAGCTTCGGCTCAAATTGAA<br>GACCGACCGCCGGAATCGGGAACTTGTCGGCTTTGACGAAC<br>GTGAAGGACTTTGTGTCGGTGTGCTGGGAATACGTGCGACCG<br>TACACGGCTAAGGGAGTGATTATTTGCTCGTCGTGCTTGTTTG<br>GACGAGAATTGTTGGAAAACCCGAACTTGTTTTCGTGGCCGTT<br>GATTTTTCGAGCTTTGTTGGGAATGTTGGCTATTTTGGGATCG<br>TGCTTTTACACGGCTGGAATTAACCAAATTTTTGACATGGACAT<br>TGACCGAATTAACAAGCCGGACTTGCCGTTGGTGTCGGGACG<br>AATTTCGGTGGAATCGGCTTGGTTGTTGACGTTGTCGCCGGC<br>TATTATTGGATTTATTTTGATTTTGAAGTTGAACTCGGGACCGT<br>TGTTGACGTCGTTGTACTGCTTGGCTATTTTGTCGGGAACGAT<br>TTACTCGGTGCCGCCGTTTCGATGGAAGAAGAACCCGATTAC<br>GGCTTTTTTGTGCATTTTGATGATTCACGCTGGATTGAACTTTT<br>CGGTGTACTACGCTTCGCGAGCTGCTTTGGGATTGGCTTTTG<br>CTTGGTCGCCGTCGTTTTCGTTTATTACGGCTTTTATTACGTTTT<br>ATGACGTTGACGTTGGCTTCGTCGAAGGACTTGTCGGACATTA<br>ACGGAGACCGAAAGTTTGGAGTGGAAACGTTTGCTACGAAGT<br>TGGGAGCTAAGAACATTACGTTGTTGGGAACGGGATTGTTGTT<br>GTTGAACTACGTGGCTGCTATTTCGACGGCTATTATTTGGCCG<br>AAGGCTTTTAAGTCGAACATTATGTTGTGTCGCACGCTATTTT<br>GGCTTTTTCGTTGATTTTTCAAGCTCGAGAATTGGACCGAACG<br>AACTACACGCCGGAAGCTTGCAAGTCGTTTTACGAATTTATTT<br>GGATTTTGTTTTCGGCTGAATACGTGGTGTACTTGTTTATTAA |
| SEQ ID NO: 61 amino acid sequence of Steely1 from *Dictyostelium discoideum* | MNKNSKIQSPNSSDVAVIGVGFRFPGNSNDPESLWNNLLDGFDA<br>ITQVPKERWATSFREMGLIKNKFGGFLKDSEWKNFDPLFFGIGPK<br>EAPFIDPQQRLLLSIVWESLEDAYIRPDELRGSNTGVFIGVSNNDY<br>TKLGFQDNYSISPYTMTGSNSSLNSNRISYCFDFRGPSITVDTAC<br>SSSLVSVNLGVQSIQMGECKIAICGGVNALFDPSTSVAFSKLGVL<br>SENGRCNSFSDQASGYVRSEGAGVVVLKSLEQAKLDGDRIYGVI<br>KGVSSNEDGASNGDKNSLTTPSCEAQSINISKAMEKASLSPSDIY<br>YIEAHGTGTPVGDPIEVKALSKIFSNSNNNQLNNFSTDGNDNDDD<br>DDDNTSPEPLLIGSFKSNIGHLESAAGIASLIKCCLMLKNRMLVPSI<br>NCSNLNPSIPFDQYNISVIREIRQFPTDKLVNIGINSFGFGGSNCHL<br>IIQEYNNNFKNNSTICNNNNNNNNIDYLIPISSKTKKSLDKYLILIK<br>TNSNYHKDISFDDFVKFQIKSKQYNLSNRMTTIANDWNSFIKGSN<br>EFHNLIESKDGEGGSSSSNRGIDSANQINTTTTSTINDIEPLLVFVF<br>CGQGPQWNGMIKTLYNSENVFKNTVDHVDSILYKYFGYSILNVLS |

TABLE 1-continued

Sequences

KIDDNDDSINHPIVAQPSLFLLQIGLVELFKYWGIYPSISVGHSFGE
VSSYYLSGIISLETACKIVYVRSSNQNKTMGSGKMLVVSMGFKQ
WNDQFSAEWSDIEIACYNAPDSIVVTGNEERLKELSIKLSDESNQI
FNTFLRSPCSFHSSHQEVIKGSMFEELSNLQSTGETEIPLFSTVT
GRQVLSGHVTAQHIYDNVREPVLFQKTIESITSYIKSHYPSNQKVI
YVEIAPHPTLFSLIKKSIPSSNKNSSSVLCPLNRKENSNNSYKKFV
SQLYFNGVNVDFNFQLNSICDNVNNDHHLNNVKQNSFKETTNSL
PRYQWEQDEYWSEPLISRKNRLEGPTTSLLGHRIIYSFPVFQSVL
DLQSDNYKYLLDHLVNGKPVFPGAGYLDIIIEFFDYQKQQLNSSD
SSNSYIINVDKIQFLNPIHLTENKLQTLQSSFEPIVTKKSAFSVNFFI
KDTVEDQSKVKSMSDETWTNTCKATISLEQQQPSPSSTLTLSKK
QDLQILRNRCDISKLDKFELYDKISKNLGLQYNSLFQVVDTIETGK
DCSFATLSLPEDTLFTTILNPCLLDNCFHGLLTLINEKGSFVVESIS
SVSIYLENIGSFNQTSVGNVQFYLYTTISKATSFSSEGTCKLFTKD
GSLILSIGKFIIKSTNPKSTKTNETIESPLDETFSIEWQSKDSPIPTP
QQIQQQSPLNSNPSFIRSTILKDIQFEQYCSSIIHKELINHEKYKNQ
QSFDINSLENHLNDDQLMESLSISKEYLRFFTRIISIIKQYPKILNEK
ELKELKEIIELKYPSEVQLLEFEVIEKVSMIIPKLLFENDKQSSMTLF
QDNLLTRFYSNSNSTRFYLERVSEMVLESIRPIVREKRVFRILEIG
AGTGSLSNVVLTKLNTYLSTLNSNGGSGYNIIIEYTFTDISANFIIGE
IQETMCNLYPNVTFKFSVLDLEKEIINSSDFLMGDYDIVLMAYVIHA
VSNIKFSIEQLYKLLSPRGWLLCIEPKSNVVFSDLVFGCFNQWWN
YYDDIRTTHCSLSESQWNQLLLNQSLNNESSSSSNCYGGFSNVS
FIGGEKDVDSHSFILHCQKESISQMKLATTINNGLSSGSIVIVLNSQ
QLTNMKSYPKVIEYIQEATSLCKTIEIIDSKDVLNSTNSVLEKIQKSL
LVFCLLGYDLLENNYQEQSFEYVKLLNLISTTASSSNDKKPPKVLL
ITKQSERISRSFYSRSLIGISRTSMNEYPNLSITSIDLDTNDYSLQSL
LKPIFSNSKFSDNEFIFKKGLMFVSRIFKNKQLLESSNAFETDSSN
LYCKASSDLSYKYAIKQSMLTENQIEIKVECVGINFKDNLFYKGLL
PQEIFRMGDIYNPPYGLECSGVITRIGSNVTEYSVGQNVFGFARH
SLGSHVVTNKDLVILKPDTISFSEAASIPVVYCTAWYSLFNIGQLS
NEESILIHSATGGVGLASLNLLKMKNQQQQPLTNVYATVGSNEKK
KFLIDNFNNLFKEDGENIFSTRDKEYSNQLESKIDVILNTLSGEFVE
SNFKSLRSFGRLIDLSATHVYANQQIGLGNFKFDHLYSAVDLERLI
DEKPKLLQSILQRITNSIVNGSLEKIPITIFPSTETKDAIELLSKRSHI
GKVVVDCTDISKCNPVGDVITNFSMRLPKPNYQLNLNSTLLITGQ
SGLSIPLLNWLLSKSGGNVKNVVIISKSTMKWKLQTMISHFVSGF
GIHFNYVQVDISNYDALSEAIKQLPSDLPPITSVFHLAAIYNDVPMD
QVTMSTVESVHNPKVLGAVNLHRISVSFGWKLNHFVLFSSITAIT
GYPDQSIYNSANSILDALSNFRRFMGLPSFSINLGPMKDEGKVST
NKSIKKLFKSRGLPSLSLNKLFGLLEVVINNPSNHVIPSQLICSPIDF
KTYIESFSTMRPKLLHLQPTISKQQSSIINDSTKASSNISLQDKITSK
VSDLLSIPISKINFDHPLKHYGLDSLLTVQFKSWIDKEFEKNLFTHI
QLATISINSFLEKVNGLSTNNNNNNNSNVKSSPSIVKEEIVTLDKD
QQPLLLKEHQHIIISPDIRINKPKRESLIRTPILNKFNQITESIITPSTP
SLSQSDVLKTPPIKSLNNTKNSSLINTPPIQSVQQHQKQQQKVQVI
QQQQQPLSRLSYKSNNNSFVLGIGISVPGEPISQQSLKDSISNDF
SDKAETNEKVKRIFEQSQIKTRHLVRDYTKPENSIKFRHLETITDV
NNQFKKVVPDLAQQACLRALKDWGGDKGDITHIVSVTSTGIIIPDV
NFKLIDLLGLNKDVERVSLNLMGCLAGLSSSLRTAASLAKASPRNRI
LVVCTEVCSLHFSNTDGGDQMVASSIFADGSAAYIIGCNPRIEETP
LYEVMCSINRSFPNTENAMVWDLEKEGWNLGLDASIPIVIGSGIE
AFVDTLLDKAKLQTSTAISAKDCEFLIHTGGKSILMNIENSLGIDPK
QTKNTWDVYHAYGNMSSASVIFVMDHARKSKSLPTYSISLAFGP
GLAFEGCFLKNVV

| | |
|---|---|
| SEQ ID NO: 62 amino acid sequence of Steely2 from *Dictyostelium discoideum* | MNNNKSINDLSGNSNNNIANSNINNYNNLLIKKEPIAIIGIGCRFPGN VSNYSDFVNIIKNGSDCLTKIPDDRWNADIISRKQWKLNNRIGGYL KNIDQFDNQFFGISPKEAQHIDPQQRLLLHLAIETLEDGKISLDEIK GKKVGVFIGSSSGDYLRGFDSSEINQFTTPGTNSSFLSNRLSYFL DVNGPSMTVNTACSASMVAIHLGLQSLWNGESELSMVGGVNIIS SPLQSLDFGKAGLLNQETDGRCYSFDPRASGYVRSEGGGILLLK PLSAALRDNDEIYSLLLNSANNSNGKTPTGITSPRSLCQEKLIQQL LRESSDQFSIDDIGYFECHGTGTQMGDLNEITAIGKSIGMLKSHD DPLIIGSVKASIGHLEGASGICGVIKSIICLKEKILPQQCKFSSYNPKI PFETLNLKVLTKTQPWNNSKRICGVNSFGVGGSNSSLFLSSFDK STTITEPTTTTTIESLPSSSSSFDNLSVSSSISTNNDNDKVSNIVNN RYGSSIDVITLSVTSPDKEDLKIRANDVLESIKTLDDNFKIRDISNLT NIRTSHFSNRVAIIGDSIDSIKLNLQSFIKGENNNNKSIILPLINNGNN NNNNNNNSSGSSSSSSNNNNICFIFSGQGQQWNKMIFDLYENNK TFKNEMNNFSKQFEMISGWSIIDKLYNSGGGGNEELINETWLAQP SIVAVQYSLIKLFSKDIGIEGSIVLGHSLGELMAAYYCGIINDFNDLL KLLYIRSTLQNKTNGSGRMHVCLSSKAEIEQLISQLGFNGRIVICG NNTMKSCTISGDNESMNQFTKLISSQQYGSVVHKEVRTNSAFHS HQMDIIKDEFFKLFNQYFPTNQISTNQIYDGKSFYSTCYGKYLTPI ECKQLLSSPNYWWKNIRESVLFKESIEQILQNHQQSLTFIEITCHPI LNYFLSQLLKSSSKSNTLLLSTLSKNSNSIDQLLILCSKLYVNNLSSI KWNWFYDKQQQQQSESLVSSNFKLPGRRWKLEKYWIENCQRQ |

TABLE 1-continued

| Sequences |
|---|
| MDRIKPPMFISLDRKLFSVTPSFEVRLNQDRFQYLNDHQIQDIPLV<br>PFSFYIELVYASIFNSITTTTNTTASTMFEIENFTIDSSIIIDQKKSTL<br>IGINFNSDLTKFEIGSINSIGSGSSSNNNFIENKWKIHSNGIIKYGTN<br>YLKSNSKSNSFNESTTTTTTTTTTTKCFKSFNSNEFYNEIIKYNYN<br>YKSTFQCVKEFKQFDKQGTFYYSEIQFKKNDKQVIDQLLSKQLPS<br>DFRCIHPCLLDAVLQSAIIPATNKTNCSWIPIKIGKLSVNIPSNSYFN<br>FKDQLLYCLIKPSTSTSPSTYFSSDIQVFDKKNNNLICELTNLEF<br>KGINSSSSSSSSSTINSNVEANYESKIEETNHDEDEDEELPLVSE<br>YVWCKEELINQSIKFTDNYQTVIFCSTNLNGNDLLDSIITSALENGH<br>DENKIFIVSPPPVESDQYNNRIIINYTNNESDFDALFAIINSTTSISG<br>KSGLFSTRFIILPNFNSITFSSGNSTPLITNVNGNGNGKSCGGGG<br>GSTNNTISNSSSSISSIDNGNNEDEEMVLKSFNDSNLSLFHLQKSII<br>KNNIKGRLFLITNGGQSISSSTPTSTYNDQSYVNLSQYQLIGQIRV<br>FSNEYPIMECSMIDIQDSTRIDLITDQLNSTKLSKLEIAFRDNIGYSY<br>KLLKPSIFDNSSLPSSSSEIETTATTKDEEKNNSINYNNNYYRVEL<br>SDNGIISDLKIKQFRQMKCGVGQVLVRVEMCTLNFRDILKSLGRD<br>YDPIHLNSMGDEFSGKVIEIGEGVNNLSVGQYVFGINMSKSMGSF<br>VCCNSDLVFPIPIPTPSSSSSSNENIDDQEIISKLLNQYCTIPIVFLT<br>SWYSIVIQGRLKKGEKILIHSGCGGVGLATIQISMMIGAEIHVTVGS<br>NEKKQYLIKEFGIDEKRIYSSRSLQFYNDLMVNTDGQGVDMVLNS<br>LSGEYLEKSIQCLSQYGRFIEIGKKDIYSNSSIHLEPFKNNLSFFAV<br>DIAQMTENRRDYLREIMIDQLLPCFKNGSLKPLNQHCFNSPCDLV<br>KAIRFMSSGNHIGKILINWSNLNNDKQFINHHSVVHLPIQSFSNRS<br>TYIFTGFGGLTQTLLKYFSTESDLTNVIIVSKNGLDDNSGSGSGNN<br>EKLKLINQLKESGLNVLVEKCDLSSIKQVYKLFNKIFDNDASGSDS<br>GDFSDIKGIFHFASLINDKRILKHNLESFNYVYNSKATSAWNLHQV<br>SLKYNLNLDHFQTIGSVITILGNIGQSNYTCANRFVEGLTHLRIGM<br>GLKSSCIHLASIPDVGMASNDNVLNDLNSMGFVPFQSLNEMNLG<br>FKKLLSSPNPIVVLGEINVDRFIEATPNFRAKDNFIITSLFNRIDPLLL<br>VNESQDFIINNNINNNGGGGDGSFDDLNQLEDEGQQGFGNGDG<br>YVDDNIDSVSMLSGTSSIFDNDFYTKSIRGMLCDILELKDKDLNNT<br>VSFSDYGLDSLLSSELSNTIQKNFSILIPSLTLVDNSTINSTVELIKN<br>KLKNSTTSSISSSVSKKVSFKKNTQPLIIPTTAPISIIKTQSYIKSEIIE<br>SLPISSSTTIKPLVFDNLVYSSSSSNNSNSKNELTSPPPSAKRESV<br>LPHSEDNNSDNDSSMATVIYEISPIAAPYHRYQTDVLKEITQLTPH<br>KEFIDNIYKKSKIRSRYCFNDFSEKSMADINKLDAGERVALFREQT<br>YQTVINAGKTVIERAGIDPMLISHVVGVTSTGIMAPSFDVVLIDKLG<br>LSINTSRTMINFMGCGAAVNSMRAATAYAKLKPGTFVLVVAVEAS<br>ATCMKFNFDSRSDLLSQAIFTDGCVATLVTCQPKSSLVGKLEIIDD<br>LSYLMPDSRDALNLFIGPTGIDLDLRPELPIAINRHINSAITSWLKK<br>NSLQKDSIEFFATHPGGAKIISAVHEGLGLSPEDLSDSYEVMKRY<br>GNMIGVSTYYVLRRILDKNQTLLQEGSLGYNYGMAMAFSPGASIE<br>AILFKLIK |
| SEQ ID NO: 63 amino acid sequence of Orf2 from *Streptomyces* Sp. Strain Cl190 | MSEAADVERVYAAMEEAAGLLGVACARDKIYPLLSTFQDTLVEG<br>GSVVVFSMASGRHSTELDFSISVPTSHGDPYATVVEKGLFPATG<br>HPVDDLLADTQKHLPVSMFAIDGEVTGGFKKTYAFFPTDNMPGV<br>AELSAIPSMPPAVAENAELFARYGLDKVQMTSMDYKKRQVNLYF<br>SELSAQTLEAESVLALVRELGLHVPNELGLKFCKRSFSVYPTLNW<br>ETGKIDRLCFAVISNDPTLVPSSDEGDIEKFHNYATKAPYAYVGEK<br>RTLVYGLTLSPKEEYYKLGAYYHITDVQRGLLKAFDSLED |
| SEQ ID NO: 64 amino acid sequence of CsPT4 from *Cannabis sativa* | MGLSLVCTFSFQTNYHTLLNPHNKNPKNSLLSYQHPKTPIIKSSY<br>DNFPSKYCLTKNFHLLGLNSHNRISSQSRSIRAGSDQIEGSPHHE<br>SDNSIATKILNFGHTCWKLQRPYVVKGMISIACGLFGRELFNNRH<br>LFSWGLMWKAFFALVPILSFNFFAAIMNQIYDVDIDRINKPDLPLV<br>SGEMSIETAWILSIIVALTGLIVTIKLKSAPLFVFIYIFGIFAGFAYSVP<br>PIRWKQYPFTNFLITISSHVGLAFTSYSATTSALGLPFVWRPAFSFI<br>IAFMTVMGMTIAFAKDISDIEGDAKYGVSTVATKLGARNMTFVVS<br>GVLLLNYLVSISIGIIWPQVFKSNIMILSHAILAFCLIFQTRELALANY<br>ASAPSRQFFEFIWLLYYAEYFVYVFI |
| SEQ ID NO: 65 amino acid sequence of HIPT1 from *Humulus lupulus* | MELSSVSSFSLGTNPFISIPHNNNNLKVSSYCCKSKSRVINSTNSK<br>HCSPNNNSNNNTSNKTTHLLGLYGQSRCLLKPLSFISCNDQRGN<br>SIRASAQIEDRPPESGNLSALTNVKDFVSVCWEYVRPYTAKGVIIC<br>SSCLFGRELLENPNLFSWPLIFRALLGMLAILGSCFYTAGINQIFD<br>MDIDRINKPDLPLVSGRISVESAWLLTLSPAIIGFILILKLNSGPLLTS<br>LYCLAILSGTIYSVPPFRWKKNPITAFLCILMIHAGLNFSVYYASRA<br>ALGLAFAWSPSFSFITAFITFMTLTLASSKDLSDINGDRKFGVETF<br>ATKLGAKNITLLGTGLLLLNYVAAISTAIIWPKAFKSNIMLLSHAILAF<br>SLIFQARELDRTNYTPEACKSFYEFIWILFSAEYVVYLFI |
| SEQ ID NO: 66 nucleic acid coding sequence of Steely1 from *Dictyostelium discoldeum* optimized for GC-rich microalgae | ATGAACAAGAACAGCAAGATCCAGTCGCCCAACTCGAGCGAC<br>GTGGCGGTGATTGGCGTCGGGTTTCGGTTCCCTGGTAACTCG<br>AACGATCCTGAGTCGCTCTGGAACAACCTGCTGGATGGCTTT<br>GACGCCATCACGCAGGTCCCGAAGGAGCGGTGGGCTACCTC<br>CTTCCGGGAGATGGGTCTGATCAAGAACAAGTTTGGTGGCTT<br>CCTGAAGGACTCCGAGTGGAAGAACTTCGACCCGCTGTTTTTT |

TABLE 1-continued

Sequences

```
GGGATCGGGCCCAAGGAGGCCCCCTTTATTGACCCTCAGCAG
CGGCTCCTCCTCTCGATCGTGTGGGAGTCCCTGGAGGATGCG
TACATCCGCCCCGATGAGCTGCGCGGCTCGAACACGGGCGT
GTTCATCGGTGTCAGCAACAACGATTACACGAAGCTGGGTTTC
CAGGACAACTACTCCATTTCCCCTTACACGATGACCGGGTCCA
ACTCCTCGCTGAACAGCAACCGCATTTCCTACTGCTTCGATTT
CCGCGGGCCGTCGATTACGGTCGACACGGCCTGCTCCAGCT
CCCTCGTCTCGGTGAACCTCGGGGTGCAGTCCATTCAGATGG
GTGAGTGCAAGATCGCTATCTGCGGGGGTGTGAACGCGCTGT
TTGATCCCTCGACGTCGGTCGCCTTCTCCAAGCTCGGCGTGC
TGTCCGAGAACGGCCGGTGCAACTCCTTTAGCGATCAGGCTT
CGGGTTACGTGCGCTCCGAGGGCGCCGGTGTCGTCGTGCTG
AAGAGCCTCGAGCAGGCCAAGCTGGACGGCGATCGGATTTAC
GGTGTCATTAAGGGCGTGTCCTCGAACGAGGACGGTGCTTCG
AACGGTGACAAGAACAGCCTCACCACGCCCAGCTGCGAGGC
CCAGTCCATCAACATTTCCAAGGCGATGGAGAAGGCCTCCCT
GAGCCCTTCCGATATCTACTACATCGAGGCCCACGGGACCGG
CACGCCGGTGGGCGATCCCATTGAGGTCAAGGCTCTCAGCAA
GATTTTCAGCAACTCCAACAACAACCAGCTGAACAACTTCAGC
ACGGACGGGAACGACAACGATGACGATGACGACGACAACACC
TCGCCCGAGCCGCTGCTCATCGGTTCGTTCAAGAGCAACATC
GGGCACCTCGAGTCGGCGGCTGGTATTGCTTCCCTGATCAAG
TGCTGCCTGATGCTCAAGAACCGCATGCTGGTCCCGTCGATC
AACTGCTCGAACCTGAACCCGTCCATTCCCTTCGACCAGTACA
ACATTAGCGTCATCCGCGAGATTCGCCAGTTCCCTACCGACAA
GCTGGTGAACATTGGTATCAACTCGTTCGGCTTCGGTGGGTC
CAACTGCCATCTGATTATTCAGGAGTACAACAACAACTTCAAG
AACAACTCCACCATCTGCAACAACAACAACAACAACAACAACA
ACATTGACTACCTGATCCCTATCTCCTCCAAGACGAAGAAGTC
GCTGGACAAGTACCTGATCCTCATTAAGACCAACAGCAACTAC
CATAAGGATATCTCGTTTGACGATTTTGTCAAGTTCCAGATCAA
GTCGAAGCAGTACAACCTGTCGAACCGGATGACCACGATTGC
CAACGATTGGAACAGCTTTATTAAGGGTTCGAACGAGTTCCAT
AACCTGATTGAGTCCAAGGACGGCGAGGGTGGTAGCTCGTCC
TCGAACCGGGGTATCGATTCCGCCAACCAGATCAACACCACC
ACCACGAGCACCATCAACGACATTGAGCCGCTCCTCGTCTTC
GTGTTTTGCGGGCAGGGCCCGCAGTGGAACGGTATGATCAAG
ACCCTGTACAACTCGGAGAACGTGTTCAAGAACACGGTGGAC
CACGTGGATTCGATTCTGTACAAGTACTTCGGTTACAGCATTC
TGAACGTGCTCTCGAAGATTGACGATAACGATGACAGCATCAA
CCACCCTATCGTCGCCCAGCCCAGCCTCTTCCTCCTCCAGATT
GGTCTCGTCGAGCTGTTTAAGTACTGGGGCATTTACCCCTCCA
TCAGCGTCGGCCATTCGTTCGGTGAGGTCTCGTCGTACTACC
TCTCGGGGATCATCTCGCTGGAGACGGCGTGCAAGATCGTGT
ACGTGCGGAGCTCGAACCAGAACAAGACGATGGGGTCCGGG
AAGATGCTCGTGGTCTCGATGGGTTTCAAGCAGTGGAACGAC
CAGTTTAGCGCGGAGTGGTCGGACATTGAGATCGCTTGCTAC
AACGCCCCCGACAGCATCGTCGTCACCGGGAACGAGGAGCG
CCTGAAGGAGCTGTCGATCAAGCTCTCGGACGAGTCGAACCA
GATTTTCAACACGTTTCTGCGCTCGCCCTGCAGCTTCCATTCC
AGCCACCAGGAGGTCATTAAGGGCTCGATGTTCGAGGAGCTC
TCCAACCTGCAGAGCACCGGCGAGACGGAGATCCCCCTGTTC
AGCACGGTGACGGGTCGGCAGGTCCTCTCCGGCCACGTCAC
CGCCCAGCACATCTACGATAACGTGCGGGAGCCCGTGCTGTT
TCAGAAGACCATTGAGAGCATTACCTCGTACATCAAGTCGCAT
TACCCGTCCAACCAGAAGGTGATCTACGTGGAGATTGCGCCT
CATCCGACCCTGTTTTCGCTCATCAAGAAGAGCATTCCGTCGT
CCAACAAGAACTCGTCGTCCGTGCTGTGCCCTCTCAACCGCA
AGGAGAACTCCAACAACAGCTACAAGAAGTTCGTCAGCCAGC
TGTACTTTAACGGCGTGAACGTCGATTTTAACTTTCAGCTCAA
CAGCATCTGCGATAACGTCAACAACGATCACCACCTCAACAAC
GTGAAGCAGAACTCGTTCAAGGAGACCACGAACTCCCTCCCC
CGGTACCAGTGGGAGCAGGATGAGTACTGGTCGGAGCCTCTC
ATTAGCCGGAAGAACCGGCTGGAGGGCCCCACGACGTCGCT
CCTGGGCCATCGGATTATCTACAGCTTTCCGGTCTTTCAGTCG
GTGCTCGATCTGCAGTCCGATAACTACAAGTACCTGCTCGATC
ACCTCGTGAACGGTAAGCCGGTGTTTCCTGGGGCTGGGTACC
TCGACATTATCATTGAGTTTTTCGACTACCAGAAGCAGCAGCT
CAACAGCTCGGACAGCTCGAACTCCTACATTATTAACGTCGAC
AAGATCCAGTTTCTGAACCCGATCCACCTGACGGAGAACAAG
CTCCAGACCCTGCAGTCGAGCTTTGAGCCTATTGTCACCAAGA
AGTCCGCTTTTAGCGTGAACTTCTTCATTAAGGATACGGTGGA
GGACCAGAGCAAGGTCAAGAGCATGTCCGACGAGACGTGGA
CCAACACGTGCAAGGCCACCATTTCCCTCGAGCAGCAGCAGC
CCTCGCCGTCGTCGACCCTGACCCTGTCCAAGAAGCAGGATC
TCCAGATTCTGCGCAACCGGTGCGATATCTCCAAGCTCGACA
AGTTTGAGCTGTACGATAAGATTTCGAAGAACCTCGGGCTCCA
GTACAACAGCCTCTTTCAGGTGGTGGACACCATTGAGACCGG
```

TABLE 1-continued

Sequences

```
GAAGGACTGCTCCTTCGCGACGCTGAGCCTGCCTGAGGATAC
GCTCTTTACCACGATTCTCAACCCTTGCCTGCTCGACAACTGC
TTTCACGGCCTCCTCACGCTCATTAACGAGAAGGGTTCGTTCG
TGGTGGAGAGCATTTCCTCCGTCTCGATTTACCTCGAGAACAT
CGGTTCCTTTAACCAGACCAGCGTGGGGAACGTGCAGTTTTA
CCTCTACACCACGATTTCGAAGGCTACGTCCTTTAGCAGCGAG
GGCACGTGCAAGCTGTTCACGAAGGATGGCTCCCTCATCCTG
TCGATCGGGAAGTTTATCATTAAGTCGACGAACCCGAAGTCGA
CGAAGACGAACGAGACGATTGAGTCGCCCCTGGATGAGACGT
TTTCGATCGAGTGGCAGTCGAAGGACTCGCCGATTCCGACCC
CTCAGCAGATTCAGCAGCAGTCCCCCCTGAACTCCAACCCGT
CCTTTATCCGGAGCACCATCCTCAAGGACATTCAGTTTGAGCA
GTACTGCTCCTCGATTATCCATAAGGAGCTGATCAACCACGAG
AAGTACAAGAACCAGCAGTCGTTTGATATTAACTCGCTGGAGA
ACCACCTCAACGACGACCAGCTCATGGAGTCCCTCTCCATTTC
CAAGGAGTACCTCCGCTTTTTCACGCGCATTATCTCCATTATC
AAGCAGTACCCCAAGATTCTCAACGAGAAGGAGCTGAAGGAG
CTCAAGGAGATCATTGAGCTGAAGTACCCCTCGGAGGTCCAG
CTGCTGGAGTTTGAGGTCATCGAGAAGGTGTCGATGATCATTC
CGAAGCTCCTGTTTGAGAACGACAAGCAGTCGTCGATGACGC
TCTTTCAGGACAACCTGCTGACCCGGTTCTACAGCAACTCCAA
CAGCACCCGGTTCTACCTGGAGCGGGTCTCCGAGATGGTGCT
GGGAGAGCATTCGGCCCATTGTGCGCGAGAAGCGGGTGTTCC
GGATCCTGGAGATCGGTGCTGGTACGGGCTCCCTCTCCAACG
TCGTGCTCACGAAGCTGAACACCTACCTCAGCACGCTCAACT
CGAACGGTGGTTCCGGCTACAACATCATTATCGAGTACACGTT
CACCGACATCTCGGCGAACTTTATCATTGGTGAGATCCAGGA
GACCATGTGCAACCTCTACCCGAACGTGACCTTCAAGTTTTCG
GTCCTGGATCTCGAGAAGGAGATTATTAACTCCAGCGACTTCC
TCATGGGTGATTACGATATCGTGCTGATGGCTTACGTGATCCA
TGCCGTCAGCAACATTAAGTTCTCCATCGAGCAGCTGTACAAG
CTGCTGTCCCCGCGGGGCTGGCTCCTCTGCATTGAGCCGAAG
TCCAACGTGGTCTTTTCGGATCTGGTGTTTGGCTGCTTCAACC
AGTGGTGGAACTACTACGATGACATCCGCACCCACCCATTGCT
CGCTGAGCGAGTCGCAGTGGAACCAGCTGCTCCTCAACCAGT
CGCTCAACAACGAGTCGTCGTCCTCGTCCAACTGCTACGGCG
GTTTTTCCAACGTGTCCTTCATCGGTGGCGAGAAGGACGTGG
ACTCCCATAGCTTTATTCTCCATTGCCAGAAGGAGTCCATCTC
CCAGATGAAGCTCGCCACCACCATCAACAACGGCCTCTCGAG
CGGCTCGATCGTCATTGTGCTGAACAGCCAGCAGCTCACGAA
CATGAAGTCCTACCCCAAGGTCATCGAGTACATCCAGGAGGC
GACCTCGCTCTGCAAGACCATTGAGATCATCGATAGCAAGGAT
GTCCTCAACTCCACCAACTCGGTCCTCGAGAAGATCCAGAAG
AGCCTGCTGGTGTTCTGCCTCCTGGGCTACGATCTGCTGGAG
AACAACTACCAGGAGCAGTCGTTCGAGTACGTCAAGCTCCTC
AACCTGATCTCCACCACGGCCAGCTCGAGCAACGACAAGAAG
CCTCCTAAGGTCCTCCTGATTACCAAGCAGTCGGAGCGGATT
AGCCGGTCGTTTTACAGCCGCTCGCTGATCGGCATTTCCCGG
ACGAGCATGAACGAGTACCCGAACCTCTCGATTACCTCGATC
GATCTCGATACCAACGACTACTCGCTCCAGTCGCTCCTCAAGC
CGATTTTTAGCAACAGCAAGTTCAGCGATAACGAGTTCATTTT
CAAGAAGGGGCTGATGTTCGTGTCCCGGATTTTTAAGAACAAG
CAGCTGCTCGAGTCCTCGAACGCCTTTGAGACGGACTCCTCG
AACCTCTACTGCAAGGCTTCGAGCGATCTGAGCTACAAGTAC
GCTATCAAGCAGAGCATGCTCACGGAGAACCAGATTGAGATT
AAGGTGGAGTGCGTCGGTATTAACTTCAAGGACAACCTCTTCT
ACAAGGGGCTCCTCCCCCAGGAGATCTTCCGGATGGGGGAC
ATTTACAACCCGCCTTACGGTCTGGAGTGCTCCGGGGTGATT
ACGCGCATCGGCTCGAACGTGACGGAGTACAGCGTCGGTCA
GAACGTGTTTGGTTTTGCGCGCCACAGCCTCGGCTCGCATGT
CGTCACGAACAAGGATCTGGTCATCCTCAAGCCCGACACGAT
TTCGTTCTCCGAGGCCGCCTCCATTCCCGTCGTGTACTGCAC
GGCCTGGTACAGCCTCTTTAACATTGGGCAGCTGAGCAACGA
GGAGAGCATTCTGATCCATAGCGCTACCGGGGTGTCGGCCT
CGCGTCCCTCAACCTCCTCAAGATGAAGAACCAGCAGCAGCA
GCCTCTGACCAACGTGTACGCCACCGTGGGTTCCAACGAGAA
GAAGAAGTTCCTGATCGACAACTTCAACAACCTGTTCAAGGAG
GACGGTGAGAACATTTTCAGCACCCGGGATAAGGAGTACAGC
AACCAGCTGGAGAGCAAGATTGATGTCATCCTGAACACGCTG
TCCGGCGAGTTCGTCGAGAGCAACTTTAAGTCGCTGCGCTCC
TTTGGGCGGCTCATCGACCTCAGCGCTACCCACGTGTACGCG
AACCAGCAGATTGGTCTCGGTAACTTTAAGTTTGACCACCTCT
ACTCGGCCGTCGACCTGGAGCGGCTCATTGATGAGAAGCCCA
AGCTCCTGCAGTCCATCCTCCAGCGGATCACGAACTCGATTG
TGAACGGGAGCCTGGAGAAGATCCCCATCACCATTTTCCCGT
CGACCGAGACCAAGGACGCGATCGAGCTGCTCTCGAAGCGC
AGCCATATCGGCAAGGTGGTGGTCGATTGCACCGACATCAGC
AAGTGCAACCCTGTGGGCGACGTGATCACCAACTTCTCCATG
```

TABLE 1-continued

Sequences

CGGCTGCCGAAGCCTAACTACCAGCTGAACCTGAACAGCACC
CTGCTGATCACGGGCCAGTCGGGGCTGTCGATTCCCCTGCTC
AACTGGCTGCTGTCGAAGAGCGGTGGCAACGTGAAGAACGTG
GTGATCATCAGCAAGAGCACCATGAAGTGGAAGCTGCAGACG
ATGATTTCGCATTTTGTGTCGGGTTTTGGCATCCATTTTAACTA
CGTGCAGGTGGACATTTCCAACTACGATGCCCTCTCCGAGGC
GATCAAGCAGCTGCCGAGCGACCTCCCGCCCATTACCTCGGT
GTTCCATCTGGCCGCTATCTACAACGATGTCCCCATGGATCAG
GTGACGATGTCGACGGTGGAGTCCGTGCACAACCCTAAGGTG
CTCGGCGCTGTCAACCTCCACCGGATCTCCGTCAGCTTCGGG
TGGAAGCTGAACCACTTCGTCCTCTTTTCGTCCATTACGGCTA
TCACGGGTTACCCGGATCAGTCGATTTACAACAGCGCCAACT
CCATCCTGGACGCTCTCTCCAACTTCCGGCGGTTCATGGGTC
TCCCTAGCTTCAGCATTAACCTGGGGCCGATGAAGGATGAGG
GCAAGGTGAGCACCAACAAGAGCATTAAGAAGCTGTTCAAGT
CCCGGGGTCTGCCTTCGCTGAGCCTGAACAAGCTGTTCGGCC
TGCTGGAGGTCGTGATCAACAACCCGAGCAACCATGTGATCC
CCTCGCAGCTGATCTGCTCGCCTATCGACTTTAAGACGTACAT
CGAGTCCTTTTCGACCATGCGCCCGAAGCTCCTCCACCTCCA
GCCCACCATCTCCAAGCAGCAGTCCTCGATCATCAACGACTC
CACCAAGGCGTCGTCGAACATTTCGCTGCAGGACAAGATTAC
CAGCAAGGTCAGCGACCTGCTCAGCATTCCCATCAGCAAGAT
TAACTTTGATCATCCGCTCAAGCATTACGGGCTGGATTCCCTG
CTCACCGTCCAGTTCAAGTCCTGGATCGACAAGGAGTTTGAG
AAGAACCTGTTTACCCATATCCAGCTGGCGACGATTAGCATCA
ACTCGTTTCTCGAGAAGGTCAACGGTCTGTCGACCAACAACAA
CAACAACAACAACAGCAACGTGAAGTCCAGCCCGAGCATTGT
GAAGGAGGAGATTGTCACGCTGGACAAGGACCAGCAGCCCCT
CCTGCTCAAGGAGCACCAGCATATTATCATTAGCCCCGACATT
CGCATCAACAAGCCTAAGCGCGAGTCCCTGATTCGCACGCCC
ATTCTGAACAAGTTTAACCAGATCACCGAGTCGATCATCACCC
CCTCGACGCCTTCCCTCAGCCAGAGCGACGTGCTGAAGACGC
CGCCTATTAAGTCGCTCAACAACACGAAGAACTCCAGCCTCAT
CAACACCCCTCCGATTCAGTCCGTCCAGCAGCATCAGAAGCA
GCAGCAGAAGGTGCAGGTCATTCAGCAGCAGCAGCAGCCGC
TCAGCCGGCTGTCCTACAAGTCCAACAACAACAGCTTTGTCCT
GGGCATCGGGATCTCCGTCCCCGGCGAGCCCATTAGCCAGC
AGTCCCTGAAGGATTCCATTAGCAACGATTTCTCGGACAAGGC
TGAGACCAACGAGAAGGTGAAGCGCATTTTCGAGCAGTCGCA
GATCAAGACGCGCCATCTCGTGCGGGATTACACGAAGCCTGA
GAACTCGATTAAGTTTCGCCATCTGGAGACCATCACCGACGTG
AACAACCAGTTCAAGAAGGTCGTCCCGGATCTCGCTCAGCAG
GCCTGCCTCCGGGCGCTGAAGGATTGGGGGGGGATAAGGG
GGATATTACCCACATTGTGTCGGTGACGAGCACCGGTATTATC
ATCCCTGACGTGAACTTTAAGCTCATCGATCTCCTCGGTCTCA
ACAAGGACGTGGAGCGCGTCTCGCTCAACCTCATGGGCTGCC
TCGCTGGCCTCTCCAGCCTCCGCACGGCTGCGTCGCTCGCG
AAGGCGTCGCCCCGGAACCGGATCCTCGTGGTCTGCACGGA
GGTGTGCAGCCTCCATTTCTCGAACACCGATGGCGGTGACCA
GATGGTCGCGTCGAGCATCTTTGCCGACGGGTCGGCCGCCTA
CATCATTGGCTGCAACCCGCGGATTGAGGAGACCCCGCTGTA
CGAGGTGATGTGCTCGATCAACCGGTCGTTTCCGAACACGGA
GAACGCGATGGTCTGGGACCTGGAGAAGGAGGGCTGGAACC
TCGGCCTGGATGCGTCGATTCCCATCGTCATCGGCTCGGGGA
TCGAGGCCTTCGTCGATACCCTCCTGGACAAGGCGAAGCTCC
AGACGTCGACCGCCATTTCGGCTAAGGACTGCGAGTTTCTCA
TCCATACGGGCGGTAAGTCGATTCTCATGAACATTGAGAACTC
GCTGGGCATCGATCCCAAGCAGACGAAGAACACCTGGGACGT
GTACCACGCCTACGGCAACATGAGCAGCGCCAGCGTGATTTT
TGTCATGGACCACGCTCGCAAGTCGAAGTCGCTCCCGACGTA
CTCCATCAGCCTCGCCTTCGGTCCTGGGCTCGCGTTCGAGGG
GTGCTTCCTCAAGAACGTCGTCTAA

| | |
|---|---|
| SEQ ID NO: 67 nucleic acid coding sequence of Steely2 from *Dictyostelium discoideum* optimized for GC-rich microalgae | ATGAACAACAACAAGAGCATCAACGATCTCAGCGGTAACTCCA<br>ACAACAACATCGCTAACAGCAACATTAACAACTACAACAACCT<br>GATTAAGAAGGAGCCTATTGCTATCATTGGCATCGGGTGCCG<br>CTTCCCTGGGAACGTGTCCAACTACTCGGACTTCGTGAACATC<br>ATTAAGAACGGCTCCGACTGCCTCACCAAGATTCCTGACGAC<br>CGCTGGAACGCTGACATCATTTCGCGGAAGCAGTGGAAGCTG<br>AACAACCGCATCGGGGGTTACCTGAAGAACATCGACCAGTTC<br>GACAACCAGTTTTTCGGCATTTCGCCTAAGGAGGCTCAGCATA<br>TCGATCCTCAGCAGCGGCTGCTCCTGCACCTCGCTATCGAGA<br>CCCTGGAGGATGGCAAGATCTCCCTGGATGAGATCAAGGGTA<br>AGAAGGTGGGCGTGTTCATCGGGTCCAGCTCCGGCGATTACC<br>TGCGGGGGTTTGATTCGAGCGAGATCAACCAGTTTACCACGC<br>CGGGGACCAACTCCAGCTTCCTGTCGAACCGGCTCTCGTACT<br>TTCTCGACGTGAACGGGCCCTCCATGACGGTGAACACCGCGT<br>GCTCGGCTAGCATGGTGGCGATTCATCTGGGGCTCCAGTCGC |

TABLE 1-continued

Sequences

```
TGTGGAACGGCGAGTCGGAGCTCAGCATGGTGGGCGGTGTG
AACATTATTTCCTCGCCGCTCCAGTCGCTGGACTTCGGGAAG
GCGGGGCTGCTCAACCAGGAGACGGATGGCCGGTGCTACAG
CTTTGATCCCCGCGCTTCCGGGTACGTCCGCTCGGAGGGTGG
CGGCATCCTCCTCCTCAAGCCTCTGTCGGCGGCTCTGCGGGA
CAACGATGAGATCTACTCCCTCCTGCTGAACTCCGCGAACAAC
TCGAACGGGAAGACGCCCACGGGTATCACCTCCCCGCGCTC
CCTCTGCCAGGAGAAGCTCATTCAGCAGCTCCTGCGCGAGAG
CTCGGACCAGTTCTCGATTGACGATATTGGTTACTTTGAGTGC
CACGGCACGGGCACCCAGATGGGGGACCTCAACGAGATTAC
GGCGATCGGCAAGTCGATTGGGATGCTGAAGTCGCACGACGA
CCCTCTCATTATCGGCTCCGTCAAGGCGTCGATTGGGCATCT
CGAGGGTGCGAGCGGCATTTGCGGTGTGATCAAGTCGATTAT
CTGCCTCAAGGAGAAGATCCTGCCGCAGCAGTGCAAGTTTAG
CTCCTACAACCCCAAGATTCCTTTTGAGACCCTGAACCTGAAG
GTCCTCACCAAGACGCAGCCGTGGAACAACTCGAAGCGGATT
TGCGGCGTCAACTCGTTTGGGGTCGGCGGTAGCAACTCCAGC
CTGTTCCTGAGCTCGTTTGATAAGAGCACGACCATCACGGAG
CCCACCACCACGACCACCATCGAGTCCCTGCCCTCCAGCTCG
TCCTCGTTCGACAACCTGAGCGTGTCCTCCTCCATTTCGACCA
ACAACGACAACGATAAGGTCAGCAACATCGTGAACAACCGCT
ACGGCAGCTCCATTGACGTCATCACGCGTGTCGGTGACGTCGC
CGGATAAGGAGGACCTGAAGATTCGGGCGAACGATGTCCTCG
AGTCGATCAAGACGCTCGATGATAACTTCAAGATTCGCGATAT
CAGCAACCTGACGAACATTCGCACCTCCCACTTCTCCAACCG
CGTCGCTATTATCGGTGACTCGATCGACTCCATTAAGCTCAAC
CTGCAGTCCTTTATCAAGGGGGAGAACAACAACAACAAGTCG
ATTATCCTGCCTCTGATTAACAACGGCAACAACAACAACAACA
ACAACAACAACTCGTCCGGGTCCTCGTCCTCCAGCAGCAACA
ACAACAACATTTGCTTCATCTTTAGCGGCCAGGGCCAGCAGTG
GAACAAGATGATCTTCGATCTGTACGAGAACAACAAGACCTTC
AAGAACGAGATGAACAACTTTTCCAAGCAGTTCGAGATGATTT
CGGGCTGGTCGATCATTGACAAGCTGTACAACTCCGGCGGTG
GTGGTAACGAGGAGCTCATTAACGAGACGTGGCTCGCCCAGC
CGTCCATTGTGGCCGTCCAGTACTCGCTGATTAAGCTGTTTAG
CAAGGACATCGGGATCGAGGGGTCGATCGTCCTCGGGCACA
GCCTGGGTGAGCTCATGGCTGCTTACTACTGCGGTATCATTAA
CGACTTTAACGATCTGCTGAAGCTGCTCTACATCCGGTCGACG
CTCCAGAACAAGACGAACGGGTCGGGTCGCATGCACGTGTGC
CTCAGCAGCAAGGCCGAGATCGAGCAGCTGATTTCGCAGCTC
GGGTTTAACGGCCGGATTGTGATTTGCGGGAACAACACGATG
AAGTCGTGCACCATCTCGGGTGATAACGAGTCGATGAACCAG
TTTACCAAGCTCATTTCGTCGCAGCAGTACGGCAGCGTCGTG
CATAAGGAGGTCCGCACGAACAGCGCCTTTCATTCGCACCAG
ATGGACATCATCAAGGACGAGTTCTTTAAGCTCTTTAACCAGT
ACTTCCCTACGAACCAGATTAGCACCAACCAGATTTACGATGG
CAAGAGCTTCTACTCGACGTGCTACGGGAAGTACCTGACGCC
TATTGAGTGCAAGCAGCTCCTCTCGTCGCCGAACTACTGGTG
GAAGAACATTCGCGAGTCGGTGCTCTTTAAGGAGTCGATTGA
GCAGATCCTGCAGAACCACCAGCAGTCGCTCACGTTTATTGA
GATCACGTGCCACCCTATCCTCAACTACTTCCTGTCGCAGCTC
CTGAAGTCGAGCAGCAAGTCGAACACCCTCCTGCTCTCCACG
CTGTCGAAGAACAGCAACTCCATCGATCAGCTGCTCATTCTGT
GCAGCAAGCTGTACGTCAACAACCTCTCCTCGATCAAGTGGA
ACTGGTTTTACGACAAGCAGCAGCAGCAGTCGGAGTCGC
TCGTGAGCAGCAACTTTAAGCTGCCTGGCCGCCGGTGGAAGC
TCGAGAAGTACTGGATCGAGAACTGCCAGCGCCAGATGGATC
GGATTAAGCCGCCGATGTTCATTAGCCTCGATCGGAAGCTGTT
TTCCGTCACGCCGTCCTTTGAGGTGCGGCTCAACCAGGATCG
CTTCCAGTACCTGAACGACCACCAGATTCAGGATATCCCCCTG
GTGCCGTTCTCCTTTTACATCGAGCTCGTGTACGCCTCCATCT
TTAACTCCATCTCCACCACCACCACGAACACGACGGCTTCGAC
CATGTTTGAGATCGAGAACTTCACCATTGATAGCAGCATCATC
ATCGACCAGAAGAAGTCGACCCTCATCGGTATTAACTTCAACT
CGGACCTCACGAAGTTTGAGATCGGCTCCATTAACTCCATCG
GGTCGGGTTCGTCGTCGAACAACAACTTTATCGAGAACAAGT
GGAAGATCCATTCGAACGGTATTATTAAGTACGGTACCAACTA
CCTCAAGAGCAACAGCAAGTCCAACAGCTTCAACGAGTCGAC
GACGACGACCACGACGACCACCACCACCACCAAGTGCTTCAA
GAGCTTCAACAGCAACGAGTTTTACAACGAGATTATTAAGTAC
AACTACAACTACAAGTCGACGTTCCAGTCGCGTCAAGGAGTTCA
AGCAGTTCGACAAGCAGGGGACGTTCTACTACTCCGAGATTC
AGTTCAAGAAGAACGATAAGCAGGTCATTGATCAGCTCCTCTC
GAAGCAGCTGCCTTCCGACTTTCGCTGCATCCACCCTTGCCT
GCTGGACGCCGTGCTCCAGAGCGCTATTATTCCTGCGACGAA
CAAGACCAACTGCTCGTGGATTCCTATCAAGATCGGGAAGCT
CAGCGTCAACATTCCCTCGAACTCCTACTTCAACTTTAAGGAT
CAGCTCCTCTACTGCCTCATTAAGCCGTCCACCTCCACCTCGA
```

TABLE 1-continued

Sequences

```
CCTCCCCTAGCACGTACTTTTCGTCGGACATCCAGGTGTTCGA
TAAGAAGAACAACAACCTGATCTGCGAGCTGACGAACCTGGA
GTTCAAGGGGATTAACAGCAGCTCCTCGAGCAGCTCGTCGTC
GTCCACGATTAACTCGAACGTGGAGGCCAACTACGAGTCCAA
GATCGAGGAGACCAACCACGATGAGGATGAGGACGAGGAGC
TCCCCCTCGTGAGCGAGTACGTGTGGTGCAAGGAGGAGCTGA
TTAACCAGAGCATCAAGTTCACCGATAACTACCAGACCGTGAT
TTTTTGCAGCACGAACCTGAACGGTAACGATCTGCTGGACTCC
ATCATCACCAGCGCCCTGGAGAACGGGCACGACGAGAACAAG
ATTTTCATTGTCTCCCCGCCCCCCGTCGAGTCGGACCAGTACA
ACAACCGGATTATTATTAACTACACGAACAACGAGAGCGACTT
CGATGCTCTGTTTGCCATCATCAACTCCACGACGTCCATCAGC
GGCAAGAGCGGCCTGTTTTCCACGCGGTTTATTATTCTGCCTA
ACTTTAACTCCATTACGTTCTCCTCCGGCAACTCCACGCCCCT
GATCACCAACGTGAACGGTAACGGCAACGGGAAGTCGTGCG
GCGGGGGCGGTGGTTCCACCAACAACACCATCTCCAACTCGT
CGTCGAGCATTTCGTCCATCGATAACGGCAACAACGAGGATG
AGGAGATGGTCCTCAAGAGCTTTAACGATAGCAACCTCAGCCT
GTTTCACCTCCAGAAGAGCATCATTAAGAACAACATTAAGGGC
CGCCTGTTTCTGATTACGAACGGGGGGCAGAGCATCAGCTCG
TCCACGCCGACCTCCACCTACAACGACCAGTCCTACGTGAAC
CTCAGCCAGTACCAGCTGATTGGCCAGATCCGCGTGTTTAGC
AACGAGTACCCGATTATGGAGTGCTCGATGATCGACATCCAG
GATTCGACGCGGATTGACCTCATTACCGATCAGCTCAACAGCA
CCAAGCTCAGCAAGCTCGAGATCGCGTTCCGGGATAACATTG
GCTACAGCTACAAGCTGCTGAAGCCCTCCATTTTTGACAACTC
GTCGCTGCCGAGCTCGTCGTCCGAGATCGAGACGACCGCTAC
CACGAAGGATGAGGAGAAGAACAACTCCATTAACTACAACAAC
AACTACTACCGGGTCGAGCTCTCCGACAACGGGATTATTAGC
GATCTCAAGATCAAGCAGTTCCGCCAGATGAAGTGCGGGGTG
GGCCAGGTGCTGGTGCGCGTCGAGATGTGCACGCTCAACTTC
CGGGACATCCTCAAGTCGCTCGGTCGCGATTACGACCCTATC
CACCTGAACTCGATGGGTGACGAGTTCTCGGGTAAGGTGATT
GAGATTGGCGAGGGGGTGAACAACCTGAGCGTCGGCCAGTA
CGTGTTCGGTATTAACATGTCCAAGTCCATGGGCAGCTTTGTG
TGCTGCAACAGCGACCTCGTCTTTCCTATTCCCATTCCGACCC
CTTCCAGCAGCAGCTCGAGCAACGAGAACATCGATGACCAGG
AGATCATTTCGAAGCTGCTGAACCAGTACTGCACGATTCCGAT
TGTCTTTCTCACGTCCTGGTACAGCATCGTCATTCAGGGCCGC
CTGAAGAAGGGTGAGAAGATTCTGATCCACTCCGGTTGCGGG
GGTGTGGGTCTGGCTACCATTCAGATTTCGATGATGATTGGC
GCGGAGATCCACGTGACGGTGGGGAGCAACGAGAAGAAGCA
GTACCTGATCAAGGAGTTCGGTATTGACGAGAAGCGGATTTAC
AGCTCGCGCTCCCTCCAGTTTTACAACGACCTGATGGTCAACA
CCGACGGTCAGGGTGTCGATATGGTGCTGAACTCCCTGAGCG
GTGAGTACCTCGAGAAGTCCATCCAGTGCCTGTCCCAGTACG
GCCGGTTTATTGAGATTGGCAAGAAGGATATCTACTCGAACTC
CAGCATTCACCTGGAGCCTTTTAAGAACAACCTGAGCTTTTTC
GCTGTGGACATTGCGCAGATGACGGAGAACCGGCGGGACTA
CCTGCGCGAGATCATGATCGATCAGCTGCTGCCTTGCTTCAA
GAACGGGTCCCTCAAGCCTCTCAACCAGCACTGCTTCAACTC
CCCCTGCGACCTCGTGAAGGCTATCCGGTTTATGTCGTCGGG
GAACCATATTGGTAAGATCCTCATCAACTGGAGCAACCTCAAC
AACGACAAGCAGTTCATCAACCACCATTCGGTCGTCCATCTCC
CTATCCAGTCGTTTTCGAACCGCAGCACGTACATTTTTACCGG
CTTCGGTGGGCTCACCCAGACGCTCCTGAAGTACTTTAGCAC
CGAGTCCGACCTGACCAACGTGATCATTGTCTCGAAGAACGG
CCTGGATGACAACTCGGGTAGCGGTAGCGGGAACAACGAGAA
GCTCAAGCTGATCAACCAGCTGAAGGAGTCCGGGCTCAACGT
GCTCGTCGAGAAGTGCGATCTGAGCTCCATTAAGCAGGTCTA
CAAGCTCTTCAACAAGATTTTCGACAACGATGCTTCGGGCTCC
GATTCGGGCGATTTCTCGGACATCAAGGGTATTTTTCACTTCG
CGTCCCTGATTAACGACAAGCGCATCCTGAAGCACAACCTGG
AGTCCTTTAACTACGTCTACAACTCCAAGGCGACGAGCGCCT
GGAACCTCCATCAGGTCTCGCTGAAGTACAACCTCAACCTCG
ACCATTTTCAGACGATCGGCAGCGTCATCACCATTCTGGGGAA
CATCGGCCAGAGCAACTACACGTGCGCCAACCGCTTTGTCGA
GGGTCTCACGCATCTCCGCATTGGCATGGGCCTGAAGAGCTC
CTGCATTCATCTCGCTAGCATTCCTGATGTGGGTATGGCGAGC
AACGACAACGTGCTGAACGACCTCAACTCCATGGGGTTCGTG
CCCTTCCAGAGCCTGAACGAGATGAACCTGGGGTTTAAGAAG
CTCCTCTCCTCGCCGAACCCGATCGTGGTCCTCGGCGAGATT
AACGTGGATCGCTTTATTGAGGCGACCCCCAACTTCCGGGCT
AAGGATAACTTTATTATTACGTCGCTGTTTAACCGGATTGACCC
CCTGCTGCTGGTCAACGAGAGCCAGGATTTTATTATTAACAAC
AACATCAACAACAACGGCGGGGGTGGTGACGGGAGCTTCGAT
GACCTGAACCAGCTCGAGGATGAGGGTCAGCAGGGTTTCGG
CAACGGGGACGGTTACGTCGACGATAACATTGACTCGGTGTC
```

TABLE 1-continued

Sequences

| | |
|---|---|
| | GATGCTCAGCGGCACCTCCAGCATTTTTGATAACGATTTCTAC<br>ACGAAGTCGATCCGGGGTATGCTCTGCGACATTCTCGAGCTC<br>AAGGACAAGGATCTGAACAACACGGTGTCGTTCAGCGACTAC<br>GGCCTGGACTCCCTGCTCTCGAGCGAGCTCAGCAACACCATC<br>CAGAAGAACTTCTCCATTCTGATCCCCTCCCTGACCCTGGTGG<br>ACAACTCGACGATCAACTCCACCGTCGAGCTCATTAAGAACAA<br>GCTCAAGAACTCCACGACCAGCTCGATCTCCTCCTCGGTGAG<br>CAAGAAGGTCTCCTTTAAGAAGAACACCCAGCCCCTGATCATC<br>CCTACGACGGCTCCGATTAGCATTATCAAGACGCAGTCGTACA<br>TTAAGTCGGAGATCATTGAGAGCCTCCCCATTAGCTCCAGCAC<br>CACGATCAAGCCTCTCGTCTTCGATAACCTCGTCTACTCCAGC<br>TCGAGCAGCAACAACAGCAACTCCAAGAACGAGCTCACGTCG<br>CCGCCCCCGAGCGCCAAGCGCGAGAGCGTGCTGCCCATCAT<br>CAGCGAGGATAACAACAGCGATAACGATAGCAGCATGGCCAC<br>CGTGATTTACGAGATCTCCCCGATTGCCGCGCCTTACCATCG<br>CTACCAGACGGATGTCCTCAAGGAGATCACCCAGCTGACGCC<br>CCACAAGGAGTTCATTGACAACATCTACAAGAAGTCGAAGATT<br>CGCAGCCGCTACTGCTTTAACGATTTCTCCGAGAAGTCGATG<br>GCGGATATCAACAAGCTGGACGCTGGTGAGCGCGTCGCGCT<br>CTTCCGGGAGCAGACGTACCAGACCGTGATTAACGCCGGGAA<br>GACCGTGATCGAGCGCGCTGGGATTGATCCGATGCTCATCTC<br>CCATGTGGTGGGGGTGACGTCGACCGGTATTATGGCTCCTTC<br>CTTTGATGTCGTGCTCATTGATAAGCTGGGCCTGTCGATTAAC<br>ACCTCCCGGACCATGATTAACTTTATGGGCTGCGGGGCTGCG<br>GTCAACAGCATGCGGGCCGCCACCGCTTACGCTAAGCTCAAG<br>CCCGGTACGTTCGTCCTGGTGGTGGCCGTCGAGGCCAGCGC<br>TACCTGCATGAAGTTCAACTTCGACTCGCGGTCGGATCTGCTG<br>TCCCAGGCCATTTTCACGGATGGGTGCGTCGCCACCCTGGTC<br>ACCTGCCAGCCTAAGTCCTCGCTGGTCGGCAAGCTGGAGATT<br>ATCGATGACCTGTCCTACCTCATGCCTGACAGCCGCGATGCG<br>CTCAACCTCTTTATTGGGCCTACGGGGATCGACCTCGACCTG<br>CGGCCCGAGCTCCCTATTGCGATTAACCGGCATATCAACTCC<br>GCGATCACGTCGTGGCTGAAGAAGAACAGCCTGCAGAAGTCG<br>GACATCGAGTTTTTTGCGACCCATCCTGGCGGCGCTAAGATC<br>ATTTCGGCCGTCCACGAGGGGCTCGGTCTGTCGCCTGAGGAC<br>CTCAGCGACTCCTACGAGGTCATGAAGCGGTACGGCAACATG<br>ATCGGTGTCTCGACGTACTACGTCCTGCGGCGCATCCTCGAC<br>AAGAACCAGACGCTCCTCCAGGAGGGGTCGCTCGGCTACAAC<br>TACGGCATGGCTATGGCTTTCAGCCCTGGGGCGTCGATCGAG<br>GCCATTCTGTTTAAGCTGATTAAGTAA |
| SEQ ID NO: 68 nucleic acid<br>coding sequence of Orf2 from<br>Streptomyces Sp. Strain C1190<br>optimized for GC-rich<br>microalgae | ATGAGCGAGGCGGCCGATGTCGAGCGGGTCTACGCTGCTAT<br>GGAGGAGGCTGCTGGGCTGCTGGGCGTGGCGTGCGCGCGC<br>GATAAGATCTACCCCCTCCTCAGCACCTTTCAGGATACCCTGG<br>TGGAGGGTGGTAGCGTGGTGGTCTTCAGCATGGCTTCCGGG<br>CGGCATTCCACCGAGCTCGATTTTTCCATCTCGGTCCCCACGT<br>CCCACGGGGACCCTTACGCGACCGTCGTGGAGAAGGGTCTC<br>TTCCCCGCTACGGGTCACCCCGTGGATGATCTGCTGGCCGAT<br>ACGCAGAAGCATCTGCCGGTGAGCATGTTCGCTATCGACGGG<br>GAGGTCACCGGCGGCTTTAAGAAGACGTACGCCTTCTTTCCT<br>ACCGATAACATGCCTGGGGTGGCCGAGCTCAGCGCCATTCCT<br>TCGATGCCGCCCGCCGTGGCCGAGAACGCTGAGCTGTTTGC<br>GCGGTACGGCCTGGATAAGGTGCAGATGACCTCCATGGATTA<br>CAAGAAGCGCCAGGTGAACCTCTACTTTTCGGAGCTCTCCGC<br>TCAGACCCTCGAGGCCGAGTCCGTCCTGGCTCTCGTGCGGG<br>AGCTGGGTCTCCATGTCCCGAACGAGCTCGGGCTCAAGTTCT<br>GCAAGCGCTCGTTCTCGGTCTACCCTACCCTCAACTGGGAGA<br>CCGGCAAGATTGACCGCCTGTGCTTCGCTGTGATTAGCAACG<br>ATCCTACCCTCGTCCCTAGCTCCGATGAGGGTGACATCGAGA<br>AGTTCCACAACTACGCTACCAAGGCGCCCTACGCTTACGTGG<br>GGGAGAAGCGCACGCTGGTCTACGGCCTCACCCTGAGCCCT<br>AAGGAGGAGTACTACAAGCTCGGCGCTTACTACCACATCACG<br>GATGTCCAGCGCGGCCTCCTCAAGGCCTTTGACTCGCTGGAG<br>GATTGA |
| SEQ ID NO: 69 nucleic acid<br>coding sequence of CsPT4<br>from Cannabis sativa optimized<br>for GC-rich microalgae | ATGGGGCTCTCGCTCGTCTGCACCTTTAGCTTTCAGACCAACT<br>ACCATACGCTGCTGAACCCGCACAACAAGAACCCGAAGAACA<br>GCCTCCTCAGCTACCAGCACCCCAAGACCCCCATTATCAAGT<br>CCAGCTACGATAACTTTCCTAGCAAGTACTGCCTCACCAAGAA<br>CTTCCACCTGCTCGGCCTCAACAGCCATAACCGCATTTCCAGC<br>CAGTCCCGCTCCATCCGCGCTGGCTCCGATCAGATCGAGGG<br>GTCCCCGCATCACGAGTCCGACAACTCGATCGCCACCAAGAT<br>TCTGAACTTTGGGCACACGTGCTGGAAGCTGCAGCGGCCGTA<br>CGTCGTCAAGGGGATGATCTCGATCGCCTGCGGGCTGTTCGG<br>TCGGGAGCTCTTCAACAACCGGCATCTGTTTAGCTGGGGCCT<br>GATGTGGAAGGCTTTTTTCGCGCTGGTGCCCATCCTCAGCTTC<br>AACTTTTTTGCCGCTATCATGAACCAGATTTACGATGTGGACAT<br>TGACCGGATTAACAAGCCCGACCTGCCCCTGGTCAGCGGTGA |

TABLE 1-continued

Sequences

| | |
|---|---|
| | GATGTCCATTGAGACCGCTTGGATTCTCAGCATTATCGTGGCG<br>CTCACGGGCCTGATCGTCACCATCAAGCTCAAGAGCGCTCCG<br>CTCTTTGTGTTCATCTACATCTTTGGCATTTTTGCGGGTTTCGC<br>TTACAGCGTGCCTCCGATCCGCTGGAAGCAGTACCCGTTCAC<br>GAACTTTCTGATTACGATTAGCTCGCATGTGGGTCTCGCTTTT<br>ACGTCGTACAGCGCTACCACCTCGGCTCTCGGCCTGCCTTTT<br>GTCTGGCGCCCCGCGTTCTCCTTTATCATTGCGTTCATGACCG<br>TCATGGGCATGACGATTGCGTTTGCTAAGGATATTTCCGATAT<br>CGAGGGTGATGCCAAGTACGGCGTCAGCACGGTCGCCACGA<br>AGCTGGGGGCGCGGAACATGACGTTTGTCGTGTCGGGCGTG<br>CTCCTCCTCAACTACCTCGTCTCGATCTCGATCGGGATCATCT<br>GGCCTCAGGTCTTTAAGAGCAACATTATGATTCTGTCCCATGC<br>CATTCTGGCCTTTTGCCTGATCTTTCAGACGCGCGAGCTCGCC<br>CTCGCGAACTACGCTAGCGCTCCTTCCCGCCAGTTCTTCGAG<br>TTTATCTGGCTCCTCTACTACGCGGAGTACTTTGTGTACGTGT<br>TCATTTAA |
| SEQ ID NO: 70 nucleic acid coding sequence of HIPT1 from *Humulus lupulus* optimized for GC-rich microalgae | ATGGAGCTGTCGTCGGTCAGCTCGTTCTCCCTGGGTACCAAC<br>CCTTTTATCTCCATCCGCACAACAACAACAACCTCAAGGTGT<br>CGTCCTACTGCTGCAAGTCCAAGTCGCGGGTCATCAACTCGA<br>CCAACTCGAAGCACTGCAGCCCCAACAACAACAGCAACAACA<br>ACACCTCGAACAAGACGACGCATCTGCTCGGCCTGTACGGGC<br>AGTCCCGGTGCCTCCTGAAGCCTCTCAGCTTTATTTCGTGCAA<br>CGATCAGCGCGGTAACTCGATTCGGGCGTCCGCTCAGATTGA<br>GGATCGGCCCCCCGAGTCGGGTAACCTCTCCGCGCTGACCA<br>ACGTCAAGGACTTTGTGTCCGTGTGCTGGGAGTACGTGCGGC<br>CTTACACCGCCAAGGGCGTCATTATCTGCTCCTCCTGCCTCTT<br>CGGCCGGGAGCTGCTGGAGAACCCCAACCTCTTTAGCTGGCC<br>TCTCATTTTTCGCGCCCTCCTCGGCATGCTGGCCATTCTGGGT<br>AGCTGCTTCTACACGGCTGGCATCAACCAGATTTTCGACATGG<br>ACATCGACCGGATTAACAAGCCTGATCTGCCGCTCGTCTCGG<br>GGCGGATTTCGGTGGAGAGCGCTTGGCTCCTGACCCTCAGCC<br>CTGCGATTATTGGTTTTATCCTGATCCTGAAGCTGAACTCCGG<br>GCCTCTCCTGACCAGCCTGTACTGCCTCGCGATTCTCAGCGG<br>GACCATTTACAGCGTCCCTCCCTTTCGGTGGAAGAAGAACCC<br>GATCACGGCTTTTCTCTGCATCCTGATGATTCACGCTGGGCTC<br>AACTTCTCCGTGTACTACGCGTCCCGGGCTGCCCTCGGTCTG<br>GCTTTTGCGTGGTCGCCGAGCTTCTCCTTCATCACCGCCTTCA<br>TTACCTTTATGACGCTGACCCTGGCTTCCAGCAAGGATCTCAG<br>CGATATTAACGGCGACCGGAAGTTCGGCGTGGAGACCTTTGC<br>TACGAAGCTGGGCGCGAAGAACATCACCCTCCTGGGGACCG<br>GGCTCCTGCTCCTCAACTACGTCGCCGCTATCAGCACGGCCA<br>TTATTTGGCCGAAGGCGTTTAAGTCGAACATCATGCTCCTGTC<br>GCATGCGATCCTGGCCTTTTCCCTGATTTTTCAGGCGCGCGA<br>GCTCGACCGCACGAACTACACGCCGGAGGCCTGCAAGTCCTT<br>CTACGAGTTCATTTGGATCCTCTTTTCGGCTGAGTACGTGGTG<br>TACCTCTTTATT |

As used herein, the term "genetically engineered" and its derivatives refer to a microorganism whose genetic material has been altered using molecular biology techniques such as but not limited to molecular cloning, recombinant DNA methods, transformation and gene transfer. The genetically engineered microorganism includes a living modified microorganism, genetically modified microorganism or a transgenic microorganism. Genetic alteration includes addition, deletion, modification and/or mutation of genetic material. Such genetic engineering as described herein in the present disclosure increases production of plant natural products such as cannabinoid biosynthetic pathway products relative to the corresponding wild-type microorganism.

The term "cannabinoid" as used herein refers to a compound that acts on a cannabinoid receptor. A cannabinoid is derived from a source including a plant or a microorganism, in particular a genetically engineered microorganisms using host cells such as microalgae and cyanobacteria disclosed herein. A cannabinoid biosynthetic pathway product is a product associated with the production of cannabinoid. Examples of cannabinoid biosynthetic pathway products include, but not limited to hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol and cannabidiol. In an embodiment, the cannabinoid biosynthetic pathway product is at least one, two, three, four, five, six, seven, eight, nine, or ten of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

In one embodiment, the genetically engineered microorganism has increased production of at least one, two, three, four, five, six, seven, eight, nine, or ten cannabinoid biosynthetic pathway products relative to the corresponding wild-type microorganism. In another embodiment, the cannabinoid biosynthetic pathway product is at least one, two, three, four, five, six, seven, eight, nine, or ten of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol. For example, the genetically engineered microorganism may have increased production of olivetolic acid, or olivetolic acid and cannabigerolic acid, relative to the corresponding wild-type microorganism. In another example, the genetically engineered microorganism may have increased production of olivetol, or olivetol and cannabigerol, relative to the corresponding wild-type microorganism The term "nucleic acid molecule" or its derivatives, as used herein, is intended to include unmodified DNA or RNA or modified DNA or RNA. For example, it is useful for the nucleic acid molecules of the disclosure to be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, it is useful for the nucleic acid molecules to be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning. In some embodiments, the genetically engineered microorganism comprises at least one nucleic acid molecule described herein.

As used herein, the term "exogenous" refers to an element that has been introduced into a cell. An exogenous element can include a protein or a nucleic acid. An exogenous nucleic acid is a nucleic acid that has been introduced into a cell, such as by a method of transformation. An exogenous nucleic acid may code for the expression of an RNA and/or a protein. An exogenous nucleic acid may have been derived from the same species (homologous) or from a different species (heterologous). An exogenous nucleic acid may comprise a homologous sequence that is altered such that it is introduced into the cell in a form that is not normally found in the cell in nature. For example, an exogenous nucleic acid that is homologous may contain mutations, being operably linked to a different control region, or being integrated into a different region of the genome, relative to the endogenous version of the nucleic acid. An exogenous nucleic acid may be incorporated into the chromosomes of the transformed cell in one or more copies, into the plastid or mitochondrial DNA of the transformed cell, or be maintained as a separate nucleic acid outside of the transformed cell genome.

The term "nucleic acid sequence" as used herein refers to a sequence of nucleoside or nucleotide monomers consisting of naturally occurring bases, sugars and intersugar (backbone) linkages and includes cDNA. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences.

Increased cannabinoid biosynthetic pathway products produced by a genetically engineered microorganism can be the result of increasing activity of one or more enzymes associated with cannabinoid biosynthetic pathway. Increase of activity of an enzyme in a microorganism can include, for example, the introduction of a nucleic acid molecule comprising a nucleic acid sequence encoding the enzyme. In an embodiment, introduction of a nucleic acid molecule comprising a nucleic acid sequence encoding an enzyme can be accomplished by transformation. Examples of cannabinoid biosynthetic pathway enzymes include, but are not limited to hexanoyl-CoA synthetase, type III polyketide synthase (e.g., tetraketide synthase, Steely 1 and Steely 2), olivetolic acid cyclase, geranyl pyrophosphate synthase, aromatic prenyltransferase, geranyl pyrophosphate:olivetolic acid geranyltransferase, tetrahydrocannabidiol synthase, cannabichromene synthase, cannabidiol synthase, tetrahydrocannabinolic acid synthase, and cannabidiolic acid synthase.

FIG. 1 shows an exemplary cannabinoid biosynthetic pathway based on enzymes from *Cannabis sativa*: Tetraketide synthase (TKS) condenses hexanoyl-CoA and malonyl-CoA to form the intermediate trioxododenacoyl-CoA; Olivetolic acid cyclase (OAC) catalyzes and intramolecular aldol condensation to yield olivetolic acid (OA); aromatic prenyltransferase transfers a geranyldiphosphate (GPP) onto OA to produce cannabigerolic acid (CBGA); tetrahydrocannabinolic acid synthase or cannabidiolic acid synthase catalyze the oxidative cyclization of CBGA into tetrahydrocannabinolic acid (THCA) or cannabidiolic acid (CBDA), respectively. Decarboxylation of THCA or CBDA to remove the carboxyl group will produce decarboxylated cannabinoids tetrahydrocannabinol (THC) or cannabidiol (CBD), respectively.

In addition to the exemplary cannabinoid biosynthetic pathway from *Cannabis sativa* shown in FIG. 1, alternative biosynthetic intermediates can be used in a cannabinoid biosynthetic pathway in a genetically engineered microorganism. For example, olivetol is an intermediate that lacks the carboxyl group of olivetolic acid. Use of olivetol instead of olivetolic acid in a cannabinoid biosynthetic pathway will produce cannabinoids that similarly lack a carboxyl group such as cannabigerol (CBG), tetrahydrocannabinol (THC), or cannabidiol (CBD).

In addition to the exemplary cannabinoid biosynthetic pathway from *Cannabis sativa* shown in FIG. 1, alternative enzymes can be used in a cannabinoid biosynthetic pathway in a genetically engineered microorganism. For example, in addition to the enzymes found in *Cannabis sativa*, alternative enzymes of a cannabinoid biosynthetic pathway may be found in other plants (e.g., *Humulus lupulus*), in bacteria (e.g., *Streptomyces*), or in protists (e.g., Dictyostelium discoideum). Enzymes that differ in structure, but perform the same function, may be used interchangeably in a cannabinoid biosynthetic pathway in a genetically engineered microorganism. For example, the aromatic prenyltransferases CsPT1 (SEQ ID NO:18) and CsPT4 (SEQ ID NO:64) from *Cannabis sativa*, HIPT1 from *Humulus lupulus* (SEQ ID NO:65), and Orf2 (SEQ ID NO:63) from *Streptomyces* Sp. Strain CI190 are all aromatic prenyltransferases that catalyze the synthesis of CBGA from GPP and OA. In a further example, the Steely1 (SEQ ID NO:61) or Steely2 (SEQ ID NO:62) polyketide synthase from Dictyostelium discoideum, or a variant thereof, can be used to condense malonyl-CoA into olivetol, and may be used in place of TKS to produce olivetol in the absence of OAC.

In addition to the wild-type enzymes found in organisms discussed herein, modified variants of these enzymes can be used in a cannabinoid biosynthetic pathway in a genetically engineered microorganism. Variants of enzymes for use in a cannabinoid biosynthetic pathway can be generated by altering the nucleic acid sequence encoding said enzyme to, for example, increase/decrease the activity of a domain, add/remove a domain, add/remove a signaling sequences, or to otherwise alter the activity or specificity of the enzyme. For example, the sequence of Steely1 can be modified to reduce the activity of a methyltransferase domain in order to produce non-methylated cannabinoids. By way of example, this can be done by mutating amino acids G1516D+G1518A or G1516R relative to SEQ ID NO:61 as disclosed in WO/2018/148849, herein incorporated by reference. In a further example, the sequences of tetrahydrocannabinolic acid synthase or cannabidiolic acid synthase can be modified to remove an N-terminal secretion peptide. By way of example, this can be done by removing amino acids 1-28 of SEQ ID NO:20 or 21 to produce a truncated enzyme as disclosed in WO/2018/200888, herein incorporated by reference.

A hexanoyl-CoA synthetase is an acyl-activating enzyme, more specifically an acyl-CoA synthetase that ligates CoA and hexanoic acid or hexanoate to produce hexanoyl-CoA. A hexanoyl-CoA synthetase may have the amino acid sequence of SEQ ID NO: 19 or an amino acid sequence with at least 90% identity to SEQ ID NO: 19.

A type III polyketide synthase is an enzyme that produces polyketides by catalyzing the condensation reaction of acetyl units to thioester-linked starter molecules. A type III polyketide synthase may have the amino acid sequence of SEQ ID NO: 15, 61 or 62 or an amino acid sequence with at least 90% identity to SEQ ID NO: 15, 61 or 62. In an embodiment, the type III polyketide synthase is tetraketide synthase from Cannabis sativa which is also known in the art as olivetol synthase and 3,5,7-trioxododecanoyl-CoA synthase. Tetraketide synthase condenses hexanoyl-CoA with three malonyl-CoA in a multi-step reaction to form 3,5,7-trioxododecanoyl-CoA. In another embodiment, the type III polyketide synthase is Steely1 or Steely 2 from Dictyostelium discoideum, comprising a domain with type III polyketide synthase activity, or a variant thereof (e.g., Steely1 (G1516D+G1518A) or Steely1 (G1516R) disclosed in WO/2018/148849). Steely1 is also known in the art as DiPKS or DiPKS1, and Steely2 is also known in the art as DiPKS37.

An olivetolic acid cyclase is an enzyme that catalyzes an intramolecular aldol condensation of trioxododecanoyl-CoA to form olivetolic acid. An olivetolic acid cyclase may have the amino acid sequence of SEQ ID NO: 16 or 17 or an amino acid sequence with at least 90% identity to SEQ ID NO: 16 or 17. Olivetolic acid cyclase from Cannabis sativa is also known in the art as olivetolic acid synthase and 3,5,7-trioxododecanoyl-CoA CoA-lyase.

An aromatic prenyltransferase, as used herein, refers to an enzyme capable of transferring a geranyl disphosphate onto olivetol to synthesize cannibergol (CBG) or onto olivetolic acid (OA) to synthesize cannabigerolic acid (CBGA). An example of an aromatic prenyltransferase is aromatic prenyltransferase from Cannabis sativa which is also known in the art as CsPT1, prenyltransferase geranylpyrophosphate-olietolic acid geranyltransferase, and geranyl-diphosphate: olivetolate geranytransferase. Further examples of aromatic prenyltransferase include HIPT1 from Humulus lupulus, CsPT4 from Cannabis sativa, and Orf2 (NphB) from Streptomyces Sp. Strain CI190. An aromatic prenyltransferase may have the amino acid sequence of SEQ ID NO: 18, 63, 64 or 65, or an amino acid sequence with at least 90% identity to SEQ ID NO: 18, 63, 64 or 65.

A tetrahydrocannabinolic acid synthase is also known in the art as Δ9-tetrahydrocannabinolic acid synthase, and synthesizes Δ9-tetrahydrocannabinolic acid by catalyzing the cyclization of the monoterpene moiety in cannabigerolic acid. A tetrahydrocannabinolic acid synthase may have the amino acid sequence of SEQ ID NO: 20 or an amino acid sequence with at least 90% identity to SEQ ID NO: 20.

A cannabidiolic acid synthase synthesizes cannabidiolic acid by catalyzing the stereoselective oxidative cyclization of the monoterpene moiety in cannabigerolic acid. A cannabidiolic acid synthase may have the amino acid sequence of SEQ ID NO: 21 or an amino acid sequence with at least 90% identity to SEQ ID NO: 21.

In an embodiment, the nucleic acid molecule encodes at least one, two, three, four, five, or six of hexanoyl-CoA synthetase, type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase; or encodes at least one, two, three, four, or five of type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase without encoding hexanoyl-CoA synthetase. In another embodiment, the at least one nucleic acid molecule comprises nucleic acid sequence encoding hexanoyl-CoA synthetase comprises at least 80%, 85%, 90%, 95%, 96%, 97%, 98%, 99%, or 100% sequence identity to a sequence shown in SEQ ID NO:5 or 12. In another embodiment, the at least one nucleic acid molecule comprises nucleic acid sequence encoding type III polyketide synthase (e.g., tetraketide synthase, Steely 1 and Steely 2) comprises at least 80%, 85%, 90%, 95%, 96%, 97%, 98%, 99%, or 100% sequence identity to a sequence shown in SEQ ID NO:1, 8, 56, 57, 66, or 67. In another embodiment, the at least one nucleic acid molecule comprises nucleic acid sequence encoding olivetolic acid cyclase comprises at least 80%, 85%, 90%, 95%, 96%, 97%, 98%, 99%, or 100% sequence identity to a sequence shown in SEQ ID NO:2, 3, 9 or 10. In another embodiment, the at least one nucleic acid molecule comprises nucleic acid sequence encoding aromatic prenyltransferase comprises at least 80%, 85%, 90%, 95%, 96%, 97%, 98%, 99%, or 100% sequence identity to a sequence shown in SEQ ID NO:4, 11, 58, 59, 60, 68, 69, or 70. In another embodiment, the at least one nucleic acid molecule comprises nucleic acid sequence encoding tetrahydrocannabinolic acid synthase comprises at least 80%, 85%, 90%, 95%, 96%, 97%, 98%, 99%, or 100% sequence identity to a sequence shown in SEQ ID NO:6 or 13. In another embodiment, the at least one nucleic acid molecule comprises nucleic acid sequence encoding cannabidiolic acid synthase comprises at least 80%, 85%, 90%, 95%, 96%, 97%, 98%, 99%, or 100% sequence identity to a sequence shown in SEQ ID NO:7 or 14. In another embodiment, the nucleic acid molecule is comprised in a genetically engineered microorganism.

In an embodiment, the nucleic acid molecule comprising nucleic acid sequence encoding at least one of hexanoyl-CoA synthetase comprises amino acid sequence with at least 90%, 95%, 96%, 97%, 98%, 99%, or 100% sequence identity to sequence as shown in SEQ ID NO:19, type III polyketide synthase comprises amino acid sequence with at least 90%, 95%, 96%, 97%, 98%, 99%, or 100% sequence identity to sequence as shown in SEQ ID NO:15, 61 or 62, olivetolic acid cyclase comprises amino acid sequence with at least 90%, 95%, 96%, 97%, 98%, 99%, or 100% sequence identity to sequence as shown in SEQ ID NO:16 or 17, aromatic prenyltransferase comprises amino acid sequence with at least 90%, 95%, 96%, 97%, 98%, 99%, or 100% sequence identity to sequence as shown in SEQ ID NO:18, 63, 64, or 65, tetrahydrocannabinolic acid synthase comprises amino acid sequence with at least 90%, 95%, 96%, 97%, 98%, 99%, or 100% sequence identity to sequence as shown in SEQ ID NO:20, and cannabidiolic acid synthetase comprises amino acid sequence with at least 90%, 95%, 96%, 97%, 98%, 99%, or 100% sequence identity to sequence as shown in SEQ ID NO:21. In another embodiment, the nucleic acid molecule does not comprise nucleic acid sequence encoding hexanoyl-CoA synthetase. In another embodiment, the nucleic acid molecule is comprised in a genetically engineered microorganism.

As used herein, the term "vector" or "nucleic acid vector" means a nucleic acid molecule, such as a plasmid, comprising regulatory elements and a site for introducing transgenic DNA, which is used to introduce said transgenic DNA into a microorganism. The transgenic DNA can encode a heterologous protein, which can be expressed in and isolated from a microorganism. The transgenic DNA can be integrated into nuclear, mitochondrial or chloroplastic genomes through homologous or non-homologous recombination. The transgenic DNA can also replicate without integrating into nuclear, mitochondrial or chloroplastic genomes. The vector can contain a single, operably-linked set of regulatory elements that includes a promoter, a 5' untranslated region (5' UTR), an insertion site for transgenic DNA, a 3' untranslated region (3' UTR) and a terminator sequence. Vectors useful in the present methods are well known in the art. In one embodiment, the nucleic acid molecule is an episomal vector.

As used herein, the term "episomal vector" refers to a DNA vector based on a bacterial episome that can be expressed in a transformed cell without integration into the transformed cell genome.

In another embodiment, the vector is a commercially-available vector. As used herein, the term "expression cassette" means a single, operably-linked set of regulatory elements that includes a promoter, a 5' untranslated region (5' UTR), an insertion site for transgenic DNA, a 3' untranslated region (3' UTR) and a terminator sequence. In an embodiment, the at least one nucleic acid molecule is an episomal vector.

The term "operably-linked", as used herein, refers to an arrangement of two or more components, wherein the components so described are in a relationship permitting them to function in a coordinated manner. For example, a transcriptional regulatory sequence or a promoter is operably-linked to a coding sequence if the transcriptional regulatory sequence or promoter facilitates aspects of the transcription of the coding sequence. The skilled person can readily recognize aspects of the transcription process, which include, but not limited to, initiation, elongation, attenuation and termination. In general, an operably-linked transcriptional regulatory sequence joined in cis with the coding sequence, but it is not necessarily directly adjacent to it.

The nucleic acid vectors encoding the cannabinoid biosynthetic pathway enzyme therefore contain elements suitable for the proper expression of the enzyme in the microorganism. Specifically, each expression vector contains a promoter that promotes transcription in microorganisms. The term "promoter," as used herein, refers to a nucleotide sequence that directs the transcription of a gene or coding sequence to which it is operably-linked. Suitable promoters include, but are not limited to, pEF-1α, p40SRPS8, pH4-1B, pγ-Tubulin, pRBCMT, pFcpB, pFcpC, pFcpD (as shown in Table 1 as SEQ ID NO:38-45; see Slattery et al, 2018), and RbcS2. The skilled person can readily appreciate inducible promoters including chemically-inducible promoters, alcohol inducible promoters, and estrogen inducible promoters can also be used. Predicted promoters, such as those that can be found from genome database mining may also be used. In addition, the nucleic acid molecule or vector may contain intron in front of the cloning site to drive a strong expression of the gene of interest. The intron includes introns of FBAC2-1 TUFA-1, EIF6-1, RPS4-1 (as shown in Table 1 as SEQ ID NO:34-37) and RbcS2. The nucleic acid molecule or vector also contains a suitable terminator such as tEF-1α, t40SRPS8, tH4-1B, tγ-Tubulin, tRBCMT, tFcpB, tFcpC, tFcpD or PAL (as shown in Table 1 as SEQ ID NO:46-53). Seletectable marker genes can also be linked on the vector, such as the kanamycin resistance gene (also known as neomycin phosphotransferase gene II, or nptII), zeocin resistance gene, hygromycin resistance gene, Basta resistance gene, hygromycin resistance gene, or others. As used herein, the term "tag" refers to an amino acid sequence that is recognized by an antibody. The tag amino acid sequence links to, for example, sequence of an enzyme, thereby allowing detection or isolation of the enzyme by the binding between the tag and the tag-specific antibody. For example, common tags known in the art include 6His, MYC, FLAG, V5, HA and HSV. These tags are useful when positioned at the N- or C-terminus.

In an embodiment, the nucleic acid molecule or vector encoding the at least one cannabinoid biosynthetic pathway enzyme comprises a promoter nucleic acid sequence selected from SEQ ID NO:38-45, wherein said promoter is operably-linked to a polynucleotide sequence with at least 80%, 85%, 90%, 95%, 96%, 97%, 98%, 99% or 100% sequence identity to a sequence selected from SEQ ID NO:1-14, 56-60, and 66-70. In another embodiment, the nucleic acid molecule comprises at least one intron sequence selected from SEQ ID NO:34-37. In another embodiment, the nucleic acid molecule comprises a terminator nucleic acid sequence selected from SEQ ID NO:46-53. In another embodiment, the genetically engineered microorganism comprises a nucleic acid molecule comprising at least one tag sequence selected from SEQ ID NO:22-33.

The nucleic acid molecule can be constructed to express at least one, two, three, four, five, or six enzymes associated with the cannabinoid biosynthetic pathway. In an embodiment, the nucleic acid molecule comprises two or more polynucleotide sequences, each of which encodes one cannabinoid biosynthetic pathway enzyme and is operably linked to the same promoter. Where at least two, three, four, five, or six enzymes are encoded in a construct, the construct can contain nucleotide sequence such as shown in SEQ ID NO:54 or 55 that encodes a self-cleaving sequence FMDV2a, which results in the enzymes being produced as separated proteins, or the construct can contain peptide linker sequences linking the enzymes, allowing substrate channeling in which the passing of the intermediary metabolic product of one enzyme directly to another enzyme or active site without its release into solution, or a combination of self-cleaving and linker sequences. In an embodiment, the nucleic acid molecule comprises at least one linker sequence between at least two polynucleotide sequences. In another embodiment, the linker sequence is a self-cleaving sequence, optionally SEQ ID NO:54 or 55.

In another embodiment, the vector comprises a nucleic acid sequence as described herein. In another embodiment, a host cell is transformed with a vector or nucleic acid molecule comprising a nucleic acid sequence as described herein. In another embodiment, the host cell is any microorganism as described herein.

Nucleic acid sequences as described herein can be provided in vectors in different arrangements or combinations. Each individual sequence that encodes an enzyme of a cannabinoid biosynthetic pathway can be provided in separate vectors. Alternatively, multiple sequences can be provided together in the same vector. For example, nucleic acid sequences encoding a type III polyketide synthase and an olivetolc acid cyclase can be provided together in a first vector, a nucleic acid sequence encoding an aromatic prenyltransferase can be provided in a second vector, and nucleic acid sequences encoding a tetrahydrocannabinolic acid synthase and/or a cannabidiolic acid synthase can be provided in a third vector. Alternatively, sequences that encode all of the enzymes of a cannabinoid biosynthetic pathway can be provided together in the same vector. Where more than one sequence that encodes an enzyme is provided in the same vector, the sequences can be provided in separate expression cassettes, or together in the same expression cassette. Where two or more sequences are in the same expression cassette, they can be provided in the same open reading frame so as to produce a fusion protein. Two or more sequences that encode a fusion protein can be separated by linker sequences that encode restriction nuclease recognition sites or self-cleaving peptide linkers. Accordingly, a genetically modified microorganism for the production of cannabinoids can be engineered by stepwise transfection with multiple vectors that each comprises nucleic acid sequences that encode one or more enzymes of a cannabinoid biosynthetic pathway, or with a single vector that comprises nucleic acid sequences that encode all of the enzymes of a cannabinoid biosynthetic pathway.

As used herein, the term "microalgae" and its derivatives, include photosynthetic and non-photosynthetic microorganisms that are eukaryotes. As used herein, the term "cyanobacteria" and its derivatives, include photosynthetic microorganisms that are prokaryotes. In an embodiment, the microalga is a GC-rich microalga. As used herein, "GC-rich microalga" refers to a microalga wherein the DNA of the nuclear genome and/or the plastid genome comprises at least 50%, at least 55%, at least 60%, at least 65%, at least 70%, or at least 75% GC content. In an embodiment, the microalga is an oleaginous microalga. As used herein "oleaginous" refers to a microalga comprising a lipid conent of at least 35%, at least 40%, at least 45%, or at least 50% by weight. In an embodiment, the microalga is a cold-adapted microalga. As used herein, "cold-adapted" refers to a microalga that grows in temperate, sub-polar, or polar regions in nature, or that has been adapted in artificial growth conditions to grow at temperatures found in temperate, sub-polar, or polar regions. In some embodiments, the cold-adapted microalga grows at a temperature lower than 24° C., lower than 20° C., lower than 16° C., or lower than 12° C. In an embodiment, the microalga is a cold-adapted microalga that exhibits increased lipid content when grown at a temperature lower than 24° C., lower than 20° C., lower than 16° C., or lower than 12° C.

In an embodiment, the microalga is from the genera Ankistrodesmus, Asteromonas, Auxenochlorella, Basichlamys, *Botryococcus*, Botryokoryne, Borodinella, Brachiomonas, Catena, Carteria, Chaetophora, Characiochloris, Characiosiphon, Chlainomonas, *Chlamydomonas, Chlorella*, Chlorochytrium, Chlorococcum, Chlorogonium, Chloromonas, Closteriopsis, Dictyochloropsis, *Dunaliella*, Ellipsoidon, Eremosphaera, Eudorina, Floydiella, Friedmania, Haematococcus, Hafniomonas, Heterochlorella, Gonium, Halosarcinochlamys, Koliella, Lobocharacium, Lobochlamys, Lobomonas, Lobosphaera, Lobosphaeropsis, Marvania, Monoraphidium, Myrmecia, Nannochloris, Oocystis, Oogamochlamys, Pabia, Pandorina, Parietochloris, Phacotus, Platydorina, Platymonas, Pleodorina, Polulichloris, Polytoma, Polytomella, Prasiola, Prasiolopsis, Prasiococcus, Prototheca, Pseudochlorella, Pseudocarteria, Pseudotrebouxia, Pteromonas, Pyrobotrys, Rosenvingiella, *Scenedesmus*, Spirogyra, Stephanosphaera, Tetrabaena, Tetraedron, *Tetraselmis*, Trebouxia, Trochisciopsis, Viridiella, Vitreochlamys, Volvox, Volvulina, Vulcanochloris, Watanabea, Yamagishiella, *Euglena, Isochrysis, Nannochloropsis*. In an embodiment, the microalga is *Chlamydomonas reinhardtii, Chlorella vulgaris, Chlorella sorokiniana, Chlorella protothecoides, Tetraselmis chui, Nannochloropsis oculate, Scenedesmus* obliquus, *Acutodesmus dimorphus, Dunaliella tertiolecta*, or *Heamatococus plucialis*. In another embodiment, the microalga is a diatom, optionally *Phaeodactylum tricornutum* or *Thalassiosira pseudonana*.

In another embodiment, the cyanobacterium is from Spirulinaceae, Phormidiaceae, Synechococcaceae, or Nostocaceae. In an embodiment, the cyanobacterium is Arthrospira plantesis, Arthrospira maxima, Synechococcus *elongatus*, or Aphanizomenon *flos-aquae*.

In another embodiment, the microorganism is a bacterium, for example from the genera *Escherichia, Bacillus, Caulobacter, Mycoplasma, Pseudomonas, Streptomyces*, or *Zymomonas*.

In another embodiment, the microorganism is a protist, for example from the genera Dictyostelium, Tetrahymena, Emiliania, or *Thalassiosira*.

In another emobodiment, the microorganism is a fungus, for example from the genera *Aspergillus, Saccharomyces, Schizosaccharomyces*, or *Fusarium*.

The present disclosure also provides a cell culture comprising a genetically engineered microorganism described herein for production of cannabinoid biosynthetic pathway products and a medium for culturing the genetically engineered microorganism. In an embodiment, the medium is substantially free of a sugar, i.e., the concentration of the sugar being less than 2%, less than 1.5%, less than 1%, less than 0.5%, or less than 0.1% by weight. In another embodiment, the medium contains no more than trace amounts of a sugar, a trace amount commonly understood in the art as referring to insignificant amounts or amounts near the limit of detection. Sugars known to be required for culturing microorganisms that are not capable of photosynthesis include, but are not limited to, monosaccharides (e.g., glucose, fructose, ribose, xylose, mannose, and galactose) and disaccharides (e.g., sucrose, lactose, maltose, lactulose, trehalose, and cellobiose).

In another embodiment, the medium is substantially free of a fixed carbon source, i.e., the concentration of the fixed carbon source being less than 2%, less than 1.5%, less than 1%, less than 0.5%, or less than 0.1% by weight. In another embodiment, the medium contains no more than trace amounts of a fixed carbon source. The term "fixed carbon source", as used herein, refers to an organic carbon molecule that provides a source of carbon for the growth and/or metabolism of a microorganism. Examples of fixed carbon sources include, but are not limited to, sugars, glycerol, and carboxylic acid (such as hexanoic acid, butyric acid and their respective salts).

Microorganisms may be cultured in conditions that are permissive to their growth. It is known that photosynthetic microorganisms are capable of carbon fixation wherein carbon dioxide (which is not a fixed carbon source) is fixed into organic molecules such as sugars using energy from a light source. The fixation of carbon dioxide using energy from a light source is photosynthesis. Suitable sources of light for the provision of energy in photosynthesis include sunlight and artificial lights. Photosynthetic microorganisms are capable of growth and/or metabolism without a fixed carbon source. Photosynthetic growth is a form of autotrophic growth, wherein a microorganism is able to produce organic molecules on its own using an external energy source such as light. This is in contrast to heterotrophic growth, wherein a microorganism must consume organic molecules for growth and/or metabolism. Heterotrophic organisms therefore require a fixed carbon source for growth and/or metabolism. Some photosynthetic organisms are capable of mixotrophic growth, wherein the microorganism fixes carbon by photosynthesis while also consuming fixed carbon sources. Microorganisms such as microalgae and cyanobacteria may be cultured using methods and conditions known in the art (see, e.g., Biofuels from Algae, eds. Pandey et al., 2014, Elsevier, ISBN 978-0-444-59558-4). Some microorganisms are capable of chemoautotrophic growth, Similar to photosynthetic microorganisms, chemoautotrophic organisms are capable of carbon dioxide fixation but using energy derived from chemical sources (e.g. hydrogen sulfide, ferrous iron, molecular hydrogen, ammonia) rather than light.

The present disclosure also provides a nucleic acid molecule comprising a nucleotide sequence encoding at least one, two, three, four, five, or six cannabinoid biosynthetic pathway enzyme, wherein the nucleic acid molecule comprises at least one polynucleotide sequence with at least 80%, 85%, 90%, 95%, 96%, 97%, 98%, 99%, or 100% sequence identity to a sequence selected from SEQ ID NO:1-14, 56-60, and 66-70. In one embodiment, the nucleic acid molecule comprises nucleic acid sequences encoding at least one, two, three, four, five or six of hexanoyl-CoA synthetase, type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase. In another embodiment, the nucleic acid molecule comprises nucleic acid sequences encoding at least one, two, three, four, or five of type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase without encoding hexanoyl-CoA synthetase.

In an embodiment, the nucleic acid molecule comprises at least a polynucleotide sequence with at least 80%, 85%, 90%, 95%, 96%, 97%, 98%, 99%, or 100% sequence identity to SEQ ID NO:1 and a polynucleotide sequence with at least 80%, 85%, 90%, 95%, 96%, 97%, 98%, 99%, or 100% sequence identity to SEQ ID NO:2. In another embodiment, the nucleic acid molecule comprises at least a polynucleotide sequence with at least 80%, 85%, 90%, 95%, 96%, 97%, 98%, 99%, or 100% sequence identity to SEQ ID NO:1 and a polynucleotide sequence with at least 80%, 85%, 90%, 95%, 96%, 97%, 98%, 99%, or 100% sequence identity to SEQ ID NO:3. In an embodiment, the nucleic acid molecule comprises at least a polynucleotide sequence with at least 80%, 85%, 90%, 95%, 96%, 97%, 98%, 99%, or 100% sequence identity to SEQ ID NO: 66 or 67. In another embodiment, the nucleic acid molecule comprises at least a polynucleotide sequence with at least 80%, 85%, 90%, 95%, 96%, 97%, 98%, 99%, or 100% sequence identity to SEQ ID NO:4, 68, 69, or 70, and optionally a polynucleotide sequence with at least 80%, 85%, 90%, 95%, 96%, 97%, 98%, 99%, or 100% sequence identity to SEQ ID NO:5. In another embodiment, the nucleic acid molecule comprises at least a polynucleotide sequence with at least 80%, 85%, 90%, 95%, 96%, 97%, 98%, 99%, or 100% sequence identity to SEQ ID NO:6 and/or a polynucleotide sequence with at least 80%, 85%, 90%, 95%, 96%, 97%, 98%, 99%, or 100% sequence identity to SEQ ID NO:7. In another embodiment, the nucleic acid molecule is comprised in a genetically engineered microorganism, optionally a GC-rich microalga, optionally *Chlamydomonas reinhardtii, Chlorella vulgaris, Chlorella sorokiniana, Chlorella protothecoides, Tetraselmis chui, Nannochloropsis oculate, Scenedesmus obliquus, Acutodesmus dimorphus, Dunaliella tertiolecta*, or *Heamatococus plucialis*.

In an embodiment, the nucleic acid molecule comprises at least a polynucleotide sequence with at least 80%, 85%, 90%, 95%, 96%, 97%, 98%, 99%, or 100% sequence identity to SEQ ID NO:8 and a polynucleotide sequence with at least 80%, 85%, 90%, 95%, 96%, 97%, 98%, 99%, or 100% sequence identity to SEQ ID NO:9. In another embodiment, the nucleic acid molecule comprises at least a polynucleotide sequence with at least 80%, 85%, 90%, 95%, 96%, 97%, 98%, 99%, or 100% sequence identity to SEQ ID NO:8 and a polynucleotide sequence with at least 80%, 85%, 90%, 95%, 96%, 97%, 98%, 99%, or 100% sequence identity to SEQ ID NO:10. In an embodiment, the nucleic acid molecule comprises at least a polynucleotide sequence with at least 80%, 85%, 90%, 95%, 96%, 97%, 98%, 99%, or 100% sequence identity to SEQ ID NO: 56 or 57. In another embodiment, the nucleic acid molecule comprises at least a polynucleotide sequence with at least 80%, 85%, 90%, 95%, 96%, 97%, 98%, 99%, or 100% sequence identity to SEQ ID NO:11, 58, 59, or 60, and optionally a polynucleotide sequence with at least 80%, 85%, 90%, 95%, 96%, 97%, 98%, 99%, or 100% sequence identity to SEQ ID NO:12. In another embodiment, the nucleic acid molecule comprises at least a polynucleotide sequence with at least 80%, 85%, 90%, 95%, 96%, 97%, 98%, 99%, or 100% sequence identity to SEQ ID NO:13 and/or a polynucleotide sequence with at least 80%, 85%, 90%, 95%, 96%, 97%, 98%, 99%, or 100% sequence identity to SEQ ID NO:14. In another embodiment, the nucleic acid molecule is comprised in a genetically engineered microorganism, optionally a diatom, optionally *Thalassiosira pseudonana* or *Phaeodactylum tricornutum*.

The phrase "introducing a nucleic acid molecule into a microorganism" includes both the stable integration of the nucleic acid molecule into the genome of a microorganism to prepare a genetically engineered microorganism as well as the transient integration of the nucleic acid into microorganism. The introduction of a nucleic acid into a cell is also known in the art as transformation. The nucleic acid vectors may be introduced into the microorganism using techniques known in the art including, without limitation, agitation with glass beads, electroporation, *agrobacterium*-mediated transformation, an accelerated particle delivery method, i.e. particle bombardment, a cell fusion method or by any other method to deliver the nucleic acid vectors to a microorganism.

Further provided is a method for producing a cannabinoid biosynthetic pathway product in a genetically engineered microorganism, comprising introducing into the microorganism at least one nucleic acid molecule encoding at least one, two, three, four, five, or six cannabinoid biosynthetic pathway enzyme, wherein the at least one nucleic acid molecule encoding the at least one, two, three, four, five, or six cannabinoid biosynthetic pathway enzyme comprises a polynucleotide sequence with at least 80%, 85%, 90%, 95%, 96%, 97%, 98%, 99%, or 100% sequence identity to a sequence selected from SEQ ID NO:1-14, 56-60, and 66-70, wherein the microorganism is a microalga or a cyanobacterium, and wherein the genetically engineered microorganism having increased production of at least one, two, three, four, five, six, seven or eight cannabinoid biosynthetic pathway products relative to the corresponding wild-type microorganism.

Further provided is a method for producing a cannabinoid biosynthetic pathway product in a genetically engineered microorganism, comprising introducing into the microorganism at least one nucleic acid molecule encoding at least one cannabinoid biosynthetic pathway enzyme, wherein the at least one cannabinoid biosynthetic pathway enzyme does not comprise hexanoyl-CoA synthetase, wherein the genetically engineered microorganism is a microalga or a cyanobacterium, and wherein the genetically engineered microorganism has increased production of at least one cannabinoid biosynthetic pathway product relative to the corresponding wild-type microorganism.

Further provided is a method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a photosynthetic microalga or a cyanobacterium, wherein the at least one nucleic acid molecule is an episomal vector, and wherein the genetically engineered microorganism has increased production of at least one cannabinoid biosynthetic pathway product relative to the corresponding wild-type microorganism.

Further provided is a method for producing a cannabinoid biosynthetic pathway product in a genetically engineered microorganism, comprising introducing into the microorganism at least one nucleic acid molecule encoding at least two cannabinoid biosynthetic pathway enzymes, wherein the at least one nucleic acid molecule comprises a promoter and at least two polynucleotide sequences, each of which encodes one cannabinoid biosynthetic pathway enzyme and is operably linked to the promoter, wherein the genetically engineered microorganism is a microalga or a cyanobacterium, and wherein the genetically engineered microorganism has increased production of at least one cannabinoid biosynthetic pathway product relative to the corresponding wild-type microorganism.

Further provided is a method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a cyanobacterium that does not belong to *Anabaena*, Gleocapsa, Phormidium, *Anacystis*, Synechococcus or Oscillatoria, and wherein the genetically engineered microorganism has increased production of at least one cannabinoid biosynthetic pathway product relative to the corresponding wild-type microorganism.

Further provided is a method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a diatom that does not belong to Amphora, Chaetoceros, Fragilaria, Cyclotella, Navicula, or *Nitzschia*, and wherein the genetically engineered microorganism has increased production of at least one cannabinoid biosynthetic pathway product relative to the corresponding wild-type microorganism.

Further provided is a method for producing a cannabinoid biosynthetic pathway product in a cell culture comprising a genetically engineered microorganism and a medium that is substantially free of a sugar, comprising introducing into the microorganism at least one nucleic acid molecule encoding at least one cannabinoid biosynthetic pathway enzyme, and incubating the genetically engineered microorganism in the medium for a period of time sufficient to produce a cannabinoid biosynthetic pathway product, wherein the genetically engineered microorganism is a microalga or a cyanobacterium, and wherein the genetically engineered microorganism has increased production of at least one cannabinoid biosynthetic pathway product relative to the corresponding wild-type microorganism.

In an embodiment, the method involves at least one nucleic acid molecule comprising nucleic acid sequence encoding at least one, two, three, four, five, or six of hexanoly-CoA synthetase, type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase. In another embodiment, the method involves at least one nucleic acid molecule comprising nucleic acid sequence encoding at least one, two, three, four, or five of type III polyketide synthase (e.g., tetraketide synthase, Steely 1 and Steely 2), olivetolic acid cyclase, aromatic prenyltransferase, tetrahydrocannabinolic acid synthase, or cannabidiolic acid synthase without encoding hexanoyl-CoA synthetase.

In another embodiment, the method involves at least one nucleic acid molecule comprising nucleic acid sequence encoding at least one, two, three, four, five, or six of hexanoyl-CoA synthetase comprises amino acid sequence with at least 90%, 95%, 96%, 97%, 98%, 99%, or 100% sequence identity to sequence as shown in SEQ ID NO:19, type III polyketide synthase comprises amino acid sequence with at least 90%, 95%, 96%, 97%, 98%, 99%, or 100% sequence identity to sequence as shown in SEQ ID NO:15, 61, or 62, olivetolic acid cyclase comprises amino acid sequence with at least 90%, 95%, 96%, 97%, 98%, 99%, or 100% sequence identity to sequence as shown in SEQ ID NO:16 or 17, aromatic prenyltransferase comprises amino acid sequence with at least 90%, 95%, 96%, 97%, 98%, 99%, or 100% sequence identity to sequence as shown in SEQ ID NO:18, 63, 64, or 65, tetrahydrocannabinolic acid synthase comprises amino acid sequence with at least 90%, 95%, 96%, 97%, 98%, 99%, or 100% sequence identity to sequence as shown in SEQ ID NO:20, and cannabidiolic acid synthetase comprises amino acid sequence with at least 90%, 95%, 96%, 97%, 98%, 99%, or 100% sequence identity to sequence as shown in SEQ ID NO:21.

In an embodiment, the method involves a promoter nucleic acid sequence selected from SEQ ID NO:38-45, wherein said promoter is operably-linked to a polynucleotide sequence with at least 80%, 85%, 90%, 95%, 96%, 97%, 98%, 99%, or 100% sequence identity to a sequence selected from SEQ ID NO:1-14, 56-60, and 66-70. In another embodiment, the method involves at least one tag sequence selected from SEQ ID NO:22-33, at least one intron sequence selected from SEQ ID NO:34-37, and/or a terminator nucleic acid sequence selected from SEQ ID NO:46-53.

In an embodiment, the method involves at least two polynucleotide sequences with at least 80%, 85%, 90%, 95%, 96%, 97%, 98%, 99%, or 100% sequence identity to a sequence selected from SEQ ID NO:1-14, 56-60, and 66-70. In another embodiment, the method involves at least one linker sequence between the at least two polynucleotide sequences. In another embodiment, the method involves a linker sequence that is a self-cleaving sequence, optionally SEQ ID NO:54 or 55.

In another embodiment, the method involves producing a cannabinoid biosynthetic pathway product in a microalga, wherein the microalga is a GC-rich microalga, optionally *Chlamydomonas reinhardtii*, or a diatom, optionally *Phaeodactylum tricornutum* or *Thalassiosira pseudonana*. In another embodiment, the method involves producing a cannabinoid biosynthetic pathway product in cyanobacteria, wherein the cyanobacteria are from Spirulinaceae, Phormidiaceae, Synechococcaceae, or Nostocaceae, optionally Arthrospira plantesis, Arthrospira maxima, Synechococcus *elongatus*, or Aphanizomenon *flos-aquae*. In another embodiment, the method involves introducing at least one nucleic acid molecule that is an episomal vector into the microorganism. In another embodiment, the method involves introducing at least one nucleic acid molecule described herein into the microorganism.

In another embodiment, the method involves production of at least one, two, three, four, five, six, seven, eight, nine, or ten cannabinoid biosynthetic pathway products including hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

The following non-limiting Example is illustrative of the present disclosure:

EMBODIMENTS

Particular embodiments of the disclosure include, without limitation, the following:

1. A genetically engineered microorganism that is capable of producing olivetolic acid, wherein the genetically engineered microorganism is a photosynthetic microalga or a cyanobacterium.

2. The genetically engineered microorganism of embodiment 1, wherein the genetically engineered microorganism does not comprise an exogenous nucleic acid molecule encoding hexanoyl-CoA synthetase.

3. The genetically engineered microorganism of embodiment 1 or 2, comprising at least one nucleic acid molecule that encodes tetraketide synthase and olivetolic acid cyclase.

4. The genetically engineered microorganism of embodiment 3, wherein the tetraketide synthase comprises amino acid sequence with at least 90% sequence identity to sequence as shown in SEQ ID NO:15, and the olivetolic acid cyclase comprises amino acid sequence with at least 90% sequence identity to sequence as shown in SEQ ID NO:16 or 17.

5. The genetically engineered microorganism of embodiment 3 or 4, wherein the at least one nucleic acid molecule comprises a promoter and two polynucleotide sequences, one encoding tetraketide synthase and the other encoding olivetolic acid cyclase, each of which is operably linked to the promoter.

6. The genetically engineered microorganism of embodiment 3 or 4, wherein the at least one nucleic acid molecule comprises a first nucleic acid molecule encoding tetraketide synthase and a second nucleic acid molecule encoding olivetolic acid cyclase.

7. The genetically engineered microorganism of any one of embodiments 3 to 6, wherein the at least one nucleic acid molecule is an episomal vector.

8. The genetically engineered microorganism of any one of embodiments 3 to 7, wherein the at least one nucleic acid molecule further encodes aromatic prenyltransferase.

9. The genetically engineered microorganism of embodiment 8, which is capable of producing cannabigerolic acid.

10. The genetically engineered microorganism of embodiment 8 or 9, wherein the aromatic prenyltransferase comprises amino acid sequence with at least 90% sequence identity to sequence as shown in SEQ ID NO:18, 63, 64, or 65.

11. The genetically engineered microorganism of any one of embodiments 8 to 10, wherein the at least one nucleic acid molecule further encodes tetrahydrocannabinolic acid synthase or cannabidiolic acid synthase.

12. The genetically engineered microorganism of embodiment 11, which is capable of producing Δ9-tetrahydrocanannabinolic acid or cannabidiolic acid.

13. The genetically engineered microorganism of embodiment 11 or 12, wherein the tetrahydrocannabinolic acid synthase comprises amino acid sequence with at least 90% sequence identity to sequence as shown in SEQ ID NO:20, and the cannabidiolic acid synthetase comprises amino acid sequence with at least 90% sequence identity to sequence as shown in SEQ ID NO:21.

14. The genetically engineered microorganism of embodiment 3 to 13, wherein the at least one nucleic acid molecule comprises at least one polynucleotide sequence with at least 80% sequence identity to a sequence selected from SEQ ID NO:1-4, 6-11, 13, 14, 58-60 and 68-70.

15. The genetically engineered microorganism of embodiment 14, wherein the at least one nucleic acid molecule comprises a promoter nucleic acid sequence, optionally selected from SEQ ID NO:38-45, wherein said promoter is operably-linked to the polynucleotide sequence with at least 80% sequence identity to a sequence selected from SEQ ID NO:1-4, 6-11, 13, 14, 58-60 and 68-70.

16. The genetically engineered microorganism of any one of embodiments 3 to 15, wherein the at least one nucleic acid molecule comprises at least one intron sequence, optionally selected from SEQ ID NO:34-37.

17. The genetically engineered microorganism of any one of embodiments 3 to 16, wherein the at least one nucleic acid molecule comprises a terminator nucleic acid sequence, optionally selected from SEQ ID NO:46-53.

18. The genetically engineered microorganism of any one of embodiments 3 to 17, wherein the at least one nucleic acid molecule comprises at least one tag sequence, optionally selected from SEQ ID NO:22-33.

19. The genetically engineered microorganism of any one of embodiments 3 to 18, wherein the at least one nucleic acid molecule comprises at least two polynucleotide sequences with at least 80% sequence identity to a sequence selected from SEQ ID NO:1-4, 6-11, 13, 14, 58-60 and 68-70.

20. The genetically engineered microorganism of embodiment 19, wherein the at least one nucleic acid molecule comprises at least one linker sequence between the at least two polynucleotide sequences.

21. The genetically engineered microorganism of embodiment 20, wherein the at least one linker sequence is a self-cleaving sequence, optionally selected from SEQ ID NO:54-55.

22. The genetically engineered microorganism of any one of embodiments 1 to 21, wherein the microalga is a GC-rich microalga, optionally *Chlamydomonas reinhardtii*, *Chlore-*

*lla vulgaris, Chlorella sorokiniana, Chlorella protothecoides, Tetraselmis chui, Nannochloropsis oculate,* Scenedesmus obliquus, *Acutodesmus dimorphus, Dunaliella tertiolecta,* or *Heamatococus plucialis.*

23. The genetically engineered microorganism of embodiment 22, wherein the microalga is *Chlamydomonas reinhardtii.*

24. The genetically engineered microorganism of any one of embodiments 1 to 21, wherein the microalga is a diatom, optionally *Phaeodactylum tricornutum* or *Thalassiosira pseudonana.*

25. The genetically engineered microorganism of embodiment 24, wherein the microalga is *Phaeodactylum tricornutum.*

26. The genetically engineered microorganism of embodiment 24, wherein the diatom does not belong to Amphora, Chaetoceros, Fragilaria, Cyclotella, Navicula, or *Nitzschia.*

27. The genetically engineered microorganism of any one of embodiments 1 to 21, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae.*

28. The genetically engineered microorganism of any one of embodiments 1 to 21, wherein the cyanobacterium does not belong to *Anabaena*, Gleocapsa, Phormidium, *Anacystis*, Synechococcus or Oscillatoria.

29. A genetically engineered microorganism that is capable of producing olivetol, wherein the genetically engineered microorganism is a microalga, optionally a photosynthetic microalga, or a cyanobacterium.

30. The genetically engineered microorganism of embodiment 29, wherein the genetically engineered microorganism does not comprise an exogenous nucleic acid molecule encoding hexanoyl-CoA synthetase.

31. The genetically engineered microorganism of embodiment 29 or 30, comprising at least one nucleic acid molecule that encodes Steely1, Steely 2, or a variant thereof.

32. The genetically engineered microorganism of embodiment 31, wherein the variant of Steely1 or Steely2 comprises amino acid sequence with at least 90% sequence identity to sequence as shown in SEQ ID NO:61 or 62, respectively.

33. The genetically engineered microorganism of any one of embodiments 31 or 32, wherein the at least one nucleic acid molecule is an episomal vector.

34. The genetically engineered microorganism of any one of embodiments 31 to 33, wherein the at least one nucleic acid molecule further encodes aromatic prenyltransferase.

35. The genetically engineered microorganism of embodiment 34, which is capable of producing cannabigerol.

36. The genetically engineered microorganism of embodiment 34 or 35, wherein the aromatic prenyltransferase comprises amino acid sequence with at least 90% sequence identity to sequence as shown in SEQ ID NO:18, 63, 64, or 65.

37. The genetically engineered microorganism of any one of embodiments 34 to 36, wherein the at least one nucleic acid molecule further encodes tetrahydrocannabinolic acid synthase or cannabidiolic acid synthase.

38. The genetically engineered microorganism of embodiment 37, which is capable of producing Δ9-tetrahydrocanannabinol or cannabidiol.

39. The genetically engineered microorganism of embodiment 37 or 38, wherein the tetrahydrocannabinolic acid synthase comprises amino acid sequence with at least 90% sequence identity to sequence as shown in SEQ ID NO:20, and the cannabidiolic acid synthetase comprises amino acid sequence with at least 90% sequence identity to sequence as shown in SEQ ID NO:21.

40. The genetically engineered microorganism of embodiment 31 to 39, wherein the at least one nucleic acid molecule comprises at least one polynucleotide sequence with at least 80% sequence identity to a sequence selected from SEQ ID NO: 4, 6, 7, 11, 13, 14, 56-60 and 66-70.

41. The genetically engineered microorganism of embodiment 40, wherein the at least one nucleic acid molecule comprises a promoter nucleic acid sequence, optionally selected from SEQ ID NO:38-45, wherein said promoter is operably-linked to the polynucleotide sequence with at least 80% sequence identity to a sequence selected from SEQ ID NO: 4, 6, 7, 11, 13, 14, 56-60 and 66-70.

42. The genetically engineered microorganism of any one of embodiments 31 to 41, wherein the at least one nucleic acid molecule comprises at least one intron sequence, optionally selected from SEQ ID NO:34-37.

43. The genetically engineered microorganism of any one of embodiments 31 to 42, wherein the at least one nucleic acid molecule comprises a terminator nucleic acid sequence, optionally selected from SEQ ID NO:46-53.

44. The genetically engineered microorganism of any one of embodiments 31 to 43, wherein the at least one nucleic acid molecule comprises at least one tag sequence, optionally selected from SEQ ID NO:22-33.

45. The genetically engineered microorganism of any one of embodiments 31 to 44, wherein the at least one nucleic acid molecule comprises at least two polynucleotide sequences with at least 80% sequence identity to a sequence selected from SEQ ID NO: 4, 6, 7, 11, 13, 14, 56-60 and 66-70.

46. The genetically engineered microorganism of embodiment 45, wherein the at least one nucleic acid molecule comprises at least one linker sequence between the at least two polynucleotide sequences.

47. The genetically engineered microorganism of embodiment 47, wherein the at least one linker sequence is a self-cleaving sequence, optionally selected from SEQ ID NO:54-55.

48. The genetically engineered microorganism of any one of embodiments 29 to 47, wherein the microalga is a GC-rich microalga, optionally *Chlamydomonas reinhardtii, Chlorella vulgaris, Chlorella sorokiniana, Chlorella protothecoides, Tetraselmis chui, Nannochloropsis oculate,* Scenedesmus obliquus, *Acutodesmus dimorphus, Dunaliella tertiolecta,* or *Heamatococus plucialis.*

49. The genetically engineered microorganism of embodiment 48, wherein the microalga is *Chlamydomonas reinhardtii.*

50. The genetically engineered microorganism of any one of embodiments 29 to 47, wherein the microalga is a diatom, optionally *Phaeodactylum tricornutum* or *Thalassiosira pseudonana.*

51. The genetically engineered microorganism of embodiment 50, wherein the microalga is *Phaeodactylum tricornutum.*

52. The genetically engineered microorganism of embodiment 50, wherein the diatom does not belong to Amphora, Chaetoceros, Fragilaria, Cyclotella, Navicula, or *Nitzschia.*

53. The genetically engineered microorganism of any one of embodiments 29 to 47, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae.*

54. The genetically engineered microorganism of any one of embodiments 29 to 47, wherein the cyanobacterium does not belong to *Anabaena*, Gleocapsa, Phormidium, *Anacystis*, Synechococcus or Oscillatoria.

55. A genetically engineered microorganism for production of cannabinoid biosynthetic pathway products comprising at least one nucleic acid molecule encoding at least one cannabinoid biosynthetic pathway enzyme, wherein the genetically engineered microorganism does not comprise an exogenous nucleic acid molecule encoding hexanoyl-CoA synthetase, wherein the genetically engineered microorganism is a microalga or a cyanobacterium, and wherein the genetically engineered microorganism has increased production of at least one cannabinoid biosynthetic pathway product relative to the corresponding wild-type microorganism.

56. The genetically engineered microorganism of embodiment 55, wherein the at least one nucleic acid molecule encodes at least one of type III polyketide synthase (e.g., tetraketide synthase, Steely 1 and Steely 2), olivetolic acid cyclase, aromatic prenyltransferase (e.g. CsPT1, Orf2, CsPT4, and HlPT1), tetrahydrocannabinolic acid synthase, or cannabidiolic acid synthase.

57. The genetically engineered microorganism of embodiment 56, wherein the at least one nucleic acid molecule encodes type III polyketide synthase and olivetolic acid cyclase.

58. The genetically engineered microorganism of embodiment 57, wherein the at least one nucleic acid molecule further encodes aromatic prenyltransferase.

59. The genetically engineered microorganism of embodiment 58, wherein the at least one nucleic acid molecule further encodes tetrahydrocannabinolic acid synthase and/or cannabidiolic acid synthase.

60. The genetically engineered microorganism of any one of embodiments 56 to 59, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

61. The genetically engineered microorganism of any one of embodiments 55 to 60, wherein the at least one nucleic acid molecule comprises at least one polynucleotide sequence with at least 80% sequence identity to a sequence selected from SEQ ID NO:1-4, 6-11, 13-14, 56-60, and 66-70.

61. The genetically engineered microorganism of embodiment 61, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:1-4, 6-11, 13-14, 56-60, and 66-70.

62. The genetically engineered microorganism of any one of embodiments 55-61, wherein the at least one nucleic acid molecule comprises at least one intron sequence, optionally selected from SEQ ID NO:34-37.

63. The genetically engineered microorganism of any one of embodiments 55-62, wherein the at least one nucleic acid molecule comprises a terminator nucleic acid sequence, optionally selected from SEQ ID NO:46-53.

64. The genetically engineered microorganism of any one of embodiments 55-63, wherein the at least one nucleic acid molecule comprises at least one tag sequence, optionally selected from SEQ ID NO:22-33.

65. The genetically engineered microorganism of any one of embodiments 55-64, wherein the at least one nucleic acid molecule comprises at least two polynucleotide sequences with at least 80% sequence identity to a sequence selected from SEQ ID NO:1-4, 6-11, 13-14, 56-60, and 66-70.

66. The genetically engineered microorganism of embodiment 65, wherein the at least one nucleic acid molecule comprises at least one linker sequence between the at least two polynucleotide sequences.

67. The genetically engineered microorganism of embodiment 66, wherein the at least one linker sequence is a self-cleaving sequence, optionally selected from SEQ ID NO:54-55.

68. The genetically engineered microorganism of any one of embodiments 55-67, wherein the microalga is a GC-rich microalga, optionally *Chlamydomonas reinhardtii*, *Chlorella vulgaris*, *Chlorella sorokiniana*, *Chlorella protothecoides*, *Tetraselmis chui*, *Nannochloropsis oculate*, *Scenedesmus obliquus*, *Acutodesmus dimorphus*, *Dunaliella tertiolecta*, or *Heamatococus plucialis*.

69. The genetically engineered microorganism of embodiment 68, wherein the microalga is *Chlamydomonas reinhardtii*.

70. The genetically engineered microorganism of any one of embodiments 55-67, wherein the microalga is a diatom, optionally *Phaeodactylum tricornutum* or *Thalassiosira pseudonana*.

71. The genetically engineered microorganism of embodiment 70, wherein the microalga is *Phaeodactylum tricornutum*.

72. The genetically engineered microorganism of any one of embodiments 55-67, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

73. The genetically engineered microorganism of any one of embodiments 55-72, wherein the at least one nucleic acid molecule is an episomal vector.

74. The genetically engineered microorganism of any one of embodiments 55-73, wherein the cannabinoid biosynthetic pathway product is at least one of trioxododecanoyl-CoA, olivetolic acid, olivetol, cannabigerolic acid, cannabigerol, Δ9-tetrahydrocanannabinolic acid, cannabidiolic acid, 49-tetrahydrocanannabinol, or cannabidiol.

75. The genetically engineered microorganism of embodiment 69, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

76. The genetically engineered microorganism of embodiment 69, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

77. The genetically engineered microorganism of embodiment 69, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is 49-tetrahydrocanannabinolic acid and cannabidiolic acid or Δ9-tetrahydrocanannabinol and cannabidiol.

78. The genetically engineered microorganism of embodiment 71, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

79. The genetically engineered microorganism of embodiment 71, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

80. The genetically engineered microorganism of embodiment 71, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

81. A method for producing a cannabinoid biosynthetic pathway product in a genetically engineered microorganism, comprising introducing into the microorganism at least one nucleic acid molecule encoding at least one cannabinoid biosynthetic pathway enzyme, wherein the at least one cannabinoid biosynthetic pathway enzyme does not comprise hexanoyl-CoA synthetase, wherein the genetically engineered microorganism is a microalga or a cyanobacterium, and wherein the genetically engineered microorganism has increased production of at least one cannabinoid biosynthetic pathway product relative to the corresponding wild-type microorganism.

82. The method of embodiment 81, wherein the at least one nucleic acid molecule encodes at least one of type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, cannabichromene synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

83. The method of embodiment 82, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

84. The method of any one of embodiments 81 to 83, wherein the at least one nucleic acid molecule comprises at least one polynucleotide sequence with at least 80% sequence identity to a sequence selected from SEQ ID NO:1-4, 6-11, 13-14, 56-60, and 66-70.

85. The method of embodiment 84, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:1-4, 6-11, 13-14, 56-60, and 66-70.

86. The method of any one of embodiments 81-85, wherein the at least one nucleic acid molecule comprises at least one intron sequence selected from SEQ ID NO:34-37.

87. The method of any one of embodiments 81-86, wherein the at least one nucleic acid molecule comprises a terminator nucleic acid sequence selected from SEQ ID NO:46-53.

88. The method of any one of embodiments 81-87, wherein the at least one nucleic acid molecule comprises at least one tag sequence selected from SEQ ID NO:22-33.

89. The method of any one of embodiments 81-88, wherein the at least one nucleic acid molecule comprises at least two polynucleotide sequences with at least 80% sequence identity to a sequence selected from SEQ ID NO:1-4, 6-11, 13-14, 56-60, and 66-70.

90. The method of embodiment 89, wherein the at least one nucleic acid molecule comprises at least one linker sequence between the at least two polynucleotide sequences.

91. The method of embodiment 90, wherein the linker sequence is a self-cleaving sequence, optionally selected from SEQ ID NO:54-55.

92. The method of any one of embodiments 81-91, wherein the microalga is a GC-rich microalga, optionally *Chlamydomonas reinhardtii, Chlorella vulgaris, Chlorella sorokiniana, Chlorella protothecoides, Tetraselmis chui, Nannochloropsis oculate, Scenedesmus* obliquus, *Acutodesmus dimorphus, Dunaliella tertiolecta,* or *Heamatococus plucialis*.

93. The method of embodiment 92, wherein the microalga is *Chlamydomonas reinhardtii*.

94. The method of any one of embodiments 81-91, wherein the microalga is a diatom, optionally *Phaeodactylum tricornutum* or *Thalassiosira pseudonana*.

95. The method of embodiment 94, wherein the microalga is *Phaeodactylum tricornutum*.

96. The method of any one of embodiments 81-91, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

97. The method of any one of embodiments 81-96, wherein the at least one nucleic acid molecule is an episomal vector.

98. The method of any one of embodiments 81-97, wherein the cannabinoid biosynthetic pathway product is at least one of trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

99. The method of embodiment 93, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or Δ9-tetrahydrocanannabinol.

100. The method of embodiment 93, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

101. The method of embodiment 93, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

102. The method of embodiment 95, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is 49-tetrahydrocanannabinolic acid or Δ9-tetrahydrocanannabinol.

103. The method of embodiment 95, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

104. The method of embodiment 95, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

105. A genetically engineered microorganism for production of cannabinoid biosynthetic pathway products comprising at least one nucleic acid molecule encoding at least one cannabinoid biosynthetic pathway enzyme, wherein the genetically engineered microorganism is a photosynthetic microalga or a cyanobacterium, wherein the at least one nucleic acid molecule is an episomal vector, and wherein the genetically engineered microorganism has increased production of at least one cannabinoid biosynthetic pathway product relative to the corresponding wild-type microorganism.

106. The genetically engineered microorganism of embodiment 105, wherein the at least one episomal vector encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

107. The genetically engineered microorganism of embodiment 106, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

108. The genetically engineered microorganism of any one of embodiments 105 to 107, wherein the at least one episomal vector comprises at least one polynucleotide sequence with at least 80% sequence identity to a sequence selected from SEQ ID NO:1-14, 56-60, and 66-70.

109. The genetically engineered microorganism of embodiment 108, wherein the at least one episomal vector comprises a promoter nucleic acid sequence selected from SEQ ID NO:38-45, wherein said promoter is operably-linked to the polynucleotide sequence with at least 80% sequence identity to a sequence selected from SEQ ID NO:1-14, 56-60, and 66-70.

110. The genetically engineered microorganism of any one of embodiments 105-109, wherein the at least one episomal vector comprises at least one intron sequence selected from SEQ ID NO:34-37.

111. The genetically engineered microorganism of any one of embodiments 105-110, wherein the at least one episomal vector comprises a terminator nucleic acid sequence selected from SEQ ID N0:46-53.

112. The genetically engineered microorganism of any one of embodiments 105-111, wherein the at least one episomal vector comprises at least one tag sequence selected from SEQ ID NO:22-33.

113. The genetically engineered microorganism of any one of embodiments 105-112, wherein the at least one episomal vector comprises at least two polynucleotide sequences with at least 80% sequence identity to a sequence selected from SEQ ID NO:1-14, 56-60, and 66-70.

114. The genetically engineered microorganism of embodiment 113, wherein the at least one episomal vector comprises at least one linker sequence between the at least two polynucleotide sequences.

115. The genetically engineered microorganism of embodiment 114, wherein the at least one linker sequence is a self-cleaving sequence, optionally selected from SEQ ID NO:54-55.

116. The genetically engineered microorganism of any one of embodiments 105-115, wherein the microalga is a GC-rich microalga, optionally *Chlamydomonas reinhardtii, Chlorella vulgaris, Chlorella sorokiniana, Chlorella prototheocoides, Tetraselmis chui, Nannochloropsis oculate, Scenedesmus* obliquus, *Acutodesmus dimorphus, Dunaliella tertiolecta,* or *Heamatococus plucialis*.

117. The genetically engineered microorganism of embodiment 116, wherein the microalga is *Chlamydomonas reinhardtii*.

118. The genetically engineered microorganism of any one of embodiments 105-115, wherein the microalga is a diatom, optionally *Phaeodactylum tricornutum* or *Thalassiosira pseudonana*.

119. The genetically engineered microorganism of embodiment 118, wherein the microalga is *Phaeodactylum tricornutum*.

120. The genetically engineered microorganism of any one of embodiments 105-115, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

121. The genetically engineered microorganism of any one of embodiments 105-120, wherein the cannabinoid biosynthetic pathway product is at least one of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

122. The genetically engineered microorganism of any one of embodiments 105-121, wherein the genetically engineered microorganism does not comprise an exogenous nucleic acid molecule encoding hexanoyl-CoA synthetase.

123. The genetically engineered microorganism of embodiment 117, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

124. The genetically engineered microorganism of embodiment 117, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

125. The genetically engineered microorganism of embodiment 117, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is 49-tetrahydrocanannabinolic acid and cannabidiolic acid or tetrahydrocanannabinol and cannabidiol.

126. The genetically engineered microorganism of embodiment 119, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

127. The genetically engineered microorganism of embodiment 119, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

128. The genetically engineered microorganism of embodiment 119, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is 49-tetrahydrocanannabinolic acid and cannabidiolic acid or tetrahydrocanannabinol and cannabidiol.

129. A method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a photosynthetic microalga or a cyanobacterium, wherein the at least one nucleic acid molecule is an episomal vector, and wherein the genetically engineered microorganism has increased production of at least one cannabinoid biosynthetic pathway product relative to the corresponding wild-type microorganism.

130. The method of embodiment 129, wherein the at least one episomal vector encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HlPT1), tetrahydrocannabinolic acid synthase, cannabichromene synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

131. The method of embodiment 130, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

132. The method of any one of embodiments 129 to 131, wherein the at least one episomal vector comprises at least one polynucleotide sequence with at least 80% sequence identity to a sequence selected from SEQ ID NO:1-14, 56-60, and 66-70.

133. The method of embodiment 132, wherein the at least one episomal vector comprises a promoter nucleic acid sequence selected from SEQ ID NO:38-45, wherein said promoter is operably-linked to the polynucleotide sequence with at least 80% sequence identity to a sequence selected from SEQ ID NO:1-14, 56-60, and 66-70.

134. The method of any one of embodiments 129-133, wherein the at least one episomal vector comprises at least one intron sequence selected from SEQ ID NO:34-37.

135. The method of any one of embodiments 129-134, wherein the at least one episomal vector comprises a terminator nucleic acid sequence selected from SEQ ID NO:46-53.

136. The method of any one of embodiments 129-135, wherein the at least one episomal vector comprises at least one tag sequence selected from SEQ ID NO:22-81.

137. The method of any one of embodiments 129-136, wherein the at least one episomal vector comprises at least two polynucleotide sequences with at least 80% sequence identity to a sequence selected from SEQ ID NO:1-14, 56-60, and 138. The method of embodiment 137, wherein the at least one episomal vector comprises at least one linker sequence between the at least two polynucleotide sequences.

139. The method of embodiment 138, wherein the linker sequence is a self-cleaving sequence, optionally selected from SEQ ID NO:54-55.

140. The method of any one of embodiments 129-139, wherein the microalga is a GC-rich microalga, optionally *Chlamydomonas reinhardtii, Chlorella vulgaris, Chlorella sorokiniana, Chlorella protothecoides, Tetraselmis chui, Nannochloropsis oculate, Scenedesmus* obliquus, *Acutodesmus dimorphus, Dunaliella tertiolecta,* or *Heamatococus plucialis*.

141. The method of embodiment 140, wherein the microalga is *Chlamydomonas reinhardtii*.

142. The method of any one of embodiments 129-139, wherein the microalga is a diatom, optionally *Phaeodactylum tricornutum* or *Thalassiosira pseudonana*.

143. The method of embodiment 142, wherein the microalga is *Phaeodactylum tricornutum*.

144. The method of any one of embodiments 129-139, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

145. The method of any one of embodiments 129-144, wherein the cannabinoid biosynthetic pathway product is at least one of hexanoyl-CoA, trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

146. The method of any one of embodiments 129-145, wherein the genetically engineered microorganism does not comprise an exogenous nucleic acid molecule encoding hexanoyl-CoA synthetase.

147. The method of embodiment 141, wherein the at least one episomal vector encodes all of type III polyketide synthase, olivetolic acid cyclase, aromatic prenyltransferase, and tetrahydrocannabinolic acid synthase, wherein the tetraketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or Δ9-tetrahydrocanannabinol.

148. The method of embodiment 141, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

149. The method of embodiment 141, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

150. The method of embodiment 143, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or Δ9-tetrahydrocanannabinol.

151. The method of embodiment 143, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

152. The method of embodiment 143, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

153. A genetically engineered microorganism for production of cannabinoid biosynthetic pathway products comprising at least one nucleic acid molecule encoding at least two cannabinoid biosynthetic pathway enzymes, wherein the at least one nucleic acid molecule comprises a promoter and at least two polynucleotide sequences, each of which encodes one cannabinoid biosynthetic pathway enzyme and is operably linked to the promoter, wherein the genetically engineered microorganism is a microalga or a cyanobacterium, and wherein the genetically engineered microorganism has increased production of at least one cannabinoid biosynthetic pathway product relative to the corresponding wild-type microorganism.

154. The genetically engineered microorganism of embodiment 153, wherein the at least one nucleic acid molecule encodes at least two of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

155. The genetically engineered microorganism of embodiment 154, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

156. The genetically engineered microorganism of any one of embodiments 153 to 155, wherein the at least one nucleic acid molecule comprises at least two polynucleotide sequences each with at least 80% sequence identity to a sequence selected from SEQ ID NO:1-14, 56-60, and 66-70.

157. The genetically engineered microorganism of any one of embodiments 153-156, wherein the promoter is selected from SEQ ID NO:38-45.

158. The genetically engineered microorganism of any one of embodiments 153-157, wherein the at least one nucleic acid molecule comprises at least one intron sequence selected from SEQ ID NO:34-37.

159. The genetically engineered microorganism of any one of embodiments 153-158, wherein the at least one nucleic acid molecule comprises a terminator nucleic acid sequence selected from SEQ ID N0:46-53.

160. The genetically engineered microorganism of any one of embodiments 153-159, wherein the at least one nucleic acid molecule comprises at least one tag sequence selected from SEQ ID NO:22-33.

161. The genetically engineered microorganism of any one of embodiments 153-160, wherein the at least one nucleic acid molecule comprises at least one linker sequence between the at least two polynucleotide sequences.

162. The genetically engineered microorganism of embodiment 161, wherein the at least one linker sequence is a self-cleaving sequence, optionally selected from SEQ ID NO:54-55.

163. The genetically engineered microorganism of any one of embodiments 153-162, wherein the microalga is a GC-rich microalga, optionally *Chlamydomonas reinhardtii, Chlorella vulgaris, Chlorella sorokiniana, Chlorella protothecoides, Tetraselmis chui, Nannochloropsis oculate, Scenedesmus obliquus, Acutodesmus dimorphus, Dunaliella tertiolecta*, or *Heamatococus plucialis*.

164. The genetically engineered microorganism of embodiment 163, wherein the microalga is *Chlamydomonas reinhardtii*.

165. The genetically engineered microorganism of any one of embodiments 153-162, wherein the microalga is a diatom, optionally *Phaeodactylum tricornutum* or *Thalassiosira pseudonana*.

166. The genetically engineered microorganism of embodiment 165, wherein the microalga is *Phaeodactylum tricornutum*.

167. The genetically engineered microorganism of any one of embodiments 153-162, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

168. The genetically engineered microorganism of any one of embodiments 153-167, wherein the at least one nucleic acid molecule is an episomal vector.

169. The genetically engineered microorganism of any one of embodiments 153-168, wherein the cannabinoid biosynthetic pathway product is at least one of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

170. The genetically engineered microorganism of any one of embodiments 153-169, wherein the genetically engineered microorganism does not comprise an exogenous nucleic acid molecule encoding hexanoyl-CoA synthetase.

171. The genetically engineered microorganism of embodiment 164, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

172. The genetically engineered microorganism of embodiment 164, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

173. The genetically engineered microorganism of embodiment 164, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is 49-tetrahydrocanannabinolic acid and cannabidiolic acid or tetrahydrocanannabinol and cannabidiol.

174. The genetically engineered microorganism of embodiment 166, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

175. The genetically engineered microorganism of embodiment 166, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

176. The genetically engineered microorganism of embodiment 166, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in type III polyketide synthase, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

177. A method for producing a cannabinoid biosynthetic pathway product in a genetically engineered microorganism, comprising introducing into the microorganism at least one nucleic acid molecule encoding at least two cannabinoid biosynthetic pathway enzymes, wherein the at least one nucleic acid molecule comprises a promoter and at least two polynucleotide sequences, each of which encodes one cannabinoid biosynthetic pathway enzyme and is operably linked to the promoter, wherein the genetically engineered microorganism is a microalga or a cyanobacterium, and wherein the genetically engineered microorganism has increased production of at least one cannabinoid biosynthetic pathway product relative to the corresponding wild-type microorganism.

178. The method of embodiment 177, wherein the at least one nucleic acid molecule encodes at least two of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, cannabichromene synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

179. The method of embodiment 178, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

180. The method of any one of embodiments 177 to 179, wherein the at least one nucleic acid molecule comprises at least two polynucleotide sequence with at least 80% sequence identity to a sequence selected from SEQ ID NO:1-14, 56-60, and 66-70.

181. The method of any one of embodiments 177-180, wherein the at least one nucleic acid molecule comprises a promoter nucleic acid sequence selected from SEQ ID NO:38-45.

182. The method of any one of embodiments 177-181, wherein the at least one nucleic acid molecule comprises at least one intron sequence selected from SEQ ID NO:34-37.

183. The method of any one of embodiments 177-182, wherein the at least one nucleic acid molecule comprises a terminator nucleic acid sequence selected from SEQ ID NO:46-53.

184. The method of any one of embodiments 177-183, wherein the at least one nucleic acid molecule comprises at least one tag sequence selected from SEQ ID NO:22-33.

185. The method of any one of embodiments 177-184, wherein the at least one nucleic acid molecule comprises at least one linker sequence between the at least two polynucleotide sequences.

186. The method of embodiment 185, wherein the linker sequence is a self-cleaving sequence, optionally selected from SEQ ID NO:54-55.

187. The method of any one of embodiments 177-186, wherein the microalga is a GC-rich microalga, optionally *Chlamydomonas reinhardtii, Chlorella vulgaris, Chlorella sorokiniana, Chlorella* protothecoides, Tetraselm is *chui, Nannochloropsis oculate, Scenedesmus* obliquus, *Acutodesmus dimorphus, Dunaliella tertiolecta*, or *Heamatococus plucialis*.

188. The method of embodiment 187, wherein the microalga is *Chlamydomonas reinhardtii*.

189. The method of any one of embodiments 177-186, wherein the microalga is a diatom, optionally *Phaeodactylum tricornutum* or *Thalassiosira pseudonana*.

190. The method of embodiment 189, wherein the microalga is *Phaeodactylum tricornutum*.

191. The method of any one of embodiments 177-186, wherein the cyanobacterium is a Spirulinaceae, Phormidiaceae, Synechococcaceae, or Nostocaceae, optionally Arthrospira plantesis, Arthrospira maxima, Synechococcus elongatus or Aphanizomenon *flos-aquae*.

192. The method of any one of embodiments 177-191, wherein the at least one nucleic acid molecule is an episomal vector.

193. The method of any one of embodiments 177-192, wherein the cannabinoid biosynthetic pathway product is at least one of hexanoyl-CoA, trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

194. The method of any one of embodiments 177-193, wherein the genetically engineered microorganism does not comprise an exogenous nucleic acid molecule encoding hexanoyl-CoA synthetase.

195. The method of embodiment 188, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or Δ9-tetrahydrocanannabinol.

196. The method of embodiment 188, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

197. The method of embodiment 188, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

198. The method of embodiment 190, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is 49-tetrahydrocanannabinolic acid or Δ9-tetrahydrocanannabinol.

199. The method of embodiment 190, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

200. The method of embodiment 190, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

201. A genetically engineered microorganism for production of cannabinoid biosynthetic pathway products comprising at least one nucleic acid molecule encoding at least one cannabinoid biosynthetic pathway enzyme, wherein the genetically engineered microorganism is a cyanobacterium that does not belong to *Anabaena*, Gleocapsa, Phormidium, *Anacystis*, Synechococcus or Oscillatoria, and wherein the genetically engineered microorganism has increased production of at least one cannabinoid biosynthetic pathway product relative to the corresponding wild-type microorganism.

202. The genetically engineered cyanobacterium of embodiment 201, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

203. The genetically engineered cyanobacterium of embodiment 202, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

204. The genetically engineered cyanobacterium of any one of embodiments 201-203, wherein the at least one nucleic acid molecule comprises a promoter nucleic acid sequence.

205. The genetically engineered cyanobacterium of any one of embodiments 201-204, wherein the at least one nucleic acid molecule comprises at least one intron sequence.

206. The genetically engineered cyanobacterium of any one of embodiments 201-205, wherein the at least one nucleic acid molecule comprises a terminator nucleic acid sequence.

207. The genetically engineered cyanobacterium of any one of embodiments 201-206, wherein the at least one nucleic acid molecule comprises at least one tag sequence.

208. The genetically engineered cyanobacterium of any one of embodiments 201-207, wherein the at least one nucleic acid molecule comprises at least two polynucleotide sequences each encoding one of hexanoyl-CoA synthetase, type III polyketide synthase, olivetolic acid cyclase, aromatic prenyltransferase, tetrahydrocannabinolic acid synthase, or cannabidiolic acid synthase.

209. The genetically engineered cyanobacterium of embodiment 208, wherein the at least one nucleic acid molecule comprises at least one linker sequence between the at least two polynucleotide sequences.

210. The genetically engineered cyanobacterium of embodiment 209, wherein the at least one linker sequence is a self-cleaving sequence.

211. The genetically engineered cyanobacterium of any one of embodiments 201-210, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flosaquae*.

212. The genetically engineered cyanobacterium of any one of embodiments 201-211, wherein the at least one nucleic acid molecule is an episomal vector.

213. The genetically engineered cyanobacterium of any one of embodiments 201-212, wherein the cannabinoid biosynthetic pathway product is at least one of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

214. The genetically engineered microorganism of any one of embodiments 201-213, wherein the genetically engineered microorganism does not comprise an exogenous nucleic acid molecule encoding hexanoyl-CoA synthetase.

215. The genetically engineered cyanobacterium of embodiment 211, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is 49-tetrahydrocanannabinolic acid or Δ9-tetrahydrocanannabinol.

216. The genetically engineered cyanobacterium of embodiment 211, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

217. The genetically engineered cyanobacterium of embodiment 211, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is 49-tetrahydrocanannabinolic acid and cannabidiolic acid or tetrahydrocanannabinol and cannabidiol.

218. A method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a cyanobacterium that does not belong to *Anabaena*, Gleocapsa, Phormidium, *Anacystis*, Synechococcus or Oscillatoria, and wherein the genetically engineered microorganism has increased production of at least one cannabinoid biosynthetic pathway product relative to the corresponding wild-type microorganism.

219. The method of embodiment 218, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, cannabichromene synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

220. The method of embodiment 219, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

221. The method of any one of embodiments 218-220, wherein the at least one nucleic acid molecule comprises a promoter nucleic acid sequence.

222. The method of any one of embodiments 218-221, wherein the at least one nucleic acid molecule comprises at least one intron sequence.

223. The method of any one of embodiments 218-222, wherein the at least one nucleic acid molecule comprises a terminator nucleic acid sequence.

224. The method of any one of embodiments 218-223, wherein the at least one nucleic acid molecule comprises at least one tag sequence.

225. The method of any one of embodiments 218-225, wherein the at least one nucleic acid molecule comprises at least two polynucleotide sequences each encoding one of hexanoyl-CoA synthetase, type III polyketide synthase, olivetolic acid cyclase, aromatic prenyltransferase, tetrahydrocannabinolic acid synthase, or cannabidiolic acid synthase.

226. The method of embodiment 225, wherein the at least one nucleic acid molecule comprises at least one linker sequence between the at least two polynucleotide sequences.

227. The method of embodiment 226 wherein the linker sequence is a self-cleaving sequence.

228. The method of any one of embodiments 218-227, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

229. The method of any one of embodiments 218-228, wherein the at least one nucleic acid molecule is an episomal vector.

230. The method of any one of embodiments 218-229, wherein the cannabinoid biosynthetic pathway product is at least one of hexanoyl-CoA, trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

231. The method of any one of embodiments 218-230, wherein the genetically engineered microorganism does not comprise an exogenous nucleic acid molecule encoding hexanoyl-CoA synthetase.

232. The method of embodiment 228, wherein the at least one nucleic acid molecule encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or Δ9-tetrahydrocanannabinol.

233. The method of embodiment 228, wherein the at least one nucleic acid molecule encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62 wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

234. The method of embodiment 228, wherein the at least one nucleic acid molecule encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

235. A genetically engineered microorganism for production of cannabinoid biosynthetic pathway products comprising at least one nucleic acid molecule encoding at least one cannabinoid biosynthetic pathway enzyme, wherein the genetically engineered microorganism is a diatom that does not belong to Amphora, Chaetoceros, Fragilaria, Cyclotella, Navicula, or *Nitzschia*, and wherein the genetically engineered microorganism has increased production of at least one cannabinoid biosynthetic pathway product relative to the corresponding wild-type microorganism.

236. The genetically engineered diatom of embodiment 235, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

237. The genetically engineered diatom of embodiment 236, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

238. The genetically engineered diatom of any one of embodiments 235 to 237, wherein the at least one nucleic acid molecule comprises at least one polynucleotide sequence with at least 80% sequence identity to a sequence selected from SEQ ID NO:8-14, 56-60.

239. The genetically engineered diatom of embodiment 238, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:8-14, 56-60.

240. The genetically engineered diatom of any one of embodiments 235-239, wherein the at least one nucleic acid molecule comprises at least one intron sequence selected from SEQ ID NO:34-37.

241. The genetically engineered diatom of any one of embodiments 235-184, wherein the at least one nucleic acid molecule comprises a terminator nucleic acid sequence selected from SEQ ID NO:46-53.

242. The genetically engineered diatom of any one of embodiments 235-241, wherein the at least one nucleic acid molecule comprises at least one tag sequence selected from SEQ ID NO:28-33.

243. The genetically engineered diatom of any one of embodiments 235-242, wherein the at least one nucleic acid molecule comprises at least two polynucleotide sequences with at least 80% sequence identity to a sequence selected from SEQ ID NO:8-14, 56-60.

245. The genetically engineered diatom of embodiment 243, wherein the at least one nucleic acid molecule comprises at least one linker sequence between the at least two polynucleotide sequences.

246. The genetically engineered diatom of embodiment 245, wherein the at least one linker sequence is a self-cleaving sequence, optionally SEQ ID NO:55.

247. The genetically engineered diatom of any one of embodiments 235-246, wherein the diatom is *Phaeodactylum tricornutum* or *Thalassiosira pseudonana*.

248. The genetically engineered diatom of embodiment 247, wherein the diatom is *Phaeodactylum tricornutum*.

249. The genetically engineered diatom of any one of embodiments 235-248, wherein the at least one nucleic acid molecule is an episomal vector.

250. The genetically engineered diatom of any one of embodiments 235-249, wherein the cannabinoid biosynthetic pathway product is at least one of trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

251. The genetically engineered microorganism of any one of embodiments 235-250, wherein the genetically engineered microorganism does not comprise an exogenous nucleic acid molecule encoding hexanoyl-CoA synthetase.

252. The genetically engineered diatom of embodiment 248, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is Δ9-tetrahydrocanannabinolic acid or 49-tetrahydrocanannabinol.

253. The genetically engineered diatom of embodiment 248, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

254. The genetically engineered diatom of embodiment 248, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65 wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

255. A method for producing a cannabinoid biosynthetic pathway product in a genetically engineered microorganism, comprising introducing into the microorganism at least one nucleic acid molecule encoding at least one cannabinoid biosynthetic pathway enzyme, wherein the genetically engineered microorganism is a diatom that does not belong to Amphora, Chaetoceros, Fragilaria, Cyclotella, Navicula, or Nitzschia, and wherein the genetically engineered microorganism has increased production of at least one cannabinoid biosynthetic pathway product relative to the corresponding wild-type microorganism.

256. The method of embodiment 255, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, cannabichromene synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

257. The method of embodiment 256, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

258. The method of any one of embodiments 255 to 257, wherein the at least one nucleic acid molecule comprises at least one polynucleotide sequence with at least 80% sequence identity to a sequence selected from SEQ ID NO:8-14, 56-60.

259. The method of embodiment 258, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:8-14, 56-60.

260. The method of any one of embodiments 255-259, wherein the at least one nucleic acid molecule comprises at least one intron sequence selected from SEQ ID NO:34-37.

261. The method of any one of embodiments 255-260, wherein the at least one nucleic acid molecule comprises a terminator nucleic acid sequence selected from SEQ ID NO:46-53.

262. The method of any one of embodiments 255-261, wherein the at least one nucleic acid molecule comprises at least one tag sequence selected from SEQ ID NO:28-33.

263. The method of any one of embodiments 255-262, wherein the at least one nucleic acid molecule comprises at least two polynucleotide sequences with at least 80% sequence identity to a sequence selected from SEQ ID NO:8-14, 56-60.

264. The method of embodiment 263, wherein the at least one nucleic acid molecule comprises at least one linker sequence between the at least two polynucleotide sequences.

265. The method of embodiment 264, wherein the linker sequence is a self-cleaving sequence, optionally SEQ ID NO:55.

266. The method of any one of embodiments 255-265, wherein the diatom is *Phaeodactylum tricornutum* or *Thalassiosira pseudonana*.

267. The method of embodiment 266, wherein the diatom is *Phaeodactylum tricornutum*.

268. The method of any one of embodiments 255-267, wherein the at least one nucleic acid molecule is an episomal vector.

269. The method of any one of embodiments 255-268, wherein the cannabinoid biosynthetic pathway product is at least one of trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

270. The method of any one of embodiments 255-269, wherein the genetically engineered microorganism does not comprise an exogenous nucleic acid molecule encoding hexanoyl-CoA synthetase.

271. The method of embodiment 267, wherein the at least one nucleic acid molecule is an episomal vector, wherein the at least one episomal vector encodes all of type III polyketide synthase, olivetolic acid cyclase, aromatic prenyltransferase, and tetrahydrocannabinolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabinoid biosynthetic pathway product is 49-tetrahydrocanannabinolic acid or Δ9-tetrahydrocanannabinol.

272. The method of embodiment 267, wherein the at least one nucleic acid molecule is an episomal vector, wherein the at least one episomal vector encodes all of type III polyketide synthase, olivetolic acid cyclase, aromatic prenyltransferase, and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the cannabidiolic acid synthetase comprises amino acid sequence with at least 90% sequence identity to sequence as shown in SEQ ID NO:21, and wherein the cannabinoid biosynthetic pathway product is cannabidiolic acid or cannabidiol.

273. The method of embodiment 267, wherein the at least one nucleic acid molecule is an episomal vector, wherein the at least one episomal vector encodes all of type III polyketide synthase, olivetolic acid cyclase, aromatic prenyltransferase, tetrahydrocannabinolic acid synthase and cannabidiolic acid synthase, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, wherein the cannabidiolic acid synthetase comprises amino acid sequence with at least 90% sequence identity to sequence as shown in SEQ ID NO:21, and wherein the cannabinoid biosynthetic pathway product is Δ9-tetrahydrocanannabinolic acid and cannabidiolic acid or tetrahydrocanannabinol and cannabidiol.

274. A cell culture comprising a genetically engineered microorganism for production of cannabinoid biosynthetic pathway products comprising at least one nucleic acid molecule encoding at least one cannabinoid biosynthetic pathway enzyme, and a medium that is substantially free of a sugar, wherein the genetically engineered microorganism is a microalga or a cyanobacterium, and wherein the genetically engineered microorganism has increased production of at least one cannabinoid biosynthetic pathway product relative to the corresponding wild-type microorganism.

275. The cell culture of embodiment 274, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

276. The cell culture of embodiment 275, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

277. The cell culture of any one of embodiments 274 to 276, wherein the at least one nucleic acid molecule comprises at least one polynucleotide sequence with at least 80% sequence identity to a sequence selected from SEQ ID NO:1-14, 56-60, and 66-70.

278. The cell culture of embodiment 277, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:1-14, 56-60, and 66-70.

279. The cell culture of any one of embodiments 274-278, wherein the at least one nucleic acid molecule comprises at least one intron sequence selected from SEQ ID NO:34-37.

280. The cell culture of any one of embodiments 274-279, wherein the at least one nucleic acid molecule comprises a terminator nucleic acid sequence selected from SEQ ID NO:46-53.

281. The cell culture of any one of embodiments 274-280, wherein the at least one nucleic acid molecule comprises at least one tag sequence selected from SEQ ID NO:22-33.

282. The cell culture of any one of embodiments 274-281, wherein the at least one nucleic acid molecule comprises at least two polynucleotide sequences with at least 80% sequence identity to a sequence selected from SEQ ID NO:1-14, 56-60, and 66-70.

283. The cell culture of embodiment 282, wherein the at least one nucleic acid molecule comprises at least one linker sequence between the at least two polynucleotide sequences.

284. The cell culture of embodiment 283, wherein the at least one linker sequence is a self-cleaving sequence, optionally selected from SEQ ID NO:54-55.

285. The cell culture of any one of embodiments 274-284, wherein the microalga is a GC-rich microalgae, optionally *Chlamydomonas reinhardtii, Chlorella vulgaris, Chlorella sorokiniana, Chlorella prototheicoides, Tetraselmis chui, Nannochloropsis oculate, Scenedesmus* obliquus, *Acutodesmus dimorphus, Dunaliella tertiolecta,* or *Heamatococus plucialis.*

286. The cell culture of embodiment 285, wherein the microalga is *Chlamydomonas reinhardtii.*

287. The cell culture of any one of embodiments 274-284, wherein the microalga is a diatom, optionally *Phaeodactylum tricornutum* or *Thalassiosira pseudonana.*

288. The cell culture of embodiment 287, wherein the microalga is *Phaeodactylum tricornutum.*

289. The cell culture of any one of embodiments 274-284, wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae*.

290. The cell culture of any one of embodiments 274-289, wherein the at least one nucleic acid molecule is an episomal vector.

291. The cell culture of any one of embodiments 274-290, wherein the cannabinoid biosynthetic pathway product is at least one of hexanoyl-CoA, trioxododecanoyl-CoA, olivetolic acid, olivetol, cannabigerolic acid, cannabigerol, 49-tetrahydrocanannabinolic acid, cannabidiolic acid, Δ9-tetrahydrocanannabinol, or cannabidiol.

292. The cell culture of any one of embodiments 274-291, wherein the genetically engineered microorganism does not comprise an exogenous nucleic acid molecule encoding hexanoyl-CoA synthetase.

293. The cell culture of any one of embodiments 274-292, wherein the sugar is present in the medium at a concentration of less than 2% by weight.

294. The cell culture of embodiment 293, wherein the sugar is present in the medium at a concentration of less than 1% by weight.

295. The cell culture of embodiment 294, wherein the sugar is present in the medium at a concentration of less than 0.5% by weight.

296. The cell culture of embodiment 295, wherein the sugar is present in the medium at a concentration of less than 0.1% by weight.

297. The cell culture of embodiment 296, wherein the sugar is present in the medium at no more than trace amounts.

298. The cell culture of any one of embodiments 274-297, wherein the sugar is a monosaccharide.

299. The cell culture of embodiment 298, wherein the monosaccharide is at least one of glucose, fructose, ribose, xylose, mannose, and galactose.

300. The cell culture of any one of embodiments 274-297, wherein the sugar is a disaccharide.

301. The cell culture of embodiment 300, wherein the disaccharide is at least one of sucrose, lactose, maltose, lactulose, trehalose, and cellobiose.

302. The cell culture of any one of embodiments 274-301, wherein the medium is substantially free of a fixed carbon source.

303. The cell culture of embodiment 302, wherein the fixed carbon source is at least one of carboxylic acid and glycerol.

304. The cell culture of embodiment 303, wherein the carboxylic acid is hexanoic acid.

305. The cell culture of any one of embodiment 274-304, wherein the cell culture undergoes autotrophic growth.

306. The cell culture of embodiment 305, wherein the autotrophic growth is photosynthetic growth.

307. The cell culture of embodiment 306, wherein the photosynthetic growth occurs in the presence of a solar light source.

308. The cell culture of embodiment 306, wherein the photosynthetic growth occurs in the presence of an artificial light source.

309. A method for producing a cannabinoid biosynthetic pathway product in a cell culture comprising a genetically engineered microorganism and a medium that is substantially free of a sugar, comprising introducing into the microorganism at least one nucleic acid molecule encoding at least one cannabinoid biosynthetic pathway enzyme, and incubating the genetically engineered microorganism in the medium for a period of time sufficient to produce a cannabinoid biosynthetic pathway product, wherein the genetically engineered microorganism is a microalga or a cyanobacterium, and wherein the genetically engineered microorganism has increased production of at least one cannabinoid biosynthetic pathway product relative to the corresponding wild-type microorganism.

310. The method of embodiment 309, wherein the at least one nucleic acid molecule encodes at least one of hexanoyl-CoA synthetase, type III polyketide synthase (e.g., tetraketide synthase, Steely 1 and Steely 2), olivetolic acid cyclase, aromatic prenyltransferase (e.g. CsPT1, Orf2, CsPT4, and HIPT1), tetrahydrocannabinolic acid synthase, or cannabidiolic acid synthase, preferably the at least one nucleic acid molecule encodes type III polyketide synthase and olivetolic acid cyclase, optionally further encodes aromatic prenyltransferase, and optionally further encodes tetrahydrocannabinolic acid synthase and/or cannabidiolic acid synthase.

311. The method of embodiment 310, wherein the hexanoyl-CoA synthetase comprises amino acid sequence with at least 90% sequence identity to sequence as shown in SEQ ID NO:19, wherein the type III polyketide synthase comprises amino acid sequence with at least 90% sequence identity to sequence as shown in SEQ ID NO:15, 61, or 62, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, 63, 64, or 65, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

312. The method of any one of embodiments 309 to 311, wherein the at least one nucleic acid molecule comprises at least one polynucleotide sequence with at least 80% sequence identity to a sequence selected from SEQ ID NO:1-14, 56-60, and 66-70.

313. The method of embodiment 312, wherein the at least one nucleic acid molecule comprises a promoter nucleic acid sequence selected from SEQ ID NO:38-45, wherein said promoter is operably-linked to the polynucleotide sequence with at least 80% sequence identity to a sequence selected from SEQ ID NO:1-14, 56-60, and 66-70.

314. The method of any one of embodiments 309-313, wherein the at least one nucleic acid molecule comprises at least one intron sequence selected from SEQ ID NO:34-37.

315. The method of any one of embodiments 309-314, wherein the at least one nucleic acid molecule comprises a terminator nucleic acid sequence selected from SEQ ID NO:46-53.

316. The method of any one of embodiments 309-315, wherein the at least one nucleic acid molecule comprises at least one tag sequence selected from SEQ ID NO:22-33.

317. The method of any one of embodiments 309-316, wherein the at least one nucleic acid molecule comprises at least two polynucleotide sequences with at least 80% sequence identity to a sequence selected from SEQ ID NO:1-14, 56-60, and 66-70.

318. The method of any one of embodiments 309-317, wherein the at least one nucleic acid molecule comprises at least one linker sequence between the at least two polynucleotide sequences.

319. The method of any one of embodiments 309-318, wherein the at least one linker sequence is a self-cleaving sequence, optionally selected from SEQ ID NO:54-55.

320. The method of any one of embodiments 309-319, wherein the microalga is a GC-rich microalgae, optionally *Chlamydomonas reinhardtii, Chlorella vulgaris, Chlorella sorokiniana, Chlorella protothecoides, Tetraselmis chui, Nannochloropsis oculate, Scenedesmus* obliquus, *Acutodesmus dimorphus, Dunaliella tertiolecta,* or *Heamatococus plucialis.*

321. The method of embodiment 320, wherein the microalga is *Chlamydomonas reinhardtii.*

322. The method of any one of embodiments 309-319, wherein the microalga is a diatom, optionally *Phaeodactylum tricornutum* or *Thalassiosira pseudonana.*

323. The method of embodiment 322, wherein the microalga is *Phaeodactylum tricornutum.*

324. The method of any one of embodiments 309-319, wherein the microalga is a cyanobacterium, and wherein the cyanobacterium is a Spirulinaceae, Phormidiaceae, Synechococcaceae, or Nostocaceae, optionally Arthrospira plantesis, Arthrospira maxima, Synechococcus *elongatus* or Aphanizomenon *flos-aquae.*

325. The method of any one of embodiments 309-324, wherein the at least one nucleic acid molecule is an episomal vector.

326. The method of any one of embodiments 309-325, wherein the cannabinoid biosynthetic pathway product is at least one of hexanoyl-CoA, trioxododecanoyl-CoA, olivetolic acid, olivetol, cannabigerolic acid, cannabigerol, Δ9-tetrahydrocanannabinolic acid, cannabidiolic acid, Δ9-tetrahydrocanannabinol, or cannabidiol.

327. The method of any one of embodiments 309-326, wherein the genetically engineered microorganism does not comprise an exogenous nucleic acid molecule encoding hexanoyl-CoA synthetase.

328. The method of any one of embodiments 309-327, wherein the sugar is present in the medium at a concentration of less than 2% by weight.

329. The method of embodiment 328, wherein the sugar is present in the medium at a concentration of less than 1% by weight.

330. The method of embodiment 329, wherein the sugar is present in the medium at a concentration of less than 0.5% by weight.

331. The method of embodiment 330, wherein the sugar is present in the medium at a concentration of less than 0.1% by weight.

332. The method of embodiment 331, wherein the sugar is present in the medium at no more than trace amounts.

333. The method of any one of embodiments 309-332, wherein the sugar is a monosaccharide.

334. The method of embodiment 333, wherein the monosaccharide is at least one of glucose, fructose, ribose, xylose, mannose, and galactose.

335. The method of any one of embodiments 309-332, wherein the sugar is a disaccharide.

336. The method of embodiment 335, wherein the disaccharide is at least one of sucrose, lactose, maltose, lactulose, trehalose, and cellobiose.

337. The method of any one of embodiments 309-336, wherein the medium is substantially free of a fixed carbon source.

338. The method of embodiment 337, wherein the fixed carbon source is at least one of carboxylic acid and glycerol.

339. The method of embodiment 338, wherein the carboxylic acid is hexanoic acid.

340. The method of any one of embodiments 309-339, wherein the cell culture undergoes autotrophic growth.

341. The method of embodiment 340, wherein the autotrophic growth is photosynthetic growth.

342. The method of embodiment 341, wherein the photosynthetic growth occurs in the presence of a solar light source.

343. The method of embodiment 341, wherein the photosynthetic growth occurs in the presence of an artificial light source.

344. A genetically engineered microorganism for production of cannabinoid biosynthetic pathway products comprising at least one nucleic acid molecule encoding at least one cannabinoid biosynthetic pathway enzyme, wherein the at least one nucleic acid molecule encoding the at least one cannabinoid biosynthetic pathway enzyme comprises a polynucleotide sequence with at least 80% sequence identity to a sequence selected from SEQ ID NO:1-14, wherein the genetically engineered microorganism is a microalga or a cyanobacterium, and wherein the genetically engineered microorganism has increased production of at least one cannabinoid biosynthetic pathway product relative to the corresponding wild-type microorganism.

345. The genetically engineered microorganism of embodiment 344, wherein the at least one nucleic acid molecule encodes at least one of hexanoyl-CoA synthetase, tetraketide synthase, olivetolic acid cyclase, aromatic prenyltransferase, tetrahydrocannabinolic acid synthase, or cannabidiolic acid synthase.

346. The genetically engineered microorganism of embodiment 345, wherein the hexanoyl-CoA synthetase comprises amino acid sequence with at least 90% sequence identity to sequence as shown in SEQ ID NO:19, wherein the tetraketide synthase comprises amino acid sequence with at least 90% sequence identity to sequence as shown in SEQ ID NO:15, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

347. The genetically engineered microorganism of any one of embodiments 344-346, wherein the at least one nucleic acid molecule encoding the at least one cannabinoid biosynthetic pathway enzyme comprises a promoter nucleic acid sequence selected from SEQ ID NO:38-45, wherein said promoter is operably-linked to a polynucleotide sequence with at least 80% sequence identity to a sequence selected from SEQ ID NO:1-14.

348. The genetically engineered microorganism of any one of embodiments 344-347, wherein the nucleic acid molecule comprises at least one intron sequence selected from SEQ ID NO:34-37.

349. The genetically engineered microorganism of any one of embodiments 344-348, wherein the nucleic acid molecule comprises a terminator nucleic acid sequence selected from SEQ ID NO:46-53.

350. The genetically engineered microorganism of any one of embodiments 344-349, wherein the nucleic acid molecule comprises at least one tag sequence selected from SEQ ID NO:22-33.

351. The genetically engineered microorganism of any one of embodiments 344-350, wherein the nucleic acid molecule comprises at least two polynucleotide sequences with at least 80% sequence identity to a sequence selected from SEQ ID NO:1-14.

352. The genetically engineered microorganism of embodiment 351, wherein the nucleic acid molecule comprises at least one linker sequence between the at least two polynucleotide sequences.

353. The genetically engineered microorganism of embodiment 352, wherein the linker sequence is a self-cleaving sequence, optionally SEQ ID NO:54 or 55.

354. The genetically engineered microorganism of any one of embodiments 344-353, wherein the microalga is a GC-rich microalga, optionally *Chlamydomonas reinhardtii*, or a diatom, optionally *Phaeodactylum tricornutum* or *Thalassiosira pseudonana*.

355. The genetically engineered microorganism of any one of embodiments 344-354, wherein the cyanobacterium is a Spirulinaceae, Phormidiaceae, Synechococcaceae, or Nostocaceae, optionally Arthrospira plantesis, Arthrospira maxima, Synechococcus *elongatus*, or Aphanizomenon *flos-aquae*.

356. The genetically engineered microorganism of any one of embodiments 344-355, wherein the at least one nucleic acid molecule is an episomal vector.

357. The genetically engineered microorganism of any one of embodiments 344-356, wherein the cannabinoid biosynthetic pathway product is at least one of hexanoyl-CoA, trioxododecanoyl-CoA, olivetolic acid, cannabigerolic acid, Δ9-tetrahydrocanannabinolic acid, cannabidiolic acid, 49-tetrahydrocanannabinol, or cannabidiol.

358. A nucleic acid molecule comprising a nucleotide sequence encoding at least one cannabinoid biosynthetic pathway enzyme, wherein the nucleic acid molecule comprises a polynucleotide sequence with at least 80% sequence identity to a sequence selected from SEQ ID NO:1-14.

359. The nucleic acid molecule of embodiment 358, wherein the at least one cannabinoid biosynthetic pathway enzyme comprises at least one of hexanoyl-CoA synthetase, tetraketide synthase, olivetolic acid cyclase, aromatic prenyltransferase, tetrahydrocannabinolic acid synthase, or cannabidiolic acid synthase.

360. The nucleic acid molecule of embodiment 359, wherein the hexanoyl-CoA synthetase comprises amino acid sequence with at least 90% sequence identity to sequence as shown in SEQ ID NO:19, wherein the tetraketide synthase comprises amino acid sequence with at least 90% sequence identity to sequence as shown in SEQ ID NO:15, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

361. The nucleic acid molecule of any one of embodiments 358-360, wherein the nucleic acid molecule encoding the at least one cannabinoid biosynthetic pathway enzyme comprises a promoter nucleic acid sequence selected from SEQ ID NO:38-45, wherein said promoter is operably-linked to a polynucleotide sequence with at least 80% sequence identity to a sequence selected from SEQ ID NO:1-14.

362. The nucleic acid molecule of any one of embodiments 358-361, wherein the nucleic acid molecule comprises at least one intron sequence selected from SEQ ID NO:34-37.

363. The nucleic acid molecule of any one of embodiments 358-362, wherein the nucleic acid molecule comprises a terminator nucleic acid sequence selected from SEQ ID NO:46-53.

364. The nucleic acid molecule of any one of embodiments 358-363, wherein the nucleic acid molecule comprises at least one tag sequence selected from SEQ ID NO:22-33.

365. The nucleic acid molecule of any one of embodiments 358-364, wherein the nucleic acid molecule comprises at least two polynucleotide sequences with at least 80% sequence identity to a sequence selected from SEQ ID NO:1-14.

366. The nucleic acid molecule of embodiment 365, wherein the nucleic acid molecule comprises at least one linker sequence between the at least two polynucleotide sequences.

367. The nucleic acid molecule of embodiment 366, wherein the linker sequence is a self-cleaving sequence, optionally SEQ ID NO:54 or 55.

368. The nucleic acid molecule of any one of embodiments 358-367, wherein the nucleic acid molecule is an episomal vector.

369. A vector comprising the nucleic acid molecule of any one of embodiments 358-368.

370. A host cell transformed with the nucleic acid molecule of any one of embodiments 358-368, or the vector of embodiment 26.

371. A method for producing a cannabinoid biosynthetic pathway product in a genetically engineered microorganism, comprising introducing into the microorganism at least one nucleic acid molecule encoding at least one cannabinoid biosynthetic pathway enzyme, wherein the at least one nucleic acid molecule encoding the at least one cannabinoid biosynthetic pathway enzyme comprises a polynucleotide sequence with at least 80% sequence identity to a sequence selected from SEQ ID NO:1-14, wherein the genetically engineered microorganism is a microalga or a cyanobacterium, and wherein the genetically engineered microorganism has increased production of at least one cannabinoid biosynthetic pathway product relative to the corresponding wild-type microorganism.

372. The method of embodiment 371, wherein the at least one nucleic acid molecule encodes at least one of hexanoly-CoA synthetase, tetraketide synthase, olivetolic acid cyclase, aromatic prenyltransferase, tetrahydrocannabinolic acid synthase, cannabichromene synthase, or cannabidiolic acid synthase.

373. The method of embodiment 372, wherein the hexanoyl-CoA synthetase comprises amino acid sequence with at least 90% sequence identity to sequence as shown in SEQ ID NO:19, wherein the tetraketide synthase comprises amino acid sequence with at least 90% sequence identity to sequence as shown in SEQ ID NO:15, wherein the olivetolic acid cyclase comprises amino acid sequence with at least 90% sequence identity to sequence as shown in SEQ ID NO:16 or 17, wherein the aromatic prenyltransferase comprises amino acid sequence with at least 90% sequence identity to sequence as shown in SEQ ID NO:18, wherein the tetrahydrocannabinolic acid synthase comprises amino acid sequence with at least 90% sequence identity to sequence as shown in SEQ ID NO:20, and wherein the cannabidiolic acid synthetase comprises amino acid sequence with at least 90% sequence identity to sequence as shown in SEQ ID NO:21.

374. The method of any one of embodiments 371-373, wherein the nucleic acid molecule encoding the at least one cannabinoid biosynthetic pathway enzyme comprises a promoter nucleic acid sequence selected from SEQ ID NO:38-45, wherein said promoter is operably-linked to a polynucleotide sequence with at least 80% sequence identity to a sequence selected from SEQ ID NO:1-14.

375. The method of any one of embodiments 371-374, wherein the nucleic acid molecule comprises at least one intron sequence selected from SEQ ID NO:34-37.

376. The method of any one of embodiments 371-375, wherein the nucleic acid molecule comprises a terminator nucleic acid sequence selected from SEQ ID NO:46-53.

377. The method of any one of embodiments 371-376, wherein the nucleic acid molecule comprises at least one tag sequence selected from SEQ ID NO:22-33.

378. The method of any one of embodiments 371-377, wherein the nucleic acid molecule comprises at least two polynucleotide sequences with at least 80% sequence identity to a sequence selected from SEQ ID NO:1-14.

379. The method of embodiment 378, wherein the nucleic acid molecule comprises at least one linker sequence between the at least two polynucleotide sequences.

380. The method of embodiment 379, wherein the linker sequence is a self-cleaving sequence, optionally SEQ ID NO:54 or 55.

381. The method of any one of embodiments 371-380, wherein the microalga is a GC-rich microalga, optionally *Chlamydomonas reinhardtii, Chlorella vulgaris, Chlorella sorokiniana, Chlorella protothecoides, Tetraselmis chui, Nannochloropsis oculate, Scenedesmus* obliquus, *Acutodesmus dimorphus, Dunaliella tertiolecta*, and *Heamatococus plucialis*; or a diatom, optionally *Phaeodactylum tricornutum* or *Thalassiosira pseudonana*.

382. The method of any one of embodiments 371-381, wherein the cyanobacterium is a Spirulinaceae, Phormidiaceae, Synechococcaceae, or Nostocaceae, optionally Arthrospira plantesis, Arthrospira maxima, Synechococcus *elongatus*, or Aphanizomenon *flos-aquae*.

383. The method of any one of embodiments 371-382, wherein the at least one nucleic acid molecule is an episomal vector.

384. The method of any one of embodiments 371-383, wherein the cannabinoid biosynthetic pathway product is at least one of hexanoyl-CoA, trioxododecanoyl-CoA, olivetolic acid, cannabigerolic acid, 49-tetrahydrocanannabinolic acid, cannabidiolic acid, Δ9-tetrahydrocanannabinol, or cannabidiol.

Example 1

Genetic Engineering of Sequences and Construction Cassettes Synthesis

The gene sequences encoding TKS and OAC were identified and the codons were optimized for maximal expression in *Chlamydomonas reinhardtii*. Genetic engineering of the DNA constructions was performed to increased expression of the transgenes.

Gene Sequences

Figure 2:
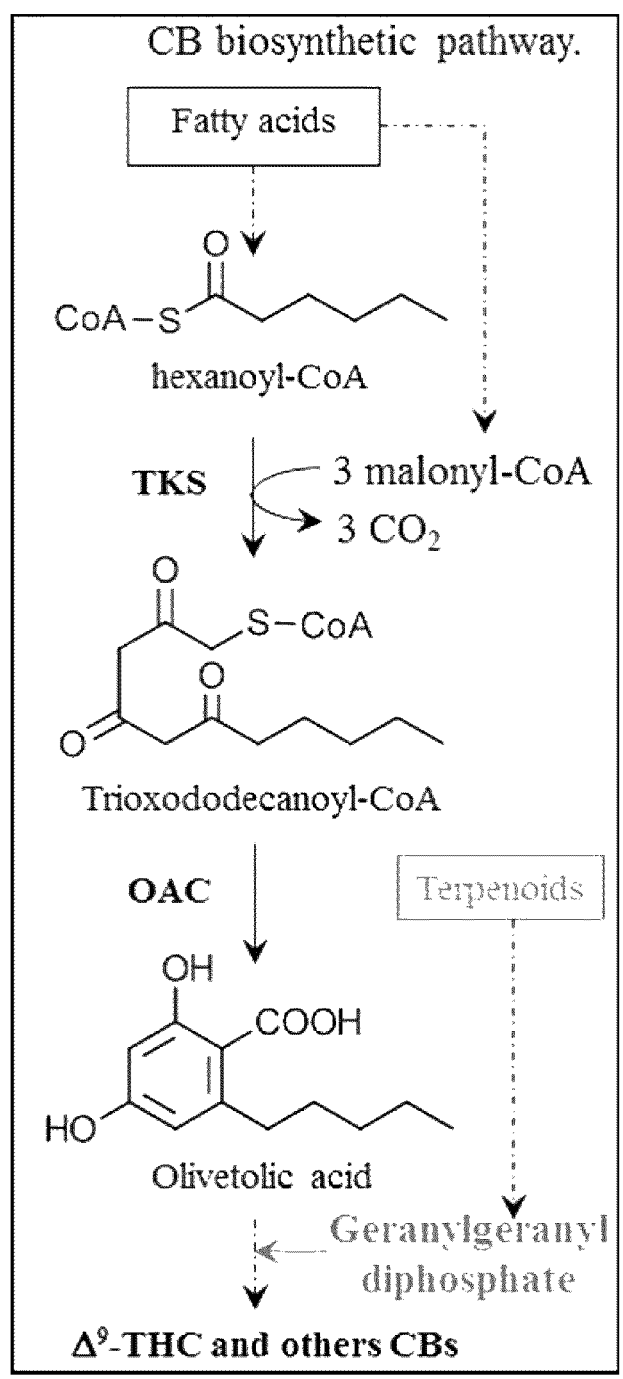
FIG. 2 shows a part of the cannabinoid biosynthetic pathway from Cannabis sativa ending in the production of olivetolic acid.

It has been suggested that hexanoyl-CoA synthetase convert hexanoic acid to hexanoyl-CoA early in CB biosynthetic pathway (FIG. 1; modified from Gagne et al 2012). Another early metabolite intermediate in the CB biosynthetic pathway is olivetolic acid (OA) that forms the polyketide skeleton of cannabinoids. Without wishing to be bound by theory, OA is produced as follows (FIG. 2): First, a type III tetra/polyketide synthase (TKS) enzyme condenses hexanoyl-CoA with three malonyl-CoA in a multi-step reaction to form trioxododecanoyl-CoA. Then, the olivetolic acid cyclase (OAC) catalyzes an intramolecular aldol condensation to yield OA. In subsequent steps, CB diversification is generated by the sequential action of "decorating" enzymes on the OA backbone, which leads to cannabinoids Δ9-tetrahydrocannabinolic acid (THCA) and cannabidiolic acid (CBDA), each of which decarboxylates to yield Δ9-tetrahydrocannabinol (THC) and cannabidiol (CBD), respectively (FIG. 1).

The gene sequence for TKS and OAC have been identified and characterized in vitro (Lussier 2012; Gagne et al 2012; Marks et al 2009; Stout et al 2012; Taura et al 2009). The complete coding sequences for non-optimized TKS (GenBank: AB164375.1) and OAC (GenBank: JN679224.1) were obtained from public databases. The open reading frame of TKS (1158 bp) encodes for a protein of 385 amino acids with a calculated MW of 42 kDa (Taura et al 2009; Flores-Sanchez et al 2010). Whereas OAC is a relatively small sequence (485 bp) encoding for a small protein of 101 amino acids and a MW of 12 kDa (Marks et al 2009). Without wishing to be bound by theory, codon optimization is suggested to improve protein expression in a host organism by replacing the nucleic acids coding for a particular amino acid (i.e. a codon) with another codon which is purportedly better expressed in the host organism. This effect may arise due to different organisms showing preferences for different codons. In particular, microalgae and cyanobacteria may prefer different codons from plants and animals. The process of altering the sequence of a nucleic acid to achieve better expression based on codon preference is called codon optimization. Statistical methods have been generated to analyze codon usage bias in various organisms and many computer algorithms have been developed to implement these statistical analyses in the design of codon optimized gene sequences (Lithwick and Margalit 2003). Other modifications in codon usage to increase protein expression that are not dependent on codon bias have also been described (Welch et al 2009). Sequences optimized for the codon usage of *Chlamydomonas reinhardtii* are shown in SEQ ID NO:1-7, 22-27, and 54. These optimized sequences can also be used for other GC-rich microalgae.

Genetic Engineering of DNA Constructions

Two engineered constructions for maximizing the expression of the transgenes are shown below.

Construction 1:

First, two genes, TKS and OAC, were included on the same open reading frame. These genes were separated with the self-cleaving sequence FMDV2A from the foot-and-mouth disease virus. This construction was named Cons1_TKS-FMDV-OAC or Construction1 (FIG. 3). It is expected that in *Chlamydomonas* cells, Construction1 will express both genes on the same mRNA, at the same level, since they are under the regulation of the same strong promoter. During the translation of the mRNA into protein, the FMDV self-cleaves, thus resulting in TKS and OAC as separated proteins. It has been suggested that in *Cannabis sativa*, these two proteins do not need to interact to produce olivetolic acid (Gagne et al 2012). Therefore, Construction1 should mimic what happens in *Cannabis*.

Construction 2:

To increase the metabolic flow of reactions, Construction 2 was built which links TKS and OAC together using a peptide linker (FIG. 3). The strategy behind this construction is to increase the efficiency of reactions by having the two proteins in the same cellular space. Without wishing to be bound by theory, enzyme fusion is considered a tool in metabolic engineering to increase pathway efficiency by reducing substrate loss and accumulation of toxic intermediates. This structural-functional complex between the sequential enzymes of CB biosynthetic metabolic pathway allows intermediate product from TKS to be passed (i.e. to promote substrate channeling) directly into the active site of the next consecutive enzyme, OAC. The restriction site BamHI was included in the sequence of Construction 2 as an additional tool and does not affect the expression of this transgene.

Gene Synthesis

Figure 4:
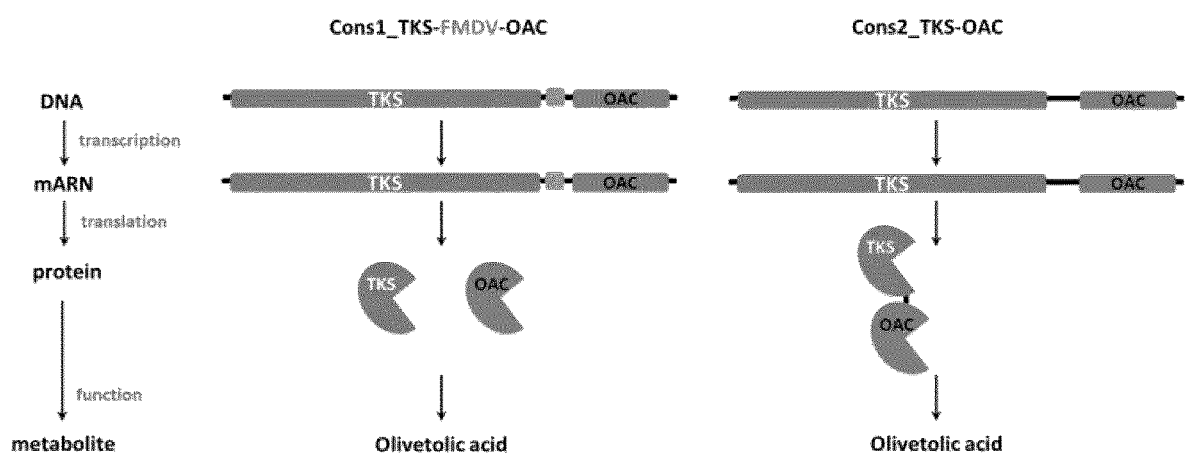
FIG. 4 shows schematic representations of the different engineered fusion genes expressed in microalgae cells.

The sequences encoding Constructions 1 and 2 were sent for synthesis. The skilled person can readily recognize the methods for synthesizing nucleic acid molecules containing the sequences. Two genetic constructions containing the genes TKS and OAC were engineered for optimal expression and synthesized by the company DNA2.0 (USA). The more the genes are expressed, the more enzymes will be made to catalyze more substrates into the desired product, olivetolic acid. FIG. 4 shows a summary of the engineered constructions functioning in cells. In *C. reinhardtii*, the genes (DNA) for each construction is transcribed into mRNA and exported to the cytosol. There in the cytosol, the mRNA is translated into proteins (enzymes TKS and OAC) which will be able to catalyze the formation of the target metabolite, olivetolic acid.

Example 2

Construction Assembly, Extraction and Purification of the Transformation Vectors The synthesized DNA constructions were assembled into integration and expression vectors to enhance expression of transgenes. Assembled vectors were transformed into *E. coli*, grown to bulk and large amount of pChlamy vectors were extracted and purified.

Assembly of the Transformation Vectors

The synthetic constructions were inserted into a default vector (KanR, high copy; FIG. 5A) which is used to transform *Escherichia coli* by electroporation. The transformed *E. coli* was grown to bulk plasmids containing the transgenes (synthetic constructions) and positive colonies confirmed by colony PCR (FIG. 5B). DNA gel of the colony-PCR from transformed *E. coli* shows the positive amplification of construction 1 (lane 1 and 2; 1213 bp), construction 2 (lane 4 and 5; 1192 bp), and lane 3 contains the DNA ladder from which the corresponding DNA size are labeled on the left of the gel (FIG. 5B). The plasmids were then extracted and ready for the synthetic constructions for assembly using the Gibson method (Gibson et al 2009). Two vectors were used for transformation of *C. reinhardtii*: pChlamy3 and pChlamy 4 (FIG. 5C). Each vector contains the strong hybrid promoter Hsp70A-RbcS2 and the intron 1 of RbcS2 in front of the cloning site to drive a strong expression of the synthetic construction (genes of interest) in *C. reinhardtii* (Schroda et al 2000; Diaz-Santos et al 2013). pChlamy 4 is a new generation of vector and, without wishing to be bound by theory, it contains additional features to allow a stronger expression. Such features include fusion (co-expression) of the selection marker zeocin resistance with the transgene, a 3' UTR for proper transcript termination and possible additional benefits like increased translation efficiency, mRNA stability, and polyadenylation signals (FIG. 5C). Thus, the synthetic constructions were PCR amplified with primers containing sequence for the Gibson assembly. The assembly was done using each synthetic construction into both pChlamy vectors. Table 2 summarizes the four possible combinations of construction/vector. Colony PCR coupled with Sanger sequencing confirmed correct reading frame of all combination of synthetic constructions/vectors (FIGS. 5D and 5E). DNA gel of the colony-PCR from transformed *E. coli* shows the positive amplification of the Gibson assembled synthetic constructions into pChlamy3 (FIG. 5D) and pChlamy4 (FIG. 5E) vectors. In particular, positive assembly of pChlamy3 with construction 1 (lane 1, 2 and 3; 1593 bp) and pChlamy3 with construction 2 (lane 4 and 5; 1557 bp) were confirmed (FIG. 5D). Also, positive assembly of pChlamy4 with construction 1 (lane 1, 2 and 3; 1615 bp) and pChlamy4 with construction 2 (lane 4 and 5; 1579 bp) were also confirmed (FIG. 5E). Lane 6 on both gels (FIGS. 5D and 5E) contains the DNA ladder from which the corresponding DNA MWs are labeled on the right of the gel.

TABLE 2

Summary of the combination between the synthetic constructions and the pChlamy vectors used.

|  | pChlamy3 | pChlamy4 |
| --- | --- | --- |
| Construction 1 (Cons1_TKS-FMDV-OAC) | pC3_1 | pC4_1 |
| Construction 2 (Cons2_TKS-OAC) | pC3_2 | pC4_2 |

Transformation of *E. coli*, Bulking and Purification of pChlamy Vectors

Figure 5:
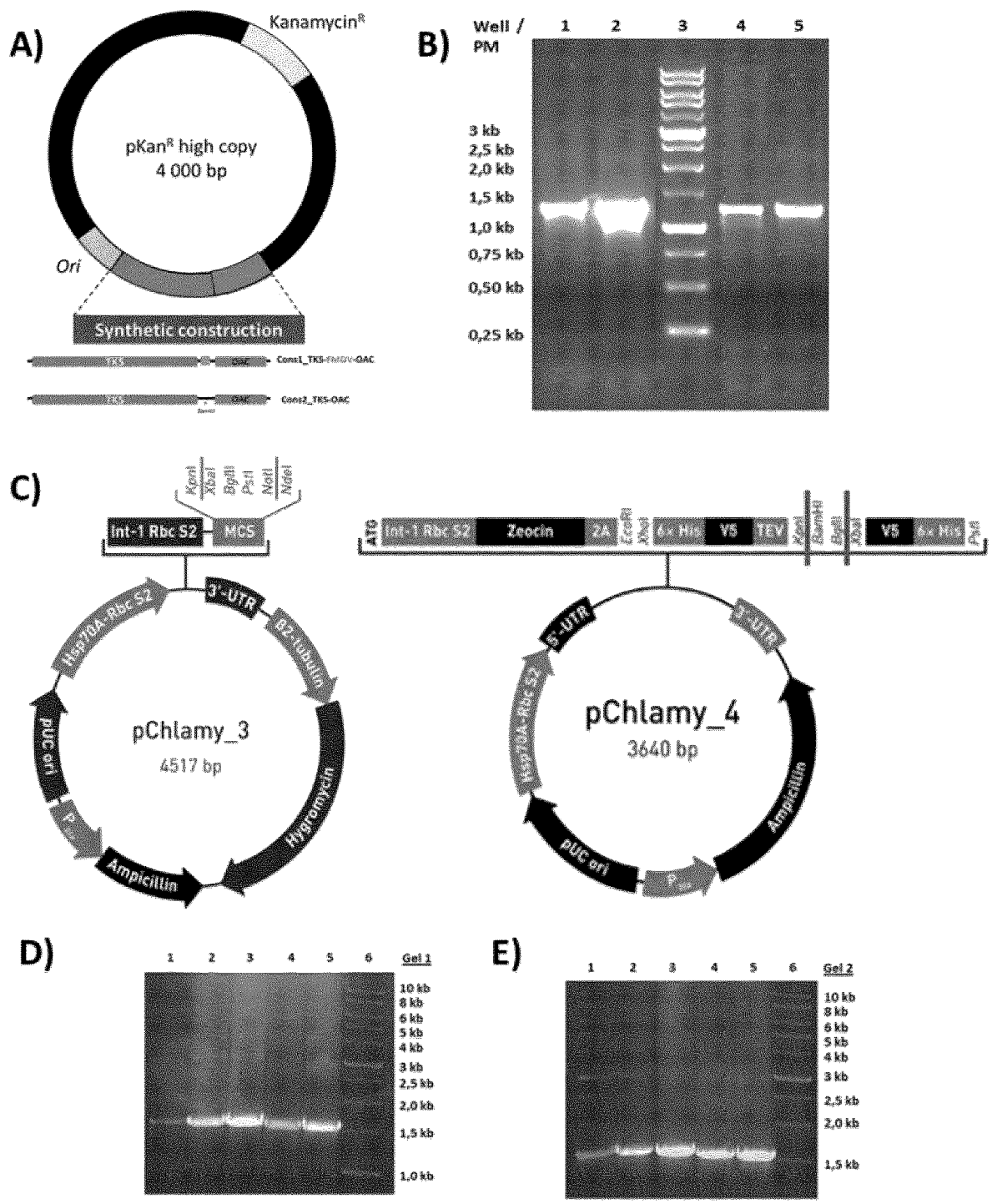
FIG. 5 shows the assembly and insertion of the synthetic constructions into pChlamy vectors. (A) The synthetic constructions were inserted into a default vector (pKan$^R$ high-copy) which is used to transform Escherichia coli. (B) The transformed E. coli was grown to bulk plasmids containing the transgenes (synthetic constructions) and positive colonies were confirmed using the colony PCR method. (C) Two vectors were used for the metabolic engineering of C. reinhardtii: pChlamy3 and pChlamy 4. (D and E) Example of gels of colony PCR results (the integrity of DNA sequences were confirmed with Sanger sequencing which confirmed successful in frame of all combination of synthetic constructions/vectors).
Figure 6:
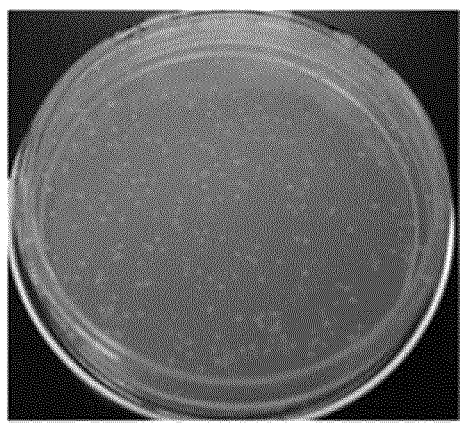
FIG. 6 shows the transformation of E. coli and extraction of the recombinant pChlamy vectors. (A) Transformed colonies for pC3_1, pC3_2, pC4-1 and pC4-2 vectors all grew on ampicillin plates. (B) Positive recombinant clones were grown and vectors were their size were verified on agarose gel.
Figure 6:
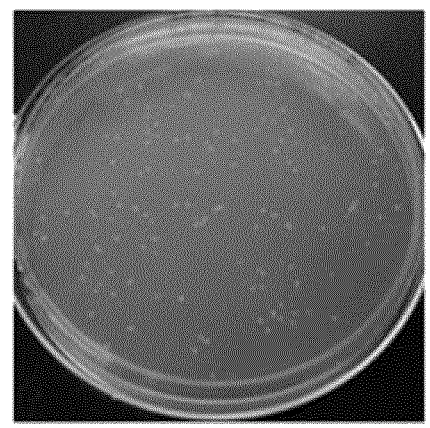
Figure 6:
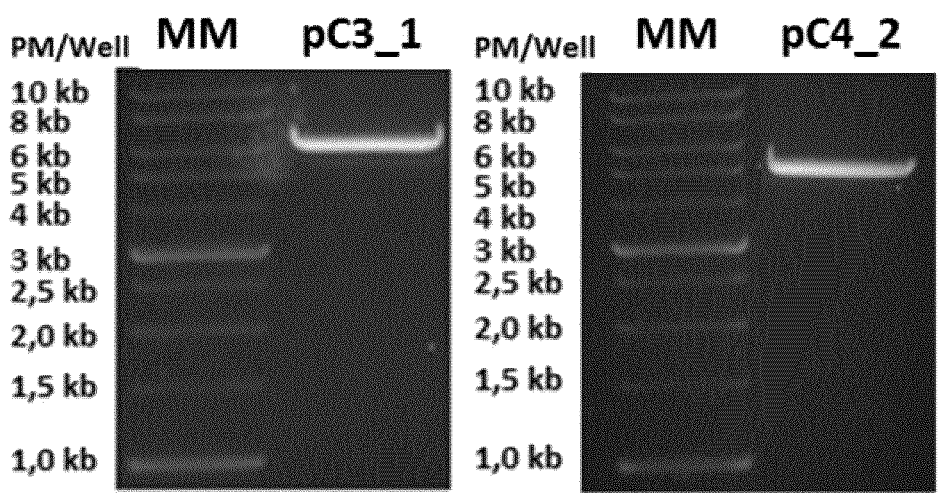

Each of the successfully assembled pChlamy vectors (FIG. 5; Table 2) were used to transform *E. coli* using the heat shock method. Transformed *E. coli* was grown to bulk vectors in order to purified large amounts for the subsequent transformation of microalgae. Transformed colonies for pC3_1, pC3_2, pC4-1 and pC4-2 vectors all grew on ampicillin plates (FIG. 6A) and positive colonies confirmed by colony PCR. Positive clones were grown and vectors were extracted and separated on agarose gel (FIG. 6B). Gel on the left shows pC3-1 at 6028 bp whereas the gel on the right shows PC4-2 at 5129 bp, and lane MM (Molecular Marker) contains the DNA ladder from which the corresponding DNA size are labeled on the left of the gel (FIG. 6B). Vectors were excised from gel and purified using columns from a vector purification kit (FroggaBio). Purified vectors were used for the transformation of *C. reinhardtii* cells as shown below. Large amount of purified *Chlamydomonas* vectors for four combinations were obtained.

Example 3

*Chlamydomonas reinhardtii* Cells Transformation and Selection of Positive Transformants Purified pChlamy vectors were used to transform *C. reinhardtii* through electroporation. Transformed cells were grown on antibiotic selection TAP solid media and the presence of the transgene was confirmed using the colony-polymerase chain reaction (PCR) method. Expression of transgenes was detected using real-time quantitative PCR (rt-qPCR) analysis and enzymes produced were detected using SDS-PAGE.

Transformation of *C. reinhardtii* with Purified pChlamy Vectors

*C. reinhardtii* cells were transformed with pChlamy vectors. Briefly, purified vectors were linearized using restriction enzyme Kpn1 and cells were electroporated in the presence of linear vector DNA. DNA was taken up by cells and integrated into the nuclear genome. Without wishing to be bound by theory, integration of exogenous DNA in *C. reinhardtii* is carried out by mechanisms involving non-homologous recombination (also known as non-homologous end joining), rather than homologous recombination (Plecenikova et al 2013). Homologous recombination is, however, the mechanism of choice when it comes to gene targeting since it allows insertion of the transgene in a very active part of the genome to bypass gene silencing mechanisms. Attempts to establish this method in *Chlamydomonas* have had limited success so far.

Figure 7:
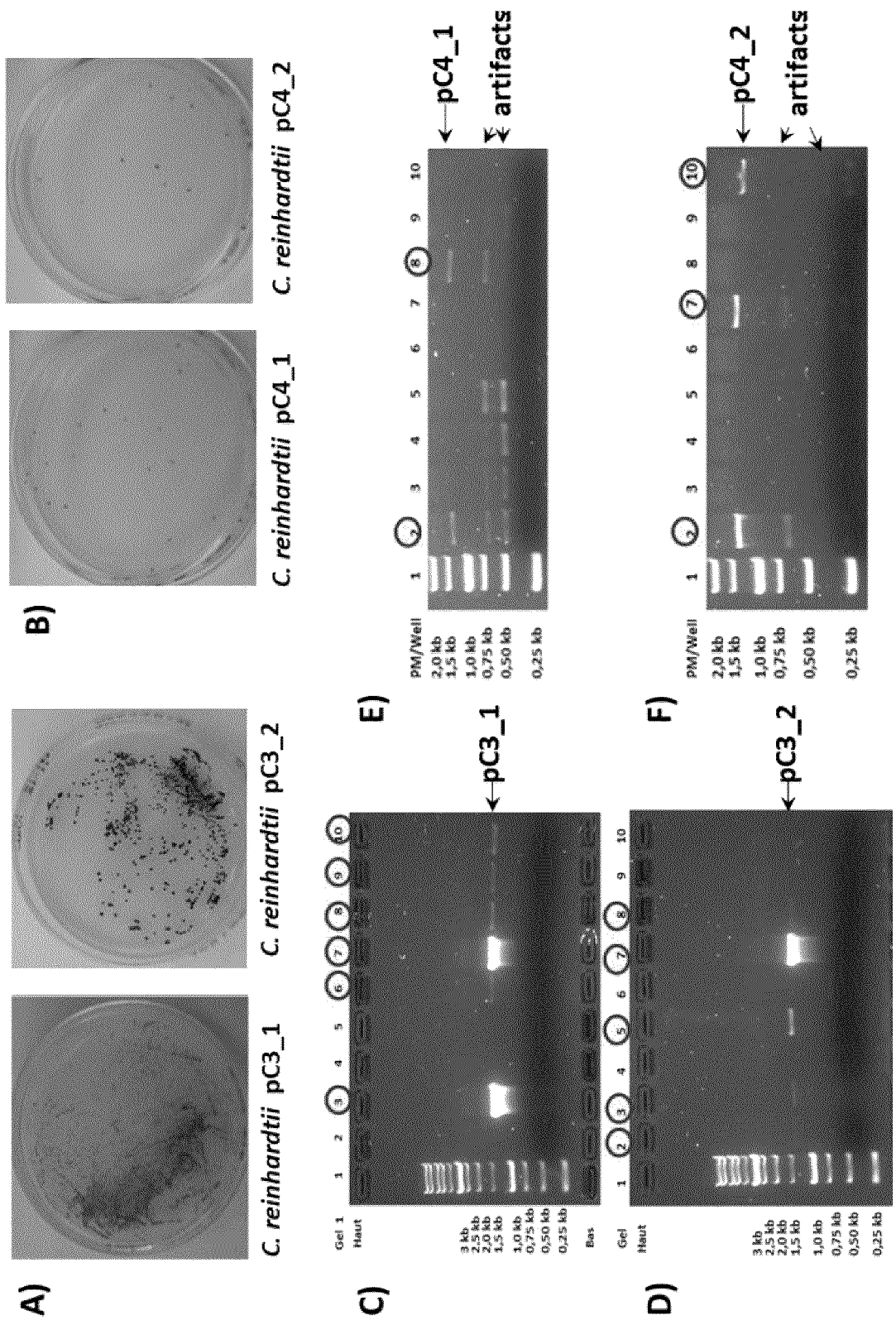
FIG. 7 shows Chlamydomonas transformation with recombinant linearized pChlamy vectors and screening by the colony PCR method. (A) Chlamydomonas transformed with recombinant pChlamy3 vectors (pC3_1, pC3_2) were grown on media containing hygromycin. (B) Cells transformed with recombinant pChlamy 4 vectors (pC4_1, pC4_2) were grown on media containing zeocin. (C-F) DNA gels of colony PCR confirms positive transformed Chlamydomonas colonies for (C) pC3_1, (D) pC3_2, (E) pC4-1 and (F) pC4_2.

Transformed cells were grown on selection media. *Chlamydomonas* transformed with pChlamy3 vectors were grown on media containing hygromycin (FIG. 7A) whereas cells transformed with pChlamy 4 vectors were grown on media containing zeocin (FIG. 7B). Positive cells were used for colony PCR to confirm the presence of the transgene (FIG. 7C-F). DNA gels of colony PCR confirm transformed *Chlamydomonas* colonies for pC3-1 (band at 1.337 kb from partial amplification of TKS-OAC sequence; FIG. 7C), pC3-2 (band at 1.304 kb from partial amplification of TKS-OAC sequence; FIG. 7D), pC4-1 (band at 1.311 kb from partial amplification of TKS-OAC sequence; FIG. 7E) and pC4-2 (band at 1.278 kb from partial amplification of TKS-OAC sequence; FIG. 7F). Lane 1 is the molecular marker that contains the DNA ladder from which the corresponding DNA sizes are labeled on the left of the gel, and lanes 2-10 correspond to different colonies where circles highlight the transformed *Chlamydomonas* containing the transgenes (FIG. 7C-F). Thus, *C. reinhardtii* cells containing the transgene randomly inserted in the nuclear genome were successfully created.

Confirmation of the Expression of TKS and OAC in *C. reinhardtii*

Figure 8:
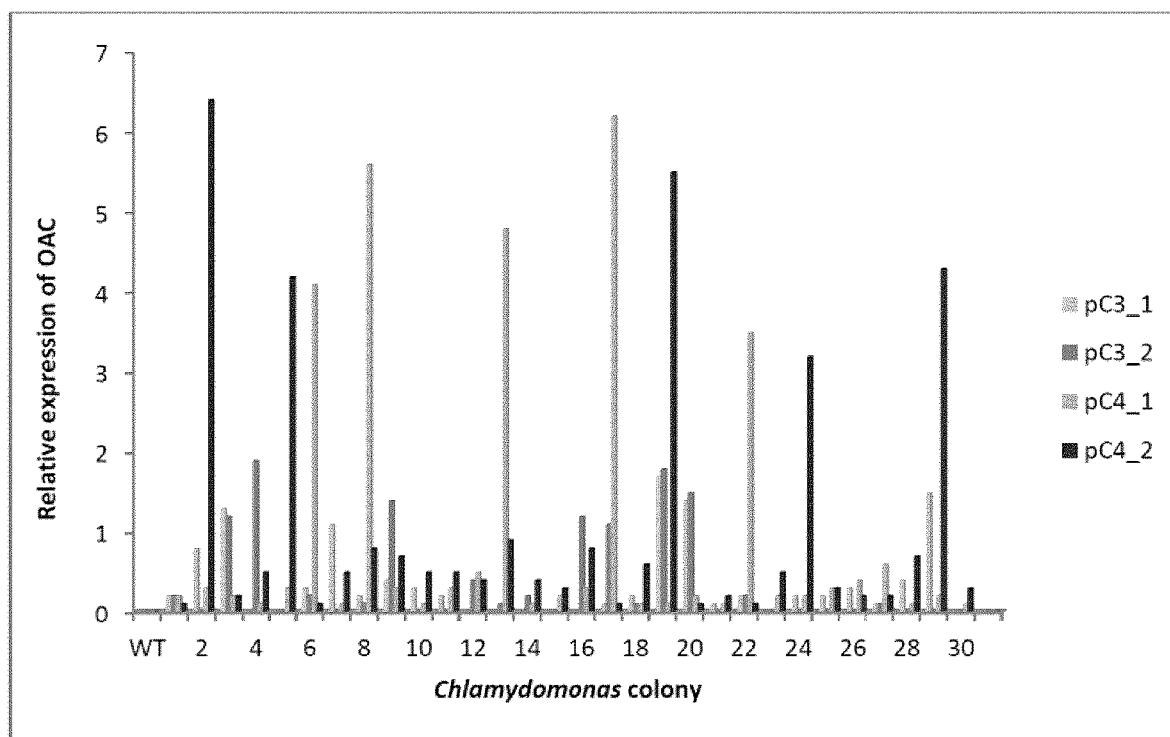
FIG. 8 shows qRT-PCR analysis of the relative expression of the OAC transgene in Chlamydomonas cells transformed with recombinant pChlamy vectors such as pC3_1, pC3_2, pC4-1 and pC4_2.

Using quantitative PCR (qPCR) analyses, the expression of OAC of 30 different colonies for each constructions was screened (FIG. 8). Colonies that were expressing OAC above 1X were detected. For pChlamy3 transformed cells, 5/30 pC3-1 colonies and 6/30 pC3-2 colonies were found to express detectable OAC transcript above the 1X. The same ratio was observed for pChlamy4 transformed cells where 5/30 (pC4_1) and 5/30 (pC4_2) colonies showed expression above 1X. Without wishing to be bound by theory, transgene expression from the *Chlamydomonas* nuclear genome via the pChlamy4 vector offers several advantages over pChlamy3, including better expression due to reduced silencing from the fusion of the transgene to the zeocin resistance gene, sh-ble. In addition, pChlamy4 vectors offer protein tags such as 6His TEV and V5-His epitopes that can be fused to the transgene for detection and purification of the translated proteins. Thus, *Chlamydomonas* transformed with pC4 vectors are candidates for production of olivetolic acid.

Figure 9:
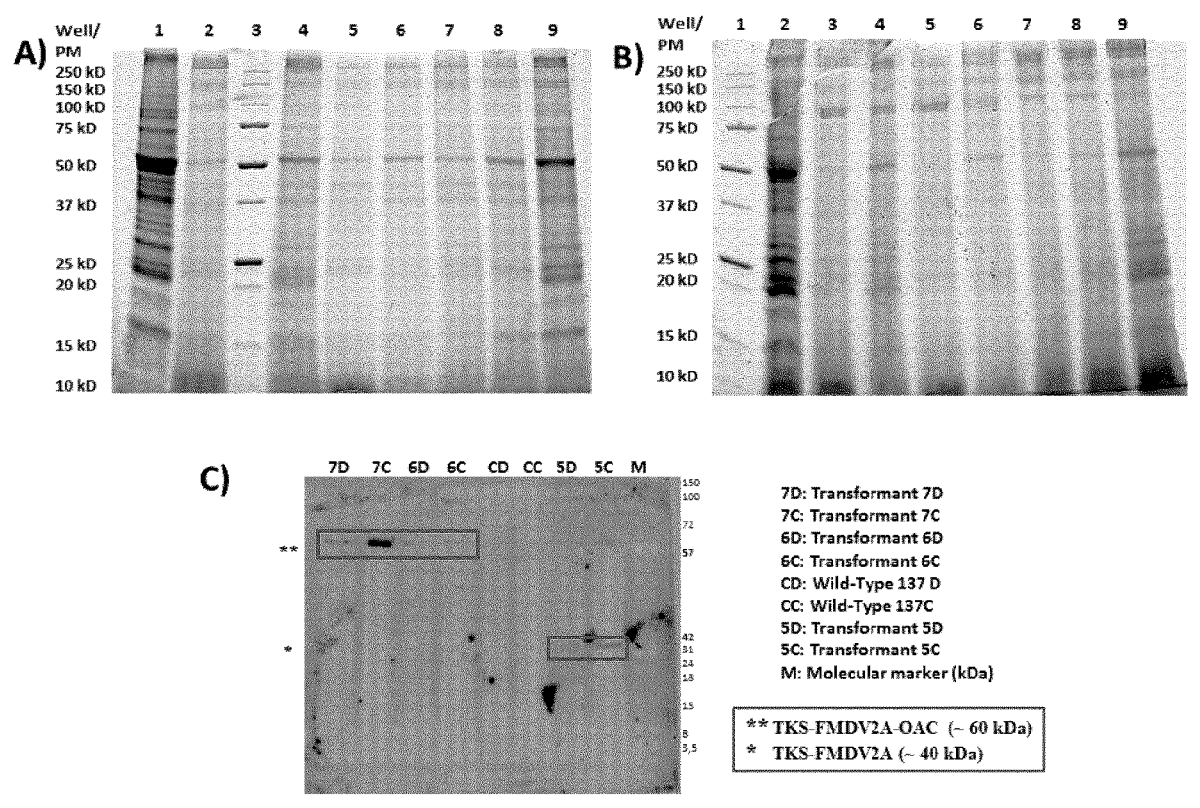

Total proteins were extracted from pChalmy4-transformed cells and separated by SDS-PAGE (FIG. 9) followed by Western blot with anti-FMDV-2A antibodies to detect TKS-FMDV2A-OAC proteins and/or the self-cleaved TKS-FMDV2A proteins produced. On SDS-PAGE gel, pC4-1 transformed cells do not show an increase of a band at 60 kDa (expected TKS-OAC fused protein) compared to control cells (lane1) (FIG. 9A; lane 3 contains the protein molecular marker). pC4-2 transformed cells do not show an increase of a band at 12 kDa (OAC protein alone) compared to control cells (lane 2) (FIG. 9B; lane 1 contains the protein molecular marker). However, Western blot analysis using anti-FMDV-2A antibodies detected TKS-FMDV2A-OAC proteins (FIG. 9C; lanes1-4) and the self-cleaved TKS-FMDV2A proteins (FIG. 9C; lanes 7-8).

Hence, this Example shows the successful transformation of *Chlamydomonas* and the transgene was integrated into the nuclear genome. Stable transformants were screen for expression of the OAC transgene and positive strains detected.

Example 4

Episomal Vectors Construction and Diatom *Phaeodactylum tricornutum* Cells Transformation Engineered Diatoms Microalgae provide a promising but challenging platform for the bioproduction of high value chemicals. Compared with model organisms such as *Escherichia coli* and *Saccharomyces cerevisiae*, characterization of the complex biology and biochemistry of algae and strain improvement has been hampered by inefficient molecular tools. To date, many microalgae are transformable but the introduced DNA is integrated randomly into the nuclear genome. Without wishing to be bound by theory, since integration of exogenous DNA in *Chlamydomonas reinhardtii* is principally carried out by mechanisms involving non-homologous recombination, the chance to encounter gene silencing is high, not the least because *Chlamydomonas* may be considered to possess high-silencing mechanisms. Hence, molecular tools to circumvent these challenges are necessary to facilitate efficient genetic engineering. Recently, an episomal vector system for diatoms was developed and shown to be highly stable (Karas et al 2015). Since episomes should not be affected by gene silencing mechanism, a diatom strain was engineered with the OAC-TKS transgene. Sequences optimized for the codon usage of *Phaeodactylum tricornutum* are shown in SEQ ID NO:8-14, 29-34 and 57. These optimized sequences can also be used for other diatoms such as *Thalassiosira pseudonana*.

Figure 10:
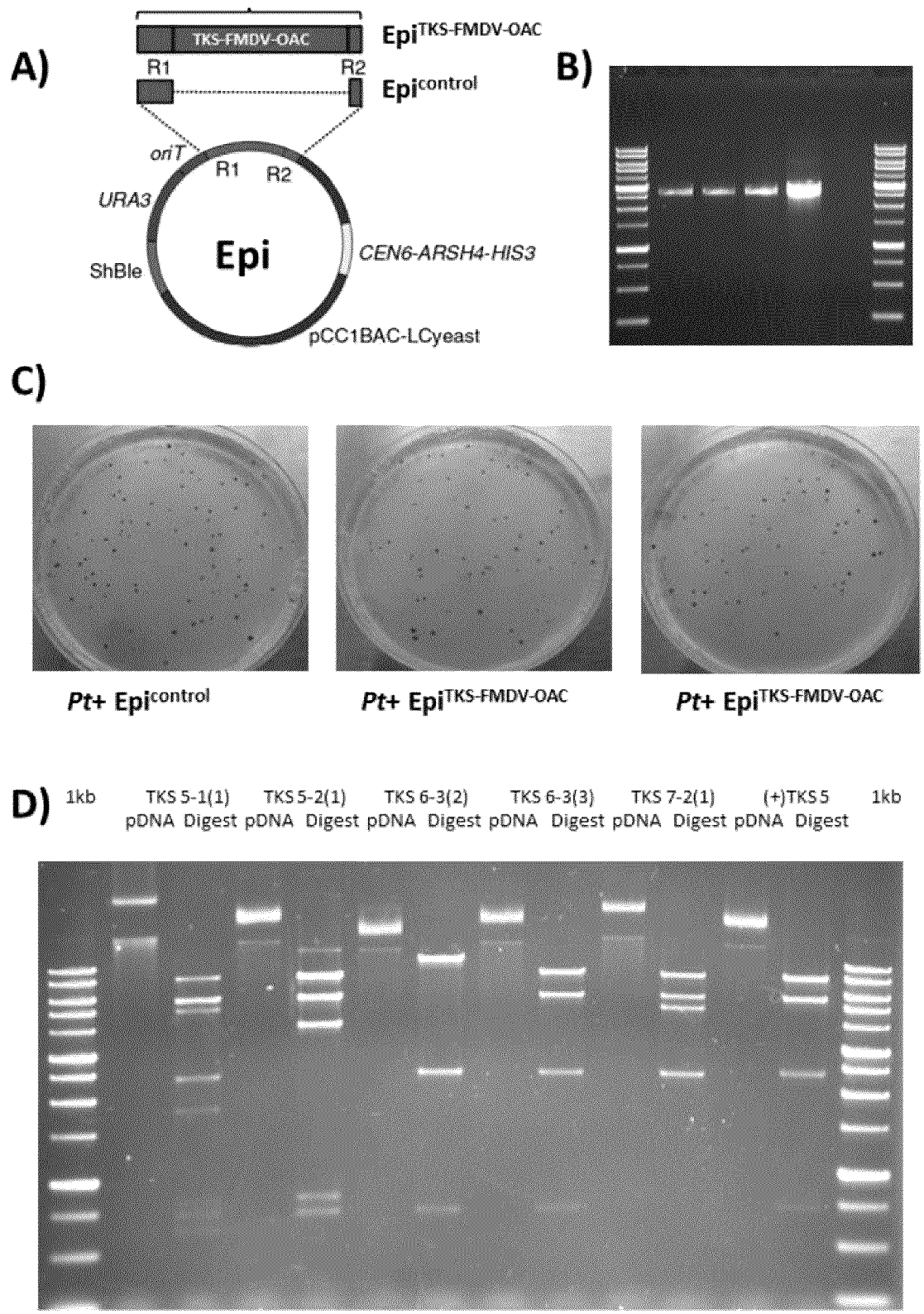
FIG. 10 shows Phaeodactylum tricornutum (Pt) episomal transformation with TKS and OAC fusion genes. (A) A map of the episome (Karas et al 2015) (Epi) empty (Epicontrol) and engineered with construction 2 of TKS and OAC genes (Epi$^{TKS\text{-}FMDV\text{-}OAC}$). (B) DNA gel of the PCR products for full fragment insert of Epi$^{TKS intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

A map of the episome (Karas et al 2015) (Epi) empty (Epicontrol) and engineered with construction 2 of TKS and OAC genes (Eptics-FMDV-OAC) is shown (FIG. 10A). DNA gel of the PCR products for full fragment insert of Epi$^{TKS\text{-}FMDV\text{-}OAC}$ construct amplified by primers annealing sites on the Epi backbone performed on Pt colonies shows the entire insert (FcpD promoter→FcpD terminator) at the correct size of 2591 bp (FIG. 10B; also includes negative control and 1 kb ladders). *P. tricornutum* colonies were grown on zeocin plates (except negative control; FIG. 10C). Each construct plate contains on average 50 colonies, while the positive control contains 92. Multiplex PCR results for colonies of Epi transformed with Pt DNA show that DNA was extracted from 1 colony of *P. tricornutum* for each isolate of TKS-FMDV-OAC (FIG. 10D). All *P. tricornutum* colonies were extracted and all 7 colonies between TKS 5-1 and 5-2 were screened (TKS colony 5 was chosen for sequencing, and it shows the correct sequence). DNA for each correct colony was extracted and digested with BamHI (FIG. 10D). Positive control of TKS colony 5 was also digested with BamHI, showing the expected sizes 8,020, 5,656, 2,346 and 725 bp. All positive *P. tricornutum* colonies were sent to the CNETE for further metabolite analysis.

Thus, three engineered diatom *P. tricornutum* were generated using the episomal vector system. The products of these engineered cells were sent for olivetolic acid analysis.

Example 5

Identification of Products from the Diatom *Phaeodactylum tricornutum*

Figure 11:
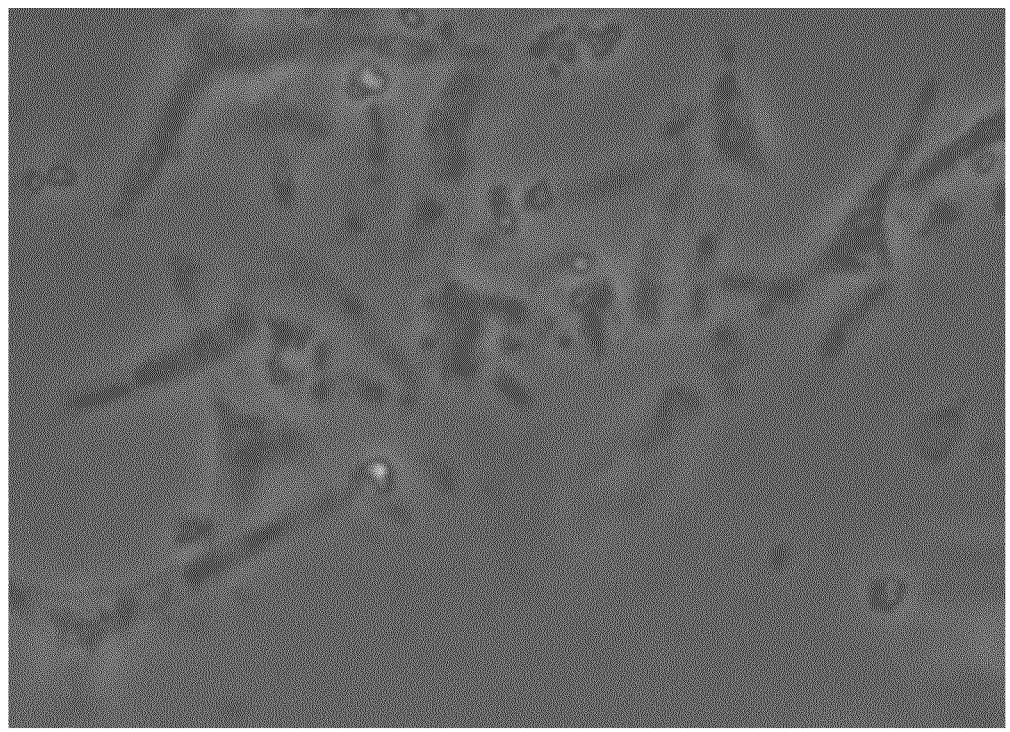

Pellets from engineered diatom *Phaeodactylum tricornutum* (either controls transfected with empty vector or transfected with EpiTKS-FMDV-OAC) were lysed. The lysis was validated by microscopic observations (FIG. 11).

Figure 12:
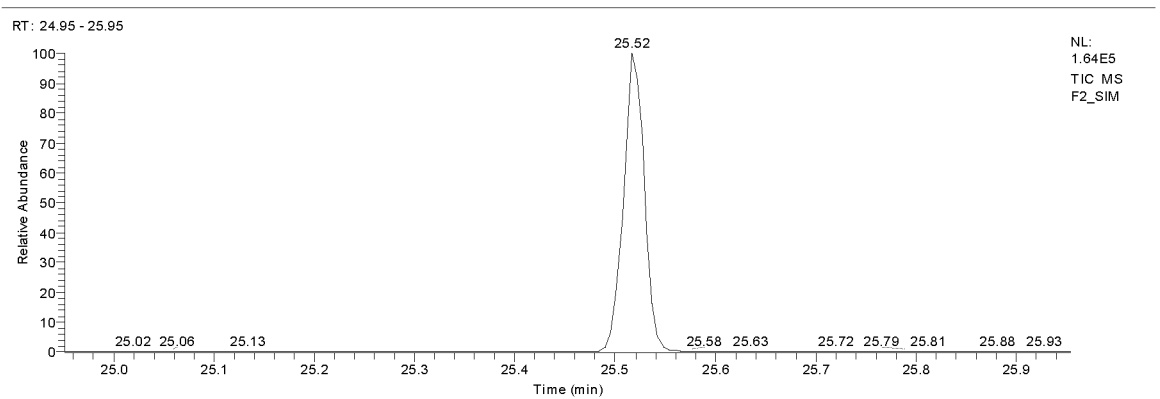
Figure 13:
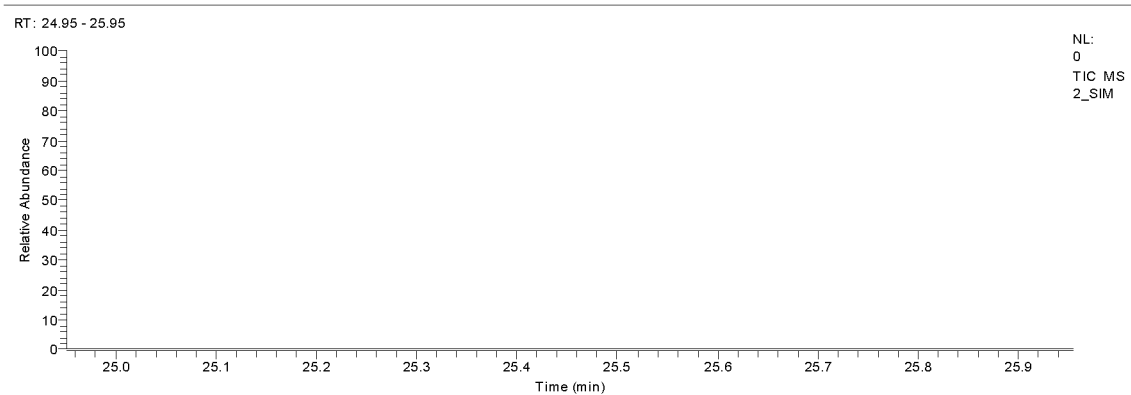
Figure 14:
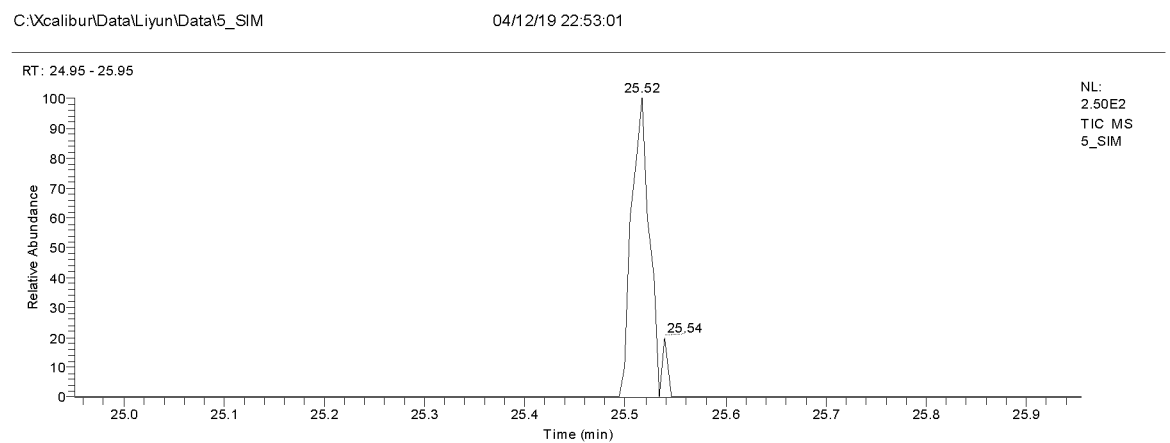
Figure 15:
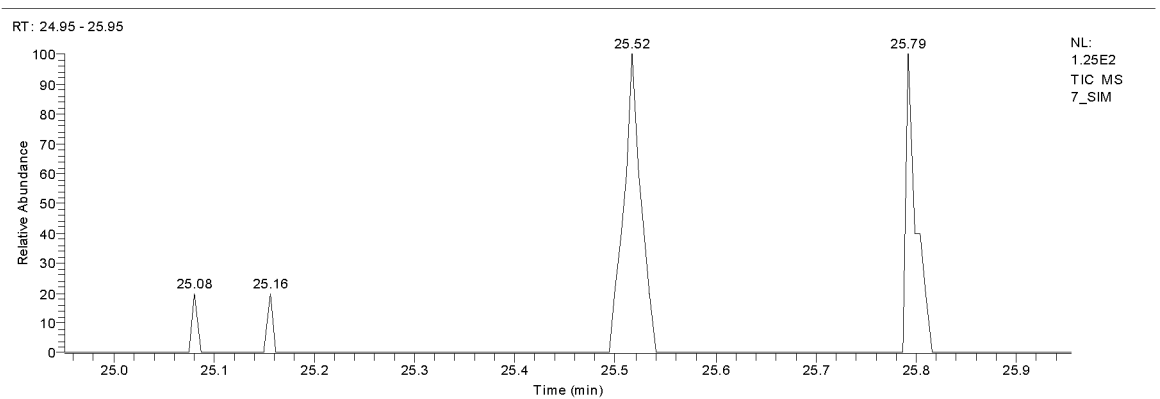
Figure 16:
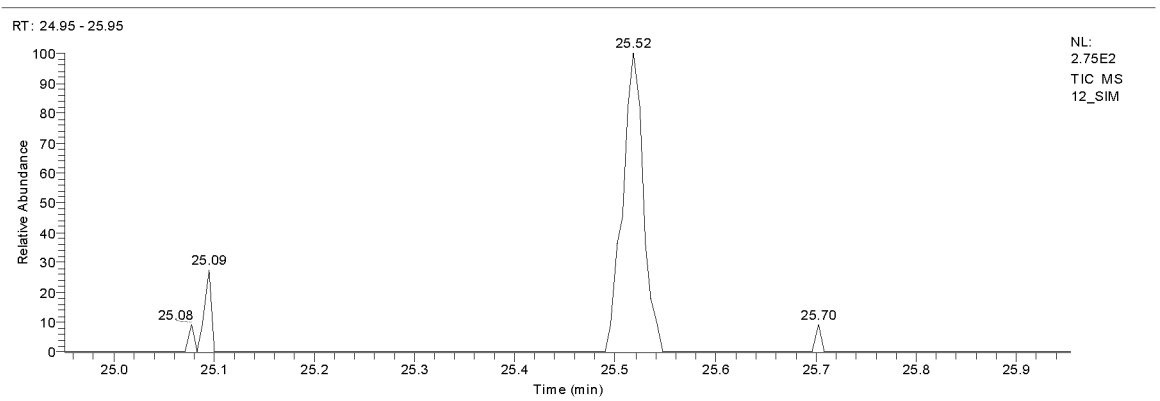

Chromatogram in selected time range in SIM mode (MS 425.3) of samples are shown in FIG. 12-16. FIG. 12 shows a lysate of control diatoms spiked with an olivetolic acid (OA) control to identify the OA peak. FIG. 13 shows the chromatogram of lysate from empty vector control diatoms indicating an absence of OA. FIGS. 14-16 show chromatograms from different lysates of diatoms transfected with EpiTKS-FMDV-OAC showing a peak corresponding to OA with the expected retention time and MS.

This shows that an engineered microorganism such as microalgae transformed with constructs for the expression of cannabinoid biosynthetic pathway enzymes can produce cannabinoid biosynthetic pathway product.

Example 6

Constructions Optimized for Expression in Diatoms and GC-Rich Microalgae

This Example provides constructions of nucleic acid sequences that are optimized for expression in GC-rich microalgae such as *Chlamydomonas reinhardtii*, and diatoms such as *Thalassiosira pseudonana* and *Phaeodactylum tricornutum* (FIG. 17). In particular, these constructs provide the co-expression of tetraketide synthase (a type III polyketide synthase) and olivetolic acid cyclase, aromatic prenyltransferase and hexanoyl-CoA synthetase, and tetrahydrocannabinolic acid synthase and cannabidiolic acid synthetase. A genetically engineered microorganism can contain a combination of these constructs, and consequently, the microorganism can co-express tetraketide synthase (a type III polyketide synthase), olivetolic acid cyclase, aromatic prenyltransferase, hexanoyl-CoA synthetase, tetrahydrocannabinolic acid synthase and cannabidiolic acid synthetase. The detection and isolation of these enzymes can be carried out by antibodies specific to the tags attached to these enzymes, which include 6His, HA, FLAG, HSV, myc and V5.

While the present disclosure has been described with reference to what are presently considered to be the preferred example, it is to be understood that the disclosure is not limited to the disclosed Examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Altschul, S. F. et al (1990) Basic local alignment search tool." Journal of molecular biology 215, 403-410.

Altschul, S. F. et al (1997) Gapped BLAST and PSI-BLAST: a new generation of protein database search programs. Nucleic acids research 25, 3389-3402.

DeLoache, W. C., et al. (2015) An enzyme-coupled biosensor enables (S)-reticuline production in yeast from glucose. Nat Chem Biol, 11(7):465.

Diaz-Santos, E., et al. (2013) Efficiency of different heterologous promoters in the unicellular microalga *Chlamydomonas reinhardtii*. Biotechnol Prog, 29(2):319-328.

ElSohly, M. A. and Slade D. (2005) Chemical constituents of marijuana: The complex mixture of natural cannabinoids. Life Sciences, 2005. 78(5):539-548.

Flores-Sanchez, I. J., et al. (2010) In silico expression analysis of PKS genes isolated from *Cannabis sativa* L. Genet Mol Biol, 33(4): 703-713.

Fossati, E., et al. (2014) Reconstitution of a 10-gene pathway for synthesis of the plant alkaloid dihydrosanguinarine in *Saccharomyces cerevisiae*. Nat Commun, (5): 3283.

Gagne, S. J., et al. (2012) Identification of olivetolic acid cyclase from *Cannabis sativa* reveals a unique catalytic route to plant polyketides. Proc Natl Acad Sci USA 109(31):12811-12816.

Gibson, D. G., et al. (2009) Enzymatic assembly of DNA molecules up to several hundred kilobases. Nat Meth, 6(5):343-345.

Karas, B. J., et al., Designer diatom episomes delivered by bacterial conjugation. Nat Commun, 2015. 6: p. 6925.

Karlin, S. and Altschul, S. F. (1990) Methods for assessing the statistical significance of molecular sequence features by using general scoring schemes. Proceedings of the National Academy of Sciences 87, 2264-2268.

Karlin, S. and Altschul, S. F. (1993) Applications and statistics for multiple high-scoring segments in molecular sequences. Proceedings of the National Academy of Sciences 90, 5873-5877.

Keasling, J. D. (2012) Synthetic biology and the development of tools for metabolic engineering. Metab Eng, 14(3):189-195.

Lithwick G, and Margalit H. (2003) Hierarchy of sequence-dependent features associated with prokaryotic translation. Genome Research 13:2665-2673.

Lussier, F. X., et al. (2012)Engineering microbes for plant polyketide biosynthesis. Comput Struct Biotechnol J 3:e201210020.

Marks, M. D., et al. (2009) Identification of candidate genes affecting Delta9-tetrahydrocannabinol biosynthesis in *Cannabis sativa*. J Exp Bot, 60(13):3715-3726.

Plecenikova, A., et al. (2013) Studies on recombination processes in two *Chlamydomonas reinhardtii* endogenous genes, NIT1 and ARG7. Protist, 164(4):570-582.

Schroda, M., et al. (2000) The HSP70A promoter as a tool for the improved expression of transgenes in *Chlamydomonas*. Plant J, 2000. 21(2): 121-131.

Singh, N. D., et al. (2009) Chloroplast-derived vaccine antigens and biopharmaceuticals: protocols for expression, purification, or oral delivery and functional evaluation. Methods Mol Biol, 483:163-192.

Slattery, S. S., et al. (2018) An expanded plasmid-based genetic toolbox enables Cas9 genome editing and stable maintenance of synthetic pathways in *Phaeodactylum tricornutum*. ACS Synthetic Biology, 7(2):328-338.

Stout, J. M., et al. (2012) The hexanoyl-CoA precursor for cannabinoid biosynthesis is formed by an acyl-activating enzyme in *Cannabis sativa* trichomes. Plant J, 71(3):353-365.

Taura, F., et al. (2009) Characterization of olivetol synthase, a polyketide synthase putatively involved in cannabinoid biosynthetic pathway. FEBS Lett, 583(12):2061-2066.

Welch et al. (2009) Design parameters to control synthetic gene expression in *Escherichia coli*. PLoS ONE 4: e7002.

The invention claimed is:

1. A genetically engineered microorganism that produces olivetolic acid in a medium that is substantially free of hexanoic acid, wherein the genetically engineered microorganism is a photosynthetic microalga or a cyanobacterium, wherein the genetically engineered microorganism does not comprise an exogenous nucleic acid molecule encoding hexanoyl-CoA synthetase, and wherein the genetically engineered microorganism comprises at least one nucleic acid molecule that encodes tetraketide synthase and olivetolic acid cyclase.

2. The genetically engineered microorganism of claim 1, wherein the tetraketide synthase comprises amino acid sequence with at least 90% sequence identity to sequence as shown in SEQ ID NO:15, and the olivetolic acid cyclase comprises amino acid sequence with at least 90% sequence identity to sequence as shown in SEQ ID NO:16 or 17.

3. The genetically engineered microorganism of claim 1, wherein the at least one nucleic acid molecule comprises a promoter and two polynucleotide sequences, one encoding tetraketide synthase and the other encoding olivetolic acid cyclase, each of which is operably linked to the promoter.

4. The genetically engineered microorganism of claim 1, wherein the at least one nucleic acid molecule comprises a first nucleic acid molecule encoding tetraketide synthase and a second nucleic acid molecule encoding olivetolic acid cyclase.

5. The genetically engineered microorganism of claim 1, wherein the at least one nucleic acid molecule is an episomal vector.

6. The genetically engineered microorganism of claim 1, wherein the at least one nucleic acid molecule further encodes aromatic prenyltransferase.

7. The genetically engineered microorganism of claim 6, wherein the aromatic prenyltransferase comprises amino acid sequence with at least 90% sequence identity to sequence as shown in SEQ ID NO:18, 63, 64, or 65.

8. The genetically engineered microorganism of claim 6, wherein the at least one nucleic acid molecule further encodes tetrahydrocannabinolic acid synthase or cannabidiolic acid synthase.

9. The genetically engineered microorganism of claim 8, wherein the tetrahydrocannabinolic acid synthase comprises amino acid sequence with at least 90% sequence identity to sequence as shown in SEQ ID NO:20, and the cannabidiolic acid synthase comprises amino acid sequence with at least 90% sequence identity to sequence as shown in SEQ ID NO:21.

10. The genetically engineered microorganism of claim 1, wherein the at least one nucleic acid molecule comprises at least one polynucleotide sequence with at least 85% sequence identity to any one of SEQ ID NO: 1-4, 6-11, 13, and 14.

11. The genetically engineered microorganism of claim 1, wherein the at least one nucleic acid molecule comprises at least two polynucleotide sequences, wherein the at least two polynucleotide sequences comprise at least 85% sequence identity to at least two sequences selected from SEQ ID NO: 1-4, 6-11, 13, and 14, and wherein the at least one nucleic acid molecule comprises at least one linker sequence between the at least two polynucleotide sequences.

12. The genetically engineered microorganism of claim 11, wherein the at least one linker sequence is a self-cleaving sequence.

13. The genetically engineered microorganism of claim 1, wherein the microalga is *Chlamydomonas reinhardtii, Chlorella vulgaris, Chlorella sorokiniana, Chlorella protothecoides, Tetraselmis chui, Nannochloropsis oculate, Scenedesmus obliquus, Acutodesmus dimorphus, Dunaliella tertiolecta,* or *Heamatococus plucialis.*

14. The genetically engineered microorganism of claim 1, wherein the microalga is a diatom.

15. The genetically engineered microorganism of claim 14, wherein the microalga is *Phaeodactylum tricornutum.*

16. A genetically engineered microorganism that produces olivetol in a medium that is substantially free of hexanoic acid, wherein the genetically engineered microorganism is a microalga or a cyanobacterium, wherein the genetically engineered microorganism does not comprise an exogenous nucleic acid molecule encoding hexanoyl-CoA synthetase, and wherein the genetically engineered microorganism comprises at least one nucleic acid molecule that encodes tetraketide synthase and olivetolic acid cyclase.

17. The genetically engineered microorganism of claim 1, wherein the cyanobacterium is Arthrospira plantesis, Arthrospira maxima, Synechococcus *elongatus* or Aphanizomenon *flos-aquae.*

* * * * *

SEQUENCE LISTING

<160> NUMBER OF SEQ ID NOS: 70

<210> SEQ ID NO 1
<211> LENGTH: 1155
<212> TYPE: DNA
<213> ORGANISM: Artificial Sequence
<220> FEATURE:
<223> OTHER INFORMATION: optimized TKS

<400> SEQUENCE: 1

| | | | | | |
|---|---|---|---|---|---|
| atgaaccacc | tgcgcgctga | gggccccgcc | tccgtcctcg | ccattgggac | ggcgaaccct | 60 |
| gagaacattc | tcctgcagga | tgagtttccg | gattactact | tcgggtcac | gaagtcggag | 120 |
| cacatgaccc | agctcaagga | gaagtttcgg | aagatttgcg | ataagagcat | gatccgcaag | 180 |
| cgcaactgct | ttctgaacga | ggagcacctg | aagcagaacc | cccggctcgt | cgagcacgag | 240 |
| atgcagacgc | tcgatgcccg | gcaggacatg | ctcgtggtcg | aggtccctaa | gctcggcaag | 300 |
| gacgcttgcg | cgaaggctat | caaggagtgg | ggtcagccca | gtccaagat | cacccatctg | 360 |
| atttttacct | ccgcgtcgac | cacggatatg | cctggggctg | actaccactg | cgcgaagctg | 420 |
| ctgggtctct | ccccgtcggt | gaagcgggtc | atgatgtacc | agctgggctg | ctacgggggg | 480 |
| ggtacggtcc | tgcgcatcgc | gaaggacatc | gctgagaaca | caagggtgc | ccgggtcctc | 540 |
| gcggtgtgct | gcgacattat | ggcttgcctg | tttcggggtc | cctcggagtc | ggacctggag | 600 |
| ctgctggtcg | gtcaggctat | ctttggggat | ggcgctgccg | ccgtgattgt | cggcgccgag | 660 |
| ccggatgagt | cggtgggtga | gcggccgatc | ttcgagctcg | tctccaccgg | gcagacgatc | 720 |
| ctccctaact | ccgagggcac | catcgggggg | cacattgcg | aggcggggct | cattttgat | 780 |
| ctgcacaagg | acgtgccgat | gctgatttcc | aacaacatcg | agaagtgcct | catcgaggct | 840 |
| ttcaccccca | ttggtatttc | cgattggaac | agcatttttt | ggatcaccca | cccgggcggt | 900 |
| aaggctattc | tggataaggt | ggaggagaag | ctccatctca | gtccgacaa | gtttgtcgat | 960 |
| agccgccatg | tcctgagcga | gcatgggaac | atgtccagct | ccacggtgct | ctttgtcatg | 1020 |
| gacgagctgc | ggaagcgctc | gctggaggag | ggcaagtcca | ccaccggcga | cggtttcgag | 1080 |
| tgggggtcc | tgttcggttt | tggtcccggt | ctcacggtgg | agcgggtggt | cgtgcgctcg | 1140 |
| gtgcccatca | agtac | | | | | 1155 |

<210> SEQ ID NO 2
<211> LENGTH: 303
<212> TYPE: DNA
<213> ORGANISM: Artificial Sequence
<220> FEATURE:
<223> OTHER INFORMATION: optimized OAC

<400> SEQUENCE: 2

| | | | | | |
|---|---|---|---|---|---|
| atggcggtga | agcacctgat | tgtcctcaag | ttcaaggacg | agatcaccga | ggcccagaag | 60 |
| gaggagtttt | tcaagaccta | cgtgaacctc | gtgaacatta | tccctgcgat | gaaggacgtg | 120 |
| tactggggga | aggatgtcac | gcagaagaac | aaggaggagg | ttacacgca | catcgtcgag | 180 |
| gtcacgttcg | agtcggtcga | gaccattcag | gattacatca | tccatcccgc | tcatgtgggt | 240 |
| tttggggacg | tgtaccgcag | cttctgggag | aagctgctga | ttttcgatta | cacccctcgc | 300 |
| aag | | | | | | 303 |

<210> SEQ ID NO 3
<211> LENGTH: 378
<212> TYPE: DNA
<213> ORGANISM: Artificial Sequence
<220> FEATURE:
<223> OTHER INFORMATION: optimized OAC2

<400> SEQUENCE: 3

```
atgaagatga aggctgcgtg gagcgcgacg atttactccc tgctgagctg gtgcgtcgtc      60
aagaacgaga agttctttcc tgagcgcacg attgacattt ccaagagcaa catggggcgc     120
atgaacaacg tcgtcctgaa ctccctccac acgctcaagt gctacctgaa ctacgtctcg     180
gtgccgtttt ttctgattct gctctcccac atttttacgc cggtgtacat ttttcatggc     240
tgggacgata ttcataagat tcacattcgc ctggagaagt tctttctcct gggttttttgc    300
gatttcatct tcgagctgca gtacaaccag atgctgcatt ccatagcct ctcgcagctg      360
tcgtccagca gcagcttt                                                   378
```

<210> SEQ ID NO 4
<211> LENGTH: 1185
<212> TYPE: DNA
<213> ORGANISM: Artificial Sequence
<220> FEATURE:
<223> OTHER INFORMATION: optimized aromatic prenyltransferase

<400> SEQUENCE: 4

```
atggggctca gctcggtgtg caccttctcg ttccagacga actaccacac gctgctgaac      60
ccccacaaca caaccctaa gacctccctg ctctgctacc gccacccgaa gaccccatt       120
aagtacagct acaacaactt cccgtccaag cactgctcca cgaagtcgtt ccacctgcag     180
aacaagtgct cggagagcct cagcatcgcg aagaacagca tccgggctgc gaccacgaac     240
cagacggagc cgcccgagtc ggataaccac tcggtcgcta cgaagattct gaacttcggt     300
aaggcgtgct ggaagctcca cgcccctac accatcattg cgtttacgag ctgcgcttgc     360
ggtctcttcg ggaaggagct cctgcacaac acgaacctga tcagctggtc cctcatgttt     420
aaggcttttt tcttcctcgt ggccatcctg tgcattgcgt cctcacgac caccatcaac     480
cagatttacg acctgcacat tgaccgcatt aacaagcctg acctgcctct ggcctcgggg    540
gagatttcgg tgaacacggc ttggatcatg tcgatcatcg tggctctctt tggtctcatt     600
atcacgatta agatgaaggg cggccccctg tacatttttg gttactgctt tgggatcttc     660
ggtgggatcg tctacagcgt gccccgttt cggtggaagc agaacccgtc gacggcctt      720
ctcctgaact tctggctca tattattacg aacttcacct tctactacgc gagccgcgct     780
gcgctcgggc tgccgttcga gctccgcccg agcttcacgt ttctcctggc ctttatgaag    840
agcatgggtt cggctctcgc cctcattaag gacgcttccg acgtggaggg ggataccaag    900
ttcggcatca gcacgctcgc gtccaagtac ggctcccgga acctcaccct gtttgctcg    960
gggattgtcc tcctgagcta cgtggccgcc atcctggctg catcatctg gccgcaggct     1020
ttcaactcca acgtcatgct cctctcgcac gcgattctgg ccttctggct gattctgcag    1080
acccgcgact tcgccctcac gaactacgac cctgaggctg gtcggcgctt ttacgagttt    1140
atgtggaagc tgtactacgc ggagtacctg gtctacgtgt ttatc                    1185
```

<210> SEQ ID NO 5
<211> LENGTH: 2160
<212> TYPE: DNA
<213> ORGANISM: Artificial Sequence
<220> FEATURE:
<223> OTHER INFORMATION: optimized hexanoyl-CoA synthetase1

<400> SEQUENCE: 5

```
atgggcaaga actacaagtc gctggattcc gtggtggctt cggacttcat cgctctgggg      60
atcaccagcg aggtcgccga gaccctccac gggcgcctcg ctgagatcgt gtgcaactac     120
ggtgccgcca cgccgcagac ctggattaac atcgccaacc atatcctgtc gccggatctc     180
cctttcagcc tgcatcagat gctgttttac gggtgctaca aggacttcgg gccggcgcct     240
cctgcttgga tccccgatcc cgagaaggtc aagagcacga acctgggcgc tctcctcgag     300
aagcgcggga aggagtttct cggggtgaag tacaaggatc ccatcagctc gtttagccat     360
tttcaggagt tctccgtccg gaaccctgag gtgtactggc ggacggtcct catggatgag     420
atgaagattt cgtttagcaa ggatccggag tgcattctcc ggcgggatga tatcaacaac     480
cctgggggca gcgagtggct ccccggtggt tacctgaact ccgccaagaa ctgcctcaac     540
gtcaactcca acaagaagct gaacgatacg atgattgtct ggcgggacga ggggaacgac     600
gatctgcccc tcaacaagct gaccctcgat cagctgcgga agggtctg ctggtcggg     660
tacgctctgg aggagatggg tctcgagaag ggctgcgcca tcgcgattga catgccgatg     720
cacgtggatg ccgtggtcat ttacctcgct attgtcctgg cgggttacgt cgtggtgtcg     780
attgctgaca gcttctccgc tcctgagatc tcgacgcggc tccggctctc gaaggccaag     840
gccatttta cgcaggacca cattattcgg gggaagaagc ggattcccct ctactcgcgg     900
gtggtcgagg cgaagtcgcc catggccatt gtcattcctt gctcggggag caacatcggc     960
gccgagctcc gcgacgggga tatcagctgg gattactttc tggagcgcgc caaggagttc    1020
aagaactgcg agtttaccgc tcgggagcag cccgtggatg cttacacgaa cattctgttc    1080
agctcgggca cgacgggtga gccgaaggcg attccttgga cgcaggctac ccctctgaag    1140
gctgctgcgg atgggtggtc ccacctcgat atccgcaagg gggacgtgat tgtctggccc    1200
accaacctgg gttggatgat ggggccttgg ctggtgtacg cctccctgct gaacggggct    1260
agcattgctc tctacaacgg gagccctctc gtctccggct ttgctaagtt tgtgcaggac    1320
gccaaggtga cgatgctcgg ggtcgtgcct agcattgtgc ggagctggaa gtcgaccaac    1380
tgcgtctcgg gctacgattg gtccaccatt cgctgctttt cctcgtccgg tgaggccagc    1440
aacgtggatg agtacctgtg gctgatgggt cgggctaact acaagccggt catcgagatg    1500
tgcggcggca cggagattgg gggggccttt tcggctgggt cgtttctgca ggctcagtcc    1560
ctgtcgtcgt tttcgtcgca gtgcatgggc tgcaccctct acatcctgga taagaacggt    1620
taccctatgc caagaacaa gcccggcatc ggggagctgg cgctgggccc ggtcatgttt    1680
ggtgcttcga agacgctgct gaacggtaac catcacgacg tgtacttcaa gggtatgcct    1740
acgctgaacg gtgaggtcct gcgccgccac ggtgacattt ttgagctcac gagcaacggt    1800
tactaccatg cgcatggtcg cgctgacgat accatgaaca ttggcggtat caagatctcg    1860
agcattgaga tcgagcgcgt ctgcaacgag gtcgacgatc gcgtgtttga ccacggct    1920
atcggtgtcc cgcctctcgg cggcggtccg gagcagctcg tcatcttttt cgtcctgaag    1980
gattcgaacg ataccacgat cgatctgaac cagctgcgcc tgtcctttaa cctgggcctc    2040
cagaagaagc tgaaccctct cttcaaggtg acccgcgtgg tccccctctc ctccctgcct    2100
cggacggcta cgaacaagat catgcgccgg gtcctgcggc agcagttctc ccacttcgag    2160
```

<210> SEQ ID NO 6
<211> LENGTH: 1635
<212> TYPE: DNA
<213> ORGANISM: Artificial Sequence
<220> FEATURE:
<223> OTHER INFORMATION: optimized tetrahydrocannabinolic acid synthase

<400> SEQUENCE: 6

```
atgaactgct cggcgttttc cttttggttt gtctgcaaga ttattttttt ttttctcagc      60
ttccacatcc agatttccat tgctaaccct cgggagaact ttctgaagtg cttttcgaag     120
cacatcccta acaacgtggc gaaccctaag ctggtctaca cgcagcatga tcagctgtac     180
atgtcgatcc tgaactccac gatccagaac ctccggttta tctcggatac gaccccctaag   240
cccctggtga ttgtgacgcc gtccaacaac agccatattc aggctacgat tctctgctcg     300
aagaaggtgg ggctccagat ccggacccgg tccgggggcc atgatgctga ggggatgagc    360
tacatctccc aggtcccctt cgtcgtggtg gatctgcgga acatgcattc gatcaagatt     420
gatgtccact cgcagaccgc gtgggtcgag gccggcgcta ccctcggtga ggtctactac    480
tggatcaacg agaagaacga gaacctcagc ttccccggcg gctactgccc gacggtcggg    540
gtcggtgggc acttttcggg tgggggctac ggcgccctca tgcggaacta cggcctcgct    600
gcggacaaca ttatcgatgc tcatctcgtc aacgtggatg caaggtgct cgatcgcaag      660
tcgatgggcg aggatctctt tgggcgatt cggggcgggg gcggcgagaa ctttggcatc      720
attgctgctt ggaagattaa gctcgtggcc gtccctagca agtcgaccat tttctcggtg     780
aagaagaaca tggagattca cggtctcgtc aagctctttta caagtggca gaacattgcc    840
tacaagtacg acaaggacct ggtgctgatg acccattttta ttaccaagaa cattacggac    900
aaccacggga agaacaagac cacggtccat ggctactttt cgagcatttt ccatgggggg    960
gtcgatagcc tcgtcgacct gatgaacaag tccttccccg agctgggcat caagaagacc   1020
gactgcaagg agtttagctg gatcgatacc acgatttttt actcgggggt cgtgaacttt   1080
aacaccgcca acttcaagaa ggagatcctg ctcgatcgct ccgctggcaa gaagacggct   1140
ttcagcatta agctcgatta cgtgaagaag cccatccctg acggctat ggtgaagatt      1200
ctggagaagc tctacgagga ggacgtcggg gctggcatgt acgtgctcta cccgtacggt   1260
ggtatcatgg aggagatctc ggagtcggcc atcccttttcc cccatcgggc gggcatcatg   1320
tacgagctgt ggtacaccgc cagctgggag aagcaggagg ataacgagaa gcatattaac   1380
tgggtccggt cggtctacaa cttcacgacg ccctacgtga gccagaaccc ccgcctcgct   1440
tacctcaact accgggacct cgatctgggc aagacgaacc atgcctcgcc caacaactac   1500
acccaggcgc ggatttgggg tgagaagtac tttgggaaga ctttaaccg cctcgtcaag    1560
gtgaagacga aggtggatcc caacaacttc ttccgcaacg agcagtccat ccccccctc    1620
ccgcctcacc accat                                                     1635
```

<210> SEQ ID NO 7
<211> LENGTH: 1632
<212> TYPE: DNA
<213> ORGANISM: Artificial Sequence
<220> FEATURE:
<223> OTHER INFORMATION: optimized cannabidiolic acid synthetase

<400> SEQUENCE: 7

```
atgaagtgct ccaccttttc cttctggttc gtctgcaaga tcattttttt tttcttctcc      60
tttaacatcc agacgtcgat cgctaaccct cgcgagaact ttctgaagtg cttttcccag    120
tacattccga acaacgctac caacctcaag ctcgtgtaca cgcagaacaa ccctctctac    180
atgtccgtgc tcaactccac gattcataac ctgcggttta cgagcgacac caccccctaag  240
cctctcgtca ttgtgacccc ttcgcacgtc tcccatatcc agggcacgat cctgtgctcc    300
```

```
aagaaggtcg gcctgcagat ccggacgcgc tccggtgggc atgattccga gggtatgtcg      360
tacatcagcc aggtgccgtt tgtcatcgtg gatctccgca acatgcgcag cattaagatt      420
gatgtccatt cgcagaccgc ttgggtcgag gcggggggcga cgctcggtga ggtgtactac     480
tgggtcaacg agaagaacga gaacctctcc ctcgctgccg gctactgccc caccgtctgc     540
gcgggggggc atttttggggg cggcggttac gggccgctca tgcggaacta cggcctggcg    600
gcggacaaca tcatcgacgc tcacctcgtc aacgtccatg gtaaggtgct cgatcggaag     660
tccatggggg aggacctgtt ttgggcgctc cgggggggcg gcgctgagag ctttggtatc     720
attgtcgcct ggaagatccg cctcgtggct gtcccgaagt cgaccatgtt cagcgtcaag     780
aagattatgg agattcacga gctggtcaag ctcgtgaaca agtggcagaa cattgcctac     840
aagtacgaca aggacctgct cctgatgacc catttcatta cgcggaacat cacgacaac     900
caggggaaga acaagaccgc gattcatacg tacttcagct ccgtcttcct cggcggcgtg     960
gatagcctgg tggacctcat gaacaagagc tttccggagc tgggcatcaa gaagacggat    1020
tgccgccagc tcagctggat tgacacgatc atctttttact cggggggtggt caactacgac  1080
acggacaact ttaacaagga gattctgctc gatcggtccg ccggtcagaa cggtgccttt    1140
aagatcaagc tcgattacgt caagaagccc attcccgaga gcgtgtttgt ccagattctc    1200
gagaagctct acgaggagga cattggtgcc ggtatgtacg cgctctaccc gtacgggggc    1260
attatgggacg agattagcga gagcgccatt cctttccctc atcgcgctgg cattctctac   1320
gagctgtggt acatttgcag ctgggagaag caggaggaca acgagaagca cctcaactgg    1380
attcgcaaca tctacaactt catgaccccg tacgtctcga agaaccctcg gctggcttac    1440
ctgaactacc gcgatctcga cattggcatt aacgatccga agaacccaa caactacacg     1500
caggcgcgga tctgggggtga aagtactttt ggtaagaact ttgatcggct cgtgaaggtc    1560
aagacgctcg tggaccctaa caacttcttt cgcaacgagc agtcgatccc ccgctgcct     1620
cgccaccggc ac                                                        1632

<210> SEQ ID NO 8
<211> LENGTH: 1155
<212> TYPE: DNA
<213> ORGANISM: Artificial Sequence
<220> FEATURE:
<223> OTHER INFORMATION: optimized TKS

<400> SEQUENCE: 8
atgaatcatc ttcgcgctga agggccggct tccgttctcg cgattgggac ggctaaccct      60
gagaacatct tgttgcaaga cgagttccca gactactatt ttcgtgttac gaaatctgag    120
cacatgacac aacttaaaga aaagttccgt aaaatctgcg acaaaagtat gattaggaag    180
agaaattgct ttctcaacga agagcacctc aagcagaacc cgaggttggt tgagcacgaa    240
atgcaaacac tcgacgcgcg tcaagatatg cttgtagttg aagtaccaaa attgggtaaa    300
gacgcttgtg ctaaagcgat caagagtgg ggacaaccta agagcaaaat tactcacttg     360
atctttactt ctgcatcgac tactgacatg cccggggcag attatcattg tgcgaagctt    420
ttgggacttt cacccagtgt caaacgcgta atgatgtatc agttggggttg ctacggcggt   480
ggtacagtgc tcagaatcgc aaaagacatt gcggaaaaca acaaggggc aagagtcctc     540
gcggttttgct gtgatatcat ggcgtgcttt tttcgaggac cgagtgaatc tgacctcgag   600
ttgcttgttg gacaagcaat ttttggagat gggggccgcag ccgtcatcgt gggagcagag   660
cctgacgagt ctgtggggga acgtcccatc tttgaactcg ttagtaccgg acagacaatt   720
```

```
ttgcccaatt ccgaaggaac tattggtggt cacatccgag aagctgggtt gatcttcgat      780
cttcataaag atgtcccgat gctcattagt aataatatcg aaaaatgtct cattgaagcg      840
tttacaccca tcggtattag cgattggaat agtattttct ggatcaccca ccccggcggc      900
aaggcgattc ttgataaggt ggaggagaaa ttgcacttga agagtgacaa atttgtagac      960
agccgccacg ttctttccga gcatggcaat atgtcatctt ctacggtact ctttgtaatg     1020
gacgaactcc gcaagcgctc tctcgaggag ggtaagtcaa caacgggtga cggctttgag     1080 tgggggttt tgtttgggtt tggccccggc ttgaccgtag aacgtgtggt cgtgcgttcc     1140
gtgccgatta agtat                                                     1155
```

<210> SEQ ID NO 9
<211> LENGTH: 303
<212> TYPE: DNA
<213> ORGANISM: Artificial Sequence
<220> FEATURE:
<223> OTHER INFORMATION: optimized OAC

<400> SEQUENCE: 9

```
atggcagtta acacctcat cgtcctcaaa ttcaaagatg agatcactga ggctcaaaag       60
gaggagttct tcaaaacgta tgtaaatctt gtgaatatta tccctgcgat gaaggatgta      120 tattgggga aggacgtgac gcaaaaaaac aaagaggaag ctacacgca tattgtcgaa       180 gttactttcg agtcggttga aaccatccag gattacatta tccaccccgc acatgtaggc     240
tttggtgatg tgtaccgatc attctgggag aaattgttga tcttcgatta tacgccaagg     300
aag                                                                    303
```

<210> SEQ ID NO 10
<211> LENGTH: 378
<212> TYPE: DNA
<213> ORGANISM: Artificial Sequence
<220> FEATURE:
<223> OTHER INFORMATION: optimized OAC2

<400> SEQUENCE: 10

```
atgaaaatga aggcagcttg gtcggcgaca atctattcac tcctctcctg gtgcgtagta      60
aaaaacgaaa aattttttcc agagcgtacc attgacatta gcaaatccaa tatgggtcga     120
atgaataacg ttgtgctcaa tagtctccac acacttaagt gttatttgaa ctacgtcagc     180
gtccccttct ttctcatcct tctttcgcac atctttacgc ctgtatacat tttccacggg     240
tgggacgaca tccataaaat tcacatccga ctcgagaagt tcttcttgtt gggcttctgc     300
gattttattt tcgagctcca atacaatcag atgcttcact gccatagcct ttctcagttg     360
tcgtccagtt catcattc                                                   378
```

<210> SEQ ID NO 11
<211> LENGTH: 1185
<212> TYPE: DNA
<213> ORGANISM: Artificial Sequence
<220> FEATURE:
<223> OTHER INFORMATION: optimized aromatic prenyltransferase

<400> SEQUENCE: 11

```
atgggcctca gcagtgtatg taccttttca ttccagacta actatcacac gttgcttaat       60
ccgcataaca ataacccgaa aacttcgttg ctttgttata ggcacccgaa gaccccatc      120 aaatatagtt ataataactt tccaagcaaa cactgttcga ctaagtcctt tcatttgcaa     180
```

| | |
|---|---|
| aataaatgtt ccgagtctct tagcattgcg aagaactcca ttcgtgctgc tactacaaat | 240 |
| caaactgagc cccccgagag tgataatcac agtgtagcaa cgaagatctt gaactttggg | 300 |
| aaggcatgct ggaaattgca acgtccttac accatcatcg cgttcacgtc ttgcgcatgc | 360 |
| ggcttgttcg gaaaggagct tttgcataat acgaatctta tcagttggtc gttgatgttc | 420 |
| aaggccttct ttttcctcgt tgcaattctt tgtattgcca gcttcacaac gacaattaac | 480 |
| cagatttatg atcttcatat cgatagaatc aataaacccg acttgccttt ggcatcagga | 540 |
| gaaatctctg tcaatacagc atggattatg tccattattg tcgcattgtt tggacttatc | 600 |
| atcaccatca agatgaaggg agggccactc tatatcttcg gttattgttt tggaatcttt | 660 |
| ggcggtatcg tatattctgt acctccgttc agatggaaac agaaccccag cacggcgttt | 720 |
| cttttgaact ttcttgctca catcatcact aattttacat tttactatgc aagtagggca | 780 |
| gccctcggac tccccttcga gttgaggccg agttttactt ttctccttgc gtttatgaaa | 840 |
| agtatgggga gtgctcttgc ccttatcaag gatgcaagtg atgttgaagg cgatactaaa | 900 |
| tttggtatca gtaccctcgc cagtaaatat gggtccagga atctcacact cttttgttca | 960 |
| gggatcgttc ttctttcata cgtggctgca atccttgctg gtattatctg gccccaagct | 1020 |
| ttcaatagta atgtcatgct ccttagccat gccatccttg cattttggct catcttgcaa | 1080 |
| acgagggatt tgctctcac caactatgat cccgaagctg aaggcgtttc tatgagtttc | 1140 |
| atgtggaagc tttactacgc agaatatctc gtatatgtat tcatt | 1185 |

<210> SEQ ID NO 12
<211> LENGTH: 2160
<212> TYPE: DNA
<213> ORGANISM: Artificial Sequence
<220> FEATURE:
<223> OTHER INFORMATION: optimized hexanoyl-CoA synthetase1

<400> SEQUENCE: 12

| | |
|---|---|
| atgggtaaga actacaagtc tttggactcg gtggtcgcct cagattttat tgcattgggc | 60 |
| atcacctcag aggttgcgga aactcttcat ggcagactcg cagaaattgt ttgcaactac | 120 |
| ggcgcggcaa ccccacaaac gtggatcaat atcgctaatc acattttgtc gccggacttg | 180 |
| cctttttcat tgcatcagat gttgttttat ggttgttaca aggacttcgg tcccgcgcct | 240 |
| ccagcttgga ttccggatcc agaaaaggtc aagagtacca atctcgggc tttgcttgaa | 300 |
| aaacgaggaa agaattcct tggcgtaaag tataaggatc ccatctctag cttttcgcac | 360 |
| ttccaggaat tcagtgtacg taatcctgag gtttactggc gtaccgttct tatggatgag | 420 |
| atgaaaattt cattttctaa ggaccccgaa tgtatccttc gtagagatga tattaacaat | 480 |
| ccagggggct cagaatggtt gccgggtggg taccttaatt ccgctaagaa ttgcttgaac | 540 |
| gtcaactcca acaaaaagct caacgacacc atgatcgttt ggcgagacga gggaaatgac | 600 |
| gacttgcctc ttaataagtt gacgctcgat caattgagaa agcgagtatg gctcgtaggc | 660 |
| tatgctctcg aggaaatggg tcttgagaag ggatgcgcga ttgcaatcga tatgccaatg | 720 |
| cacgtcgatg cagtagttat ttaccttgct atcgtgctcg ccggatatgt ggtggtatca | 780 |
| attgcagatt cgtttagtgc gcccgagatt caacccgcc ttcgcctttc aaaagccaaa | 840 |
| gccatcttca cccaagatca catcattagg ggaaagaaac gcatcccatt gtattcaagg | 900 |
| gttgtagaag cgaagagccc aatggcgatc gtaattccct gttccggttc caacatcggg | 960 |
| gcggaacttc gtgacggtga cattagttgg gattattttc tcgagagagc taaggaattt | 1020 |
| aaaaactgcg aattcactgc aagggagcag ccggttgacg cgtacacaaa tattctcttt | 1080 |

```
tcctccggaa ctacgggggga accaaaggcg atcccttgga cgcaagcgac accacttaag    1140
gcagccgccg acggttggtc ccaccttgat attaggaagg gggatgtcat cgtgtggcca    1200
actaacctcg gctggatgat gggaccgtgg ctcgtctatg cgtccctcct aacggagca    1260 tcgatcgcac tctacaatgg atctcctttg gtatcaggat tcgcgaagtt cgtacaggat    1320
gcaaaggtaa ccatgcttgg tgtggtacca tcaattgtga aagctggaa aagcactaat    1380 tgcgtgagcg gttatgattg gtcaacaatt cgctgtttct cgtctagtgg agaggcgtcc    1440
aatgtagatg aatatctctg gcttatgggt agagccaact acaaaccagt tattgagatg    1500
tgcggcggaa ccgagattgg aggcgccttc agtgccggat ccttccttca ggcgcagtca    1560
ttgtcgtcct tctccagtca gtgtatgggc tgtactctct atattcttga caagaacgga    1620
tacccgatgc cgaagaacaa gcctggaatt ggtgagctcg cactcggacc agtaatgttt    1680
ggggcgtcaa aaactcttct caacggcaac catcacgatg tttatttaa gggtatgccg    1740 acccttaatg gtgaggtatt gcgccgccac ggtgacattt cgagctcac ttcaaatgga    1800 tactaccacg cgcatgggcg agcagacgac acaatgaaca ttgggggaat taagatcagt    1860
tcgatcgaga ttgaaagagt gtgtaacgaa gttgacgaca gggtcttcga gaccacagcc    1920
atcggggtac ctccgctcgg tggcggcccg gagcagctcg tgatttttt tgtccttaaa    1980 gactcaaacg ataccactat cgatttgaat caacttagac tcagttttaa tctcggactt    2040
caaaaaaagt gaacccct cttcaaagtc accagagtgg tgcccctctc gagtcttccc    2100
cgcaccgcta caaataagat catgcgccga gttcttcgcc aacagttcag tcactttgaa    2160
```

<210> SEQ ID NO 13
<211> LENGTH: 1635
<212> TYPE: DNA
<213> ORGANISM: Artificial Sequence
<220> FEATURE:
<223> OTHER INFORMATION: optimized tetrahydrocannabinolic acid synthase

<400> SEQUENCE: 13

```
atgaactgtt ccgctttcag cttttggttc gtgtgtaaaa tcatcttctt tttcctctca     60
ttccatattc agatctctat cgcaaacccg cgagagaatt cctcaaatg cttctcgaaa    120 cacattccta taatgtagc caatccaaaa cttgtgtata cgcagcacga tcagctctat    180
atgtccattc ttaactctac tatccagaac ttgagattca tctctgatac cacacccaag    240
ccgttggtga tcgtaacacc tagtaataat agtcacatcc aggcgacgat cctctgctca    300
aagaaggtag gactccaaat tagaacgaga tcgggcggac acgatgccga aggaatgagt    360
tatatctccc aagtaccgtt cgtagttgtt gaccttagga atatgcactc aattaagatt    420
gatgtccaca gtcaaacagc atgggttgag gcaggagcca ctcttggtga agtctactac    480
tggattaacg agaaaaatga gaacctctcg tttcctggcg gttactgtcc tacagtggga    540
gtgggaggtc atttttcggg cggaggatac ggggctttga tgagaaacta tgggcttgca    600
gcagataaca ttattgacgc ccacctcgtc aacgtagacg gtaaggtatt ggataggaag    660
tctatgggag aagacttgtt ctgggcgatt cgcggaggag gcggtgaaaa cttcggaatc    720
atcgcagcgt ggaaaatcaa actcgtagca gtgccatcga aaagtactat cttcagtgtt    780
aagaaaaaca tggaaatcca cggacttgtt aaacttttta acaaatggca aacattgcc    840 tataagtatg ataagatt ggtgctcatg actcacttca ttaccaagaa tattacagac    900
aaccacggta aaaataagac gactgtacat ggatacttta gctcgatttt ccacggcggc    960
```

```
gtcgacagcc ttgtagatct tatgaacaaa tcatttcccg aactcggaat taagaaaacg    1020
gactgtaagg aattcagttg gatcgatacc accatttttt actccggcgt cgttaatttc    1080
aacactgcca acttcaagaa ggaaattctc ctcgatagga gcgcgggtaa gaaaacagca    1140
ttttcgatta agttggatta tgttaaaaaa cccatccctg agactgccat ggtaaaaatt    1200
cttgaaaaac tctatgagga ggacgttggg gctggcatgt acgtacttta tccatacgga    1260
ggtatcatgg aggaaattag cgagtcggca atcccttcc cgcaccgcgc tggcatcatg     1320
tatgaacttt ggtacacagc aagctgggaa aagcaggaag ataacgaaaa acatatcaac    1380
tgggttaggt cagtctataa ctttacgacc ccctacgtgt cacagaatcc tagattggcg    1440
taccttaatt atcgtgacct tgacttgggc aagacgaacc acgcttcccc caacaactat    1500
actcaggctc gtatctgggg tgaaaaatat tttggaaaaa atttcaacag gttggtcaaa    1560
gtcaaaacca aggtggatcc gaacaatttc ttccgaaacg aacaatctat tccgccgctt    1620
ccaccgcacc accac                                                    1635

<210> SEQ ID NO 14
<211> LENGTH: 1632
<212> TYPE: DNA
<213> ORGANISM: Artificial Sequence
<220> FEATURE:
<223> OTHER INFORMATION: optimized cannabidiolic acid synthetase

<400> SEQUENCE: 14
atgaagtgtt ctacgttctc cttctggttc gtttgcaaaa tcattttctt cttctttagc      60
tttaatatcc agacttccat cgcgaacccg cgcgagaact tcctcaagtg cttctcacaa     120
tatattccga ataatgcgac gaaccttaag ctcgtatata cgcaaaataa tccactttac     180
atgagtgtgc tcaatagtac tattcataac ttgcgcttta cgtctgatac cacaccgaag     240
cccctcgtaa tcgtcacacc ttcacacgtg tcgcatattc aggggactat tttgtgctcg     300
aagaaggtgg gcttgcaaat cagaacgcgt tcaggaggtc atgactctga agggatgagc     360
tacatttcac aggtaccttt tgtgattgtc gacttgcgaa acatgagatc tatcaagatc    420
gacgtccata gccaaactgc gtgggtagaa gcgggcgcta cattggggga ggtgtattac    480
tgggtgaatg aaaagaacga gaacctctct ctcgctgccg gttactgccc cacagtctgt    540
gctggtggac actttggagg tggagggtac ggtcctctta tgcgaaacta tggattggct    600
gccgacaaca ttattgacgc tcacttggta aacgttcatg gtaaggtact tgaccgtaag    660
tctatgggcg aagacctctt tgggcactt cgcggtggtg gcgctgaatc tttcggtatc    720
atcgtcgcgt ggaagattag attggtagcg gtccctaagt ccacaatgtt cagtgtgaaa    780
aagattatgg atccacgaac cttgttaaaa cttgtcaaca atggcaaaaa cattgcgtat    840
aagtacgaca aggatttgtt gctcatgacg cactttatca cacgaaacat cactgacaac    900
caggggaaga acaaaacagc aatccacacg tacttctcgt ctgtgttcct ggcggggta    960 gattcactcg tcgatctcat gaataaaagc ttccggagt tggggattaa aaaaacagat    1020
tgcaggcaac tctcctggat cgatacaatt atttttaca gcggagtggt caattacgac    1080
acggacaact tcaataagga gatcctcctc gataggtcag ccgggcagaa cggagccttt    1140
aagatcaaac tcgattacgt caagaagccg atcccagagt ctgtatttgt tcaaattctt    1200
gaaaaacttt acgaagagga tattggggct gggatgtacg cttttgtatcc ttatgggggt    1260 attatggacg agatctcaga atcggcaatc cccttccccc atagggccgg aatcttgtac    1320
gaactttggt acatctgctc ctgggaaaag caggaggata acgagaagca cttgaactgg    1380
```

```
atcagaaaca tttataattt tatgacccct tacgtctcga aaaccctcg acttgcctac    1440 ttgaattaca gggatctcga catcggtatt aatgaccccta gaatccaaa taactatacg   1500 caggcccgta tttggggaga aaatatttt ggtaagaact ttgatcgctt ggtcaaagtt    1560
aaaacgttgg ttgatcccaa taacttcttc agaaatgagc agtcgatccc cccattgcct   1620
agacatcgcc at                                                      1632

<210> SEQ ID NO 15
<211> LENGTH: 385
<212> TYPE: PRT
<213> ORGANISM: Cannabis sativa

<400> SEQUENCE: 15
```

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

```
Ser Arg His Val Leu Ser Glu His Gly Asn Met Ser Ser Ser Thr Val
            325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
            355                 360                 365

Pro Gly Leu Thr Val Glu Arg Val Val Arg Ser Val Pro Ile Lys
            370                 375                 380

Tyr
385

<210> SEQ ID NO 16
<211> LENGTH: 101
<212> TYPE: PRT
<213> ORGANISM: Cannabis sativa

<400> SEQUENCE: 16

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
            35                  40                  45

Lys Asn Lys Glu Glu Gly Tyr Thr His Ile Val Glu Val Thr Phe Glu
        50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Arg Lys
            100

<210> SEQ ID NO 17
<211> LENGTH: 126
<212> TYPE: PRT
<213> ORGANISM: Artificial Sequence
<220> FEATURE:
<223> OTHER INFORMATION: OAC2

<400> SEQUENCE: 17

Met Lys Met Lys Ala Ala Trp Ser Ala Thr Ile Tyr Ser Leu Leu Ser
1               5                   10                  15

Trp Cys Val Val Lys Asn Glu Lys Phe Phe Pro Glu Arg Thr Ile Asp
            20                  25                  30

Ile Ser Lys Ser Asn Met Gly Arg Met Asn Asn Val Val Leu Asn Ser
            35                  40                  45

Leu His Thr Leu Lys Cys Tyr Leu Asn Tyr Val Ser Val Pro Phe Phe
        50                  55                  60

Leu Ile Leu Leu Ser His Ile Phe Thr Pro Val Tyr Ile Phe His Gly
65                  70                  75                  80

Trp Asp Asp Ile His Lys Ile His Ile Arg Leu Glu Lys Phe Phe Leu
                85                  90                  95

Leu Gly Phe Cys Asp Phe Ile Phe Glu Leu Gln Tyr Asn Gln Met Leu
            100                 105                 110

His Cys His Ser Leu Ser Gln Leu Ser Ser Ser Ser Phe
            115                 120                 125
```

<210> SEQ ID NO 18
<211> LENGTH: 403
<212> TYPE: PRT
<213> ORGANISM: Cannabis sativa

<400> SEQUENCE: 18

```
Met Gly Leu Ser Ser Val Cys Thr Phe Ser Phe Gln Thr Asn Tyr His
1               5                   10                  15

Thr Leu Leu Asn Pro His Asn Asn Pro Lys Thr Ser Leu Leu Cys
            20                  25                  30

Tyr Arg His Pro Lys Thr Pro Ile Lys Tyr Ser Tyr Asn Asn Phe Pro
            35                  40                  45

Ser Lys His Cys Ser Thr Lys Ser Phe His Leu Gln Asn Lys Cys Ser
    50                  55                  60

Glu Ser Leu Ser Ile Ala Lys Asn Ser Ile Arg Ala Ala Thr Thr Asn
65                  70                  75                  80

Gln Thr Glu Pro Pro Glu Ser Asp Asn His Ser Val Ala Thr Lys Ile
                85                  90                  95

Leu Asn Phe Gly Lys Ala Cys Trp Lys Leu Gln Arg Pro Tyr Thr Ile
            100                 105                 110

Ile Ala Phe Thr Ser Cys Ala Cys Gly Leu Phe Gly Lys Glu Leu Leu
            115                 120                 125

His Asn Thr Asn Leu Ile Ser Trp Ser Leu Met Phe Lys Ala Phe Phe
            130                 135                 140

Phe Leu Val Ala Ile Leu Cys Ile Ala Ser Phe Thr Thr Thr Ile Asn
145                 150                 155                 160

Gln Ile Tyr Asp Leu His Ile Asp Arg Ile Asn Lys Pro Asp Leu Pro
                165                 170                 175

Leu Ala Ser Gly Glu Ile Ser Val Asn Thr Ala Trp Ile Met Ser Ile
            180                 185                 190

Ile Val Ala Leu Phe Gly Leu Ile Ile Thr Ile Lys Met Lys Gly Gly
            195                 200                 205

Pro Leu Tyr Ile Phe Gly Tyr Cys Phe Gly Ile Phe Gly Gly Ile Val
            210                 215                 220

Tyr Ser Val Pro Pro Phe Arg Trp Lys Gln Asn Pro Ser Thr Ala Phe
225                 230                 235                 240

Leu Leu Asn Phe Leu Ala His Ile Ile Thr Asn Phe Thr Phe Tyr Tyr
            245                 250                 255

Ala Ser Arg Ala Ala Leu Gly Leu Pro Phe Glu Leu Arg Pro Ser Phe
            260                 265                 270

Thr Phe Leu Leu Ala Phe Met Lys Ser Met Gly Ser Ala Leu Ala Leu
            275                 280                 285

Ile Lys Asp Ala Ser Asp Val Glu Gly Asp Thr Lys Phe Gly Ile Ser
            290                 295                 300

Thr Leu Ala Ser Lys Tyr Gly Ser Arg Asn Leu Thr Leu Phe Cys Ser
305                 310                 315                 320

Gly Ile Val Leu Leu Ser Tyr Val Ala Ala Ile Leu Ala Gly Ile Ile
                325                 330                 335

Trp Pro Gln Ala Phe Asn Ser Asn Val Met Leu Leu Ser His Ala Ile
            340                 345                 350

Leu Ala Phe Trp Leu Ile Leu Gln Thr Arg Asp Phe Ala Leu Thr Asn
            355                 360                 365

Tyr Asp Pro Glu Ala Gly Arg Arg Phe Tyr Glu Phe Met Trp Lys Leu
            370                 375                 380
```

Tyr Tyr Ala Glu Tyr Leu Val Tyr Val Phe Ile Asp Tyr Lys Asp Asp
385                 390                 395                 400

Asp Asp Lys

<210> SEQ ID NO 19
<211> LENGTH: 720
<212> TYPE: PRT
<213> ORGANISM: Cannabis sativa

<400> SEQUENCE: 19

Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
                20                  25                  30

Leu Ala Glu Ile Val Cys Asn Tyr Gly Ala Ala Thr Pro Gln Thr Trp
            35                  40                  45

Ile Asn Ile Ala Asn His Ile Leu Ser Pro Asp Leu Pro Phe Ser Leu
        50                  55                  60

His Gln Met Leu Phe Tyr Gly Cys Tyr Lys Asp Phe Gly Pro Ala Pro
65              70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
210                 215                 220

Glu Met Gly Leu Glu Lys Gly Cys Ala Ile Ala Ile Asp Met Pro Met
225                 230                 235                 240

His Val Asp Ala Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
        290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

-continued

Asp Ala Tyr Thr Asn Ile Leu Phe Ser Ser Gly Thr Gly Glu Pro
        355                 360                 365

Lys Ala Ile Pro Trp Thr Gln Ala Thr Pro Leu Lys Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415

Leu Asn Gly Ala Ser Ile Ala Leu Tyr Asn Gly Ser Pro Leu Val Ser
            420                 425                 430

Gly Phe Ala Lys Phe Val Gln Asp Ala Lys Val Thr Met Leu Gly Val
        435                 440                 445

Val Pro Ser Ile Val Arg Ser Trp Lys Ser Thr Asn Cys Val Ser Gly
    450                 455                 460

Tyr Asp Trp Ser Thr Ile Arg Cys Phe Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720

<210> SEQ ID NO 20
<211> LENGTH: 555
<212> TYPE: PRT
<213> ORGANISM: Cannabis sativa

<400> SEQUENCE: 20

Met Asn Cys Ser Ala Phe Ser Phe Trp Phe Val Cys Lys Ile Ile Phe
1               5                   10                  15

```
Phe Phe Leu Ser Phe His Ile Gln Ile Ser Ile Ala Asn Pro Arg Glu
             20                  25                  30

Asn Phe Leu Lys Cys Phe Ser Lys His Ile Pro Asn Asn Val Ala Asn
         35                  40                  45

Pro Lys Leu Val Tyr Thr Gln His Asp Gln Leu Tyr Met Ser Ile Leu
 50                  55                  60

Asn Ser Thr Ile Gln Asn Leu Arg Phe Ile Ser Asp Thr Thr Pro Lys
 65              70                  75                  80

Pro Leu Val Ile Val Thr Pro Ser Asn Asn Ser His Ile Gln Ala Thr
                 85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
            115                 120                 125

Val Val Asp Leu Arg Asn Met His Ser Ile Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Tyr Gly Ala
            180                 185                 190

Leu Met Arg Asn Tyr Gly Leu Ala Ala Asp Asn Ile Ile Asp Ala His
            195                 200                 205

Leu Val Asn Val Asp Gly Val Leu Asp Arg Lys Ser Met Gly Glu
            210                 215                 220

Asp Leu Phe Trp Ala Ile Arg Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
            275                 280                 285

Leu Met Thr His Phe Ile Thr Lys Asn Ile Thr Asp Asn His Gly Lys
            290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
            355                 360                 365

Ile Leu Leu Asp Arg Ser Ala Gly Lys Lys Thr Ala Phe Ser Ile Lys
            370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415

Tyr Pro Tyr Gly Gly Ile Met Glu Glu Ile Ser Glu Ser Ala Ile Pro
            420                 425                 430
```

```
Phe Pro His Arg Ala Gly Ile Met Tyr Glu Leu Trp Tyr Thr Ala Ser
            435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
                500                 505                 510

Lys Asn Phe Asn Arg Leu Val Lys Val Lys Thr Lys Val Asp Pro Asn
            515                 520                 525

Asn Phe Phe Arg Asn Glu Gln Ser Ile Pro Pro Leu Pro Pro His His
        530                 535                 540

His Glu Gln Lys Leu Ile Ser Glu Glu Asp Leu
545                 550                 555

<210> SEQ ID NO 21
<211> LENGTH: 544
<212> TYPE: PRT
<213> ORGANISM: Cannabis sativa

<400> SEQUENCE: 21

Met Lys Cys Ser Thr Phe Ser Phe Trp Phe Val Cys Lys Ile Ile Phe
1                   5                   10                  15

Phe Phe Phe Ser Phe Asn Ile Gln Thr Ser Ile Ala Asn Pro Arg Glu
                20                  25                  30

Asn Phe Leu Lys Cys Phe Ser Gln Tyr Ile Pro Asn Asn Ala Thr Asn
            35                  40                  45

Leu Lys Leu Val Tyr Thr Gln Asn Asn Pro Leu Tyr Met Ser Val Leu
        50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
                100                 105                 110

Gly His Asp Ser Glu Gly Met Ser Tyr Ile Ser Gln Val Pro Phe Val
            115                 120                 125

Ile Val Asp Leu Arg Asn Met Arg Ser Ile Lys Ile Asp Val His Ser
        130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255
```

-continued

```
Phe Ser Val Lys Lys Ile Met Glu Ile His Glu Leu Val Lys Leu Val
            260                 265                 270

Asn Lys Trp Gln Asn Ile Ala Tyr Lys Tyr Asp Lys Asp Leu Leu Leu
        275                 280                 285

Met Thr His Phe Ile Thr Arg Asn Ile Thr Asp Asn Gln Gly Lys Asn
290                 295                 300

Lys Thr Ala Ile His Thr Tyr Phe Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
            340                 345                 350

Tyr Ser Gly Val Val Asn Tyr Asp Thr Asp Asn Phe Asn Lys Glu Ile
        355                 360                 365

Leu Leu Asp Arg Ser Ala Gly Gln Asn Gly Ala Phe Lys Ile Lys Leu
370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
            420                 425                 430

Pro His Arg Ala Gly Ile Leu Tyr Glu Leu Trp Tyr Ile Cys Ser Trp
        435                 440                 445

Glu Lys Gln Glu Asp Asn Glu Lys His Leu Asn Trp Ile Arg Asn Ile
450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495

Asn Asn Tyr Thr Gln Ala Arg Ile Trp Gly Glu Lys Tyr Phe Gly Lys
            500                 505                 510

Asn Phe Asp Arg Leu Val Lys Val Lys Thr Leu Val Asp Pro Asn Asn
        515                 520                 525

Phe Phe Arg Asn Glu Gln Ser Ile Pro Pro Leu Pro Arg His Arg His
530                 535                 540
```

<210> SEQ ID NO 22
<211> LENGTH: 18
<212> TYPE: DNA
<213> ORGANISM: Artificial Sequence
<220> FEATURE:
<223> OTHER INFORMATION: 6His

<400> SEQUENCE: 22
catcaccacc atcaccat                                              18

<210> SEQ ID NO 23
<211> LENGTH: 30
<212> TYPE: DNA
<213> ORGANISM: Artificial Sequence
<220> FEATURE:
<223> OTHER INFORMATION: MYC

<400> SEQUENCE: 23
gagcagaagc tcatttccga ggaggacctg                                 30

<210> SEQ ID NO 24
<211> LENGTH: 24
<212> TYPE: DNA
<213> ORGANISM: Artificial Sequence
<220> FEATURE:
<223> OTHER INFORMATION: FLAG

<400> SEQUENCE: 24
gattacaagg atgatgatga caag                                            24

<210> SEQ ID NO 25
<211> LENGTH: 42
<212> TYPE: DNA
<213> ORGANISM: Artificial Sequence
<220> FEATURE:
<223> OTHER INFORMATION: V5

<400> SEQUENCE: 25
gggaagccca tccctaaccc tctcctgggg ctcgactcga cg                        42

<210> SEQ ID NO 26
<211> LENGTH: 42
<212> TYPE: DNA
<213> ORGANISM: Artificial Sequence
<220> FEATURE:
<223> OTHER INFORMATION: HA

<400> SEQUENCE: 26
gggaagccca tccctaaccc tctcctgggg ctcgactcga cg                        42

<210> SEQ ID NO 27
<211> LENGTH: 36
<212> TYPE: DNA
<213> ORGANISM: Artificial Sequence
<220> FEATURE:
<223> OTHER INFORMATION: HSV

<400> SEQUENCE: 27
cagcctgagc tcgcgcctga ggaccccgag gactgc                               36

<210> SEQ ID NO 28
<211> LENGTH: 18
<212> TYPE: DNA
<213> ORGANISM: Artificial Sequence
<220> FEATURE:
<223> OTHER INFORMATION: 6His

<400> SEQUENCE: 28
catcaccatc atcaccat                                                   18

<210> SEQ ID NO 29
<211> LENGTH: 30
<212> TYPE: DNA
<213> ORGANISM: Artificial Sequence
<220> FEATURE:
<223> OTHER INFORMATION: MYC

<400> SEQUENCE: 29
gaacagaagc tcatttcaga agaggacttg                                      30

<210> SEQ ID NO 30
<211> LENGTH: 24
<212> TYPE: DNA
<213> ORGANISM: Artificial Sequence
<220> FEATURE:
<223> OTHER INFORMATION: FLAG

```
<400> SEQUENCE: 30
gattacaaag acgacgacga caag                                          24

<210> SEQ ID NO 31
<211> LENGTH: 42
<212> TYPE: DNA
<213> ORGANISM: Artificial Sequence
<220> FEATURE:
<223> OTHER INFORMATION: V5

<400> SEQUENCE: 31
ggtaaaccga ttccgaatcc ccttttgggt ctcgactcca ca                      42

<210> SEQ ID NO 32
<211> LENGTH: 27
<212> TYPE: DNA
<213> ORGANISM: Artificial Sequence
<220> FEATURE:
<223> OTHER INFORMATION: HA

<400> SEQUENCE: 32
tatccctatg acgtgccgga ctacgcc                                       27

<210> SEQ ID NO 33
<211> LENGTH: 36
<212> TYPE: DNA
<213> ORGANISM: Artificial Sequence
<220> FEATURE:
<223> OTHER INFORMATION: HSV

<400> SEQUENCE: 33
caaccagagc ttgcacctga agaccctgag gattgc                             36

<210> SEQ ID NO 34
<211> LENGTH: 482
<212> TYPE: DNA
<213> ORGANISM: Artificial Sequence
<220> FEATURE:
<223> OTHER INFORMATION: FBAC2-1

<400> SEQUENCE: 34
gtacgtacgc gtaacatatt gtagccaatt tggtgtcgac ggcatggtct cgcagggaac    60
gatagaaaaa cgttgacacc tagaaacggg ggctctggca cggcagctct ccacggattc   120
tctcgcagta ttacacgggc tatgcagtgg acagggatac caaacgtatg ttggtgtctt   180
aatgtaaact ttgcccgtaa attccgtcca tatcgatcga atccttaccg tcaagggaga   240
cctccagttc ccatggtcga ggggctttcg tggaccatcc cgccgcaaga tccatccgct   300
ggtgtgacgt cgagcagcgc cgaacggtgt cagtgacgtg gcatccctcc cccatccaca   360
gcaaacacga gtagttttgg tcgcgtttat accgcgctcc aaacccccaga attggccgtc   420 gcggttttcc gtaccgttgg tctcacactg gtcccgcgtt ttttctttga ttccacaatc   480
ag                                                                 482

<210> SEQ ID NO 35
<211> LENGTH: 136
<212> TYPE: DNA
<213> ORGANISM: Artificial Sequence
<220> FEATURE:
<223> OTHER INFORMATION: TUFA-1

<400> SEQUENCE: 35
```

```
gtaagactct gcaggctcca cgtgaacgag tacctcgaac ggtatggtac cgtcacaata    60
cacggtttct gcccttgtta gctcacacgt ttgctgtcct ttctactcgt tcttccctgt   120
tgttgatcct tgttag                                                   136

<210> SEQ ID NO 36
<211> LENGTH: 92
<212> TYPE: DNA
<213> ORGANISM: Artificial Sequence
<220> FEATURE:
<223> OTHER INFORMATION: EIF6-1

<400> SEQUENCE: 36
gtacgttttg ttgtggtcta ttgacaactg tagagtgcgt gaagcattta catcttgaaa    60
tggtacatct gacgcttttt gtcatcttga ag                                  92

<210> SEQ ID NO 37
<211> LENGTH: 196
<212> TYPE: DNA
<213> ORGANISM: Artificial Sequence
<220> FEATURE:
<223> OTHER INFORMATION: RPS4-1

<400> SEQUENCE: 37
gtaagaatac tcattcttcg tcaatgagat tgttgagtct ctgataggaa ccgaaaatgt    60
aggaaggaag cgctggcaac tttctgatga agatgtttc tgatgaaaga cgtttgccgt   120
tgacaaacat ccgtcccacg aaagtagtgt cgggaaacgt tggctcactc ggttgattct   180
tttctccttt taatag                                                   196

<210> SEQ ID NO 38
<211> LENGTH: 605
<212> TYPE: DNA
<213> ORGANISM: Artificial Sequence
<220> FEATURE:
<223> OTHER INFORMATION: pEF-1a

<400> SEQUENCE: 38
cgaaacgaat agaagctccc cgaggtcggg tgttgtttgg gaggttcatg gtggtttcgg    60
tgtcgcttgc tcgctcgctc gttcgcagtg acagacagtt cgtgagacac gagaaccgtt   120
ggcgtccgag ttcgggtgcc gcatttcgtc gtctccacga ttcaattctt gcccatcaga   180
cgagtcccga attccgtgac tctggatgcg atttactttc taactgtaag cgaaactcaa   240
cgattccgta cgttgttttc tattttacag tgagtcttcg ataccaccgt acaaccatcg   300
ttcgtgtacc gtctggtagt cccacgtgtc gacaacgtgt ggctctggac cgatgagttg   360
tttgccgttc ggaaacgagc agtaccaagg aattcacaga aacacagccc atgtaacaca   420
acgaccgcga atcgtttcgg tgctctcgct tcgcgtacgg gcgggcggtc ctcccgagca   480
gcgagaggag tccgcagcgt catagttgca atccgggccc ccctcgcgtt gttcactctc   540
tcgtctagta gagaaacttc catcggatcg tatcataata ttgtatcgta taatatcacg   600
taatc                                                               605

<210> SEQ ID NO 39
<211> LENGTH: 600
<212> TYPE: DNA
<213> ORGANISM: Artificial Sequence
<220> FEATURE:
<223> OTHER INFORMATION: p40SRPS8

<400> SEQUENCE: 39
```

```
ccctgcgata gacctttcc aaactcacgc agtccaagaa acaaaggggg tgagaagtat      60 acgcacctt cggtttcggc ataattctta aactcttgtg gtcactttct tgtgaagaag     120
ctaggggcac tcgttttccc tcagagcctg caaacacaaa attcctgcag tcaattgtcc    180
caacactcgg caaaccgtat gcgcaagcaa cgatgcgcag aaggccgtgg atggatggcg    240
actcgcgata tggcttcttg ggtcgccagt gtggtacgtc cggcgtatgt caatacgcga    300
attcggacga ctggcatctc taggaggagg attccttctt ttatgacatg ttatttttat   360
atacattgat gctttccgac agtcggaagt aataaatgaa tttatttcaa gactacctat    420
actcctttga cttgttcgac taatcttacc gcttactaaa atctcgaaat cacgcttgac    480
ctctcgcacg caaattttg ctgctggacg ctacgcactc ggcccaattc ttctcggtcc     540
tcgtcgtcgc aattgtcgtt gcgttgatct tgcaccgaag gaatcagaga atagaatacc    600
```

<210> SEQ ID NO 40
<211> LENGTH: 603
<212> TYPE: DNA
<213> ORGANISM: Artificial Sequence
<220> FEATURE:
<223> OTHER INFORMATION: pH4-1B

<400> SEQUENCE: 40

```
cgtcggtctc tttcccggga aacgggtaca ctcctccgcg ccaacaacat attactacta      60
ctaccaagaa cgtccacggc cttgtcgtgc gttacgctct cccaacgcgt gcggggtaaa    120
ttacgtctcg gtttgctaag tagcgcacag ctaaatagat gaccgttatt gtatttaaga    180
tcattcaata ttgattgcat tgtactttgc gtcaaactga aattccctcg tactaacggt    240
taacccgtca accctaagcg ttcgcccaaa gtagtcaacc gggacacgcg aaccgacatt    300
gggcagatct ttcacagaca gaaaaccatt tccaatccaa ataagcatga ctattacaca    360
cccattcgta gcgcgaggac aaactgatag ctccaacaaa atgcgccaac atcgtacatt    420
gtaagaagct tacggaacac tatgtatgta gaaccatacg aacagcaact agtactggcc    480
atcgagcagc ggtgactccc ggctttcgta gcgctgtgaa ggttacactc tcacaattcg    540
ctctcggcta caaccgacaa aagtcttact cacagtcaat accgaaaaca acaacagcc     600 aac                                                                  603
```

<210> SEQ ID NO 41
<211> LENGTH: 600
<212> TYPE: DNA
<213> ORGANISM: Artificial Sequence
<220> FEATURE:
<223> OTHER INFORMATION: py-Tubulin

<400> SEQUENCE: 41

```
ttcgttgata tttttattca aatgtatcgg gaggagtaga ggttgattaa ctgtaaacaa      60
tttcctattt actgttaagg accagctgct gcagtaggta tggcctatcc actaaacgca    120
ctcacggaac gcctcgcgaa atttacccac ggccaactta cattaccgcc ttttgtgaat    180
tggaaacgcc gcatgattct caaatgcgca gaatttcaaa cggtagcttg cggtggagac    240
tcgctcattg acagtgaaac taccttgtgt cctcggattt tcagatatac ctatacagtt    300
catggcaaaa tttcgttcat gaacgcacgt gatccattgc tcgcgattcc cgttttttgat   360 tgtgaacgcg ggattacatg cgtgcggtga cggtagtcca gacacagata tttgcaatac    420
cgggcccttt tcactacaga ccctgtaggg gtatgttgac gagaatgaac tcgcagactg    480
```

```
ccaaaatcgc tttggctgat cccaagtttt ggcactccat cgtaatttgt catattccat      540
acggtagctt cgactgaatc cagacaaaca atttagtcca gctgcgcttc tacttgcaat      600

<210> SEQ ID NO 42
<211> LENGTH: 504
<212> TYPE: DNA
<213> ORGANISM: Artificial Sequence
<220> FEATURE:
<223> OTHER INFORMATION: pRBCMT

<400> SEQUENCE: 42
acacggagga tctatctaca gcagcgatga gggcgcccga gaaagaaaga acgattgccg       60
tactattctc tttgaccttt gggcgctcgc tcgtatcttt gaagcgactg ttggggtctc      120
agggtccaaa aaacagaaac tggattgaca gtgtgtctgg accttgtcga accttacagt      180
tacattacag ttaattgtca ctgtaaatag tctatcgctg gattacgtca tcgcgtgact      240
gggtgggaat ccttcttgtt gacagtgaat ctacggtata ctattccttg ggcgcttgta      300
cttgtgtctc gagattgccg acagtgacgt caattcggca cccacacctt ccacccgccg      360
aaccaaaatc aacaacacga agcacacgac cgaccgactg tacacgtgaa ggagcaaacc      420
atcgaacgaa aggagccttc cacggacaca acccgaaagc tcgacaccct tcacccacgc      480
aaagtatctc ttcgtgatcc tacc                                            504

<210> SEQ ID NO 43
<211> LENGTH: 250
<212> TYPE: DNA
<213> ORGANISM: Artificial Sequence
<220> FEATURE:
<223> OTHER INFORMATION: pFcpB

<400> SEQUENCE: 43
gaaacatacc ttcagcgtcg tcttcactgt cacagtcaac tgacagtaat ctttggcccg       60
tagaggttcg aaattcaatc tattaaatac agcaggataa gacacaagag cgacatcctg      120
acatcaactc cgtgaacagc aaatcctggt tgaacacgta tccttttggg ggcctccagc      180
tacgacgctc gccccagctg gggcttcctt actatacaca gcgcatattt cgcggttgcc      240
agaagtcaag                                                            250

<210> SEQ ID NO 44
<211> LENGTH: 599
<212> TYPE: DNA
<213> ORGANISM: Artificial Sequence
<220> FEATURE:
<223> OTHER INFORMATION: pFcpC

<400> SEQUENCE: 44
gagcacaaga ggtgacaaaa gccaccggct ggatcgcact tctcggaatt tccccctac        60 tatcaaacaa attcgaattg ccaaaggtga agggactaac tgtaaatcct gatcaatcaa      120
ggtctcaatc aagtacaatg ggctacaatg atatttagat gggaacacaa tgaaacaaat      180
tgaaacttct actgacagga gcgcaattga cttgtgtagc ttttcatgag cacttgattg      240
ctaccaattg tgaacgggat ggggaaagac tcgaaaaggt gcatgcttcc gataatctac      300
tatattttct agaatcaaat aatatttaaa tgaatgaggt cctcagcgta cgttaagcct      360
acttatttag aacagaagt cagaccgagg ggtactaaaa ttctaagggt tgagaggtat       420
cttgattccg ggtctatgga agcccatcct tgttgaagct tgaacacgat ccttgtgaaa      480
ggccgacgtt gcgcgaaaaa acagcctgcc gatttctttc cttctttctc gtctcaacct      540
```

```
atatactttc ataatctctg ttagagttta ccaacaacac atatatacat ttcgacaaa      599
```

<210> SEQ ID NO 45
<211> LENGTH: 593
<212> TYPE: DNA
<213> ORGANISM: Artificial Sequence
<220> FEATURE:
<223> OTHER INFORMATION: pFcpD

<400> SEQUENCE: 45

```
actagcttga ttgggatatc tcgctcatgt ttgtcgcgtg ctatgtcttt ttaggtactt       60
tgaacctacg ttcgtacttg tataatatga tcatcgtatt atcgtttttc atccgtccag      120
cgcaaaatgc attagcagct agtcctagcg tgcggagcta cctggacagg tgcatgacgg      180
atgcgtgtcc ttcagtgact ttctaattaa cagtaacttc tttacttatg tttcagtttg      240
taagaagcgg gattcgctcg tcggttgaca tctgattgga ctgcgtcggc acatgaaaac      300
tacattgtga aatctgctaa aactccgggt atctctgaca caaaacgatt cggcttcgca      360
atttcaacat tacggtcaag gctaacgtat cttcctcggt caacttcaga ttatgccgat      420
taaattgtcg tagcttttcaa ggcgttttga gtactgcggc agttgttgaa cctgcaagga      480
gaagatctcg acaacagaat aaagcgaaaa atgggtctca tgcactaaca ctcaggcctc      540
cctcataatc tctgtttgag tttaccaaca acacatatat acatttcgac aaa             593
```

<210> SEQ ID NO 46
<211> LENGTH: 499
<212> TYPE: DNA
<213> ORGANISM: Artificial Sequence
<220> FEATURE:
<223> OTHER INFORMATION: tEF-1a

<400> SEQUENCE: 46

```
atgcgggagt ggaccgcgac gatccgtccg gaaaacaata ctaggtgcta tcacaggggc       60
gcgttttgga gagacgttct gcggaaacac gaatttagaa tacgtaacta acatataaac      120
tggatagccc tcgcatcgga acttagaatg ttcgcctcaa ttttttagttt agcgtggagc      180
agagatacct ttccatttgg caaaatctac ctttcgtgag ggacatcttg agaaataagc      240
ggacttgtag actaggaccg tggtaacctc ctctcaatct accaatgttg tctgatttcc      300
gagccgcgcg gctgaaaatc gtctagcact tggatgcgag agcaaatgtc aagtcctgct      360
ctgtcctgtt ggacgctttc ctctcaccgc gagagggctt tcactcgcga aacacgtatt      420
tcatattcaa actctatgaa gtttaaagta gatgtatcta caaacggtcc taagtttggg      480
taagaatttt cgactgcat                                                   499
```

<210> SEQ ID NO 47
<211> LENGTH: 499
<212> TYPE: DNA
<213> ORGANISM: Artificial Sequence
<220> FEATURE:
<223> OTHER INFORMATION: t40SRPS8

<400> SEQUENCE: 47

```
agataagaat atctcattgt gaacatctat gatttaccaa ttttattctt tgtttacagt       60
tagacgccag taattgtgct gtttctctca gtctgtgtc aatacaaact acgaaacttg       120
gcaatttttc tcttgaatat gagcacgaga ttgaaacgca caaggaaat tagtttccat       180
cctttgacaa agtttgttgc tgtttagaga acagatgtca aaattaacgt gccatggaat      240
```

```
tgaaccatgg tgcgctatcc ccaaatcacg tcgtttgacc tcgtcacatt taaggtatat    300
caagcatatt cacttatatc ttgacatcct ccctgcttga tattcctttg cccttgagcc    360
atcttcccca cacgctggag atgacccctg cccctccttt ctttatccac ccgagtaagg    420
tgtcgacaag tcactttgcc cctgagccat cctccccact caggagatga cccctacccc    480
tttcttcttt atccacccc                                                 499

<210> SEQ ID NO 48
<211> LENGTH: 500
<212> TYPE: DNA
<213> ORGANISM: Artificial Sequence
<220> FEATURE:
<223> OTHER INFORMATION: tH4-1B

<400> SEQUENCE: 48
gcttgcgctt gatcctcgac tttgttgctc gtctttaaaa ccttggaacg attatataca    60
atcaccaact caaaaaccgg attttctaaa atccacccaa acaaccaaag aaaatacttc    120
tcattgcatt tatgaatcac agcagacctg cgtcctttta aaacttagat cctgttttct    180
tataaaaaac agatcaaatt ttctgggagt tcattgactc tgccagtcag aatcaatcct    240
gcagtaattc tttatttaca ggtgaaagta aagagaatc ccaatttttt gcttgtacat     300
taaggtcctc cttacattac agctaatttc aaaataagat gaagttggat tcgtgtcctt    360
tcatggtgat gtgatattct gcactatacc aaacaccgtg aaatgtcagc tagagcttgt    420
catgaggcag ttgctgccaa tcactacata tagatccttc acggagaaaa gttggcttca    480
ttctctgttg ctaatcggct                                                500

<210> SEQ ID NO 49
<211> LENGTH: 500
<212> TYPE: DNA
<213> ORGANISM: Artificial Sequence
<220> FEATURE:
<223> OTHER INFORMATION: ty-Tubulin

<400> SEQUENCE: 49
agcaaactca ttatgatgca tgggagtgcg accgagtttc gaacgatgct aacgaacatt    60
attagtggaa ggcagtcatt gttgtatgcg tcaaagtata taatcagacg gacagtagtt    120
cattttaaac ttttgttcgg aaagcgttga tcattcatcg gggaatcgcg ctaacgagca    180
gtaattggag ttgtaactgc aggctcaacg cgtttctggc tcccgtgggt taccataatg    240
ctaactatca ttctttattt gcagtatcac cagtccaaga attattcgtg gtcatttctg    300
atgctactgt ggagaagtga gagtaatttc gccgactttg aagtgaagac gcgtctccga    360
acgtagattg ttggtattgt accattgaag gagagttttt gaactcaggt tgttgatcgt    420
aatgtccgcg acatcctggc gcactacacg ccaatgacca taacatgtct tggtcgccct    480
cctcgtaagt catcgccatt                                                500

<210> SEQ ID NO 50
<211> LENGTH: 501
<212> TYPE: DNA
<213> ORGANISM: Artificial Sequence
<220> FEATURE:
<223> OTHER INFORMATION: tRBCMT

<400> SEQUENCE: 50
aaatacaaat tcatgtacct aaacgatagt atggatgatg ggagtaattg cactataatt    60
gtagaacctt gtaagaggaa aaaatgatct tactgtgtta tttcctcttg aaagaatcta    120
```

```
tggataaaat aagagaggac gctaggtggt aacattccgg caaaacactg gcgcctaaat      180
ttttgccgga atcgtcaatt gcaacggttg taccggtgct ttgttttagt gtttcgcctt      240
gctacccttc aggaaccggt aacgaacacc tccgccaccc cggacccgct ctgttttagt      300
ttgaatggac ttgcgcaaag aatccttatc attcgcctgt gaccgggttc cttccttggc      360
caaatttgcc agaaaggttt cccgatcaat gctaggggtg cttccgcctc cacttgccgt      420
gggagtgttc ccaccgctac ttgccgttgg agtgctatca ctatcggagc cttggatcgt      480
gttgggcgta ccggtagtgc c                                                501
```

<210> SEQ ID NO 51
<211> LENGTH: 502
<212> TYPE: DNA
<213> ORGANISM: Artificial Sequence
<220> FEATURE:
<223> OTHER INFORMATION: tFcpB

<400> SEQUENCE: 51

```
tttacttgct gggtaggccg tttctggaat aacatattag attctaactg gttcgaagca       60
ttgcgttgct gtaacattcc cgttcacaaa aatacagaac agtctagaag ttcgcgacga      120
cataattttt ctctttagga ggccggggtt gtaattgttc tagggctgtt ccaatagaga      180
agataagatg atcaaacata ccagccgcgc ttgattggac ggagtacgtt tgcatcagct      240
atttttcaaa agcgctgcac gacgcacact ctatgaacac ttcaagactc tcaacgcaag      300
tgacaaccat cctctccaaa aggctatctt tcggggcacc tgtaatataa aaaagcatgg      360
cagtgcattc catgcaaaaa atgtctaatc tggttgggtt ttaaagtccg tatcgagcac      420
agaggtgaca aaagccaccg gctggatcgc acttctcgga atttcccccc tactatcaaa      480
caaattcgaa ttgccaaagg tg                                               502
```

<210> SEQ ID NO 52
<211> LENGTH: 492
<212> TYPE: DNA
<213> ORGANISM: Artificial Sequence
<220> FEATURE:
<223> OTHER INFORMATION: tFcpC

<400> SEQUENCE: 52

```
ttttgttaca ttgacttcaa ggagtcgagg aatcgatact gccgtcgttt ccaggatccg       60
aggtttctat agactctcta tagactctgt taacctaata gaatcagaca tacctctcct      120
gctattttgt tttatgaat ttggcttttg cctctctagt cagatttgaa tgttattttc       180
cgccaggtgt gttagtcggg ctctcgtttg agttacaaga gggattgagt ggcgaggatt      240
cactctaatg taaatatgac tgtgaacaaa actttaaaat tactacgcat cttctttgac      300
tgtcagatat tcgtcggtga cagcagtcaa tgcctgcaaa ttgtcctcct gggtcgcaat      360
ttggttttgg attgacctgg tatgcattat gaagaaaaaa attcgttatt agccaactgc      420
ctagcgtgca cattgcatgg ttagacctcc ttgacgactg tgagcctaca tccttctgca      480
acaagctgca at                                                          492
```

<210> SEQ ID NO 53
<211> LENGTH: 336
<212> TYPE: DNA
<213> ORGANISM: Artificial Sequence
<220> FEATURE:
<223> OTHER INFORMATION: tFcpD

<400> SEQUENCE: 53
ttttgttaca tttactgact tcaaggagtc gaggaatcga tactgccgtc gtttccagga 60
tccgaggttt cataaactct gttaacgtta tagaaacaga cttacctctc ctacgccatt 120
cacgtaatat tcgcaatatg ctattcttcc tctgaagacc aggtttatgt gctgcctgaa 180
actatttcaa taagtcagct gcacttgcac agggtttcac aaggaaagcg tgtctttttt 240
tccaacgtag gcgtcgcttt cgtctgactc ttactcttac attcacagcc aatacttaca 300
attagtaaaa aacctgtgct cgagagtgaa aacgtc 336

<210> SEQ ID NO 54
<211> LENGTH: 72
<212> TYPE: DNA
<213> ORGANISM: Artificial Sequence
<220> FEATURE:
<223> OTHER INFORMATION: FMDV2a

<400> SEQUENCE: 54
gctcctgtca agcagaccct gaactttgac ctgctcaagc tcgccggtga tgtggagagc 60
aaccccggcc cc 72

<210> SEQ ID NO 55
<211> LENGTH: 72
<212> TYPE: DNA
<213> ORGANISM: Artificial Sequence
<220> FEATURE:
<223> OTHER INFORMATION: FMDV2a

<400> SEQUENCE: 55
gccccggtga aacaaaccct taatttcgat ttgttgaaat tggctggaga tgttgagtct 60
aatccaggcc cc 72

<210> SEQ ID NO 56
<211> LENGTH: 9444
<212> TYPE: DNA
<213> ORGANISM: Artificial Sequence
<220> FEATURE:
<223> OTHER INFORMATION: optimized Steely1

<400> SEQUENCE: 56
atgaacaaga actcgaagat tcaatcgccg aactcgtcgg acgtggctgt gattggagtg 60
ggatttcgat ttccgggaaa ctcgaacgac ccggaatcgt tgtggaacaa cttgttggac 120
ggatttgacg ctattacgca agtgccgaag gaacgatggg ctacgtcgtt tcgagaaatg 180
ggattgatta agaacaagtt tggaggattt ttgaaggact cggaatggaa gaactttgac 240
ccgttgtttt ttggaattgg accgaaggaa gctccgttta ttgacccgca acaacgattg 300
ttgttgtcga ttgtgtggga atcgttggaa gacgcttaca ttcgaccgga cgaattgcga 360
ggatcgaaca cgggagtgtt tattggagtg tcgaacaacg actacacgaa gttgggattt 420
caagacaact actcgatttc gccgtacacg atgacgggat cgaactcgtc gttgaactcg 480
aaccgaattt cgtactgctt tgactttcga ggaccgtcga ttacggtgga cacggcttgc 540
tcgtcgtcgt tggtgtcggt gaacttggga gtgcaatcga ttcaaatggg agaatgcaag 600
attgctattt gcggaggagt gaacgctttg tttgacccgt cgacgtcggt ggctttttcg 660
aagttgggag tgttgtcgga aaacggacga tgcaactcgt tttcggacca agcttcggga 720
tacgtgcgat cggaaggagc tggagtggtg gtgttgaagt cgttggaaca agctaagttg 780
gacggagacc gaatttacgg agtgattaag ggagtgtcgt cgaacgaaga cggagcttcg 840

```
aacggagaca agaactcgtt gacgacgccg tcgtgcgaag ctcaatcgat taacatttcg    900
aaggctatgg aaaaggcttc gttgtcgccg tcggacattt actacattga agctcacgga    960
acgggaacgc cggtgggaga cccgattgaa gtgaaggctt tgtcgaagat tttttcgaac   1020
tcgaacaaca accaattgaa caacttttcg acggacggaa acgacaacga cgacgacgac   1080
gacgacaaca cgtcgccgga accgttgttg attggatcgt ttaagtcgaa cattggacac   1140
ttggaatcgg ctgctggaat tgcttcgttg attaagtgct gcttgatgtt gaagaaccga   1200
atgttggtgc cgtcgattaa ctgctcgaac ttgaacccgt cgattccgtt tgaccaatac   1260
aacatttcgg tgattcgaga aattcgacaa ttttccgacgg acaagttggt gaacattgga   1320
attaactcgt ttggatttgg aggatcgaac tgccacttga ttattcaaga atacaacaac   1380
aactttaaga caactcgac gatttgcaac aacaacaaca caacaacaa caacattgac    1440
tacttgattc cgatttcgtc gaagacgaag aagtcgttgg acaagtactt gattttgatt   1500
aagacgaact cgaactacca caaggacatt tcgtttgacg actttgtgaa gtttcaaatt   1560
aagtcgaagc aatacaactt gtcgaaccga atgacgacga ttgctaacga ctggaactcg   1620
tttattaagg gatcgaacga atttcacaac ttgattgaat cgaaggacgg agaaggagga   1680
tcgtcgtcgt cgaaccgagg aattgactcg gctaaccaaa ttaacacgac gacgacgtcg   1740
acgattaacg acattgaacc gttgttggtg tttgtgtttt gcggacaagg accgcaatgg   1800
aacggaatga ttaagacgtt gtacaactcg gaaaacgtgt ttaagaacac ggtggaccac   1860
gtggactcga ttttgtacaa gtactttgga tactcgattt tgaacgtgtt gtcgaagatt   1920
gacgacaacg acgactcgat taaccacccg attgtggctc aaccgtcgtt gttttgttg    1980
caaattggat tggtggaatt gtttaagtac tggggaattt acccgtcgat ttcgtgggga   2040
cactcgtttg gagaagtgtc gtcgtactac ttgtcgggaa ttatttcgtt ggaaacggct   2100
tgcaagattg tgtacgtgcg atcgtcgaac caaaacaaga cgatgggatc gggaaagatg   2160
ttggtggtgt cgatgggatt taagcaatgg aacgaccaat tttcggctga atggtcggac   2220
attgaaattg cttgctacaa cgctccggac tcgattgtgg tgacgggaaa cgaagaacga   2280
ttgaaggaat tgtcgattaa gttgtcggac gaatcgaacc aaattttaa cacgttttg    2340
cgatcgccgt gctcgtttca ctcgtcgcac aagaagtga ttaagggatc gatgtttgaa   2400
gaattgtcga acttgcaatc gacgggagaa acggaaattc cgttgttttc gacggtgacg   2460
ggacgacaag tgttgtcggg acacgtgacg gctcaacaca tttacgacaa cgtgcgagaa   2520
ccggtgttgt ttcaaaagac gattgaatcg attacgtcgt acattaagtc gcactacccg   2580
tcgaaccaaa aggtgattta cgtggaaatt gctccgcacc cgacgttgtt ttcgttgatt   2640
aagaagtcga ttccgtcgtc gaacaagaac tcgtcgtcgg tgttgtgccc gttgaaccga   2700
aaggaaaact cgaacaactc gtacaagaag tttgtgtcgc aattgtactt taacggagtg   2760
aacgtggact ttaactttca attgaactcg atttgcgaca acgtgaacaa cgaccaccac   2820
ttgaacaacg tgaagcaaaa ctcgtttaag gaaacgacga actcgttgcc gcgataccaa   2880
tgggaacaag acgaatactg gtcggaaccg ttgatttcgc gaaagaaccg attggaagga   2940
ccgacgacgt cgttgttggg acaccgaatt atttactcgt ttccggtgtt tcaatcggtg   3000
ttggacttgc aatcggacaa ctacaagtac ttgttggacc acttggtgaa cggaaagccg   3060
gtgtttccgg gagctggata cttggacatt attattgaat ttttgactga ccaaaagcaa   3120
caattgaact cgtcggactc gtcgaactcg tacattatta acgtggacaa gattcaattt   3180
```

```
ttgaacccga ttcacttgac ggaaaacaag ttgcaaacgt tgcaatcgtc gtttgaaccg    3240
attgtgacga agaagtcggc ttttcggtg  aactttttta ttaaggacac ggtggaagac    3300
caatcgaagg tgaagtcgat gtcggacgaa acgtggacga acacgtgcaa ggctacgatt    3360
tcgttggaac aacaacaacc gtcgccgtcg tcgacgttga cgttgtcgaa gaagcaagac    3420
ttgcaaattt tgcgaaaccg atgcgacatt tcgaagttgg acaagtttga attgtacgac    3480
aagatttcga agaacttggg attgcaatac aactcgttgt ttcaagtggt ggacacgatt    3540
gaaacgggaa aggactgctc gtttgctacg ttgtcgttgc cggaagacac gttgtttacg    3600
acgattttga acccgtgctt gttggacaac tgctttcacg gattgttgac gttgattaac    3660
gaaaagggat cgtttgtggt ggaatcgatt tcgtcggtgt cgatttactt ggaaaacatt    3720
ggatcgttta accaaacgtc ggtgggaaac gtgcaatttt acttgtacac gacgatttcg    3780
aaggctacgt cgttttcgtc ggaaggaacg tgcaagttgt ttacgaagga cggatcgttg    3840
attttgtcga ttggaaagtt tattattaag tcgacgaacc cgaagtcgac gaagacgaac    3900
gaaacgattg aatcgccgtt ggacgaaacg ttttcgattg aatggcaatc gaaggactcg    3960
ccgattccga cgccgcaaca aattcaacaa caatcgccgt tgaactcgaa cccgtcgttt    4020
attcgatcga cgattttgaa ggacattcaa tttgaacaat actgctcgtc gattattcac    4080
aaggaattga ttaaccacga aaagtacaag aaccaacaat cgtttgacat taactcgttg    4140
gaaaaccact tgaacgacga ccaattgatg gaatcgttgt cgatttcgaa ggaatacttg    4200
cgatttttta cgcgaattat ttcgattatt aagcaatacc cgaagatttt gaacgaaaag    4260
gaattgaagg aattgaagga aattattgaa ttgaagtacc cgtcggaagt gcaattgttg    4320
gaatttgaag tgattgaaaa ggtgtcgatg attattccga agttgttgtt tgaaaacgac    4380
aagcaatcgt cgatgacgtt gtttcaagac aacttgttga cgcgatttta ctcgaactcg    4440
aactcgacgc gattttactt ggaacgagtg tcggaaatgg tgttggaatc gattcgaccg    4500
attgtgcgag aaaagcgagt gttttcgaat ttggaaattg gagctggaac gggatcgttg    4560
tcgaacgtgg tgttgacgaa gttgaacacg tacttgtcga cgttgaactc gaacggagga    4620
tcgggataca acattattat tgaatacacg tttacggaca tttcggctaa ctttattatt    4680
ggagaaattc aagaaacgat gtgcaacttg tacccgaacg tgacgtttaa gttttcggtg    4740
ttggacttgg aaaaggaaat tattaactcg tcggacttt  tgatgggaga ctacgacatt    4800
gtgttgatgg cttacgtgat tcacgctgtg tcgaacatta agttttcgat tgaacaattg    4860
tacaagttgt tgtcgccgcg aggatggttg ttgtgcattg aaccgaagtc gaacgtggtg    4920
ttttcggact tggtgtttgg atgctttaac caatggtgga actactacga cgacattcga    4980
acgacgcact gctcgttgtc ggaatcgcaa tggaaccaat tgttgttgaa ccaatcgttg    5040
aacaacgaat cgtcgtcgtc gtcgaactgc tacggaggat tttcgaacgt gtcgtttatt    5100
ggaggagaaa aggacgtgga ctcgcactcg tttatttttgc actgccaaaa ggaatcgatt    5160
tcgcaaatga agttggctac gacgattaac aacggattgc cgtcgggatc gattgtgatt    5220
gtgttgaact cgcaacaatt gacgaacatg aagtcgtacc cgaaggtgat tgaatacatt    5280
caagaagcta cgtcgttgtg caagacgatt gaaattattg actcgaagga cgtgttgaac    5340
tcgacgaact cggtgttgga aaagattcaa aagtcgttgt tggtgttttg cttgttggga    5400
tacgacttgt tggaaaacaa ctaccaagaa caatcgtttg aatacgtgaa gttgttgaac    5460
ttgatttcga cgacggcttc gtcgtcgaac gacaagaagc cgccgaaggt gttgttgatt    5520
acgaagcaat cggaacgaat ttcgcgatcg tttttactcgc gatcgttgat tggaatttcg    5580
```

```
cgaacgtcga tgaacgaata cccgaacttg tcgattacgt cgattgactt ggacacgaac   5640
gactactcgt tgcaatcgtt gttgaagccg attttttcga actcgaagtt ttcggacaac   5700
gaatttattt ttaagaaggg attgatgttt gtgtcgcgaa ttttttaagaa caagcaattg   5760 ttggaatcgt cgaacgcttt tgaaacggac tcgtcgaact tgtactgcaa ggcttcgtcg   5820
gacttgtcgt acaagtacgc tattaagcaa tcgatgttga cggaaaacca aattgaaatt   5880
aaggtggaat gcgtgggaat taactttaag gacaacttgt tttacaaggg attgttgccg   5940
caagaaattt ttcgaatggg agacatttac aacccgccgt acggattgga atgctcggga   6000
gtgattacgc gaattggatc gaacgtgacg gaatactcgg tgggacaaaa cgtgtttgga   6060
tttgctcgac actcgttggg atcgcacgtg gtgacgaaca aggacttggt gattttgaag   6120
ccggacacga tttcgttttc ggaagctgct tcgattccgg tggtgtactg cacggcttgg   6180
tactcgttgt ttaacattgg acaattgtcg aacgaagaat cgattttgat tcactcggcc   6240
acgggaggag tgggattggc ttcgttgaac ttgttgaaga tgaagaacca acaacaacaa   6300
ccgttgacga acgtgtacgc tacggtggga tcgaacgaaa agaagaagtt tttgattgac   6360
aactttaaca acttgtttaa ggaagacgga gaaaacattt tttcgacgcg agacaaggaa   6420
tactcgaacc aattggaatc gaagattgac gtgattttga acacgttgtc gggagaattt   6480
gtggaatcga actttaagtc gttgcgatcg tttggacgat tgattgactt gtcggctacg   6540
cacgtgtacg ctaaccaaca aattggattg ggaaacttta gtttgacca cttgtactcg   6600 gctgtggact tggaacgatt gattgacgaa aagccgaagt tgttgcaatc gattttgcaa   6660
cgaattacga actcgattgt gaacggatcg ttggaaaaga ttccgattac gattttttccg   6720 tcgacgaaa cgaaggacgc tattgaattg ttgtcgaagc gatcgcacat tggaaaggtg   6780
gtggtggact gcacggacat ttcgaagtgc aacccggtgg gagacgtgat tacgaacttt   6840
tcgatgcgat tgccgaagcc gaactaccaa ttgaacttga actcgacgtt gttgattacg   6900
ggacaatcgg gattgtcgat tccgttgttg aactggttgt tgtcgaagtc gggaggaaac   6960
gtgaagaacg tggtgattat ttcgaagtcg acgatgaagt ggaagttgca acgatgatt   7020 tcgcactttg tgtcgggatt tggaattcac tttaactacg tgcaagtgga catttcgaac   7080
tacgacgctt tgtcggaagc tattaagcaa ttgccgtcgg acttgccgcc gattacgtcg   7140
gtgtttcact tggctgctat ttacaacgac gtgccgatgg accaagtgac gatgtcgacg   7200
gtggaatcgg tgcacaaccc gaaggtgttg ggagctgtga acttgcaccg aatttcggtg   7260
tcgtttggat ggaagttgaa ccactttgtg ttgttttcgt cgattacggc tattacggga   7320
tacccggacc aatcgattta caactcggct aactcgattt tggacgcttt gtcgaacttt   7380
cgacgattta tgggattgcc gtcgtttccg attaacttgg gaccgatgaa ggacgaagga   7440
aaggtgtcga cgaacaagtc gattaagaag ttgtttaagt cgcgaggatt gccgtcgttg   7500
tcgttgaaca agttgtttgg attgttggaa gtggtgatta caacccgtcg gaaccacgtg   7560
attccgtcgc aattgatttg ctcgccgatt gactttaaga cgtacattga atcgttttcg   7620
acgatgcgac cgaagttgtt gcacttgcaa ccgacgattt cgaagcaaca atcgtcgatt   7680
attaacgact cgacgaaggc ttcgtcgaac atttcgttgc aagacaagat tacgtcgaag   7740
gtgtcggact tgttgtcgat tccgatttcg aagattaact ttgaccaccc gttgaagcac   7800
tacggattgg actcgttgtt gacggtgcaa tttaagtcgt ggattgacaa ggaatttgaa   7860
aagaacttgt ttacgcacat tcaattggct acgatttcga ttaactcgtt tttggaaaag   7920
```

```
gtgaacggat tgtcgacgaa caacaacaac aacaacaact cgaacgtgaa gtcgtcgccg    7980
tcgattgtga aggaagaaat tgtgacgttg gacaaggacc aacaaccgtt gttgttgaag    8040
gaacaccaac acattattat ttcgccggac attcgaatta acaagccgaa gcgagaatcg    8100
ttgattcgaa cgccgatttt gaacaagttt aaccaaatta cggaatcgat tattacgccg    8160
tcgacgccgt cgttgtcgca atcggacgtg ttgaagacgc cgccgattaa gtcgttgaac    8220
aacacgaaga actcgtcgtt gattaacacg ccgccgattc aatcggtgca acaacaccaa    8280
aagcaacaac aaaaggtgca agtgattcaa caacaacaac aaccgttgtc gcgattgtcg    8340
tacaagtcga acaacaactc gtttgtgttg ggaattggaa tttcggtgcc gggagaaccg    8400
atttcgcaac aatcgttgaa ggactcgatt tcgaacgact tttcggacaa ggctgaaacg    8460
aacgaaaagg tgaagcgaat ttttgaacaa tcgcaaatta agacgcgaca cttggtgcga    8520
gactacacga agccggaaaa ctcgattaag tttcgacact tggaaacgat tacggacgtg    8580
aacaaccaat ttaagaaggt ggtgccggac ttggctcaac aagcttgctt gcgagctttg    8640
aaggactggg gaggagacaa gggagacatt acgcacattg tgtcggtgac gtcgacggga    8700
attattattc cggacgtgaa cttttaagtt attgacttgt tgggattgaa caaggacgtg    8760
gaacgagtgt cgttgaactt gatgggatgc ttggctggat tgtcgtcgtt gcgaacggct    8820
gcttcgttgg ctaaggcttc gccgcgaaac cgaattttgg tggtgtgcac ggaagtgtgc    8880
tcgttgcact tttcgaacac ggacggagga gaccaaatgg tggcttcgtc gattttttgct    8940 gacggatcgg ctgcttacat tattggatgc aacccgcgaa ttgaagaaac gccgttgtac    9000
gaagtgatgt gctcgattaa ccgatcgttt ccgaacacgg aaaacgctat ggtgtgggac    9060
ttggaaaagg aaggatggaa cttgggattg gacgcttcga ttccgattgt gattggatcg    9120
ggaattgaag cttttgtgga cacgttgttg gacaaggcta gttgcaaac gtcgacggct    9180 atttcggcta aggactgcga atttttgatt cacacgggag gaaagtcgat tttgatgaac    9240
attgaaaact cgttgggaat tgacccgaag caaacgaaga acacgtggga cgtgtaccac    9300
gcttacggaa acatgtcgtc ggcttcggtg attttttgtga tggaccacgc tcgaaagtcg    9360
aagtcgttgc cgacgtactc gatttcgttg gcttttggac cgggattggc ttttgaagga    9420 tgcttttttga agaacgtggt gtaa                                          9444
```

<210> SEQ ID NO 57
<211> LENGTH: 8907
<212> TYPE: DNA
<213> ORGANISM: Artificial Sequence
<220> FEATURE:
<223> OTHER INFORMATION: optimized Steely2

<400> SEQUENCE: 57

```
atgaacaaca acaagtcgat taacgacttg tcgggaaact cgaacaacaa cattgctaac      60
tcgaacatta acaactacaa caacttgatt aagaaggaac cgattgctat tattggaatt     120
ggatgccgat ttccgggaaa cgtgtcgaac tactcggact ttgtgaacat tattaagaac     180
ggatcggact gcttgacgaa gattccggac gaccgatgga acgctgacat tatttcgcga     240
aagcaatgga agttgaacaa ccgaattgga ggatacttga gaacattga ccaatttgac      300 aaccaatttt ttggaatttc gccgaaggaa gctcaacaca ttgacccgca caacgattg      360 ttgttgcact ggctattga aacgttgaa gacggaaaga tttcgttgga cgaaattaag       420
ggaaagaagg tgggagtgtt tattggatcg tcgtcgggag actacttgcg aggatttgac     480
tcgtcggaaa ttaaccaatt tacgacgccg ggaacgaact cgtcgttttt gtcgaaccga     540
```

```
ttgtcgtact ttttggacgt gaacggaccg tcgatgacgg tgaacacggc ttgctcggct    600
tcgatggtgg ctattcactt gggattgcaa tcgttgtgga acggagaatc ggaattgtcg    660
atggtgggag gagtgaacat tatttcgtcg ccgttgcaat cgttggactt tggaaaggct    720
ggattgttga accaagaaac ggacggacga tgctactcgt ttgacccgcg agcttcggga    780
tacgtgcgat cggaaggagg aggaattttg ttgttgaagc cgttgtcggc tgctttgcga    840
gacaacgacg aaatttactc gttgttgttg aactcggcta acaactcgaa cggaaagacg    900
ccgacgggaa ttacgtcgcc gcgatcgttg tgccaagaaa agttgattca acaattgttg    960
cgagaatcgt cggaccaatt ttcgattgac gacattggat actttgaatg ccacggaacg   1020
ggaacgcaaa tgggagactt gaacgaaatt acggctattg gaaagtcgat tggaatgttg   1080
aagtcgcacg acgacccgtt gattattgga tcggtgaagg cttcgattgg acacttggaa   1140
ggagcttcgg gaatttgcgg agtgattaag tcgattattt gcttgaagga aaagattttg   1200
ccgcaacaat gcaagttttc gtcgtacaac ccgaagattc cgtttgaaac gttgaacttg   1260
aaggtgttga cgaagacgca accgtggaac aactcgaagc gaatttgcgg agtgaactcg   1320
tttggagtgg gaggatcgaa ctcgtcgttg tttttgtcgt cgtttgacaa gtcgacgacg   1380
attacggaac cgacgacgac gacgacgatt gaatcgttgc cgtcgtcgtc gtcgtcgttt   1440
gacaacttgt cggtgtcgtc gtcgatttcg acgaacaacg acaacgacaa ggtgtcgaac   1500
attgtgaaca accgatacgg atcgtcgatt gacgtgatta cgttgtcggt gacgtcgccg   1560
gacaaggaag acttgaagat tcgagctaac gacgtgttgg aatcgattaa gacgttggac   1620
gacaacttta agattcgaga catttcgaac ttgacgaaca ttcgaacgtc gcacttttcg   1680
aaccgagtgg ctattattgg agactcgatt gactcgatta agttgaactt gcaatcgttt   1740
attaagggag aaaacaacaa caacaagtcg attattttgc cgttgattaa caacggaaac   1800
aacaacaaca acaacaacaa caactcgtcg ggatcgtcgt cgtcgtcgtc gaacaacaac   1860
aacatttgct ttattttttc gggacaagga caacaatgga acaagatgat ttttgacttg   1920
tacgaaaaca acaagacgtt taagaacgaa atgaacaact tttcgaagca atttgaaatg   1980
atttcgggat ggtcgattat tgacaagttg tacaactcgg gaggaggagg aaacgaagaa   2040
ttgattaacg aaacgtggtt ggctcaaccg tcgattgtgg ctgtgcaata ctcgttgatt   2100
aagttgtttt cgaaggacat tggaattgaa ggatcgattg tgttgggaca ctcgttggga   2160
gaattgatgg ctgcttacta ctgcggaatt attaacgact ttaacgactt gttgaagttg   2220
ttgtacattc gatcgacgtt gcaaaacaag acgaacggat cggacgaatt gcacgtgtgc   2280
ttgtcgtcga aggctgaaat tgaacaattg atttcgcaat gggatttaa cggacgaatt   2340 gtgatttgcg gaaacaacac gatgaagtcg tgcacgattt cggagacaa cgaatcgatg   2400 aaccaatttta cgaagttgat ttcgtcgcaa caatacggat cggtggtgca caaggaagtg   2460
cgaacgaact cggcttttca ctcgcaccaa atggacatta ttaaggacga attttttaag   2520
ttgtttaacc aatactttcc gacgaaccaa atttcgacga accaaattta cgacggaaag   2580 tcgtttttact cgacgtgcta cggaaagtac ttgacgccga ttgaatgcaa gcaattgttg   2640
tcgtcgccga actactggtg gaagaacatt cgagaatcgg tgttgtttaa ggaatcgatt   2700
gaacaaattt tgcaaaacca ccaacaatcg ttgacgttta ttgaaattac gtgccacccg   2760
attttgaact acttttttgtc gcaattgttg aagtcgtcgt cgaagtcgaa cacgttgttg   2820
ttgtcgacgt tgtcgaagaa ctcgaactcg attgaccaat tgttgatttt tgtgctcgaag   2880
```

```
ttgtacgtga caacttgtc gtcgattaag tggaactggt tttacgacaa gcaacaacaa    2940
caacaatcgg aatcgttggt gtcgtcgaac tttaagttgc cgggacgacg atggaagttg    3000
gaaaagtact ggattgaaaa ctgccaacga caaatggacc gaattaagcc gccgatgttt    3060
atttcgttgg accgaaagtt gttttcggtg acgccgtcg ttgaagtgcg attgaaccaa    3120
gaccgatttc aatacttgaa cgaccaccaa attcaagaca ttccgttggt gccgttttcg    3180
ttttacattg aattggtgta cgcttcgatt tttaactcga tttcgacgac gacgacgaac    3240
acgacggctt cgacgatgtt tgaaattgaa aactttacga ttgactcgtc gattattatt    3300
gaccaaaaga gtcgacgtt gattggaatt aactttaact cggacttgac gaagtttgaa    3360
attggatcga ttaactcgat tggatcggga tcgtcgtcga caacaacttt tattgaaaac    3420
aagtggaaga ttcactcgaa cggaattatt aagtacggaa cgaactactt gaagtcgaac    3480
tcgaagtcga actcgtttaa cgaatcgacg acgacgacga cgacgacgac gacgacgacg    3540
aagtgcttta agtcgtttaa ctcgaacgaa ttttacaacg aaattattaa gtacaactac    3600
aactacaagt cgacgtttca atgcgtgaag gaatttaagc aatttgacaa gcaaggaacg    3660
ttttactact cggaaattca atttaagaag aacgacaagc aagtgattga ccaattgttg    3720
tcgaagcaat tgccgtcgga ctttcgatgc attcacccgt gcttgttgga cgctgtgttg    3780
caatcggcta ttattccggc tacgaacaag acgaactgct cgtggattcc gattaagatt    3840
ggaaagttgt cggtgaacat tccgtcgaac tcgtacttta actttaagga ccaattgttg    3900
tactgcttga ttaagccgtc gacgtcgacg tcgacgtcgc cgtcgacgta ctttcgtcg    3960 gacattcaag tgtttgacaa gaagaacaac aacttgattt gcgaattgac gaacttggaa    4020
tttaagggaa ttaactcgtc gtcgtcgtcg tcgtcgtcgt cgtcgacgat taactcgaac    4080
gtggaagcta actacgaatc gaagattgaa gaaacgaacc acgacgaaga cgaagacgaa    4140
gaattgccgt tggtgtcgga atacgtgtgg tgcaaggaag aattgattaa ccaatcgatt    4200
aagtttacgg acaactacca aacggtgatt ttttgctcga cgaacttgaa cggaaacgac    4260
ttgttggact cgattattac gtcggctttg gaaaacggac acgacgaaaa caagattttt    4320
attgtgtcgc cgccgccggt ggaatcggac caatacaaca accgaattat tattaactac    4380
acgaacaacg aatcggactt tgacgctttg tttgctatta ttaactcgac gacgtcgatt    4440 tcggaaagt cgggattgtt ttcgacgcga tttattattt tgccgaactt taactcgatt    4500
acgttttcgt cgggaaactc gacgccgttg attacgaacg tgaacggaaa cggaaacgga    4560
aagtcgtgcg gaggaggagg aggatcgacg aacaacacga tttcgaactc gtcgtcgtcg    4620
atttcgtcga ttgacaacgg aaacaacgaa gacgaagaaa tggtgttgaa gtcgtttaac    4680
gactcgaact tgtcgttgtt tcacttgcaa aagtcgatta ttaagaacaa cattaaggga    4740
cgattgtttt tgattacgaa cggaggacaa tcgatttcgt cgtcgacgcc gacgtcgacg    4800
tacaacgacc aatcgtacgt gaacttgtcg caataccaat tgattggaca aattcgagtg    4860
ttttcgaacg aatacccgat tatggaatgc tcgatgattg acattcaaga ctcgacgcga    4920
attgacttga ttacggacca attgaactcg acgaagttgt cgaagttgga aattgctttt    4980
cgagacaaca ttggatactc gtacaagttg ttgaagccgt cgattttttga caactcgtcg    5040 ttgccgtcgt cgtcgtcgga aattgaaacg acggctacga cgaaggacga agaaaagaac    5100
aactcgatta actacaacaa caactactac cgagtggaat tgtcggacaa cggaattatt    5160
tcggacttga agattaagca atttcgacaa atgaagtgcg gagtgggaca agtgttggtg    5220
cgagtggaaa tgtgcacgtt gaactttcga gacatttga agtcgttggg acgagactac    5280
```

```
gacccgattc acttgaactc gatgggagac gaattttcgg gaaaggtgat tgaaattgga    5340
gaaggagtga acaacttgtc ggtgggacaa tacgtgtttg gaattaacat gtcgaagtcg    5400
atgggatcgt ttgtgtgctg caactcggac ttggtgtttc cgattccgat tccgacgccg    5460
tcgtcgtcgt cgtcgtcgaa cgaaaacatt gacgaccaag aaattatttc gaagttgttg    5520
aaccaatact gcacgattcc gattgtgttt ttgacgtcgt ggtactcgat tgtgattcaa    5580
ggacgattga agaagggaga aaagattttg attcactcgg gatgcggagg agtgggattg    5640
gctacgattc aaatttcgat gatgattgga gctgaaattc acgtgacggt gggatcgaac    5700
gaaaagaagc aatacttgat taaggaattt ggaattgacg aaaagcgaat ttactcgtcg    5760
cgatcgttgc aattttacaa cgacttgatg gtgaacacgg acggacaagg agtggacatg    5820
gtgttgaact cgttgtcggg agaatacttg gaaaagtcga ttcaatgctt gtcgcaatac    5880
ggacgattta ttgaaattgg aaagaaggac atttactcga actcgtcgat tcacttggaa    5940
ccgtttaaga caacttgtc gttttttgct gtggacattg ctcaaatgac ggaaaaccga    6000
cgagactact tgcgagaaat tatgattgac caattgttgc cgtgctttaa gaacggatcg    6060
ttgaagccgt tgaaccaaca ctgctttaac tcgccgtgcg acttggtgaa ggctattcga    6120
tttatgtcgt cgggaaacca cattggaaag attttgatta actggtcgaa cttgaacaac    6180
gacaagcaat ttattaacca ccactcggtg gtgcacttgc cgattcaatc gttttcgaac    6240
cgatcgacgt acatttttac gggatttgga ggattgacgc aaacgttgtt gaagtacttt    6300
tcgacggaat cggacttgac gaacgtgatt attgtgtcga gaacggatt ggacgacaac     6360
tcgggatcgg gatcgggaaa caacgaaaag ttgaagttga ttaaccaatt gaaggaatcg    6420
ggattgaacg tgttggtgga aaagtgcgac ttgtcgtcga ttaagcaagt gtacaagttg    6480
tttaacaaga ttttttgacaa cgacgcttcg ggatcggact cgggagactt tcggacatt    6540
aagggaattt ttcactttgc ttcgttgatt aacgacaagc gaattttgaa gcacaacttg    6600
gaatcgttta actacgtgta caactcgaag gctacgtcgg cttggaactt gcaccaagtg    6660
tcgttgaagt acaacttgaa cttggaccac tttcaaacga ttggatcggt gattacgatt    6720
ttgggaaaca ttgacaatc gaactacacg tgcgctaacc gatttgtgga aggattgacg    6780
cacttgcgaa ttggaatggg attgaagtcg tcgtgcattc acttggcttc gattccggac    6840
gtgggaatgg cttcgaacga caacgtgttg aacgacttga actcgatggg atttgtgccg    6900
tttcaatcgt tgaacgaaat gaacttggga tttaagaagt tgttgtcgtc gccgaacccg    6960
attgtggtgt tgggagaaat taacgtggac cgatttattg aagctacgcc gaactttcga    7020
gctaaggaca acttttattat tacgtcgttg tttaaccgaa ttgacccgtt gttgttggtg    7080
aacgaatcgc aagactttat tattaacaac aacattaaca caacggagg aggaggagac     7140
ggatcgtttg acgacttgaa ccaattggaa gacgaaggac aacaaggatt tggaaacgga    7200
gacgatacg tggacgacaa cattgactcg gtgtcgatgt tgtcgggaac gtcgtcgatt     7260
tttgacaacg acttttacac gaagtcgatt cgaggaatgt tgtgcgacat tttggaattg    7320
aaggacaagg acttgaacaa cacggtgtcg ttttcggact acggattgga ctcgttgttg    7380
tcgtcggaat tgtcgaacac gattcaaaag aactttcga ttttgattcc gtcgttgacg     7440
ttggtggaca actcgacgat taactcgacg gtggaattga ttaagaacaa gttgaagaac    7500
tcgacgacgt cgtcgatttc gtcgtcggtg tcgaagaagg tgtcgtttaa gaagaacacg    7560
caaccgttga ttattccgac gacggctccg atttcgatta ttaagacgca atcgtacatt    7620
```

| | |
|---|---|
| aagtcggaaa ttattgaatc gttgccgatt tcgtcgtcga cgacgattaa gccgttggtg | 7680 |
| tttgacaact tggtgtactc gtcgtcgtcg tcgaacaact cgaactcgaa gaacgaattg | 7740 |
| acgtcgccgc cgccgtcggc taagcgagaa tcggtgttgc cgattatttc ggaagacaac | 7800 |
| aactcggaca cgactcgtc gatggctacg gtgatttacg aaatttcgcc gattgctgct | 7860 |
| ccgtaccacc gataccaaac ggacgtgttg aaggaaatta cgcaattgac gccgcacaag | 7920 |
| gaatttattg acaacattta caagaagtcg aagattcgat cgcgatactg ctttaacgac | 7980 |
| ttttcggaaa agtcgatggc tgacattaac aagttggacg ctggagaacg agtggctttg | 8040 |
| tttcgagaac aaacgtacca aacggtgatt aacgctggaa agacggtgat tgaacgagct | 8100 |
| ggaattgacc cgatgttgat tcgcacgtg gtgggagtga cgtcgacggg aattatggct | 8160 |
| ccgtcgtttg acgtggtgtt gattgacaag ttgggattgt cgattaacac gtcgcgaacg | 8220 |
| atgattaact ttatgggatg cggagctgct gtgaactcga tgcgagctgc tacggcttac | 8280 |
| gctaagttga agccgggaac gtttgtgttg gtggtggctg tggaagcttc ggctacgtgc | 8340 |
| atgaagttta actttgactc gcgatcggac ttgttgtcgc aagctatttt tacggacgga | 8400 |
| tgcgtggcta cgttggtgac gtgccaaccg aagtcgtcgt tggtgggaaa gttggaaatt | 8460 |
| attgacgact tgtcgtactt gatgccggac tcgcgagacg ctttgaactt gtttattgga | 8520 |
| ccgacgggaa ttgacttgga cttgcgaccg gaattgccga ttgctattaa ccgacacatt | 8580 |
| aactcggcta ttacgtcgtg gttgaagaag aactcgttgc aaaagtcgga cattgaattt | 8640 |
| tttgctacgc acccgggagg agctaagatt atttcggctg tgcacgaagg attgggattg | 8700 |
| tcgccggaag acttgtcgga ctcgtacgaa gtgatgaagc gatacggaaa catgattgga | 8760 |
| gtgtcgacgt actacgtgtt gcgacgaatt ttggacaaga ccaaacgtt gttgcaagaa | 8820 |
| ggatcgttgg gatacaacta cggaatggct atggcttttt cgccgggagc ttcgattgaa | 8880 |
| gctattttgt ttaagttgat taagtaa | 8907 |

<210> SEQ ID NO 58
<211> LENGTH: 924
<212> TYPE: DNA
<213> ORGANISM: Artificial Sequence
<220> FEATURE:
<223> OTHER INFORMATION: optimized Orf2

<400> SEQUENCE: 58

| | |
|---|---|
| atgtcggaag ctgctgacgt ggaacgagtg tacgctgcta tggaagaagc tgctggattg | 60 |
| ttgggagtgg cttgcgctcg agacaagatt tacccgttgt tgtcgacgtt tcaagacacg | 120 |
| ttggtggaag gaggatcggt ggtggtgttt tcgatggctt cgggacgaca ctcgacggaa | 180 |
| ttggactttt cgatttcggt gccgacgtcg cacggagacc cgtacgctac ggtggtggaa | 240 |
| aagggattgt tccggctac gggacacccg gtggacgact gttggctga cacgcaaaag | 300 |
| cacttgccgg tgtcgatgtt tgctattgac ggagaagtga cgggaggatt taagaagacg | 360 |
| tacgcttttt ttccgacgga caacatgccg ggagtggctg aattgtcggc tattccgtcg | 420 |
| atgccgccgg ctgtggctga aaacgctgaa ttgtttgctc gatacggatt ggacaaggtg | 480 |
| caaatgacgt cgatggacta caagaagcga caagtgaact tgtactttc ggaattgtcg | 540 |
| gctcaaacgt tggaagctga atcggtgttg gctttggtgc gagaattggg attgcacgtg | 600 |
| ccgaacgaat tgggattgaa gttttgcaag cgatcgtttt cggtgtaccc gacgttgaac | 660 |
| tgggaaacgg gaaagattga ccgattgtgc tttgctgtga tttcgaacga cccgacgttg | 720 |
| gtgccgtcgt cggacgaagg agacattgaa aagtttcaca actacgctac gaaggctccg | 780 |

| | |
|---|---:|
| tacgcttacg tgggagaaaa gcgaacgttg gtgtacggat tgacgttgtc gccgaaggaa | 840 |
| gaatactaca agttgggagc ttactaccac attacggacg tgcaacgagg attgttgaag | 900 |
| gcttttgact cgttggaaga ctaa | 924 |

<210> SEQ ID NO 59
<211> LENGTH: 1197
<212> TYPE: DNA
<213> ORGANISM: Artificial Sequence
<220> FEATURE:
<223> OTHER INFORMATION: optimized CsPT4

<400> SEQUENCE: 59

| | |
|---|---:|
| atgggattgt cgttggtgtg cacgttttcg tttcaaacga actaccacac gttgttgaac | 60 |
| ccgcacaaca agaacccgaa gaactcgttg ttgtcgtacc aacacccgaa gacgccgatt | 120 |
| attaagtcgt cgtacgacaa cttttccgtcg aagtactgct tgacgaagaa ctttcacttg | 180 |
| ttgggattga actcgcacaa ccgaatttcg tcgcaatcgc gatcgattcg agctggatcg | 240 |
| gaccaaattg aaggatcgcc gcaccacgaa tcggacaact cgattgctac gaagattttg | 300 |
| aactttggac acacgtgctg gaagttgcaa cgaccgtacg tggtgaaggg aatgatttcg | 360 |
| attgcttgcg gattgtttgg acgagaattg tttaacaacc gacacttgtt ttcgtgggga | 420 |
| ttgatgtgga aggcttttt tgctttggtg ccgattttgt cgtttaactt ttttgctgct | 480 |
| attatgaacc aaatttacga cgtggacatt gaccgaatta caagccgga cttgccgttg | 540 |
| gtgtcgggag aaatgtcgat tgaaacggct tggattttgt cgattattgt ggctttgacg | 600 |
| ggattgattg tgacgattaa gttgaagtcg gctccgttgt tgtgtttat ttacatttt | 660 |
| ggaattttg ctggatttgc ttactcggtg ccgccgattc gatggaagca atacccgttt | 720 |
| acgaactttt tgattacgat ttcgtcgcac gtgggattgg cttttacgtc gtactcggct | 780 |
| acgacgtcgg cttgggatt gccgtttgtg tggcgaccgg cttttcgtt tattattgct | 840 |
| tttatgacgg tgatgggaat gacgattgct tttgctaagg acatttcgga cattgaagga | 900 |
| gacgctaagt acgagtgtc gacggtggct acgaagttgg gagctcgaaa catgacgttt | 960 |
| gtggtgtcgg gagtgttgtt gttgaactac ttggtgtcga tttcgattgg aattatttgg | 1020 |
| ccgcaagtgt ttaagtcgaa cattatgatt ttgtcgcacg ctattttggc ttttttgcttg | 1080 |
| atttttcaaa cgcgagaatt ggctttggct aactacgctt cggctccgtc gcgacaattt | 1140 |
| tttgaattta tttggttgtt gtactacgct gaatactttg tgtacgtgtt tatttaa | 1197 |

<210> SEQ ID NO 60
<211> LENGTH: 1241
<212> TYPE: DNA
<213> ORGANISM: Artificial Sequence
<220> FEATURE:
<223> OTHER INFORMATION: optimized H1PT4

<400> SEQUENCE: 60

| | |
|---|---:|
| atggaattgt cgtcggtgtc gtcgttttcg ttgggaacga acccgtttat ttcgattccg | 60 |
| cacaacaaca caaacttgaa ggtgtcgtcg tactgctgca agtcgaagtc gcgagtgatt | 120 |
| aactcgacga actcgaagca ctgctcgccg aacaacaact cgaacaacaa cacgtcgaac | 180 |
| aagacgacgc acttgttggg attgtacgga caatcgcgat gcttgttgaa gccgttgtcg | 240 |
| tttatttcgt gcaacgacca acgaggaaac tcgattcgag cttcggctca aattgaagac | 300 |
| cgaccgccgg aatcgggaaa cttgtcggct ttgacgaacg tgaaggactt tgtgtcggtg | 360 |

```
tgctgggaat acgtgcgacc gtacacggct aagggagtga ttatttgctc gtcgtgcttg    420
tttggacgag aattgttgga aaacccgaac ttgttttcgt ggccgttgat ttttcgagct    480
ttgttgggaa tgttggctat tttgggatcg tgcttttaca cggctggaat taaccaaatt    540
tttgacatgg acattgaccg aattaacaag ccggacttgc cgttggtgtc gggacgaatt    600
tcggtggaat cggcttggtt gttgacgttg tcgccggcta ttattggatt tattttgatt    660
ttgaagttga actcgggacc gttgttgacg tcgttgtact gcttggctat tttgtcggga    720
acgatttact cggtgccgcc gtttcgatgg aagaagaacc cgattacggc ttttttgtgc    780
attttgatga ttcacgctgg attgaacttt tcggtgtact acgcttcgcg agctgctttg    840
ggattggctt ttgcttggtc gccgtcgttt tcgtttatta cggcttttat tacgtttatg    900
acgttgacgt tggcttcgtc gaaggacttg tcggacatta cggagaccg aaagtttgga     960 gtggaaacgt ttgctacgaa gttgggagct aagaacatta cgttgttggg aacgggattg   1020
ttgttgttga actacgtggc tgctatttcg acggctatta tttggccgaa ggcttttaag   1080
tcgaacatta tgttgttgtc gcacgctatt ttggcttttt cgttgatttt tcaagctcga   1140
gaattggacc gaacgaacta cacgccggaa gcttgcaagt cgttttacga atttatttgg   1200
attttgtttt cggctgaata cgtggtgtac ttgtttatta a                       1241
```

<210> SEQ ID NO 61
<211> LENGTH: 3147
<212> TYPE: PRT
<213> ORGANISM: Dictyostelium discoideum

<400> SEQUENCE: 61

```
Met Asn Lys Asn Ser Lys Ile Gln Ser Pro Asn Ser Ser Asp Val Ala
1               5                   10                  15

Val Ile Gly Val Gly Phe Arg Phe Pro Gly Asn Ser Asn Asp Pro Glu
            20                  25                  30

Ser Leu Trp Asn Asn Leu Leu Asp Gly Phe Asp Ala Ile Thr Gln Val
        35                  40                  45

Pro Lys Glu Arg Trp Ala Thr Ser Phe Arg Glu Met Gly Leu Ile Lys
    50                  55                  60

Asn Lys Phe Gly Gly Phe Leu Lys Asp Ser Glu Trp Lys Asn Phe Asp
65                  70                  75                  80

Pro Leu Phe Phe Gly Ile Gly Pro Lys Glu Ala Pro Phe Ile Asp Pro
                85                  90                  95

Gln Gln Arg Leu Leu Leu Ser Ile Val Trp Glu Ser Leu Glu Asp Ala
            100                 105                 110

Tyr Ile Arg Pro Asp Glu Leu Arg Gly Ser Asn Thr Gly Val Phe Ile
        115                 120                 125

Gly Val Ser Asn Asn Asp Tyr Thr Lys Leu Gly Phe Gln Asp Asn Tyr
    130                 135                 140

Ser Ile Ser Pro Tyr Thr Met Thr Gly Ser Asn Ser Ser Leu Asn Ser
145                 150                 155                 160

Asn Arg Ile Ser Tyr Cys Phe Asp Phe Arg Gly Pro Ser Ile Thr Val
                165                 170                 175

Asp Thr Ala Cys Ser Ser Leu Val Ser Val Asn Leu Gly Val Gln
            180                 185                 190

Ser Ile Gln Met Gly Glu Cys Lys Ile Ala Ile Cys Gly Gly Val Asn
        195                 200                 205

Ala Leu Phe Asp Pro Ser Thr Ser Val Ala Phe Ser Lys Leu Gly Val
    210                 215                 220
```

```
Leu Ser Glu Asn Gly Arg Cys Asn Ser Phe Ser Asp Gln Ala Ser Gly
225                 230                 235                 240

Tyr Val Arg Ser Glu Gly Ala Gly Val Val Leu Lys Ser Leu Glu
            245                 250                 255

Gln Ala Lys Leu Asp Gly Asp Arg Ile Tyr Gly Val Ile Lys Gly Val
            260                 265                 270

Ser Ser Asn Glu Asp Gly Ala Ser Asn Gly Asp Lys Asn Ser Leu Thr
            275                 280                 285

Thr Pro Ser Cys Glu Ala Gln Ser Ile Asn Ile Ser Lys Ala Met Glu
            290                 295                 300

Lys Ala Ser Leu Ser Pro Ser Asp Ile Tyr Tyr Ile Glu Ala His Gly
305                 310                 315                 320

Thr Gly Thr Pro Val Gly Asp Pro Ile Glu Val Lys Ala Leu Ser Lys
            325                 330                 335

Ile Phe Ser Asn Ser Asn Asn Gln Leu Asn Asn Phe Ser Thr Asp
            340                 345                 350

Gly Asn Asp Asn Asp Asp Asp Asp Asn Thr Ser Pro Glu Pro
            355                 360                 365

Leu Leu Ile Gly Ser Phe Lys Ser Asn Ile Gly His Leu Glu Ser Ala
370                 375                 380

Ala Gly Ile Ala Ser Leu Ile Lys Cys Cys Leu Met Leu Lys Asn Arg
385                 390                 395                 400

Met Leu Val Pro Ser Ile Asn Cys Ser Asn Leu Asn Pro Ser Ile Pro
            405                 410                 415

Phe Asp Gln Tyr Asn Ile Ser Val Ile Arg Glu Ile Arg Gln Phe Pro
            420                 425                 430

Thr Asp Lys Leu Val Asn Ile Gly Ile Asn Ser Phe Gly Phe Gly Gly
            435                 440                 445

Ser Asn Cys His Leu Ile Ile Gln Glu Tyr Asn Asn Asn Phe Lys Asn
450                 455                 460

Asn Ser Thr Ile Cys Asn Asn Asn Asn Asn Asn Asn Asn Ile Asp
465                 470                 475                 480

Tyr Leu Ile Pro Ile Ser Ser Lys Thr Lys Ser Leu Asp Lys Tyr
            485                 490                 495

Leu Ile Leu Ile Lys Thr Asn Ser Asn Tyr His Lys Asp Ile Ser Phe
            500                 505                 510

Asp Asp Phe Val Lys Phe Gln Ile Lys Ser Lys Gln Tyr Asn Leu Ser
            515                 520                 525

Asn Arg Met Thr Thr Ile Ala Asn Asp Trp Asn Ser Phe Ile Lys Gly
530                 535                 540

Ser Asn Glu Phe His Asn Leu Ile Glu Ser Lys Asp Gly Glu Gly Gly
545                 550                 555                 560

Ser Ser Ser Ser Asn Arg Gly Ile Asp Ser Ala Asn Gln Ile Asn Thr
            565                 570                 575

Thr Thr Thr Ser Thr Ile Asn Asp Ile Glu Pro Leu Leu Val Phe Val
            580                 585                 590

Phe Cys Gly Gln Gly Pro Gln Trp Asn Gly Met Ile Lys Thr Leu Tyr
            595                 600                 605

Asn Ser Glu Asn Val Phe Lys Asn Thr Val Asp His Val Asp Ser Ile
            610                 615                 620

Leu Tyr Lys Tyr Phe Gly Tyr Ser Ile Leu Asn Val Leu Ser Lys Ile
625                 630                 635                 640
```

```
Asp Asp Asn Asp Asp Ser Ile Asn His Pro Ile Val Ala Gln Pro Ser
                645                 650                 655

Leu Phe Leu Leu Gln Ile Gly Leu Val Glu Leu Phe Lys Tyr Trp Gly
            660                 665                 670

Ile Tyr Pro Ser Ile Ser Val Gly His Ser Phe Gly Glu Val Ser Ser
            675                 680                 685

Tyr Tyr Leu Ser Gly Ile Ile Ser Leu Glu Thr Ala Cys Lys Ile Val
            690                 695                 700

Tyr Val Arg Ser Ser Asn Gln Asn Lys Thr Met Gly Ser Gly Lys Met
705                 710                 715                 720

Leu Val Val Ser Met Gly Phe Lys Gln Trp Asn Asp Gln Phe Ser Ala
                725                 730                 735

Glu Trp Ser Asp Ile Glu Ile Ala Cys Tyr Asn Ala Pro Asp Ser Ile
            740                 745                 750

Val Val Thr Gly Asn Glu Glu Arg Leu Lys Glu Leu Ser Ile Lys Leu
            755                 760                 765

Ser Asp Glu Ser Asn Gln Ile Phe Asn Thr Phe Leu Arg Ser Pro Cys
            770                 775                 780

Ser Phe His Ser Ser His Gln Glu Val Ile Lys Gly Ser Met Phe Glu
785                 790                 795                 800

Glu Leu Ser Asn Leu Gln Ser Thr Gly Glu Thr Glu Ile Pro Leu Phe
                805                 810                 815

Ser Thr Val Thr Gly Arg Gln Val Leu Ser Gly His Val Thr Ala Gln
            820                 825                 830

His Ile Tyr Asp Asn Val Arg Glu Pro Val Leu Phe Gln Lys Thr Ile
            835                 840                 845

Glu Ser Ile Thr Ser Tyr Ile Lys Ser His Tyr Pro Ser Asn Gln Lys
850                 855                 860

Val Ile Tyr Val Glu Ile Ala Pro His Pro Thr Leu Phe Ser Leu Ile
865                 870                 875                 880

Lys Lys Ser Ile Pro Ser Ser Asn Lys Asn Ser Ser Val Leu Cys
                885                 890                 895

Pro Leu Asn Arg Lys Glu Asn Ser Asn Ser Tyr Lys Lys Phe Val
            900                 905                 910

Ser Gln Leu Tyr Phe Asn Gly Val Asn Val Asp Phe Asn Phe Gln Leu
            915                 920                 925

Asn Ser Ile Cys Asp Asn Val Asn Asp His His Leu Asn Asn Val
            930                 935                 940

Lys Gln Asn Ser Phe Lys Glu Thr Thr Asn Ser Leu Pro Arg Tyr Gln
945                 950                 955                 960

Trp Glu Gln Asp Glu Tyr Trp Ser Glu Pro Leu Ile Ser Arg Lys Asn
                965                 970                 975

Arg Leu Glu Gly Pro Thr Thr Ser Leu Leu Gly His Arg Ile Ile Tyr
            980                 985                 990

Ser Phe Pro Val Phe Gln Ser Val  Leu Asp Leu Gln Ser  Asp Asn Tyr
            995                 1000                1005

Lys Tyr Leu Leu Asp His Leu  Val Asn Gly Lys Pro  Val Phe Pro
        1010                1015                1020

Gly Ala Gly Tyr Leu Asp Ile  Ile Ile Glu Phe Phe  Asp Tyr Gln
        1025                1030                1035

Lys Gln Gln Leu Asn Ser Ser  Asp Ser Ser Asn Ser  Tyr Ile Ile
        1040                1045                1050

Asn Val Asp Lys Ile Gln Phe  Leu Asn Pro Ile His  Leu Thr Glu
```

```
            1055                1060                1065
Asn Lys Leu Gln Thr Leu Gln Ser Ser Phe Glu Pro Ile Val Thr
        1070                1075                1080
Lys Lys Ser Ala Phe Ser Val Asn Phe Phe Ile Lys Asp Thr Val
        1085                1090                1095
Glu Asp Gln Ser Lys Val Lys Ser Met Ser Asp Glu Thr Trp Thr
        1100                1105                1110
Asn Thr Cys Lys Ala Thr Ile Ser Leu Glu Gln Gln Gln Pro Ser
        1115                1120                1125
Pro Ser Ser Thr Leu Thr Leu Ser Lys Lys Gln Asp Leu Gln Ile
        1130                1135                1140
Leu Arg Asn Arg Cys Asp Ile Ser Lys Leu Asp Lys Phe Glu Leu
        1145                1150                1155
Tyr Asp Lys Ile Ser Lys Asn Leu Gly Leu Gln Tyr Asn Ser Leu
        1160                1165                1170
Phe Gln Val Val Asp Thr Ile Glu Thr Gly Lys Asp Cys Ser Phe
        1175                1180                1185
Ala Thr Leu Ser Leu Pro Glu Asp Thr Leu Phe Thr Thr Ile Leu
        1190                1195                1200
Asn Pro Cys Leu Leu Asp Asn Cys Phe His Gly Leu Leu Thr Leu
        1205                1210                1215
Ile Asn Glu Lys Gly Ser Phe Val Val Glu Ser Ile Ser Ser Val
        1220                1225                1230
Ser Ile Tyr Leu Glu Asn Ile Gly Ser Phe Asn Gln Thr Ser Val
        1235                1240                1245
Gly Asn Val Gln Phe Tyr Leu Tyr Thr Thr Ile Ser Lys Ala Thr
        1250                1255                1260
Ser Phe Ser Ser Glu Gly Thr Cys Lys Leu Phe Thr Lys Asp Gly
        1265                1270                1275
Ser Leu Ile Leu Ser Ile Gly Lys Phe Ile Ile Lys Ser Thr Asn
        1280                1285                1290
Pro Lys Ser Thr Lys Thr Asn Glu Thr Ile Glu Ser Pro Leu Asp
        1295                1300                1305
Glu Thr Phe Ser Ile Glu Trp Gln Ser Lys Asp Ser Pro Ile Pro
        1310                1315                1320
Thr Pro Gln Gln Ile Gln Gln Gln Ser Pro Leu Asn Ser Asn Pro
        1325                1330                1335
Ser Phe Ile Arg Ser Thr Ile Leu Lys Asp Ile Gln Phe Glu Gln
        1340                1345                1350
Tyr Cys Ser Ser Ile Ile His Lys Glu Leu Ile Asn His Glu Lys
        1355                1360                1365
Tyr Lys Asn Gln Gln Ser Phe Asp Ile Asn Ser Leu Glu Asn His
        1370                1375                1380
Leu Asn Asp Asp Gln Leu Met Glu Ser Leu Ser Ile Ser Lys Glu
        1385                1390                1395
Tyr Leu Arg Phe Phe Thr Arg Ile Ile Ser Ile Ile Lys Gln Tyr
        1400                1405                1410
Pro Lys Ile Leu Asn Glu Lys Glu Leu Lys Glu Leu Lys Glu Ile
        1415                1420                1425
Ile Glu Leu Lys Tyr Pro Ser Glu Val Gln Leu Leu Glu Phe Glu
        1430                1435                1440
Val Ile Glu Lys Val Ser Met Ile Ile Pro Lys Leu Leu Phe Glu
        1445                1450                1455
```

```
Asn Asp Lys Gln Ser Ser Met Thr Leu Phe Gln Asp Asn Leu Leu
    1460                1465                1470

Thr Arg Phe Tyr Ser Asn Ser Asn Ser Thr Arg Phe Tyr Leu Glu
    1475                1480                1485

Arg Val Ser Glu Met Val Leu Glu Ser Ile Arg Pro Ile Val Arg
    1490                1495                1500

Glu Lys Arg Val Phe Arg Ile Leu Glu Ile Gly Ala Gly Thr Gly
    1505                1510                1515

Ser Leu Ser Asn Val Val Leu Thr Lys Leu Asn Thr Tyr Leu Ser
    1520                1525                1530

Thr Leu Asn Ser Asn Gly Gly Ser Gly Tyr Asn Ile Ile Ile Glu
    1535                1540                1545

Tyr Thr Phe Thr Asp Ile Ser Ala Asn Phe Ile Ile Gly Glu Ile
    1550                1555                1560

Gln Glu Thr Met Cys Asn Leu Tyr Pro Asn Val Thr Phe Lys Phe
    1565                1570                1575

Ser Val Leu Asp Leu Glu Lys Glu Ile Ile Asn Ser Ser Asp Phe
    1580                1585                1590

Leu Met Gly Asp Tyr Asp Ile Val Leu Met Ala Tyr Val Ile His
    1595                1600                1605

Ala Val Ser Asn Ile Lys Phe Ser Ile Glu Gln Leu Tyr Lys Leu
    1610                1615                1620

Leu Ser Pro Arg Gly Trp Leu Leu Cys Ile Glu Pro Lys Ser Asn
    1625                1630                1635

Val Val Phe Ser Asp Leu Val Phe Gly Cys Phe Asn Gln Trp Trp
    1640                1645                1650

Asn Tyr Tyr Asp Asp Ile Arg Thr Thr His Cys Ser Leu Ser Glu
    1655                1660                1665

Ser Gln Trp Asn Gln Leu Leu Leu Asn Gln Ser Leu Asn Asn Glu
    1670                1675                1680

Ser Ser Ser Ser Ser Asn Cys Tyr Gly Gly Phe Ser Asn Val Ser
    1685                1690                1695

Phe Ile Gly Gly Glu Lys Asp Val Asp Ser His Ser Phe Ile Leu
    1700                1705                1710

His Cys Gln Lys Glu Ser Ile Ser Gln Met Lys Leu Ala Thr Thr
    1715                1720                1725

Ile Asn Asn Gly Leu Ser Ser Gly Ser Ile Val Ile Val Leu Asn
    1730                1735                1740

Ser Gln Gln Leu Thr Asn Met Lys Ser Tyr Pro Lys Val Ile Glu
    1745                1750                1755

Tyr Ile Gln Glu Ala Thr Ser Leu Cys Lys Thr Ile Glu Ile Ile
    1760                1765                1770

Asp Ser Lys Asp Val Leu Asn Ser Thr Asn Ser Val Leu Glu Lys
    1775                1780                1785

Ile Gln Lys Ser Leu Leu Val Phe Cys Leu Leu Gly Tyr Asp Leu
    1790                1795                1800

Leu Glu Asn Asn Tyr Gln Glu Gln Ser Phe Glu Tyr Val Lys Leu
    1805                1810                1815

Leu Asn Leu Ile Ser Thr Thr Ala Ser Ser Ser Asn Asp Lys Lys
    1820                1825                1830

Pro Pro Lys Val Leu Leu Ile Thr Lys Gln Ser Glu Arg Ile Ser
    1835                1840                1845
```

```
Arg Ser Phe Tyr Ser Arg Ser Leu Ile Gly Ile Ser Arg Thr Ser
    1850                1855                1860

Met Asn Glu Tyr Pro Asn Leu Ser Ile Thr Ser Ile Asp Leu Asp
    1865                1870                1875

Thr Asn Asp Tyr Ser Leu Gln Ser Leu Leu Lys Pro Ile Phe Ser
    1880                1885                1890

Asn Ser Lys Phe Ser Asp Asn Glu Phe Ile Phe Lys Lys Gly Leu
    1895                1900                1905

Met Phe Val Ser Arg Ile Phe Lys Asn Lys Gln Leu Leu Glu Ser
    1910                1915                1920

Ser Asn Ala Phe Glu Thr Asp Ser Ser Asn Leu Tyr Cys Lys Ala
    1925                1930                1935

Ser Ser Asp Leu Ser Tyr Lys Tyr Ala Ile Lys Gln Ser Met Leu
    1940                1945                1950

Thr Glu Asn Gln Ile Glu Ile Lys Val Glu Cys Val Gly Ile Asn
    1955                1960                1965

Phe Lys Asp Asn Leu Phe Tyr Lys Gly Leu Leu Pro Gln Glu Ile
    1970                1975                1980

Phe Arg Met Gly Asp Ile Tyr Asn Pro Pro Tyr Gly Leu Glu Cys
    1985                1990                1995

Ser Gly Val Ile Thr Arg Ile Gly Ser Asn Val Thr Glu Tyr Ser
    2000                2005                2010

Val Gly Gln Asn Val Phe Gly Phe Ala Arg His Ser Leu Gly Ser
    2015                2020                2025

His Val Val Thr Asn Lys Asp Leu Val Ile Leu Lys Pro Asp Thr
    2030                2035                2040

Ile Ser Phe Ser Glu Ala Ala Ser Ile Pro Val Val Tyr Cys Thr
    2045                2050                2055

Ala Trp Tyr Ser Leu Phe Asn Ile Gly Gln Leu Ser Asn Glu Glu
    2060                2065                2070

Ser Ile Leu Ile His Ser Ala Thr Gly Gly Val Gly Leu Ala Ser
    2075                2080                2085

Leu Asn Leu Leu Lys Met Lys Asn Gln Gln Gln Pro Leu Thr
    2090                2095                2100

Asn Val Tyr Ala Thr Val Gly Ser Asn Glu Lys Lys Lys Phe Leu
    2105                2110                2115

Ile Asp Asn Phe Asn Asn Leu Phe Lys Glu Asp Gly Glu Asn Ile
    2120                2125                2130

Phe Ser Thr Arg Asp Lys Glu Tyr Ser Asn Gln Leu Glu Ser Lys
    2135                2140                2145

Ile Asp Val Ile Leu Asn Thr Leu Ser Gly Glu Phe Val Glu Ser
    2150                2155                2160

Asn Phe Lys Ser Leu Arg Ser Phe Gly Arg Leu Ile Asp Leu Ser
    2165                2170                2175

Ala Thr His Val Tyr Ala Asn Gln Gln Ile Gly Leu Gly Asn Phe
    2180                2185                2190

Lys Phe Asp His Leu Tyr Ser Ala Val Asp Leu Glu Arg Leu Ile
    2195                2200                2205

Asp Glu Lys Pro Lys Leu Leu Gln Ser Ile Leu Gln Arg Ile Thr
    2210                2215                2220

Asn Ser Ile Val Asn Gly Ser Leu Glu Lys Ile Pro Ile Thr Ile
    2225                2230                2235

Phe Pro Ser Thr Glu Thr Lys Asp Ala Ile Glu Leu Leu Ser Lys
```

-continued

```
                2240                2245                2250

Arg Ser His Ile Gly Lys Val Val Asp Cys Thr Asp Ile Ser
    2255                2260                2265

Lys Cys Asn Pro Val Gly Asp Val Ile Thr Asn Phe Ser Met Arg
    2270                2275                2280

Leu Pro Lys Pro Asn Tyr Gln Leu Asn Leu Asn Ser Thr Leu Leu
    2285                2290                2295

Ile Thr Gly Gln Ser Gly Leu Ser Ile Pro Leu Leu Asn Trp Leu
    2300                2305                2310

Leu Ser Lys Ser Gly Gly Asn Val Lys Asn Val Ile Ile Ser
    2315                2320                2325

Lys Ser Thr Met Lys Trp Lys Leu Gln Thr Met Ile Ser His Phe
    2330                2335                2340

Val Ser Gly Phe Gly Ile His Phe Asn Tyr Val Gln Val Asp Ile
    2345                2350                2355

Ser Asn Tyr Asp Ala Leu Ser Glu Ala Ile Lys Gln Leu Pro Ser
    2360                2365                2370

Asp Leu Pro Pro Ile Thr Ser Val Phe His Leu Ala Ala Ile Tyr
    2375                2380                2385

Asn Asp Val Pro Met Asp Gln Val Thr Met Ser Thr Val Glu Ser
    2390                2395                2400

Val His Asn Pro Lys Val Leu Gly Ala Val Asn Leu His Arg Ile
    2405                2410                2415

Ser Val Ser Phe Gly Trp Lys Leu Asn His Phe Val Leu Phe Ser
    2420                2425                2430

Ser Ile Thr Ala Ile Thr Gly Tyr Pro Asp Gln Ser Ile Tyr Asn
    2435                2440                2445

Ser Ala Asn Ser Ile Leu Asp Ala Leu Ser Asn Phe Arg Arg Phe
    2450                2455                2460

Met Gly Leu Pro Ser Phe Ser Ile Asn Leu Gly Pro Met Lys Asp
    2465                2470                2475

Glu Gly Lys Val Ser Thr Asn Lys Ser Ile Lys Lys Leu Phe Lys
    2480                2485                2490

Ser Arg Gly Leu Pro Ser Leu Ser Leu Asn Lys Leu Phe Gly Leu
    2495                2500                2505

Leu Glu Val Val Ile Asn Asn Pro Ser Asn His Val Ile Pro Ser
    2510                2515                2520

Gln Leu Ile Cys Ser Pro Ile Asp Phe Lys Thr Tyr Ile Glu Ser
    2525                2530                2535

Phe Ser Thr Met Arg Pro Lys Leu Leu His Leu Gln Pro Thr Ile
    2540                2545                2550

Ser Lys Gln Gln Ser Ser Ile Ile Asn Asp Ser Thr Lys Ala Ser
    2555                2560                2565

Ser Asn Ile Ser Leu Gln Asp Lys Ile Thr Ser Lys Val Ser Asp
    2570                2575                2580

Leu Leu Ser Ile Pro Ile Ser Lys Ile Asn Phe Asp His Pro Leu
    2585                2590                2595

Lys His Tyr Gly Leu Asp Ser Leu Leu Thr Val Gln Phe Lys Ser
    2600                2605                2610

Trp Ile Asp Lys Glu Phe Glu Lys Asn Leu Phe Thr His Ile Gln
    2615                2620                2625

Leu Ala Thr Ile Ser Ile Asn Ser Phe Leu Glu Lys Val Asn Gly
    2630                2635                2640
```

```
Leu Ser Thr Asn Asn Asn Asn Asn Asn Ser Asn Val Lys Ser
    2645            2650            2655

Ser Pro Ser Ile Val Lys Glu Glu Ile Val Thr Leu Asp Lys Asp
    2660            2665            2670

Gln Gln Pro Leu Leu Leu Lys Glu His Gln His Ile Ile Ile Ser
    2675            2680            2685

Pro Asp Ile Arg Ile Asn Lys Pro Lys Arg Glu Ser Leu Ile Arg
    2690            2695            2700

Thr Pro Ile Leu Asn Lys Phe Asn Gln Ile Thr Glu Ser Ile Ile
    2705            2710            2715

Thr Pro Ser Thr Pro Ser Leu Ser Gln Ser Asp Val Leu Lys Thr
    2720            2725            2730

Pro Pro Ile Lys Ser Leu Asn Asn Thr Lys Asn Ser Ser Leu Ile
    2735            2740            2745

Asn Thr Pro Pro Ile Gln Ser Val Gln Gln His Gln Lys Gln Gln
    2750            2755            2760

Gln Lys Val Gln Val Ile Gln Gln Gln Gln Pro Leu Ser Arg
    2765            2770            2775

Leu Ser Tyr Lys Ser Asn Asn Asn Ser Phe Val Leu Gly Ile Gly
    2780            2785            2790

Ile Ser Val Pro Gly Glu Pro Ile Ser Gln Gln Ser Leu Lys Asp
    2795            2800            2805

Ser Ile Ser Asn Asp Phe Ser Asp Lys Ala Glu Thr Asn Glu Lys
    2810            2815            2820

Val Lys Arg Ile Phe Glu Gln Ser Gln Ile Lys Thr Arg His Leu
    2825            2830            2835

Val Arg Asp Tyr Thr Lys Pro Glu Asn Ser Ile Lys Phe Arg His
    2840            2845            2850

Leu Glu Thr Ile Thr Asp Val Asn Asn Gln Phe Lys Lys Val Val
    2855            2860            2865

Pro Asp Leu Ala Gln Gln Ala Cys Leu Arg Ala Leu Lys Asp Trp
    2870            2875            2880

Gly Gly Asp Lys Gly Asp Ile Thr His Ile Val Ser Val Thr Ser
    2885            2890            2895

Thr Gly Ile Ile Ile Pro Asp Val Asn Phe Lys Leu Ile Asp Leu
    2900            2905            2910

Leu Gly Leu Asn Lys Asp Val Glu Arg Val Ser Leu Asn Leu Met
    2915            2920            2925

Gly Cys Leu Ala Gly Leu Ser Ser Leu Arg Thr Ala Ala Ser Leu
    2930            2935            2940

Ala Lys Ala Ser Pro Arg Asn Arg Ile Leu Val Val Cys Thr Glu
    2945            2950            2955

Val Cys Ser Leu His Phe Ser Asn Thr Asp Gly Gly Asp Gln Met
    2960            2965            2970

Val Ala Ser Ser Ile Phe Ala Asp Gly Ser Ala Ala Tyr Ile Ile
    2975            2980            2985

Gly Cys Asn Pro Arg Ile Glu Glu Thr Pro Leu Tyr Glu Val Met
    2990            2995            3000

Cys Ser Ile Asn Arg Ser Phe Pro Asn Thr Glu Asn Ala Met Val
    3005            3010            3015

Trp Asp Leu Glu Lys Glu Gly Trp Asn Leu Gly Leu Asp Ala Ser
    3020            3025            3030
```

-continued

```
Ile Pro Ile Val Ile Gly Ser Gly Ile Glu Ala Phe Val Asp Thr
    3035            3040            3045

Leu Leu Asp Lys Ala Lys Leu Gln Thr Ser Thr Ala Ile Ser Ala
    3050            3055            3060

Lys Asp Cys Glu Phe Leu Ile His Thr Gly Gly Lys Ser Ile Leu
    3065            3070            3075

Met Asn Ile Glu Asn Ser Leu Gly Ile Asp Pro Lys Gln Thr Lys
    3080            3085            3090

Asn Thr Trp Asp Val Tyr His Ala Tyr Gly Asn Met Ser Ser Ala
    3095            3100            3105

Ser Val Ile Phe Val Met Asp His Ala Arg Lys Ser Lys Ser Leu
    3110            3115            3120

Pro Thr Tyr Ser Ile Ser Leu Ala Phe Gly Pro Gly Leu Ala Phe
    3125            3130            3135

Glu Gly Cys Phe Leu Lys Asn Val Val
    3140            3145
```

<210> SEQ ID NO 62
<211> LENGTH: 2968
<212> TYPE: PRT
<213> ORGANISM: Dictyostelium discoideum

<400> SEQUENCE: 62

```
Met Asn Asn Asn Lys Ser Ile Asn Asp Leu Ser Gly Asn Ser Asn Asn
1               5                   10                  15

Asn Ile Ala Asn Ser Asn Ile Asn Asn Tyr Asn Asn Leu Ile Lys Lys
            20                  25                  30

Glu Pro Ile Ala Ile Ile Gly Ile Gly Cys Arg Phe Pro Gly Asn Val
        35                  40                  45

Ser Asn Tyr Ser Asp Phe Val Asn Ile Ile Lys Asn Gly Ser Asp Cys
    50                  55                  60

Leu Thr Lys Ile Pro Asp Asp Arg Trp Asn Ala Asp Ile Ile Ser Arg
65                  70                  75                  80

Lys Gln Trp Lys Leu Asn Asn Arg Ile Gly Gly Tyr Leu Lys Asn Ile
                85                  90                  95

Asp Gln Phe Asp Asn Gln Phe Phe Gly Ile Ser Pro Lys Glu Ala Gln
            100                 105                 110

His Ile Asp Pro Gln Gln Arg Leu Leu Leu His Leu Ala Ile Glu Thr
        115                 120                 125

Leu Glu Asp Gly Lys Ile Ser Leu Asp Glu Ile Lys Gly Lys Lys Val
    130                 135                 140

Gly Val Phe Ile Gly Ser Ser Gly Asp Tyr Leu Arg Gly Phe Asp
145                 150                 155                 160

Ser Ser Glu Ile Asn Gln Phe Thr Thr Pro Gly Thr Asn Ser Ser Phe
                165                 170                 175

Leu Ser Asn Arg Leu Ser Tyr Phe Leu Asp Val Asn Gly Pro Ser Met
            180                 185                 190

Thr Val Asn Thr Ala Cys Ser Ala Ser Met Val Ala Ile His Leu Gly
        195                 200                 205

Leu Gln Ser Leu Trp Asn Gly Glu Ser Glu Leu Ser Met Val Gly Gly
    210                 215                 220

Val Asn Ile Ile Ser Ser Pro Leu Gln Ser Leu Asp Phe Gly Lys Ala
225                 230                 235                 240

Gly Leu Leu Asn Gln Glu Thr Asp Gly Arg Cys Tyr Ser Phe Asp Pro
                245                 250                 255
```

-continued

```
Arg Ala Ser Gly Tyr Val Arg Ser Glu Gly Gly Ile Leu Leu Leu
        260                 265                 270
Lys Pro Leu Ser Ala Ala Leu Arg Asp Asn Asp Glu Ile Tyr Ser Leu
            275                 280                 285
Leu Leu Asn Ser Ala Asn Asn Ser Asn Gly Lys Thr Pro Thr Gly Ile
    290                 295                 300
Thr Ser Pro Arg Ser Leu Cys Gln Glu Lys Leu Ile Gln Gln Leu Leu
305                 310                 315                 320
Arg Glu Ser Ser Asp Gln Phe Ser Ile Asp Asp Ile Gly Tyr Phe Glu
                325                 330                 335
Cys His Gly Thr Gly Thr Gln Met Gly Asp Leu Asn Glu Ile Thr Ala
            340                 345                 350
Ile Gly Lys Ser Ile Gly Met Leu Lys Ser His Asp Asp Pro Leu Ile
        355                 360                 365
Ile Gly Ser Val Lys Ala Ser Ile Gly His Leu Glu Gly Ala Ser Gly
    370                 375                 380
Ile Cys Gly Val Ile Lys Ser Ile Ile Cys Leu Lys Glu Lys Ile Leu
385                 390                 395                 400
Pro Gln Gln Cys Lys Phe Ser Ser Tyr Asn Pro Lys Ile Pro Phe Glu
                405                 410                 415
Thr Leu Asn Leu Lys Val Leu Thr Lys Thr Gln Pro Trp Asn Asn Ser
            420                 425                 430
Lys Arg Ile Cys Gly Val Asn Ser Phe Gly Val Gly Gly Ser Asn Ser
        435                 440                 445
Ser Leu Phe Leu Ser Ser Phe Asp Lys Ser Thr Thr Ile Thr Glu Pro
    450                 455                 460
Thr Thr Thr Thr Thr Ile Glu Ser Leu Pro Ser Ser Ser Ser Ser Phe
465                 470                 475                 480
Asp Asn Leu Ser Val Ser Ser Ser Ile Ser Thr Asn Asp Asn Asp
                485                 490                 495
Lys Val Ser Asn Ile Val Asn Asn Arg Tyr Gly Ser Ser Ile Asp Val
            500                 505                 510
Ile Thr Leu Ser Val Thr Ser Pro Asp Lys Glu Asp Leu Lys Ile Arg
        515                 520                 525
Ala Asn Asp Val Leu Glu Ser Ile Lys Thr Leu Asp Asp Asn Phe Lys
    530                 535                 540
Ile Arg Asp Ile Ser Asn Leu Thr Asn Ile Arg Thr Ser His Phe Ser
545                 550                 555                 560
Asn Arg Val Ala Ile Ile Gly Asp Ser Ile Asp Ser Ile Lys Leu Asn
                565                 570                 575
Leu Gln Ser Phe Ile Lys Gly Glu Asn Asn Asn Lys Ser Ile Ile
            580                 585                 590
Leu Pro Leu Ile Asn Asn Gly Asn Asn Asn Asn Asn Asn Asn Asn
        595                 600                 605
Ser Ser Gly Ser Ser Ser Ser Ser Asn Asn Asn Asn Ile Cys Phe
    610                 615                 620
Ile Phe Ser Gly Gln Gly Gln Gln Trp Asn Lys Met Ile Phe Asp Leu
625                 630                 635                 640
Tyr Glu Asn Asn Lys Thr Phe Lys Asn Glu Met Asn Asn Phe Ser Lys
                645                 650                 655
Gln Phe Glu Met Ile Ser Gly Trp Ser Ile Ile Asp Lys Leu Tyr Asn
            660                 665                 670
```

```
Ser Gly Gly Gly Gly Asn Glu Glu Leu Ile Asn Glu Thr Trp Leu Ala
            675                 680                 685

Gln Pro Ser Ile Val Ala Val Gln Tyr Ser Leu Ile Lys Leu Phe Ser
        690                 695                 700

Lys Asp Ile Gly Ile Glu Gly Ser Ile Val Leu Gly His Ser Leu Gly
705                 710                 715                 720

Glu Leu Met Ala Ala Tyr Tyr Cys Gly Ile Ile Asn Asp Phe Asn Asp
                725                 730                 735

Leu Leu Lys Leu Leu Tyr Ile Arg Ser Thr Leu Gln Asn Lys Thr Asn
            740                 745                 750

Gly Ser Gly Arg Met His Val Cys Leu Ser Ser Lys Ala Glu Ile Glu
        755                 760                 765

Gln Leu Ile Ser Gln Leu Gly Phe Asn Gly Arg Ile Val Ile Cys Gly
        770                 775                 780

Asn Asn Thr Met Lys Ser Cys Thr Ile Ser Gly Asp Asn Glu Ser Met
785                 790                 795                 800

Asn Gln Phe Thr Lys Leu Ile Ser Ser Gln Tyr Gly Ser Val Val
                805                 810                 815

His Lys Glu Val Arg Thr Asn Ser Ala Phe His Ser His Gln Met Asp
            820                 825                 830

Ile Ile Lys Asp Glu Phe Phe Lys Leu Phe Asn Gln Tyr Phe Pro Thr
            835                 840                 845

Asn Gln Ile Ser Thr Asn Gln Ile Tyr Asp Gly Lys Ser Phe Tyr Ser
            850                 855                 860

Thr Cys Tyr Gly Lys Tyr Leu Thr Pro Ile Glu Cys Lys Gln Leu Leu
865                 870                 875                 880

Ser Ser Pro Asn Tyr Trp Trp Lys Asn Ile Arg Glu Ser Val Leu Phe
            885                 890                 895

Lys Glu Ser Ile Glu Gln Ile Leu Gln Asn His Gln Ser Leu Thr
                900                 905                 910

Phe Ile Glu Ile Thr Cys His Pro Ile Leu Asn Tyr Phe Leu Ser Gln
            915                 920                 925

Leu Leu Lys Ser Ser Ser Lys Ser Asn Thr Leu Leu Leu Ser Thr Leu
            930                 935                 940

Ser Lys Asn Ser Asn Ser Ile Asp Gln Leu Leu Ile Leu Cys Ser Lys
945                 950                 955                 960

Leu Tyr Val Asn Asn Leu Ser Ser Ile Lys Trp Asn Trp Phe Tyr Asp
                965                 970                 975

Lys Gln Gln Gln Gln Ser Gly Ser Leu Val Ser Ser Asn Phe Lys
            980                 985                 990

Leu Pro Gly Arg Arg Trp Lys Leu Glu Lys Tyr Trp Ile Glu Asn Cys
            995                1000                1005

Gln Arg Gln Met Asp Arg Ile Lys Pro Pro Met Phe Ile Ser Leu
            1010                1015                1020

Asp Arg Lys Leu Phe Ser Val Thr Pro Ser Phe Glu Val Arg Leu
            1025                1030                1035

Asn Gln Asp Arg Phe Gln Tyr Leu Asn Asp His Gln Ile Gln Asp
            1040                1045                1050

Ile Pro Leu Val Pro Phe Ser Phe Tyr Ile Glu Leu Val Tyr Ala
            1055                1060                1065

Ser Ile Phe Asn Ser Ile Ser Thr Thr Thr Thr Asn Thr Thr Ala
            1070                1075                1080

Ser Thr Met Phe Glu Ile Glu Asn Phe Thr Ile Asp Ser Ser Ile
```

```
                1085                1090                1095
Ile Ile Asp Gln Lys Lys Ser Thr Leu Ile Gly Ile Asn Phe Asn
        1100                1105                1110
Ser Asp Leu Thr Lys Phe Glu Ile Gly Ser Ile Asn Ser Ile Gly
        1115                1120                1125
Ser Gly Ser Ser Ser Asn Asn Asn Phe Ile Glu Asn Lys Trp Lys
        1130                1135                1140
Ile His Ser Asn Gly Ile Ile Lys Tyr Gly Thr Asn Tyr Leu Lys
        1145                1150                1155
Ser Asn Ser Lys Ser Asn Ser Phe Asn Glu Ser Thr Thr Thr Thr
        1160                1165                1170
Thr Thr Thr Thr Thr Thr Thr Lys Cys Phe Lys Ser Phe Asn Ser
        1175                1180                1185
Asn Glu Phe Tyr Asn Glu Ile Ile Lys Tyr Asn Tyr Asn Tyr Lys
        1190                1195                1200
Ser Thr Phe Gln Cys Val Lys Glu Phe Lys Gln Phe Asp Lys Gln
        1205                1210                1215
Gly Thr Phe Tyr Tyr Ser Glu Ile Gln Phe Lys Lys Asn Asp Lys
        1220                1225                1230
Gln Val Ile Asp Gln Leu Leu Ser Lys Gln Leu Pro Ser Asp Phe
        1235                1240                1245
Arg Cys Ile His Pro Cys Leu Leu Asp Ala Val Leu Gln Ser Ala
        1250                1255                1260
Ile Ile Pro Ala Thr Asn Lys Thr Asn Cys Ser Trp Ile Pro Ile
        1265                1270                1275
Lys Ile Gly Lys Leu Ser Val Asn Ile Pro Ser Asn Ser Tyr Phe
        1280                1285                1290
Asn Phe Lys Asp Gln Leu Leu Tyr Cys Leu Ile Lys Pro Ser Thr
        1295                1300                1305
Ser Thr Ser Thr Ser Pro Ser Thr Tyr Phe Ser Ser Asp Ile Gln
        1310                1315                1320
Val Phe Asp Lys Lys Asn Asn Asn Leu Ile Cys Glu Leu Thr Asn
        1325                1330                1335
Leu Glu Phe Lys Gly Ile Asn Ser Ser Ser Ser Ser Ser Ser Ser
        1340                1345                1350
Ser Ser Thr Ile Asn Ser Asn Val Glu Ala Asn Tyr Glu Ser Lys
        1355                1360                1365
Ile Glu Glu Thr Asn His Asp Glu Asp Glu Asp Glu Glu Leu Pro
        1370                1375                1380
Leu Val Ser Glu Tyr Val Trp Cys Lys Glu Glu Leu Ile Asn Gln
        1385                1390                1395
Ser Ile Lys Phe Thr Asp Asn Tyr Gln Thr Val Ile Phe Cys Ser
        1400                1405                1410
Thr Asn Leu Asn Gly Asn Asp Leu Leu Asp Ser Ile Ile Thr Ser
        1415                1420                1425
Ala Leu Glu Asn Gly His Asp Glu Asn Lys Ile Phe Ile Val Ser
        1430                1435                1440
Pro Pro Pro Val Glu Ser Asp Gln Tyr Asn Asn Arg Ile Ile Ile
        1445                1450                1455
Asn Tyr Thr Asn Asn Glu Ser Asp Phe Asp Ala Leu Phe Ala Ile
        1460                1465                1470
Ile Asn Ser Thr Thr Ser Ile Ser Gly Lys Ser Gly Leu Phe Ser
        1475                1480                1485
```

-continued

Thr Arg Phe Ile Ile Leu Pro Asn Phe Asn Ser Ile Thr Phe Ser
    1490            1495                1500

Ser Gly Asn Ser Thr Pro Leu Ile Thr Asn Val Asn Gly Asn Gly
    1505            1510                1515

Asn Gly Lys Ser Cys Gly Gly Gly Gly Ser Thr Asn Asn Thr
    1520            1525                1530

Ile Ser Asn Ser Ser Ser Ile Ser Ser Ile Asp Asn Gly Asn
    1535            1540                1545

Asn Glu Asp Glu Glu Met Val Leu Lys Ser Phe Asn Asp Ser Asn
    1550            1555                1560

Leu Ser Leu Phe His Leu Gln Lys Ser Ile Ile Lys Asn Asn Ile
    1565            1570                1575

Lys Gly Arg Leu Phe Leu Ile Thr Asn Gly Gly Gln Ser Ile Ser
    1580            1585                1590

Ser Ser Thr Pro Thr Ser Thr Tyr Asn Asp Gln Ser Tyr Val Asn
    1595            1600                1605

Leu Ser Gln Tyr Gln Leu Ile Gly Gln Ile Arg Val Phe Ser Asn
    1610            1615                1620

Glu Tyr Pro Ile Met Glu Cys Ser Met Ile Asp Ile Gln Asp Ser
    1625            1630                1635

Thr Arg Ile Asp Leu Ile Thr Asp Gln Leu Asn Ser Thr Lys Leu
    1640            1645                1650

Ser Lys Leu Glu Ile Ala Phe Arg Asp Asn Ile Gly Tyr Ser Tyr
    1655            1660                1665

Lys Leu Leu Lys Pro Ser Ile Phe Asp Asn Ser Ser Leu Pro Ser
    1670            1675                1680

Ser Ser Ser Glu Ile Glu Thr Thr Ala Thr Thr Lys Asp Glu Glu
    1685            1690                1695

Lys Asn Asn Ser Ile Asn Tyr Asn Asn Asn Tyr Tyr Arg Val Glu
    1700            1705                1710

Leu Ser Asp Asn Gly Ile Ile Ser Asp Leu Lys Ile Lys Gln Phe
    1715            1720                1725

Arg Gln Met Lys Cys Gly Val Gly Gln Val Leu Val Arg Val Glu
    1730            1735                1740

Met Cys Thr Leu Asn Phe Arg Asp Ile Leu Lys Ser Leu Gly Arg
    1745            1750                1755

Asp Tyr Asp Pro Ile His Leu Asn Ser Met Gly Asp Glu Phe Ser
    1760            1765                1770

Gly Lys Val Ile Glu Ile Gly Glu Gly Val Asn Asn Leu Ser Val
    1775            1780                1785

Gly Gln Tyr Val Phe Gly Ile Asn Met Ser Lys Ser Met Gly Ser
    1790            1795                1800

Phe Val Cys Cys Asn Ser Asp Leu Val Phe Pro Ile Pro Ile Pro
    1805            1810                1815

Thr Pro Ser Ser Ser Ser Ser Ser Asn Glu Asn Ile Asp Asp Gln
    1820            1825                1830

Glu Ile Ile Ser Lys Leu Leu Asn Gln Tyr Cys Thr Ile Pro Ile
    1835            1840                1845

Val Phe Leu Thr Ser Trp Tyr Ser Ile Val Ile Gln Gly Arg Leu
    1850            1855                1860

Lys Lys Gly Glu Lys Ile Leu Ile His Ser Gly Cys Gly Gly Val
    1865            1870                1875

```
Gly Leu Ala Thr Ile Gln Ile Ser Met Met Ile Gly Ala Glu Ile
    1880            1885                1890

His Val Thr Val Gly Ser Asn Glu Lys Lys Gln Tyr Leu Ile Lys
    1895            1900                1905

Glu Phe Gly Ile Asp Glu Lys Arg Ile Tyr Ser Ser Arg Ser Leu
    1910            1915                1920

Gln Phe Tyr Asn Asp Leu Met Val Asn Thr Asp Gly Gln Gly Val
    1925            1930                1935

Asp Met Val Leu Asn Ser Leu Ser Gly Glu Tyr Leu Glu Lys Ser
    1940            1945                1950

Ile Gln Cys Leu Ser Gln Tyr Gly Arg Phe Ile Glu Ile Gly Lys
    1955            1960                1965

Lys Asp Ile Tyr Ser Asn Ser Ser Ile His Leu Glu Pro Phe Lys
    1970            1975                1980

Asn Asn Leu Ser Phe Phe Ala Val Asp Ile Ala Gln Met Thr Glu
    1985            1990                1995

Asn Arg Arg Asp Tyr Leu Arg Glu Ile Met Ile Asp Gln Leu Leu
    2000            2005                2010

Pro Cys Phe Lys Asn Gly Ser Leu Lys Pro Leu Asn Gln His Cys
    2015            2020                2025

Phe Asn Ser Pro Cys Asp Leu Val Lys Ala Ile Arg Phe Met Ser
    2030            2035                2040

Ser Gly Asn His Ile Gly Lys Ile Leu Ile Asn Trp Ser Asn Leu
    2045            2050                2055

Asn Asn Asp Lys Gln Phe Ile Asn His His Ser Val Val His Leu
    2060            2065                2070

Pro Ile Gln Ser Phe Ser Asn Arg Ser Thr Tyr Ile Phe Thr Gly
    2075            2080                2085

Phe Gly Gly Leu Thr Gln Thr Leu Leu Lys Tyr Phe Ser Thr Glu
    2090            2095                2100

Ser Asp Leu Thr Asn Val Ile Ile Val Ser Lys Asn Gly Leu Asp
    2105            2110                2115

Asp Asn Ser Gly Ser Gly Ser Gly Asn Asn Glu Lys Leu Lys Leu
    2120            2125                2130

Ile Asn Gln Leu Lys Glu Ser Gly Leu Asn Val Leu Val Glu Lys
    2135            2140                2145

Cys Asp Leu Ser Ser Ile Lys Gln Val Tyr Lys Leu Phe Asn Lys
    2150            2155                2160

Ile Phe Asp Asn Asp Ala Ser Gly Ser Asp Ser Gly Asp Phe Ser
    2165            2170                2175

Asp Ile Lys Gly Ile Phe His Phe Ala Ser Leu Ile Asn Asp Lys
    2180            2185                2190

Arg Ile Leu Lys His Asn Leu Glu Ser Phe Asn Tyr Val Tyr Asn
    2195            2200                2205

Ser Lys Ala Thr Ser Ala Trp Asn Leu His Gln Val Ser Leu Lys
    2210            2215                2220

Tyr Asn Leu Asn Leu Asp His Phe Gln Thr Ile Gly Ser Val Ile
    2225            2230                2235

Thr Ile Leu Gly Asn Ile Gly Gln Ser Asn Tyr Thr Cys Ala Asn
    2240            2245                2250

Arg Phe Val Glu Gly Leu Thr His Leu Arg Ile Gly Met Gly Leu
    2255            2260                2265

Lys Ser Ser Cys Ile His Leu Ala Ser Ile Pro Asp Val Gly Met
```

2270                2275                2280

Ala Ser Asn Asp Asn Val Leu Asn Asp Leu Asn Ser Met Gly Phe
    2285                2290                2295

Val Pro Phe Gln Ser Leu Asn Glu Met Asn Leu Gly Phe Lys Lys
    2300                2305                2310

Leu Leu Ser Ser Pro Asn Pro Ile Val Val Leu Gly Glu Ile Asn
    2315                2320                2325

Val Asp Arg Phe Ile Glu Ala Thr Pro Asn Phe Arg Ala Lys Asp
    2330                2335                2340

Asn Phe Ile Ile Thr Ser Leu Phe Asn Arg Ile Asp Pro Leu Leu
    2345                2350                2355

Leu Val Asn Glu Ser Gln Asp Phe Ile Ile Asn Asn Asn Ile Asn
    2360                2365                2370

Asn Asn Gly Gly Gly Gly Asp Gly Ser Phe Asp Asp Leu Asn Gln
    2375                2380                2385

Leu Glu Asp Glu Gly Gln Gln Gly Phe Gly Asn Gly Asp Gly Tyr
    2390                2395                2400

Val Asp Asp Asn Ile Asp Ser Val Ser Met Leu Ser Gly Thr Ser
    2405                2410                2415

Ser Ile Phe Asp Asn Asp Phe Tyr Thr Lys Ser Ile Arg Gly Met
    2420                2425                2430

Leu Cys Asp Ile Leu Glu Leu Lys Asp Lys Asp Leu Asn Asn Thr
    2435                2440                2445

Val Ser Phe Ser Asp Tyr Gly Leu Asp Ser Leu Leu Ser Ser Glu
    2450                2455                2460

Leu Ser Asn Thr Ile Gln Lys Asn Phe Ser Ile Leu Ile Pro Ser
    2465                2470                2475

Leu Thr Leu Val Asp Asn Ser Thr Ile Asn Ser Thr Val Glu Leu
    2480                2485                2490

Ile Lys Asn Lys Leu Lys Asn Ser Thr Thr Ser Ser Ile Ser Ser
    2495                2500                2505

Ser Val Ser Lys Lys Val Ser Phe Lys Lys Asn Thr Gln Pro Leu
    2510                2515                2520

Ile Ile Pro Thr Thr Ala Pro Ile Ser Ile Ile Lys Thr Gln Ser
    2525                2530                2535

Tyr Ile Lys Ser Glu Ile Ile Glu Ser Leu Pro Ile Ser Ser Ser
    2540                2545                2550

Thr Thr Ile Lys Pro Leu Val Phe Asp Asn Leu Val Tyr Ser Ser
    2555                2560                2565

Ser Ser Ser Asn Asn Ser Asn Ser Lys Asn Glu Leu Thr Ser Pro
    2570                2575                2580

Pro Pro Ser Ala Lys Arg Glu Ser Val Leu Pro Ile Ile Ser Glu
    2585                2590                2595

Asp Asn Asn Ser Asp Asn Asp Ser Ser Met Ala Thr Val Ile Tyr
    2600                2605                2610

Glu Ile Ser Pro Ile Ala Ala Pro Tyr His Arg Tyr Gln Thr Asp
    2615                2620                2625

Val Leu Lys Glu Ile Thr Gln Leu Thr Pro His Lys Glu Phe Ile
    2630                2635                2640

Asp Asn Ile Tyr Lys Lys Ser Lys Ile Arg Ser Arg Tyr Cys Phe
    2645                2650                2655

Asn Asp Phe Ser Glu Lys Ser Met Ala Asp Ile Asn Lys Leu Asp
    2660                2665                2670

Ala Gly Glu Arg Val Ala Leu Phe Arg Glu Gln Thr Tyr Gln Thr
                2675                2680                2685

Val Ile Asn Ala Gly Lys Thr Val Ile Glu Arg Ala Gly Ile Asp
        2690                2695                2700

Pro Met Leu Ile Ser His Val Val Gly Val Thr Ser Thr Gly Ile
    2705                2710                2715

Met Ala Pro Ser Phe Asp Val Val Leu Ile Asp Lys Leu Gly Leu
    2720                2725                2730

Ser Ile Asn Thr Ser Arg Thr Met Ile Asn Phe Met Gly Cys Gly
    2735                2740                2745

Ala Ala Val Asn Ser Met Arg Ala Ala Thr Ala Tyr Ala Lys Leu
    2750                2755                2760

Lys Pro Gly Thr Phe Val Leu Val Val Ala Val Glu Ala Ser Ala
    2765                2770                2775

Thr Cys Met Lys Phe Asn Phe Asp Ser Arg Ser Asp Leu Leu Ser
    2780                2785                2790

Gln Ala Ile Phe Thr Asp Gly Cys Val Ala Thr Leu Val Thr Cys
    2795                2800                2805

Gln Pro Lys Ser Ser Leu Val Gly Lys Leu Glu Ile Ile Asp Asp
    2810                2815                2820

Leu Ser Tyr Leu Met Pro Asp Ser Arg Asp Ala Leu Asn Leu Phe
    2825                2830                2835

Ile Gly Pro Thr Gly Ile Asp Leu Asp Leu Arg Pro Glu Leu Pro
    2840                2845                2850

Ile Ala Ile Asn Arg His Ile Asn Ser Ala Ile Thr Ser Trp Leu
    2855                2860                2865

Lys Lys Asn Ser Leu Gln Lys Ser Asp Ile Glu Phe Phe Ala Thr
    2870                2875                2880

His Pro Gly Gly Ala Lys Ile Ile Ser Ala Val His Glu Gly Leu
    2885                2890                2895

Gly Leu Ser Pro Glu Asp Leu Ser Asp Ser Tyr Glu Val Met Lys
    2900                2905                2910

Arg Tyr Gly Asn Met Ile Gly Val Ser Thr Tyr Tyr Val Leu Arg
    2915                2920                2925

Arg Ile Leu Asp Lys Asn Gln Thr Leu Leu Gln Glu Gly Ser Leu
    2930                2935                2940

Gly Tyr Asn Tyr Gly Met Ala Met Ala Phe Ser Pro Gly Ala Ser
    2945                2950                2955

Ile Glu Ala Ile Leu Phe Lys Leu Ile Lys
    2960                2965

<210> SEQ ID NO 63
<211> LENGTH: 307
<212> TYPE: PRT
<213> ORGANISM: Streptomyces sp. strain CL190

<400> SEQUENCE: 63

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser

```
            50                  55                  60
Ile Ser Val Pro Thr Ser His Gly Asp Pro Tyr Ala Thr Val Glu
 65                  70                  75                  80

Lys Gly Leu Phe Pro Ala Thr Gly His Pro Val Asp Leu Leu Ala
                 85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
            115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
                180                 185                 190

Val Arg Glu Leu Gly Leu His Val Pro Asn Glu Leu Gly Leu Lys Phe
            195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
                260                 265                 270

Gly Leu Thr Leu Ser Pro Lys Glu Glu Tyr Tyr Lys Leu Gly Ala Tyr
            275                 280                 285

Tyr His Ile Thr Asp Val Gln Arg Gly Leu Leu Lys Ala Phe Asp Ser
    290                 295                 300

Leu Glu Asp
305

<210> SEQ ID NO 64
<211> LENGTH: 398
<212> TYPE: PRT
<213> ORGANISM: Cannabis sativa

<400> SEQUENCE: 64

Met Gly Leu Ser Leu Val Cys Thr Phe Ser Phe Gln Thr Asn Tyr His
  1               5                  10                  15

Thr Leu Leu Asn Pro His Asn Lys Asn Pro Lys Asn Ser Leu Leu Ser
                 20                  25                  30

Tyr Gln His Pro Lys Thr Pro Ile Ile Lys Ser Ser Tyr Asp Asn Phe
             35                  40                  45

Pro Ser Lys Tyr Cys Leu Thr Lys Asn Phe His Leu Leu Gly Leu Asn
 50                  55                  60

Ser His Asn Arg Ile Ser Ser Gln Ser Arg Ser Ile Arg Ala Gly Ser
 65                  70                  75                  80

Asp Gln Ile Glu Gly Ser Pro His His Glu Ser Asp Asn Ser Ile Ala
             85                  90                  95

Thr Lys Ile Leu Asn Phe Gly His Thr Cys Trp Lys Leu Gln Arg Pro
            100                 105                 110
```

```
Tyr Val Val Lys Gly Met Ile Ser Ile Ala Cys Gly Leu Phe Gly Arg
            115                 120                 125

Glu Leu Phe Asn Asn Arg His Leu Phe Ser Trp Gly Leu Met Trp Lys
130                 135                 140

Ala Phe Phe Ala Leu Val Pro Ile Leu Ser Phe Asn Phe Phe Ala Ala
145                 150                 155                 160

Ile Met Asn Gln Ile Tyr Asp Val Asp Ile Asp Arg Ile Asn Lys Pro
            165                 170                 175

Asp Leu Pro Leu Val Ser Gly Glu Met Ser Ile Glu Thr Ala Trp Ile
            180                 185                 190

Leu Ser Ile Ile Val Ala Leu Thr Gly Leu Ile Val Thr Ile Lys Leu
            195                 200                 205

Lys Ser Ala Pro Leu Phe Val Phe Ile Tyr Ile Phe Gly Ile Phe Ala
210                 215                 220

Gly Phe Ala Tyr Ser Val Pro Pro Ile Arg Trp Lys Gln Tyr Pro Phe
225                 230                 235                 240

Thr Asn Phe Leu Ile Thr Ile Ser Ser His Val Gly Leu Ala Phe Thr
            245                 250                 255

Ser Tyr Ser Ala Thr Thr Ser Ala Leu Gly Leu Pro Phe Val Trp Arg
            260                 265                 270

Pro Ala Phe Ser Phe Ile Ile Ala Phe Met Thr Val Met Gly Met Thr
            275                 280                 285

Ile Ala Phe Ala Lys Asp Ile Ser Asp Ile Glu Gly Asp Ala Lys Tyr
            290                 295                 300

Gly Val Ser Thr Val Ala Thr Lys Leu Gly Ala Arg Asn Met Thr Phe
305                 310                 315                 320

Val Val Ser Gly Val Leu Leu Leu Asn Tyr Leu Val Ser Ile Ser Ile
            325                 330                 335

Gly Ile Ile Trp Pro Gln Val Phe Lys Ser Asn Ile Met Ile Leu Ser
            340                 345                 350

His Ala Ile Leu Ala Phe Cys Leu Ile Phe Gln Thr Arg Glu Leu Ala
            355                 360                 365

Leu Ala Asn Tyr Ala Ser Ala Pro Ser Arg Gln Phe Phe Glu Phe Ile
            370                 375                 380

Trp Leu Leu Tyr Tyr Ala Glu Tyr Phe Val Tyr Val Phe Ile
385                 390                 395

<210> SEQ ID NO 65
<211> LENGTH: 413
<212> TYPE: PRT
<213> ORGANISM: Humulus lupulus

<400> SEQUENCE: 65

Met Glu Leu Ser Ser Val Ser Ser Phe Ser Leu Gly Thr Asn Pro Phe
1               5                   10                  15

Ile Ser Ile Pro His Asn Asn Asn Leu Lys Val Ser Ser Tyr Cys
            20                  25                  30

Cys Lys Ser Lys Ser Arg Val Ile Asn Ser Thr Asn Ser Lys His Cys
            35                  40                  45

Ser Pro Asn Asn Asn Ser Asn Asn Thr Ser Asn Lys Thr Thr His
            50                  55                  60

Leu Leu Gly Leu Tyr Gly Gln Ser Arg Cys Leu Leu Lys Pro Leu Ser
65                  70                  75                  80

Phe Ile Ser Cys Asn Asp Gln Arg Gly Asn Ser Ile Arg Ala Ser Ala
                85                  90                  95
```

Gln Ile Glu Asp Arg Pro Pro Glu Ser Gly Asn Leu Ser Ala Leu Thr
            100                 105                 110

Asn Val Lys Asp Phe Val Ser Val Cys Trp Glu Tyr Val Arg Pro Tyr
        115                 120                 125

Thr Ala Lys Gly Val Ile Ile Cys Ser Ser Cys Leu Phe Gly Arg Glu
    130                 135                 140

Leu Leu Glu Asn Pro Asn Leu Phe Ser Trp Pro Leu Ile Phe Arg Ala
145                 150                 155                 160

Leu Leu Gly Met Leu Ala Ile Leu Gly Ser Cys Phe Tyr Thr Ala Gly
            165                 170                 175

Ile Asn Gln Ile Phe Asp Met Asp Ile Asp Arg Ile Asn Lys Pro Asp
        180                 185                 190

Leu Pro Leu Val Ser Gly Arg Ile Ser Val Glu Ser Ala Trp Leu Leu
    195                 200                 205

Thr Leu Ser Pro Ala Ile Ile Gly Phe Ile Leu Ile Leu Lys Leu Asn
210                 215                 220

Ser Gly Pro Leu Leu Thr Ser Leu Tyr Cys Leu Ala Ile Leu Ser Gly
225                 230                 235                 240

Thr Ile Tyr Ser Val Pro Pro Phe Arg Trp Lys Lys Asn Pro Ile Thr
            245                 250                 255

Ala Phe Leu Cys Ile Leu Met Ile His Ala Gly Leu Asn Phe Ser Val
        260                 265                 270

Tyr Tyr Ala Ser Arg Ala Ala Leu Gly Leu Ala Phe Ala Trp Ser Pro
    275                 280                 285

Ser Phe Ser Phe Ile Thr Ala Phe Ile Thr Phe Met Thr Leu Thr Leu
290                 295                 300

Ala Ser Ser Lys Asp Leu Ser Asp Ile Asn Gly Asp Arg Lys Phe Gly
305                 310                 315                 320

Val Glu Thr Phe Ala Thr Lys Leu Gly Ala Lys Asn Ile Thr Leu Leu
            325                 330                 335

Gly Thr Gly Leu Leu Leu Leu Asn Tyr Val Ala Ala Ile Ser Thr Ala
        340                 345                 350

Ile Ile Trp Pro Lys Ala Phe Lys Ser Asn Ile Met Leu Leu Ser His
    355                 360                 365

Ala Ile Leu Ala Phe Ser Leu Ile Phe Gln Ala Arg Glu Leu Asp Arg
370                 375                 380

Thr Asn Tyr Thr Pro Glu Ala Cys Lys Ser Phe Tyr Glu Phe Ile Trp
385                 390                 395                 400

Ile Leu Phe Ser Ala Glu Tyr Val Val Tyr Leu Phe Ile
            405                 410

<210> SEQ ID NO 66
<211> LENGTH: 9444
<212> TYPE: DNA
<213> ORGANISM: Artificial Sequence
<220> FEATURE:
<223> OTHER INFORMATION: optimized Steely1

<400> SEQUENCE: 66
atgaacaaga acagcaagat ccagtcgccc aactcgagcg acgtggcggt gattggcgtc    60
gggtttcggt tccctggtaa ctcgaacgat cctgagtcgc tctggaacaa cctgctggat   120
ggctttgacg ccatcacgca ggtcccgaag gagcggtggg ctacctcctt ccgggagatg   180
ggtctgatca agaacaagtt tggtggcttc ctgaaggact ccgagtggaa gaacttcgac   240

```
ccgctgtttt ttgggatcgg gcccaaggag gcccccttta ttgaccctca gcagcggctc    300
ctcctctcga tcgtgtggga gtccctggag gatgcgtaca tccgcccgga tgagctgcgc    360
ggctcgaaca cgggcgtgtt catcggtgtc agcaacaacg attacacgaa gctgggtttc    420
caggacaact actccatttc cccttacacg atgaccgggt ccaactcctc gctgaacagc    480
aaccgcattt cctactgctt cgatttccgc gggccgtcga ttacggtcga cacggcctgc    540
tccagctccc tcgtctcggt gaacctcggg gtgcagtcca ttcagatggg tgagtgcaag    600
atcgctatct gcggggtgt gaacgcgctg tttgatccct cgacgtcggt cgccttctcc     660
aagctcggcg tgctgtccga aacggccgg tgcaactcct ttagcgatca ggcttcgggt     720
tacgtgcgct ccgagggcgc cggtgtcgtc gtgctgaaga gcctcgagca ggccaagctg    780
gacggcgatc ggatttacgg tgtcattaag ggcgtgtcct cgaacgagga cggtgcttcg    840
aacggtgaca agaacagcct caccacgccc agctgcgagg cccagtccat caacatttcc    900
aaggcgatgg agaaggcctc cctgagccct tccgatatct actacatcga ggcccacggg    960
accggcacgc cggtgggcga tcccattgag gtcaaggctc tcagcaagat tttcagcaac   1020
tccaacaaca accagctgaa caacttcagc acggacggga acgacaacga tgacgatgac   1080
gacgacaaca cctcgcccga gccgctgctc atcggttcgt tcaagagcaa catcgggcac   1140
ctcgagtcgg cggctggtat tgcttccctg atcaagtgct gcctgatgct caagaaccgc   1200
atgctggtcc gtcgatcaa ctgctcgaac ctgaacccgt ccattccctt cgaccagtac    1260
aacattagcg tcatccgcga gattcgccag ttccctaccg acaagctggt gaacattggt   1320
atcaactcgt tcggcttcgg tgggtccaac tgccatctga ttattcagga gtacaacaac   1380
aacttcaaga acaactccac catctgcaac aacaacaaca acaacaacaa caacattgac   1440
tacctgatcc ctatctcctc caagacgaag aagtcgctgg acaagtacct gatcctcatt   1500
aagaccaaca gcaactacca taaggatatc tcgtttgacg attttgtcaa gttccagatc   1560
aagtcgaagc agtacaacct gtcgaaccgg atgaccacga ttgccaacga ttggaacagc   1620
tttattaagg gttcgaacga gttccataac ctgattgagt ccaaggacgg cgagggtggt   1680
agctcgtcct cgaaccgggg tatcgattcc gccaaccaga tcaacaccac caccacgagc   1740
accatcaacg acattgagcc gctcctcgtc ttcgtgtttt gcgggcaggg cccgcagtgg   1800
aacggtatga tcaagaccct gtacaactcg gagaacgtgt tcaagaacac ggtggaccac   1860
gtggattcga ttctgtacaa gtacttcggt tacagcattc tgaacgtgct ctcgaagatt   1920
gacgataacg atgacagcat caaccaccct atcgtcgccc agcccagcct cttcctcctc   1980
cagattggtc tcgtcgagct gttttaagtac tggggcattt acccctccat cagcgtcggc   2040
cattcgttcg gtgaggtctc gtcgtactac ctctcgggga tcatctcgct ggagacggcg   2100
tgcaagatcg tgtacgtgcg gagctcgaac cagaacaaga cgatggggtc cgggaagatg   2160
ctcgtggtct cgatgggttt caagcagtgg aacgaccagt ttagcgcgga gtggtcggac   2220
attgagatcg cttgctacaa cgcccccgac agcatcgtcg tcaccgggaa cgaggagcgc   2280
ctgaaggagc tgtcgatcaa gctctcggac gagtcgaacc agattttcaa cacgtttctg   2340
cgctcgccct gcagcttcca ttccagccac caggaggtca ttaagggctc gatgttcgag   2400
gagctctcca acctgcagag caccggcgag acggagatcc ccctgttcag cacggtgacg   2460
ggtcggcagg tcctctccgg ccacgtcacc gcccagcaca tctacgataa cgtgcgggag   2520
cccgtgctgt tcagaagac cattgagagc attacctcgt acatcaagtc gcattacccg    2580
tccaaccaga aggtgatcta cgtggagatt gcgcctcatc cgaccctgtt ttcgctcatc   2640
```

```
aagaagagca ttccgtcgtc caacaagaac tcgtcgtccg tgctgtgccc tctcaaccgc    2700
aaggagaact ccaacaacag ctacaagaag ttcgtcagcc agctgtactt taacggcgtg    2760
aacgtcgatt ttaactttca gctcaacagc atctgcgata acgtcaacaa cgatcaccac    2820
ctcaacaacg tgaagcagaa ctcgttcaag gagaccacga actccctccc ccggtaccag    2880
tgggagcagg atgagtactg gtcggagcct ctcattagcc ggaagaaccg gctggagggc    2940
cccacgacgt cgctcctggg ccatcggatt atctacagct ttccggtctt tcagtcggtg    3000
ctcgatctgc agtccgataa ctacaagtac ctgctcgatc acctcgtgaa cggtaagccg    3060
gtgtttcctg gggctgggta cctcgacatt atcattgagt ttttcgacta ccagaagcag    3120
cagctcaaca gctcggacag ctcgaactcc tacattatta acgtcgacaa gatccagttt    3180
ctgaacccga tccacctgac ggagaacaag ctccagaccc tgcagtcgag ctttgagcct    3240
attgtcacca agaagtccgc ttttagcgtg aacttcttca ttaaggatac ggtggaggac    3300
cagagcaagg tcaagagcat gtccgacgag acgtggacca acacgtgcaa ggccaccatt    3360
tccctcgagc agcagcagcc ctcgccgtcg tcgaccctga ccctgtccaa gaagcaggat    3420
ctccagattc tgcgcaaccg gtgcgatatc tccaagctcg acaagtttga gctgtacgat    3480
aagatttcga gaacctcggg gctccagtac aacagcctct tcaggtggt ggacaccatt    3540 gagaccggga aggactgctc cttcgcgacg ctgagcctgc tgaggatac gctctttacc    3600 acgattctca accccttgcct gctcgacaac tgctttcacg gcctcctcac gctcattaac    3660
gagaagggtt cgttcgtggt ggagagcatt tcctccgtct cgatttacct cgagaacatc    3720 ggttcctta accagaccag cgtggggaac gtgcagtttt acctctacac cacgatttcg    3780
aaggctacgt cctttagcag cgagggcacg tgcaagctgt tcacgaagga tggctcccctc    3840 atcctgtcga tcgggaagtt tatcattaag tcgacgaacc cgaagtcgac gaagacgaac    3900
gagacgattg agtcgcccct ggatgagacg ttttcgatcg agtggcagtc gaaggactcg    3960
ccgattccga cccctcagca gattcagcag cagtcccccc tgaactccaa cccgtcctt    4020 atccggagca ccatcctcaa ggacattcag tttgagcagt actgctcctc gattatccat    4080
aaggagctga tcaaccacga gaagtacaag aaccagcagt cgtttgatat taactcgctg    4140
gagaaccacc tcaacgacga ccagctcatg gagtccctct ccatttccaa ggagtacctc    4200 cgcttttca cgcgcattat ctccattatc aagcagtacc ccaagattct caacgagaag    4260
gagctgaagg agctcaagga gatcattgag ctgaagtacc cctcggaggt ccagctgctg    4320
gagtttgagg tcatcgagaa ggtgtcgatg atcattccga agctcctgtt tgagaacgac    4380
aagcagtcgt cgatgacgct ctttcaggac aacctgctga cccggttcta cagcaactcc    4440
aacagcaccc ggttctacct ggagcgggtc tccgagatgg tgctggagag cattcggccc    4500
attgtgcgcg agaagcgggt gttccggatc ctggagatcg gtgctggtac gggctccctc    4560
tccaacgtcg tgctcacgaa gctgaacacc tacctcagca cgctcaactc gaacggtggt    4620
tccggctaca acatcattat cgagtacacg ttcaccgaca tctcggcgaa ctttatcatt    4680
ggtgagatcc aggagaccat gtgcaacctc tacccgaacg tgaccttcaa gttttcggtc    4740
ctggatctcg agaaggagat tattaactcc agcgacttcc tcatgggtga ttacgatatc    4800
gtgctgatgg cttacgtgat ccatgccgtc agcaacatta agttctccat cgagcagctg    4860
tacaagctgc tgtccccgcg gggctggctc tctctgcattg agccgaagtc caacgtggtc    4920
ttttcggatc tggtgtttgg ctgcttcaac cagtggtgga actactacga tgacatccgc    4980
```

```
accacccatt gctcgctgag cgagtcgcag tggaaccagc tgctcctcaa ccagtcgctc    5040
aacaacgagt cgtcgtcctc gtccaactgc tacggcggtt tttccaacgt gtccttcatc    5100
ggtggcgaga aggacgtgga ctcccatagc tttattctcc attgccagaa ggagtccatc    5160
tcccagatga agctcgccac caccatcaac aacggcctct cgagcggctc gatcgtcatt    5220
gtgctgaaca gccagcagct cacgaacatg aagtcctacc ccaaggtcat cgagtacatc    5280
caggaggcga cctcgctctg caagaccatt gagatcatcg atagcaagga tgtcctcaac    5340
tccaccaact cggtcctcga aagatccag aagagcctgc tggtgttctg cctcctgggc    5400
tacgatctgc tggagaacaa ctaccaggag cagtcgttcg agtacgtcaa gctcctcaac    5460
ctgatctcca ccacggccag ctcgagcaac gacaagaagc ctcctaaggt cctcctgatt    5520
accaagcagt cggagcggat tagccggtcg ttttacagcc gctcgctgat cggcatttcc    5580
cggacgagca tgaacgagta cccgaacctc tcgattacct cgatcgatct cgataccaac    5640
gactactcgc tccagtcgct cctcaagccg attttagca acagcaagtt cagcgataac    5700
gagttcattt tcaagaaggg gctgatgttc gtgtcccgga tttttaagaa caagcagctg    5760
ctcgagtcct cgaacgcctt tgagacggac tcctcgaacc tctactgcaa ggcttcgagc    5820
gatctgagct acaagtacgc tatcaagcag agcatgctca cggagaacca gattgagatt    5880
aaggtggagt gcgtcggtat taacttcaag gacaacctct tctacaaggg gctcctcccc    5940
caggagatct tccggatggg ggacatttac aacccgcctt acggtctgga gtgctccggg    6000
gtgattacgc gcatcggctc gaacgtgacg gagtacagcg tcggtcagaa cgtgtttggt    6060
tttgcgcgcc acagcctcgg ctcgcatgtc gtcacgaaca aggatctggt catcctcaag    6120
cccgacacga tttcgttctc cgaggccgcc tccattcccg tcgtgtactg cacggcctgg    6180
tacagcctct ttaacattgg gcagctgagc aacgaggaga gcattctgat ccatagcgct    6240
accgggggtg tcggcctcgc gtccctcaac ctcctcaaga tgaagaacca gcagcagcag    6300
cctctgacca acgtgtacgc caccgtgggt tccaacgaga agaagaagtt cctgatcgac    6360
aacttcaaca acctgttcaa ggaggacggt gagaacattt tcagcacccg ggataaggag    6420
tacagcaacc agctggagag caagattgat gtcatcctga acacgctgtc cggcgagttc    6480
gtcgagagca actttaagtc gctgcgctcc tttgggcggc tcatcgacct cagcgctacc    6540
cacgtgtacg cgaaccagca gattggtctc ggtaacttta gtttgacca cctctactcg    6600 gccgtcgacc tggagcggct cattgatgag aagcccaagc tcctgcagtc catcctccag    6660
cggatcacga actcgattgt gaacgggagc ctggagaaga tccccatcac catttttccg    6720
tcgaccgaga ccaaggacgc gatcgagctg ctctcgaagc gcagccatat cggcaaggtg    6780
gtggtcgatt gcaccgacat cagcaagtgc aaccctgtgg gcgacgtgat caccaacttc    6840
tccatgcggc tgccgaagcc taactaccag ctgaacctga acagcaccct gctgatcacg    6900
ggccagtcgg ggctgtcgat tcccctgctc aactggctgc tgtcgaagag cggtggcaac    6960
gtgaagaacg tggtgatcat cagcaagagc accatgaagt ggaagctgca gacgatgatt    7020
tcgcattttg tgtcgggttt tggcatccat tttaactacg tgcaggtgga catttccaac    7080
tacgatgccc tctccgaggc gatcaagcag ctgccgagcg acctcccgcc cattacctcg    7140
gtgttccatc tggccgctat ctacaacgat gtccccatgg atcaggtgac gatgtcgacg    7200
gtggagtccg tgcacaaccc taaggtgctc ggcgctgtca acctccaccg gatctccgtc    7260
agcttcgggt ggaagctgaa ccacttcgtc ctcttttcgt ccattacggc tatcacgggt    7320 taccccggatc agtcgattta caacagcgcc aactccatcc tggacgctct ctccaacttc    7380
```

```
cggcggttca tgggtctccc tagcttcagc attaacctgg ggccgatgaa ggatgagggc    7440
aaggtgagca ccaacaagag cattaagaag ctgttcaagt cccggggtct gccttcgctg    7500
agcctgaaca agctgttcgg cctgctggag gtcgtgatca acaacccgag caaccatgtg    7560
atcccctcgc agctgatctg ctcgcctatc gactttaaga cgtacatcga gtccttttcg    7620
accatgcgcc cgaagctcct ccacctccag cccaccatct ccaagcagca gtcctcgatc    7680
atcaacgact ccaccaaggc gtcgtcgaac atttcgctgc aggacaagat taccagcaag    7740
gtcagcgacc tgctcagcat tcccatcagc aagattaact ttgatcatcc gctcaagcat    7800
tacgggctgg attccctgct caccgtccag ttcaagtcct ggatcgacaa ggagtttgag    7860
aagaacctgt ttacccatat ccagctggcg acgattagca tcaactcgtt tctcgagaag    7920
gtcaacggtc tgtcgaccaa caacaacaac aacaacaaca gcaacgtgaa gtccagcccg    7980
agcattgtga aggaggagat tgtcacgctg acaaggacc agcagcccct cctgctcaag    8040
gagcaccagc atattatcat tagccccgac attcgcatca caagcctaa gcgcgagtcc    8100 ctgattcgca cgcccattct gaacaagttt aaccagatca ccgagtcgat catcaccccc    8160
tcgacgcctt ccctcagcca gagcgacgtg ctgaagacgc cgcctattaa gtcgctcaac    8220
aacacgaaga actccagcct catcaacacc cctccgattc agtccgtcca gcagcatcag    8280
aagcagcagc agaaggtgca ggtcattcag cagcagcagc agccgctcag ccggctgtcc    8340
tacaagtcca caacaacag cttttgtcctg ggcatcggga tctccgtccc cggcgagccc    8400
attagccagc agtccctgaa ggattccatt agcaacgatt tctcggacaa ggctgagacc    8460
aacgagaagg tgaagcgcat tttcgagcag tcgcagatca agacgcgcca tctcgtgcgg    8520
gattacacga agcctgagaa ctcgattaag tttcgccatc tggagaccat caccgacgtg    8580
aacaaccagt tcaagaaggt cgtcccggat ctcgctcagc aggcctgcct ccgggcgctg    8640
aaggattggg gggggataa ggggggatatt acccacattg tgtcggtgac gagcaccggt    8700
attatcatcc ctgacgtgaa cttttaagctc atcgatctcc tcggtctcaa caaggacgtg    8760
gagcgcgtct cgctcaacct catgggctgc ctcgctggcc tctccagcct ccgcacggct    8820
gcgtcgctcg cgaaggcgtc gccccggaac cggatcctcg tggtctgcac ggaggtgtgc    8880
agcctccatt tctcgaacac cgatggcggt gaccagatgg tcgcgtcgag catctttgcc    8940
gacgggtcgg ccgcctacat cattggctgc aacccgcgga ttgaggagac cccgctgtac    9000
gaggtgatgt gctcgatcaa ccggtcgttt ccgaacacgg agaacgcgat ggtctgggac    9060
ctggagaagg agggctggaa cctcggcctg gatgcgtcga ttcccatcgt catcggctcg    9120
gggatcgagg ccttcgtcga taccctcctg gacaaggcga agctccagac gtcgaccgcc    9180
atttcggcta aggactgcga gtttctcatc catacgggcg gtaagtcgat tctcatgaac    9240
attgagaact cgctgggcat cgatcccaag cagacgaaga acacctggga cgtgtaccac    9300
gcctacggca acatgagcag cgccagcgtg attttttgtca tggaccacgc tcgcaagtcg    9360
aagtcgctcc cgacgtactc catcagcctc gccttcggtc ctgggctcgc gttcgagggg    9420
tgcttcctca agaacgtcgt ctaa                                          9444
```

<210> SEQ ID NO 67
<211> LENGTH: 8907
<212> TYPE: DNA
<213> ORGANISM: Artificial Sequence
<220> FEATURE:
<223> OTHER INFORMATION: optimized Steely2

<400> SEQUENCE: 67

```
atgaacaaca acaagagcat caacgatctc agcggtaact ccaacaacaa catcgctaac    60
agcaacatta acaactacaa caacctgatt aagaaggagc ctattgctat cattggcatc   120
gggtgccgct tccctgggaa cgtgtccaac tactcggact tcgtgaacat cattaagaac   180
ggctccgact gcctcaccaa gattcctgac gaccgctgga acgctgacat catttcgcgg   240
aagcagtgga agctgaacaa ccgcatcggg ggttacctga agaacatcga ccagttcgac   300
aaccagtttt tcggcatttc gcctaaggag gctcagcata tcgatcctca gcagcggctg   360
ctcctgcacc tcgctatcga gaccctggag gatggcaaga tctccctgga tgagatcaag   420
ggtaagaagg tgggcgtgtt catcgggtcc agctccggcg attacctgcg ggggtttgat   480
tcgagcgaga tcaaccagtt taccacgccg gggaccaact ccagcttcct gtcgaaccgg   540
ctctcgtact ttctcgacgt gaacgggccc tccatgacgg tgaacaccgc gtgctcggct   600
agcatggtgg cgattcatct ggggctccag tcgctgtgga acggcgagtc ggagctcagc   660
atggtgggcg gtgtgaacat tatttcctcg ccgctccagt cgctggactt cgggaaggcg   720
gggctgctca accaggagac ggatggccgg tgctacagct ttgatccccg cgcttccggg   780
tacgtccgct cggagggtgg cggcatcctc ctcctcaagc ctctgtcggc ggctctgcgg   840
gacaacgatg agatctactc cctcctgctg aactccgcga caactcgaa cgggaagacg   900
cccacgggta tcacctcccc gcgctccctc tgccaggaga gctcattca gcagctcctg   960
cgcgagagct cggaccagtt ctcgattgac gatattggtt actttgagtg ccacggcacg  1020
ggcacccaga tgggggacct caacgagatt acggcgatcg gcaagtcgat tgggatgctg  1080
aagtcgcacg acgaccctct cattatcggc tccgtcaagg cgtcgattgg gcatctcgag  1140
ggtgcgagcg gcatttgcgg tgtgatcaag tcgattatct gcctcaagga gaagatcctg  1200
ccgcagcagt gcaagtttag ctcctacaac cccaagattc cttttgagac cctgaacctg  1260
aaggtcctca ccaagacgca gccgtggaac aactcgaagc ggatttgcgg cgtcaactcg  1320
tttggggtcg gcggtagcaa ctccagcctg ttcctgagct cgtttgataa gagcacgacc  1380
atcacggagc ccaccaccac gaccaccatc gagtccctgc cctccagctc gtcctcgttc  1440
gacaacctga gcgtgtcctc ctccatttcg accaacaacg acaacgataa ggtcagcaac  1500
atcgtgaaca accgctacgg cagctccatt gacgtcatca cgctgtcggt gacgtcgccg  1560
gataaggagg acctgaagat tcgggcgaac gatgtcctcg agtcgatcaa gacgctcgat  1620
gataacttca agattcgcga tatcagcaac ctgacgaaca ttcgcacctc ccacttctcc  1680
aaccgcgtcg ctattatcgg tgactcgatc gactccatta agctcaacct gcagtccttt  1740
atcaagggg agaacaacaa caacaagtcg attatcctgc ctctgattaa caacggcaac  1800
aacaacaaca acaacaacaa caactcgtcc gggtcctcgt cctccagcag caacaacaac  1860
aacatttgct tcatctttag cggccagggc cagcagtgga acaagatgat cttcgatctg  1920
tacgagaaca acaagacctt caagaacgag atgaacaact tttccaagca gttcgagatg  1980
atttcgggct ggtcgatcat tgacaagctg tacaactccg gcggtggtgg taacgaggag  2040
ctcattaacg agacgtggct cgcccagccg tccattgtgg ccgtccagta tcgctgatt  2100
aagctgttta gcaaggacat cgggatcgag gggtcgatcg tcctcgggca gcctgggt   2160
gagctcatgg ctgcttacta ctgcggtatc attaacgact ttaacgatct gctgaagctg  2220
ctctacatcc ggtcgacgct ccagaacaag acgaacgggc cggtcgcat gcacgtgtgc  2280
ctcagcagca aggccgagat cgagcagctg atttcgcagc tcgggtttaa cggccggatt  2340
```

```
gtgatttgcg ggaacaacac gatgaagtcg tgcaccatct cgggtgataa cgagtcgatg    2400
aaccagttta ccaagctcat ttcgtcgcag cagtacggca gcgtcgtgca taaggaggtc    2460
cgcacgaaca gcgcctttca ttcgcaccag atggacatca tcaaggacga gttctttaag    2520
ctctttaacc agtactttcc tacgaaccag attagcacca accagattta cgatggcaag    2580
agcttctact cgacgtgcta cgggaagtac ctgacgccta ttgagtgcaa gcagctcctc    2640
tcgtcgccga actactggtg gaagaacatt cgcgagtcgg tgctctttaa ggagtcgatt    2700
gagcagatcc tgcagaacca ccagcagtcg ctcacgttta ttgagatcac gtgccaccct    2760
atcctcaact acttcctgtc gcagctcctg aagtcgagca gcaagtcgaa cacctcctg    2820 ctctccacgc tgtcgaagaa cagcaactcc atcgatcagc tgctcattct gtgcagcaag    2880
ctgtacgtca acaacctctc ctcgatcaag tggaactggt tttacgacaa gcagcagcag    2940
cagcagtcgg agtcgctcgt gagcagcaac tttaagctgc ctggccgccg gtggaagctc    3000
gagaagtact ggatcgagaa ctgccagcgc cagatggatc ggattaagcc gccgatgttc    3060
attagcctcg atcggaagct gttttccgtc acgccgtcct ttgaggtgcg gctcaaccag    3120
gatcgcttcc agtacctgaa cgaccaccag attcaggata tccccctggt gccgttctcc    3180
ttttacatcg agctcgtgta cgcctccatc tttaactcca tctccaccac caccacgaac    3240
acgacggctt cgaccatgtt tgagatcgag aacttcacca ttgatagcag catcatcatc    3300
gaccagaaga agtcgaccct catcggtatt aacttcaact cggacctcac gaagtttgag    3360
atcggctcca ttaactccat cgggtcgggt tcgtcgtcga acaacaactt tatcgagaac    3420
aagtggaaga tccattcgaa cggtattatt aagtacggta ccaactacct caagagcaac    3480
agcaagtcca acagcttcaa cgagtcgacg acgacgacca cgacgaccac caccaccacc    3540
aagtgcttca agagcttcaa cagcaacgag ttttacaacg agattattaa gtacaactac    3600
aactacaagt cgacgttcca gtgcgtcaag gagttcaagc agttcgacaa gcaggggacg    3660
ttctactact ccgagattca gttcaagaag aacgataagc aggtcattga tcagctcctc    3720
tcgaagcagc tgccttccga cttttcgctgc atccaccctt gcctgctgga cgccgtgctc    3780
cagagcgcta ttattcctgc gacgaacaag accaactgct cgtggattcc tatcaagatc    3840
gggaagctca gcgtcaacat tccctcgaac tcctacttca actttaagga tcagctcctc    3900
tactgcctca ttaagccgtc cacctccacc tcgacctccc ctagcacgta cttttcgtcg    3960
gacatccagg tgttcgataa gaagaacaac aacctgatct gcgagctgac gaacctggag    4020
ttcaagggga ttaacagcag ctcctcgagc agctcgtcgt cgtccacgat taactcgaac    4080
gtggaggcca actacgagtc caagatcgag gagaccaacc acgatgagga tgaggacgag    4140
gagctccccc tcgtgagcga gtacgtgtgg tgcaaggagg agctgattaa ccagagcatc    4200
aagttcaccg ataactacca gaccgtgatt ttttgcagca cgaacctgaa cggtaacgat    4260
ctgctggact ccatcatcac cagcgccctg gagaacgggc acgacgagaa caagattttc    4320
attgtctccc cgcccccccgt cgagtcggac cagtacaaca accggattat tattaactac    4380
acgaacaacg agagcgactt cgatgctctg tttgccatca tcaactccac gacgtccatc    4440
agcggcaaga gcggcctgtt ttccacgcgg tttattattc tgcctaactt taactccatt    4500
acgttctcct ccggcaactc cacgcccctg atcaccaacg tgaacggtaa cggcaacggg    4560
aagtcgtgcg gcggggcgg tggttccacc aacaacacca tctccaactc gtcgtcgagc    4620
atttcgtcca tcgataacgg caacaacgag gatgaggaga tggtcctcaa gagctttaac    4680
```

```
gatagcaacc tcagcctgtt tcacctccag aagagcatca ttaagaacaa cattaagggc    4740
cgcctgtttc tgattacgaa cgggggggcag agcatcagct cgtccacgcc gacctccacc    4800
tacaacgacc agtcctacgt gaacctcagc cagtaccagc tgattggcca gatccgcgtg    4860
tttagcaacg agtacccgat tatggagtgc tcgatgatcg acatccagga ttcgacgcgg    4920
attgacctca ttaccgatca gctcaacagc accaagctca gcaagctcga gatcgcgttc    4980
cgggataaca ttggctacag ctacaagctg ctgaagccct ccattttga caactcgtcg    5040 ctgccgagct cgtcgtccga gatcgagacg accgctacca cgaaggatga ggagaagaac    5100
aactccatta actacaacaa caactactac cgggtcgagc tctccgacaa cgggattatt    5160
agcgatctca agatcaagca gttccgccag atgaagtgcg gggtgggcca ggtgctggtg    5220
cgcgtcgaga tgtgcacgct caacttccgg gacatcctca agtcgctcgg tcgcgattac    5280
gaccctatcc acctgaactc gatgggtgac gagttctcgg gtaaggtgat tgagattggc    5340 gaggggggtga acaacctgag cgtcggccag tacgtgttcg gtattaacat gtccaagtcc    5400
atgggcagct ttgtgtgctg caacagcgac ctcgtctttc ctattcccat tccgacccct    5460
tccagcagca gctcgagcaa cgagaacatc gatgaccagg agatcatttc gaagctgctg    5520
aaccagtact gcacgattcc gattgtcttt ctcacgtcct ggtacagcat cgtcattcag    5580
ggccgcctga agaagggtga gaagattctg atccactccg gttgcggggg tgtgggtctg    5640
gctaccattc agatttcgat gatgattggc gcggagatcc acgtgacggt ggggagcaac    5700
gagaagaagc agtacctgat caaggagttc ggtattgacg agaagcggat ttacagctcg    5760
cgctccctcc agttttacaa cgacctgatg gtcaacaccg acggtcaggg tgtcgatatg    5820
gtgctgaact ccctgagcgg tgagtacctc gagaagtcca tccagtgcct gtcccagtac    5880
ggccggttta ttgagattgg caagaaggat atctactcga actccagcat tcacctggag    5940
ccttttaaga caacctgag cttttttcgct gtggacattg cgcagatgac ggagaaccgg    6000
cgggactacc tgcgcgagat catgatcgat cagctgctgc cttgcttcaa gaacgggtcc    6060
ctcaagcctc tcaaccagca ctgcttcaac tcccctgcg acctcgtgaa ggctatccgg    6120
tttatgtcgt cggggaacca tattggtaag atcctcatca actggagcaa cctcaacaac    6180
gacaagcagt tcatcaacca ccattcggtc gtccatctcc ctatccagtc gtttttcgaac    6240 cgcagcacgt acattttac cggcttcggt gggctcaccc agacgctcct gaagtacttt    6300
agcaccgagt ccgacctgac caacgtgatc attgtctcga gaacggcct ggatgacaac    6360 tcgggtagcg gtagcgggaa caacgagaag ctcaagctga tcaaccagct gaaggagtcc    6420
gggctcaacg tgctcgtcga gaagtgcgat ctgagctcca ttaagcaggt ctacaagctc    6480
ttcaacaaga ttttcgacaa cgatgcttcg ggctccgatt cggcgatttt tcggacatc    6540 aagggtattt ttcacttcgc gtccctgatt aacgacaagc gcatcctgaa gcacaacctg    6600
gagtccttta actacgtcta caactccaag gcgacgagcg cctggaacct ccatcaggtc    6660
tcgctgaagt acaacctcaa cctcgaccat tttcagacga tcgcagcgt catcaccatt    6720 ctggggaaca tcggccagag caactacacg tgcgccaacc gctttgtcga gggtctcacg    6780
catctccgca ttggcatggg cctgaagagc tcctgcattc atctcgctag cattcctgat    6840
gtgggtatgg cgagcaacga caacgtgctg aacgacctca actccatggg gttcgtgccc    6900
ttccagagcc tgaacgagat gaacctgggg tttaagaagc tcctctcctc gccgaacccg    6960
atcgtggtcc tcgcgagat taacgtggat cgctttattg aggcgacccc caacttccgg    7020
gctaaggata actttattat tacgtcgctg tttaaccgga ttgaccccct gctgctggtc    7080
```

```
aacgagagcc aggattttat tattaacaac aacatcaaca acaacggcgg gggtggtgac    7140
gggagcttcg atgacctgaa ccagctcgag gatgagggtc agcagggttt cggcaacggg    7200
gacggttacg tcgacgataa cattgactcg gtgtcgatgc tcagcggcac ctccagcatt    7260
tttgataacg atttctacac gaagtcgatc cggggtatgc tctgcgacat tctcgagctc    7320
aaggacaagg atctgaacaa cacggtgtcg ttcagcgact acggcctgga ctccctgctc    7380
tcgagcgagc tcagcaacac catccagaag aacttctcca ttctgatccc ctccctgacc    7440
ctggtggaca actcgacgat caactccacc gtcgagctca ttaagaacaa gctcaagaac    7500
tccacgacca gctcgatctc ctcctcggtg agcaagaagg tctcctttaa gaagaacacc    7560
cagcccctga tcatccctac gacggctccg attagcatta tcaagacgca gtcgtacatt    7620
aagtcggaga tcattgagag cctccccatt agctccagca ccacgatcaa gcctctcgtc    7680
ttcgataacc tcgtctactc cagctcgagc agcaacaaca gcaactccaa gaacgagctc    7740
acgtcgccgc ccccgagcgc caagcgcgag agcgtgctgc ccatcatcag cgaggataac    7800
aacagcgata acgatagcag catggccacc gtgatttacg agatctcccc gattgccgcg    7860
ccttaccatc gctaccagac ggatgtcctc aaggagatca cccagctgac gccccacaag    7920
gagttcattg acaacatcta caagaagtcg aagattcgca gccgctactg ctttaacgat    7980
ttctccgaga gtcgatggc ggatatcaac aagctggacg ctggtgagcg cgtcgcgctc    8040
ttccgggagc agacgtacca gaccgtgatt aacgccggga agaccgtgat cgagcgcgct    8100
gggattgatc cgatgctcat ctcccatgtg gtggggtga cgtcgaccgg tattatggct    8160
ccttcctttg atgtcgtgct cattgataag ctgggcctgt cgattaacac ctcccggacc    8220
atgattaact ttatgggctg cggggctgcg gtcaacagca tgcggccgc caccgcttac    8280 gctaagctca agcccggtac gttcgtcctg gtggtggccg tcgaggccag cgctacctgc    8340
atgaagttca acttcgactc gcggtcggat ctgctgtccc aggccatttt cacggatggg    8400
tgcgtcgcca ccctggtcac ctgccagcct aagtcctcgc tggtcggcaa gctggagatt    8460
atcgatgacc tgtcctacct catgcctgac agccgcgatg cgctcaacct ctttattggg    8520
cctacgggga tcgacctcga cctgcggccc gagctcccta ttgcgattaa ccggcatatc    8580
aactccgcga tcacgtcgtg gctgaagaag aacagcctgc agaagtcgga catcgagttt    8640
tttgcgaccc atcctggcgg cgctaagatc atttcggccg tccacgaggg gctcggtctg    8700
tcgcctgagg acctcagcga ctcctacgag gtcatgaagc ggtacggcaa catgatcggt    8760
gtctcgacgt actacgtcct gcggcgcatc ctcgacaaga accagacgct cctccaggag    8820
gggtcgctcg gctacaacta cggcatggct atggctttca gccctggggc gtcgatcgag    8880
gccattctgt ttaagctgat taagtaa                                        8907
```

<210> SEQ ID NO 68
<211> LENGTH: 924
<212> TYPE: DNA
<213> ORGANISM: Artificial Sequence
<220> FEATURE:
<223> OTHER INFORMATION: optimized Orf2

<400> SEQUENCE: 68

```
atgagcgagg cggccgatgt cgagcgggtc tacgctgcta tggaggaggc tgctgggctg      60
ctgggcgtgg cgtgcgcgcg cgataagatc taccccctcc tcagcacctt tcaggatacc     120
ctggtggagg gtggtagcgt ggtggtcttc agcatggcct ccgggcggca ttccaccgag     180
```

```
ctcgattttt ccatctcggt ccccacgtcc cacggggacc cttacgcgac cgtcgtggag      240
aagggtctct tccccgctac gggtcacccc gtggatgatc tgctggccga tacgcagaag      300
catctgccgg tgagcatgtt cgctatcgac ggggaggtca ccggcggctt taagaagacg      360
tacgccttct ttcctaccga taacatgcct ggggtggccg agctcagcgc cattccttcg      420
atgccgcccg ccgtggccga gaacgctgag ctgtttgcgc ggtacggcct ggataaggtg      480
cagatgacct ccatggatta caagaagcgc caggtgaacc tctactttc ggagctctcc       540 gctcagaccc tcgaggccga gtccgtcctg gctctcgtgc gggagctggg tctccatgtc      600
ccgaacgagc tcgggctcaa gttctgcaag cgctcgttct cggtctaccc taccctcaac      660
tgggagaccg gcaagattga ccgcctgtgc ttcgctgtga ttagcaacga tcctacccctc    720 gtccctagct ccgatgaggg tgacatcgag aagttccaca actacgctac caaggcgccc     780
tacgcttacg tgggggagaa cgcacgctg gtctacggcc tcaccctgag ccctaaggag       840
gagtactaca agctcggcgc ttactaccac atcacggatg tccagcgcgg cctcctcaag      900
gcctttgact cgctggagga ttga                                            924

<210> SEQ ID NO 69
<211> LENGTH: 1197
<212> TYPE: DNA
<213> ORGANISM: Artificial Sequence
<220> FEATURE:
<223> OTHER INFORMATION: optimized CsPT4

<400> SEQUENCE: 69
atggggctct cgctcgtctg caccttagc tttcagacca actaccatac gctgctgaac        60
ccgcacaaca agaacccgaa gaacagcctc ctcagctacc agcaccccaa gacccccatt      120
atcaagtcca gctacgataa ctttcctagc aagtactgcc tcaccaagaa cttccacctg      180
ctcggcctca acagccataa ccgcattttcc agccagtccc gctccatccg cgctggctcc     240
gatcagatcg aggggtcccc gcatcacgag tccgacaact cgatcgccac caagattctg      300
aactttgggc acacgtgctg gaagctgcag cggccgtacg tcgtcaaggg gatgatctcg      360
atcgcctgcg ggctgttcgg tcgggagctc ttcaacaacc ggcatctgtt tagctggggc      420
ctgatgtgga aggctttttt cgcgctggtg cccatcctca gcttcaactt ttttgccgct      480
atcatgaacc agatttacga tgtggacatt gaccggatta caagcccga cctgcccctg      540 gtcagcggtg agatgtccat tgagaccgct tggattctca gcattatcgt ggcgctcacg      600
ggcctgatcg tcaccatcaa gctcaagagc gctccgctct tgtgttcat ctacatctt       660 ggcattttg cgggttttcgc ttacagcgtg cctccgatcc gctggaagca gtacccgttc     720
acgaactttc tgattacgat tagctcgcat gtgggtctcg ctttttacgtc gtacagcgct    780 accacctcgg ctctcggcct gccttttgtc tggcgccccg cgttctcctt tatcattgcg    840
ttcatgaccg tcatgggcat gacgattgcg tttgctaagg atatttccga tatcgagggt     900
gatgccaagt acggcgtcag cacggtcgcc acgaagctgg gggcgcggaa catgacgttt     960
gtcgtgtcgg gcgtgctcct cctcaactac ctcgtctcga tctcgatcgg gatcatctgg    1020
cctcaggtct ttaagagcaa cattatgatt ctgtcccatg ccattctggc cttttgcctg    1080
atctttcaga cgcgcgagct cgcccctcgcg aactacgcta gcgctccttc ccgccagttc   1140
ttcgagttta tctggctcct ctactacgcg gagtactttg tgtacgtgtt cattaa         1197

<210> SEQ ID NO 70
<211> LENGTH: 1239
```

<212> TYPE: DNA
<213> ORGANISM: Artificial Sequence
<220> FEATURE:
<223> OTHER INFORMATION: optimized H1PT1

<400> SEQUENCE: 70

```
atggagctgt cgtcggtcag ctcgttctcc ctgggtacca acccttttat ctccatcccg        60
cacaacaaca acaacctcaa ggtgtcgtcc tactgctgca agtccaagtc gcgggtcatc       120
aactcgacca actcgaagca ctgcagcccc aacaacaaca gcaacaacaa cacctcgaac       180
aagacgacgc atctgctcgg cctgtacggg cagtcccggt gcctcctgaa gcctctcagc       240
tttatttcgt gcaacgatca gcgcggtaac tcgattcggg cgtccgctca gattgaggat       300
cggcccccg agtcgggtaa cctctccgcg ctgaccaacg tcaaggactt tgtgtccgtg        360
tgctgggagt acgtgcggcc ttacaccgcc aagggcgtca ttatctgctc ctcctgcctc       420
ttcggccggg agctgctgga gaaccccaac ctctttagct ggcctctcat ttttcgcgcc       480
ctcctcggca tgctggccat tctgggtagc tgcttctaca cggctggcat caaccagatt       540
ttcgacatgg acatcgaccg gattaacaag cctgatctgc cgctcgtctc ggggcggatt       600
tcggtggaga gcgcttggct cctgaccctc agcctgcga ttattggttt tatcctgatc        660
ctgaagctga actccgggcc tctcctgacc agcctgtact gcctcgcgat tctcagcggg       720
accatttaca gcgtccctcc ctttcggtgg aagaagaacc cgatcacggc tttctctgc        780
atcctgatga ttcacgctgg gctcaacttc tccgtgtact acgcgtcccg ggctgccctc       840
ggtctggctt ttgcgtggtc gccgagcttc tccttcatca ccgccttcat tacctttatg       900
acgctgaccc tggcttccag caaggatctc agcgatatta acggcgaccg gaagttcggc       960
gtggagacct ttgctacgaa gctgggcgcg aagaacatca ccctcctggg gaccgggctc      1020
ctgctcctca actacgtcgc cgctatcagc acggccatta tttggccgaa ggcgtttaag      1080
tcgaacatca tgctcctgtc gcatgcgatc ctggcctttt ccctgatttt tcaggcgcgc      1140
gagctcgacc gcacgaacta cacgccggag gcctgcaagt ccttctacga gttcatttgg      1200
atcctctttt cggctgagta cgtggtgtac ctctttatt                             1239
```